(12) United States Patent
Endo et al.

(10) Patent No.: US 11,390,652 B2
(45) Date of Patent: Jul. 19, 2022

(54) TRANSCRIPTIONAL REGULATORY FUSION POLYPEPTIDE

(71) Applicants: Astellas Pharma Inc., Tokyo (JP); National Center for Global Health and Medicine, Tokyo (JP); Hiroshima University, Higashihiroshima (JP)

(72) Inventors: Hideki Endo, Tokyo (JP); Yukihito Ishizaka, Tokyo (JP); Takashi Yamamoto, Hiroshima (JP); Tetsushi Sakuma, Hiroshima (JP)

(73) Assignees: Astellas Pharma Inc., Tokyo (JP); National Center for Global Health and Medicine, Tokyo (JP); Hiroshima University, Hiroshima (JP)

( * ) Notice: Subject to any disclaimer, the term of this patent is extended or adjusted under 35 U.S.C. 154(b) by 520 days.

(21) Appl. No.: 16/468,245

(22) PCT Filed: Dec. 11, 2017

(86) PCT No.: PCT/JP2017/044266
§ 371 (c)(1),
(2) Date: Jun. 10, 2019

(87) PCT Pub. No.: WO2018/110471
PCT Pub. Date: Jun. 21, 2018

(65) Prior Publication Data
US 2019/0330280 A1 Oct. 31, 2019

(30) Foreign Application Priority Data
Dec. 12, 2016 (JP) .............................. JP2016-240097

(51) Int. Cl.
| | | |
|---|---|---|
| C07K 14/195 | (2006.01) | |
| C12N 5/0735 | (2010.01) | |
| C12N 5/077 | (2010.01) | |
| C12N 5/0775 | (2010.01) | |
| C12N 9/50 | (2006.01) | |
| C12N 15/113 | (2010.01) | |
| C07K 14/00 | (2006.01) | |

(52) U.S. Cl.
CPC ............ *C07K 14/195* (2013.01); *C07K 14/00* (2013.01); *C12N 5/0606* (2013.01); *C12N 5/0656* (2013.01); *C12N 5/0662* (2013.01); *C12N 9/506* (2013.01); *C12N 15/113* (2013.01); *C12Y 304/22044* (2013.01); *C07K 2319/00* (2013.01); *C12N 2310/20* (2017.05); *C12N 2501/998* (2013.01); *C12Y 301/00* (2013.01); *C12Y 301/21004* (2013.01)

(58) Field of Classification Search
None
See application file for complete search history.

(56) References Cited

FOREIGN PATENT DOCUMENTS

WO WO-2014/197748 A2 12/2014

OTHER PUBLICATIONS

Ramsey et al., "Cell-penetrating peptides transport therapeutics into cells," Pharmacology & Therapeutics, Jul. 22, 2015, 154:78-86.
Akincilar et al., "Reactivation of telomerase in cancer," Cellular and Molecular Life Sciences, Feb. 4, 2016, 73:1659-1670.
Chavez et al., "Supplementary Figures: Highly efficient Cas9-mediated transcriptional programming," Nature Methods, Mar. 2, 2015, 12(4):326-328, 30 pages.
Wick et al., "Genomic organization and promoter characterization f the gene encoding the human telomerase reverse transcriptase (hTERT)," Gene, May 17, 1999, 232(1):97-106.
Accession No. AH007699, *Homo sapiens* telomerase reverse transciptse (TERI) gene, complete cds, [online], Jun. 10, 2016, retrieval date Feb. 21, 2018, database GenBank/EMBL/DDBJ/GeneSeq, internet: URL:www.ncbi.nlm.nih.gov/nuccore/103630446.
Chavez et al., "Highly efficient Cas9-mediated transcriptional programming," Nature Methods, Apr. 2015, 12(4):326-328.
Hilton et al., "Epigenome editing by CRISPR-Cas-0-based acetyltransferase activates genes from promoters and enhancers," Nature Biotechnology, May 2015, 33(5):510-517.
Horikawa et al., "Transcriptional regulation of the telomerase hTERT gene as a target for cellular and viral oncogenic mechanisms," Carcinogenesis, 2003, 24(7):1167-1176.
Liu et al., "Emerging landscape of cell penetrating peptide in reprogramming and gene editing," Journal of Controlled Release, 2016, 226:124-137.
Liu et al., "Cell-Penetrating Peptide-Mediated Delivery of TALEN Proteins via Bioconjugation for Genome Engineering," PLOS One, Jan. 2014, 9(1):e85755, 1-7.
Ru et al., "Targeted genome engineering in human induced pluripotent stem cells by penetrating TALENs," Cell Regeneration, 2013, 2:5, 8 pages.
Sohn et al., "Repression of Human Telomerase Reverse Transcriptase Using Artificial Zing Finger Transcription Factors," Molecular Cancer Research, Feb. 2010, 8(2):246-253.
Tachikawa et al., "Regulation of the engodenous VEGF-A gene by exogenous designed regulatory proteins," PNAS, Oct. 19, 2004, 101(42):15225-15230.
Wilson et al., "Design and Development of Artificial Zing Finger Transcription Factors and Zinc Finger Nucleases to the hTERT Locus," Molecular Therapy—Nucleic Acids, 2013, 2:e87, 1-10.
International Search Report dated Mar. 6, 2018 in PCT/JP2017/044266.
Office Action dated Jun. 1, 2021 in EP 17880759.0.
Supplementary European Search Report dated May 28, 2020 in EP 17880759.0.
Office Action dated Aug. 24, 2021 in JP 2018-556649, with English translation.

*Primary Examiner* — Anand U Desai
(74) *Attorney, Agent, or Firm* — Foley & Lardner LLP

(57) ABSTRACT

It is intended to provide a fusion polypeptide that regulates the transcription of a target gene.
The present inventors have provided a fusion polypeptide comprising: a cell-penetrating peptide; a DNA-binding polypeptide; and a transcriptional regulator.

15 Claims, 4 Drawing Sheets
Specification includes a Sequence Listing.

[Figure 1]
(1)
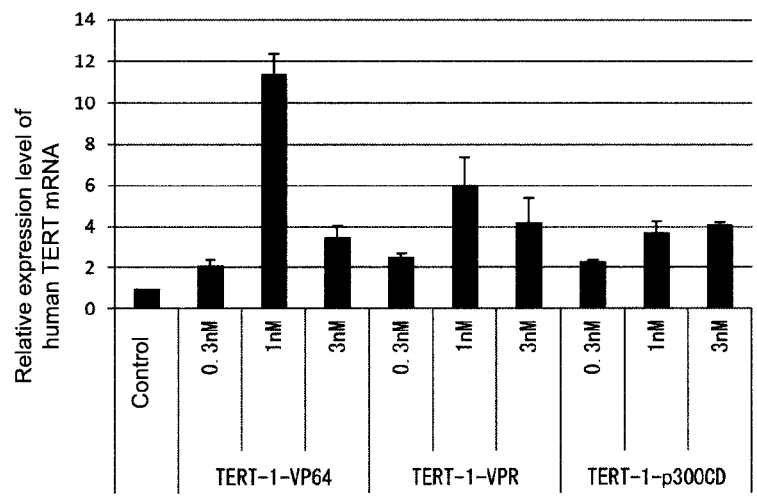
(2)
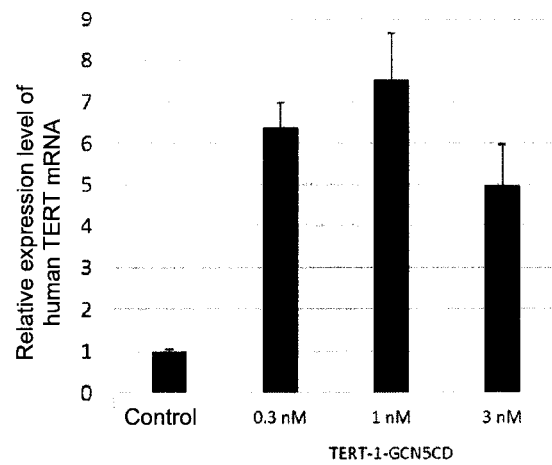

[Figure 2]
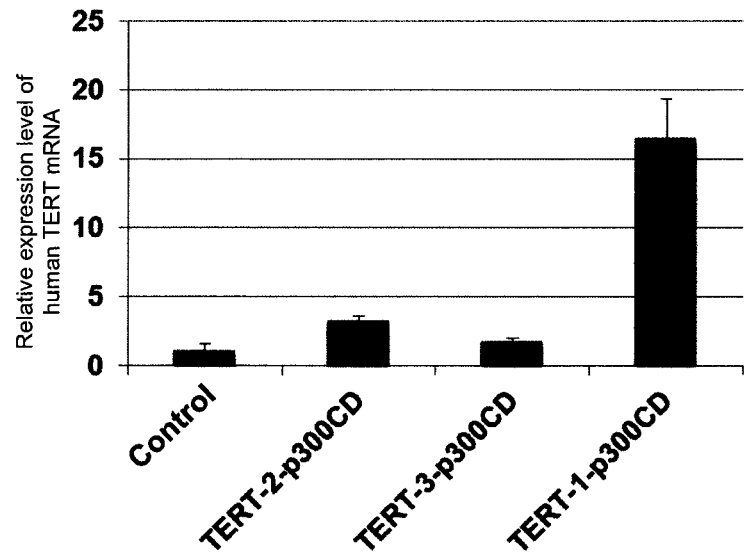
[Figure 3]
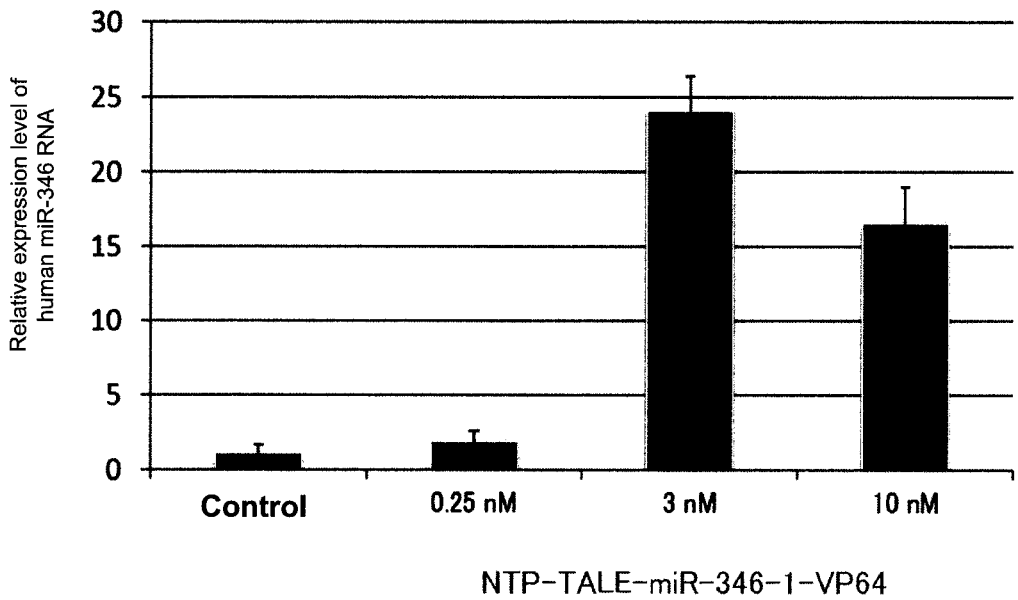
NTP-TALE-miR-346-1-VP64

[Figure 4]
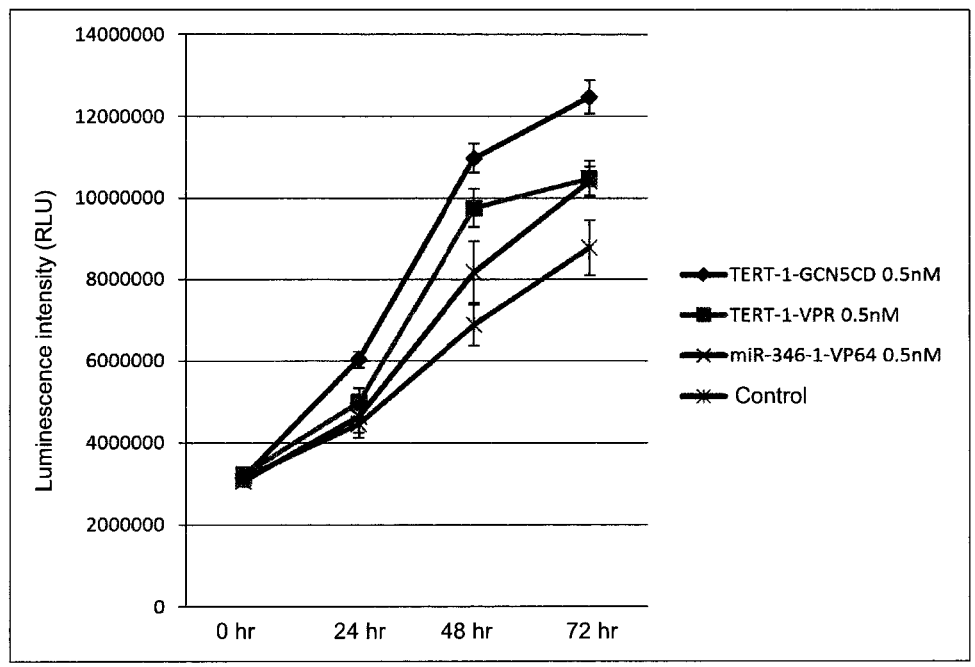
[Figure 5]
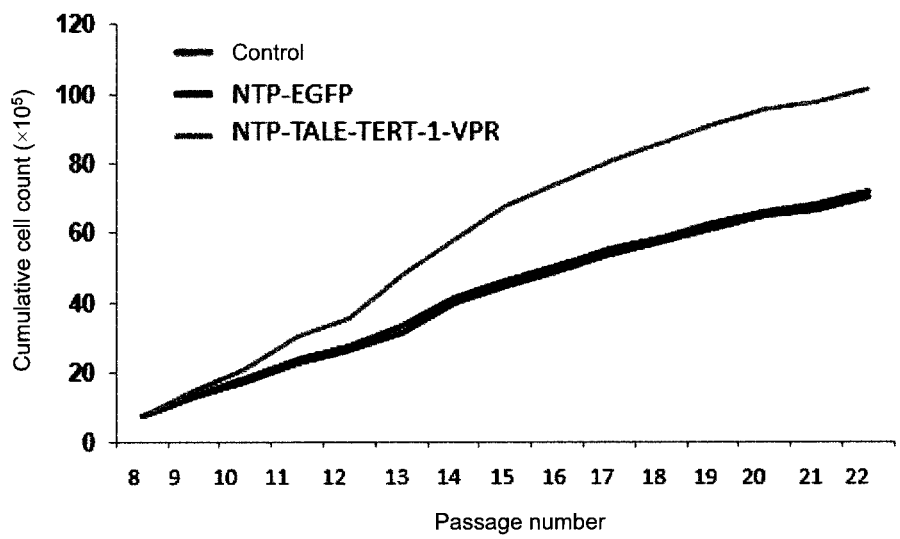

[Figure 6]
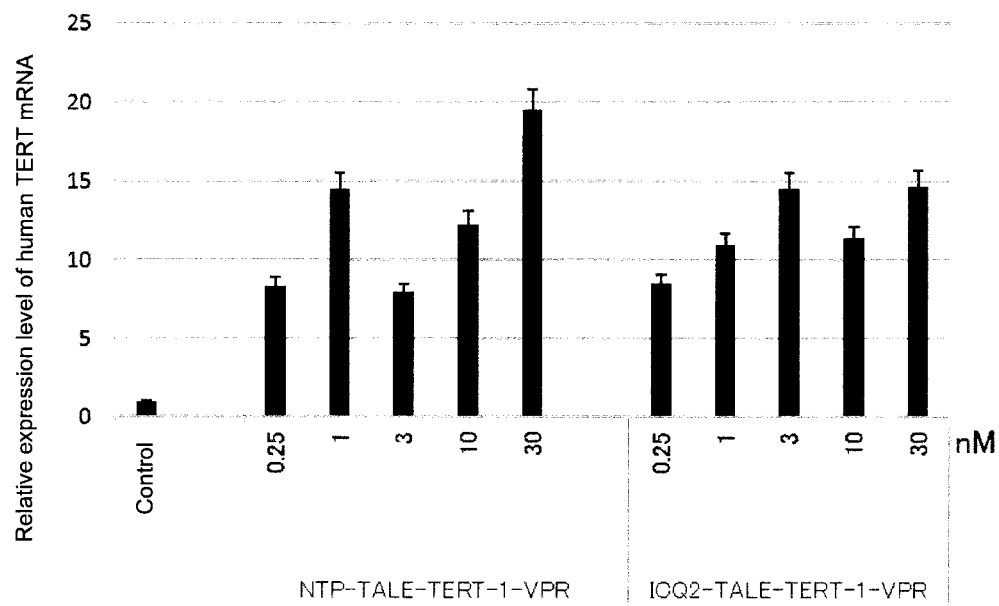
[Figure 7]
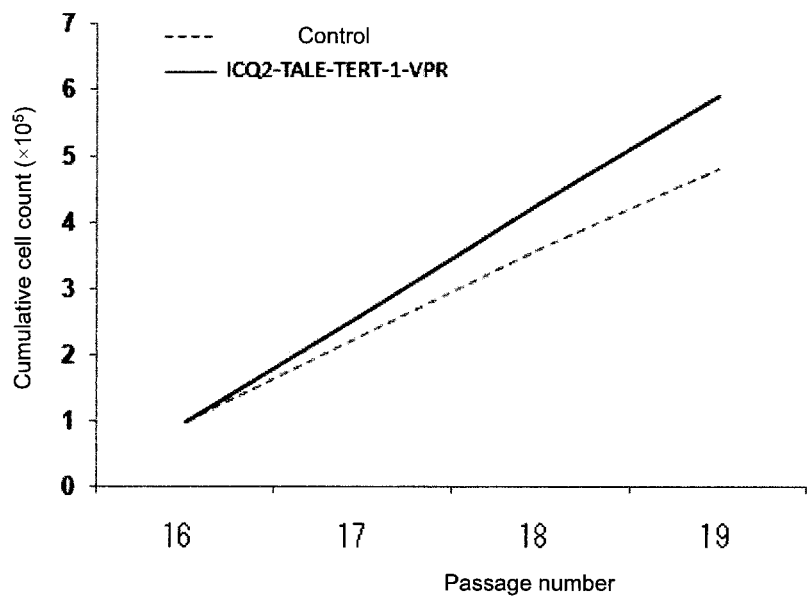

SEQUENCE LISTING

```
<160> NUMBER OF SEQ ID NOS: 71

<210> SEQ ID NO 1
<211> LENGTH: 2661
<212> TYPE: DNA
<213> ORGANISM: Artificial Sequence
<220> FEATURE:
<223> OTHER INFORMATION: TALE_TERT-1
<220> FEATURE:
<221> NAME/KEY: CDS
<222> LOCATION: (1)..(2661)

<400> SEQUENCE: 1 atc cac gga gtc cca gca gcc gta gat ttg aga act ttg gga tat tca        48
```

-continued

```
                Ile His Gly Val Pro Ala Ala Val Asp Leu Arg Thr Leu Gly Tyr Ser
                 1               5                  10                  15 cag cag cag cag gaa aag atc aag ccc aaa gtg agg tcg aca gtc gcg              96
Gln Gln Gln Gln Glu Lys Ile Lys Pro Lys Val Arg Ser Thr Val Ala
                 20                  25                  30 cag cat cac gaa gcg ctg gtg ggt cat ggg ttt aca cat gcc cac atc             144
Gln His His Glu Ala Leu Val Gly His Gly Phe Thr His Ala His Ile
         35                  40                  45 gta gcc ttg tcg cag cac cct gca gcc ctt ggc acg gtc gcc gtc aag             192
Val Ala Leu Ser Gln His Pro Ala Ala Leu Gly Thr Val Ala Val Lys
     50                  55                  60 tac cag gac atg att gcg gcg ttg ccg gaa gcc aca cat gag gcg atc             240
Tyr Gln Asp Met Ile Ala Ala Leu Pro Glu Ala Thr His Glu Ala Ile
 65                  70                  75                  80 gtc ggt gtg ggg aaa cag tgg agc gga gcc cga gcg ctt gag gcc ctg             288
Val Gly Val Gly Lys Gln Trp Ser Gly Ala Arg Ala Leu Glu Ala Leu
                 85                  90                  95 ttg acg gtc gcg gga gag ctg aga ggg cct ccc ctt cag ctg gac acg             336
Leu Thr Val Ala Gly Glu Leu Arg Gly Pro Pro Leu Gln Leu Asp Thr
                100                 105                 110 ggc cag ttg ctg aag atc gcg aag cgg gga gga gtc acg gcg gtc gag             384
Gly Gln Leu Leu Lys Ile Ala Lys Arg Gly Gly Val Thr Ala Val Glu
        115                 120                 125 gcg gta cac gcg tgg cgc aat gcg ctc acg gga gca ccc ctc aac ctg             432
Ala Val His Ala Trp Arg Asn Ala Leu Thr Gly Ala Pro Leu Asn Leu
    130                 135                 140 acc ccg gac cag gtg gtt gca atc gcg tca cac gat ggg gga aag cag             480
Thr Pro Asp Gln Val Val Ala Ile Ala Ser His Asp Gly Gly Lys Gln
145                 150                 155                 160 gcc cta gaa acc gtt cag cga ctc ctg ccc gtc ctg tgc cag gac cac             528
Ala Leu Glu Thr Val Gln Arg Leu Leu Pro Val Leu Cys Gln Asp His
                165                 170                 175 ggc ctg acc cca gaa cag gtt gtg gcc atc gcc agc aac ata ggt ggc             576
Gly Leu Thr Pro Glu Gln Val Val Ala Ile Ala Ser Asn Ile Gly Gly
                180                 185                 190 aag cag gcc ctc gaa acc gtc cag aga ctg tta ccg gtt ctc tgc cag             624
Lys Gln Ala Leu Glu Thr Val Gln Arg Leu Leu Pro Val Leu Cys Gln
        195                 200                 205 gcc cac ggc ctg acc cca gac caa gtt gtc gcg att gca agc aac aac             672
Ala His Gly Leu Thr Pro Asp Gln Val Val Ala Ile Ala Ser Asn Asn
    210                 215                 220 gga ggc aaa caa gcc tta gaa aca gtc cag aga ttg ttg cct gtg ctg             720
Gly Gly Lys Gln Ala Leu Glu Thr Val Gln Arg Leu Leu Pro Val Leu
225                 230                 235                 240 tgc caa gcc cac ggc ctg acc cca gcc cag gtt gtg gcc atc gcc agc             768
Cys Gln Ala His Gly Leu Thr Pro Ala Gln Val Val Ala Ile Ala Ser
                245                 250                 255 aac ata ggt ggc aag cag gcc ctc gaa acc gtc cag aga ctg tta ccg             816
Asn Ile Gly Gly Lys Gln Ala Leu Glu Thr Val Gln Arg Leu Leu Pro
                260                 265                 270 gtt ctc tgc cag gac cac ggc ctg acc cca gac caa gtt gtc gcg att             864
Val Leu Cys Gln Asp His Gly Leu Thr Pro Asp Gln Val Val Ala Ile
        275                 280                 285 gca agc aac aac gga ggc aaa caa gcc tta gaa aca gtc cag aga ttg             912
Ala Ser Asn Asn Gly Gly Lys Gln Ala Leu Glu Thr Val Gln Arg Leu
    290                 295                 300 ttg ccg gtg ctg tgc caa gac cac ggc ctg acc cca gaa caa gtt gtc             960
Leu Pro Val Leu Cys Gln Asp His Gly Leu Thr Pro Glu Gln Val Val
305                 310                 315                 320
```

```
gcg att gca agc aac aac gga ggc aaa caa gcc tta gaa aca gtc cag      1008
Ala Ile Ala Ser Asn Asn Gly Gly Lys Gln Ala Leu Glu Thr Val Gln
            325                 330                 335 aga ttg ttg ccg gtg ctg tgc caa gcc cac ggc ctg acc cca gac caa      1056
Arg Leu Leu Pro Val Leu Cys Gln Ala His Gly Leu Thr Pro Asp Gln
            340                 345                 350 gtt gtc gcg att gca agc aac aac gga ggc aaa caa gcc tta gaa aca      1104
Val Val Ala Ile Ala Ser Asn Asn Gly Gly Lys Gln Ala Leu Glu Thr
            355                 360                 365 gtc cag aga ttg ttg cct gtg ctg tgc caa gcc cac ggc ctg acc cca      1152
Val Gln Arg Leu Leu Pro Val Leu Cys Gln Ala His Gly Leu Thr Pro
            370                 375                 380 gcc cag gtt gtg gcc atc gcc agc aac ata ggt ggc aag cag gcc ctc      1200
Ala Gln Val Val Ala Ile Ala Ser Asn Ile Gly Gly Lys Gln Ala Leu
385                 390                 395                 400 gaa acc gtc cag aga ctg tta ccg gtt ctc tgc cag gac cac ggc ctg      1248
Glu Thr Val Gln Arg Leu Leu Pro Val Leu Cys Gln Asp His Gly Leu
                405                 410                 415 acc ccg gac cag gtg gtt gca atc gcg tca cac gat ggg gga aag cag      1296
Thr Pro Asp Gln Val Val Ala Ile Ala Ser His Asp Gly Gly Lys Gln
            420                 425                 430 gcc cta gaa acc gtt cag cga ctc ctg ccc gtc ctg tgc cag gac cac      1344
Ala Leu Glu Thr Val Gln Arg Leu Leu Pro Val Leu Cys Gln Asp His
            435                 440                 445 ggc ctg acc cca gaa caa gtt gtc gcg att gca agc aac aac gga ggc      1392
Gly Leu Thr Pro Glu Gln Val Val Ala Ile Ala Ser Asn Asn Gly Gly
450                 455                 460 aaa caa gcc tta gaa aca gtc cag aga ttg ttg ccg gtg ctg tgc caa      1440
Lys Gln Ala Leu Glu Thr Val Gln Arg Leu Leu Pro Val Leu Cys Gln
465                 470                 475                 480 gcc cac ggc ctg acc ccg gac cag gtg gtt gca atc gcg tca cac gat      1488
Ala His Gly Leu Thr Pro Asp Gln Val Val Ala Ile Ala Ser His Asp
                485                 490                 495 ggg gga aag cag gcc cta gaa acc gtt cag cga ctc ctg ccc gtc ctg      1536
Gly Gly Lys Gln Ala Leu Glu Thr Val Gln Arg Leu Leu Pro Val Leu
            500                 505                 510 tgc cag gcc cac ggc ctg acc cca gcc cag gtt gtg gcc atc gcc agc      1584
Cys Gln Ala His Gly Leu Thr Pro Ala Gln Val Val Ala Ile Ala Ser
            515                 520                 525 aac ata ggt ggc aag cag gcc ctc gaa acc gtc cag aga ctg tta ccg      1632
Asn Ile Gly Gly Lys Gln Ala Leu Glu Thr Val Gln Arg Leu Leu Pro
            530                 535                 540 gtt ctc tgc cag gac cac ggc ctg acc cca gac caa gtt gtc gcg att      1680
Val Leu Cys Gln Asp His Gly Leu Thr Pro Asp Gln Val Val Ala Ile
545                 550                 555                 560 gca agc aac aac gga ggc aaa caa gcc tta gaa aca gtc cag aga ttg      1728
Ala Ser Asn Asn Gly Gly Lys Gln Ala Leu Glu Thr Val Gln Arg Leu
                565                 570                 575 ttg ccg gtg ctg tgc caa gac cac ggc ctg acc ccc gaa cag gtt gtc      1776
Leu Pro Val Leu Cys Gln Asp His Gly Leu Thr Pro Glu Gln Val Val
            580                 585                 590 gct att gct agt aac ggc gga ggc aaa cag gcg ctg gaa aca gtt cag      1824
Ala Ile Ala Ser Asn Gly Gly Gly Lys Gln Ala Leu Glu Thr Val Gln
            595                 600                 605 cgc ctc ttg ccg gtc ttg tgt cag gcc cac ggc ctg acc ccg gac cag      1872
Arg Leu Leu Pro Val Leu Cys Gln Ala His Gly Leu Thr Pro Asp Gln
            610                 615                 620 gtg gtt gca atc gcg tca cac gat ggg gga aag cag gcc cta gaa acc      1920
Val Val Ala Ile Ala Ser His Asp Gly Gly Lys Gln Ala Leu Glu Thr
625                 630                 635                 640
```

```
gtt cag cga ctc ctg ccc gtc ctg tgc cag gcc cac ggc ctg acc ccc    1968
Val Gln Arg Leu Leu Pro Val Leu Cys Gln Ala His Gly Leu Thr Pro
            645                 650                 655 gcc cag gtt gtc gct att gct agt aac ggc gga ggc aaa cag gcg ctg    2016
Ala Gln Val Val Ala Ile Ala Ser Asn Gly Gly Gly Lys Gln Ala Leu
        660                 665                 670 gaa aca gtt cag cgc ctc ttg ccg gtc ttg tgt cag gac cac ggc ctg    2064
Glu Thr Val Gln Arg Leu Leu Pro Val Leu Cys Gln Asp His Gly Leu
    675                 680                 685 acc cct gag cag gta gtg gct att gca tcc cac gac ggg ggc aga ccc    2112
Thr Pro Glu Gln Val Val Ala Ile Ala Ser His Asp Gly Gly Arg Pro
690                 695                 700 gca ctg gag tca atc gtg gcc cag ctc tcg agg ccg gac ccc gcg ctg    2160
Ala Leu Glu Ser Ile Val Ala Gln Leu Ser Arg Pro Asp Pro Ala Leu
705                 710                 715                 720 gcc gca ctc act aat gat cat ctt gta gcg ctg gcc tgc ctc ggc gga    2208
Ala Ala Leu Thr Asn Asp His Leu Val Ala Leu Ala Cys Leu Gly Gly
                725                 730                 735 cga ccc gcc ttg gat gcg gtg aag aag ggg ctc ccg cac gcg cct gca    2256
Arg Pro Ala Leu Asp Ala Val Lys Lys Gly Leu Pro His Ala Pro Ala
            740                 745                 750 ttg att aag cgg acc aac aga agg atc ccc gag agg aca tca cat cga    2304
Leu Ile Lys Arg Thr Asn Arg Arg Ile Pro Glu Arg Thr Ser His Arg
        755                 760                 765 gtg gca gat cac gcg caa gtg gtc cgc gtg ctc gga ttc ttc cag tgt    2352
Val Ala Asp His Ala Gln Val Val Arg Val Leu Gly Phe Phe Gln Cys
    770                 775                 780 cac tcc cac ccc gca caa gcg ttc gat gac gcc atg act caa ttt ggt    2400
His Ser His Pro Ala Gln Ala Phe Asp Asp Ala Met Thr Gln Phe Gly
785                 790                 795                 800 atg tcg aga cac gga ctg ctg cag ctc ttt cgt aga gtc ggt gtc aca    2448
Met Ser Arg His Gly Leu Leu Gln Leu Phe Arg Arg Val Gly Val Thr
                805                 810                 815 gaa ctg gag gcc cgc tcg ggc aca ctg cct ccc gcc tcc cag cgg tgg    2496
Glu Leu Glu Ala Arg Ser Gly Thr Leu Pro Pro Ala Ser Gln Arg Trp
            820                 825                 830 gac agg att ctc caa gcg agc ggt atg aaa cgc gcg aag cct tca cct    2544
Asp Arg Ile Leu Gln Ala Ser Gly Met Lys Arg Ala Lys Pro Ser Pro
        835                 840                 845 acg tca act cag aca cct gac cag gcg agc ctt cat gcg ttc gca gac    2592
Thr Ser Thr Gln Thr Pro Asp Gln Ala Ser Leu His Ala Phe Ala Asp
    850                 855                 860 tcg ctg gag agg gat ttg gac gcg ccc tcg ccc atg cat gaa ggg gac    2640
Ser Leu Glu Arg Asp Leu Asp Ala Pro Ser Pro Met His Glu Gly Asp
865                 870                 875                 880 caa act cgc gcg tca gcc agc                                        2661
Gln Thr Arg Ala Ser Ala Ser
                885
```

<210> SEQ ID NO 2
<211> LENGTH: 887
<212> TYPE: PRT
<213> ORGANISM: Artificial Sequence
<220> FEATURE:
<223> OTHER INFORMATION: Synthetic Construct

<400> SEQUENCE: 2

```
Ile His Gly Val Pro Ala Ala Val Asp Leu Arg Thr Leu Gly Tyr Ser
1               5                   10                  15

Gln Gln Gln Gln Glu Lys Ile Lys Pro Lys Val Arg Ser Thr Val Ala
```

-continued

```
                20                  25                  30
    Gln His His Glu Ala Leu Val Gly His Gly Phe Thr His Ala His Ile
                35                  40                  45
    Val Ala Leu Ser Gln His Pro Ala Ala Leu Gly Thr Ala Val Lys
    50                  55                  60
    Tyr Gln Asp Met Ile Ala Ala Leu Pro Glu Ala Thr His Glu Ala Ile
    65                  70                  75                  80
    Val Gly Val Gly Lys Gln Trp Ser Gly Ala Arg Ala Leu Glu Ala Leu
                    85                  90                  95
    Leu Thr Val Ala Gly Glu Leu Arg Gly Pro Leu Gln Leu Asp Thr
                    100                 105                 110
    Gly Gln Leu Leu Lys Ile Ala Lys Arg Gly Gly Val Thr Ala Val Glu
                    115                 120                 125
    Ala Val His Ala Trp Arg Asn Ala Leu Thr Gly Ala Pro Leu Asn Leu
                    130                 135                 140
    Thr Pro Asp Gln Val Val Ala Ile Ala Ser His Asp Gly Gly Lys Gln
    145                 150                 155                 160
    Ala Leu Glu Thr Val Gln Arg Leu Leu Pro Val Leu Cys Gln Asp His
                    165                 170                 175
    Gly Leu Thr Pro Glu Gln Val Val Ala Ile Ala Ser Asn Ile Gly Gly
                    180                 185                 190
    Lys Gln Ala Leu Glu Thr Val Gln Arg Leu Leu Pro Val Leu Cys Gln
                    195                 200                 205
    Ala His Gly Leu Thr Pro Asp Gln Val Val Ala Ile Ala Ser Asn Asn
                    210                 215                 220
    Gly Gly Lys Gln Ala Leu Glu Thr Val Gln Arg Leu Leu Pro Val Leu
    225                 230                 235                 240
    Cys Gln Ala His Gly Leu Thr Pro Ala Gln Val Val Ala Ile Ala Ser
                    245                 250                 255
    Asn Ile Gly Gly Lys Gln Ala Leu Glu Thr Val Gln Arg Leu Leu Pro
                    260                 265                 270
    Val Leu Cys Gln Asp His Gly Leu Thr Pro Asp Gln Val Val Ala Ile
                    275                 280                 285
    Ala Ser Asn Asn Gly Gly Lys Gln Ala Leu Glu Thr Val Gln Arg Leu
                    290                 295                 300
    Leu Pro Val Leu Cys Gln Asp His Gly Leu Thr Pro Glu Gln Val Val
    305                 310                 315                 320
    Ala Ile Ala Ser Asn Asn Gly Gly Lys Gln Ala Leu Glu Thr Val Gln
                    325                 330                 335
    Arg Leu Leu Pro Val Leu Cys Gln Ala His Gly Leu Thr Pro Asp Gln
                    340                 345                 350
    Val Val Ala Ile Ala Ser Asn Gly Gly Lys Gln Ala Leu Glu Thr
                    355                 360                 365
    Val Gln Arg Leu Leu Pro Val Leu Cys Gln Ala His Gly Leu Thr Pro
                    370                 375                 380
    Ala Gln Val Val Ala Ile Ala Ser Asn Ile Gly Gly Lys Gln Ala Leu
    385                 390                 395                 400
    Glu Thr Val Gln Arg Leu Leu Pro Val Leu Cys Gln Asp His Gly Leu
                    405                 410                 415
    Thr Pro Asp Gln Val Val Ala Ile Ala Ser His Asp Gly Gly Lys Gln
                    420                 425                 430
    Ala Leu Glu Thr Val Gln Arg Leu Leu Pro Val Leu Cys Gln Asp His
                    435                 440                 445
```

```
Gly Leu Thr Pro Glu Gln Val Ala Ile Ala Ser Asn Asn Gly Gly
    450                 455                 460

Lys Gln Ala Leu Glu Thr Val Gln Arg Leu Leu Pro Val Leu Cys Gln
465                 470                 475                 480

Ala His Gly Leu Thr Pro Asp Gln Val Val Ala Ile Ala Ser His Asp
                485                 490                 495

Gly Gly Lys Gln Ala Leu Glu Thr Val Gln Arg Leu Leu Pro Val Leu
                500                 505                 510

Cys Gln Ala His Gly Leu Thr Pro Ala Gln Val Val Ala Ile Ala Ser
            515                 520                 525

Asn Ile Gly Gly Lys Gln Ala Leu Glu Thr Val Gln Arg Leu Leu Pro
    530                 535                 540

Val Leu Cys Gln Asp His Gly Leu Thr Pro Asp Gln Val Val Ala Ile
545                 550                 555                 560

Ala Ser Asn Asn Gly Gly Lys Gln Ala Leu Glu Thr Val Gln Arg Leu
                565                 570                 575

Leu Pro Val Leu Cys Gln Asp His Gly Leu Thr Pro Glu Gln Val Val
                580                 585                 590

Ala Ile Ala Ser Asn Gly Gly Lys Gln Ala Leu Glu Thr Val Gln
    595                 600                 605

Arg Leu Leu Pro Val Leu Cys Gln Ala His Gly Leu Thr Pro Asp Gln
610                 615                 620

Val Val Ala Ile Ala Ser His Asp Gly Gly Lys Gln Ala Leu Glu Thr
625                 630                 635                 640

Val Gln Arg Leu Leu Pro Val Leu Cys Gln Ala His Gly Leu Thr Pro
                645                 650                 655

Ala Gln Val Val Ala Ile Ala Ser Asn Gly Gly Gly Lys Gln Ala Leu
                660                 665                 670

Glu Thr Val Gln Arg Leu Leu Pro Val Leu Cys Gln Asp His Gly Leu
            675                 680                 685

Thr Pro Glu Gln Val Val Ala Ile Ala Ser His Asp Gly Gly Arg Pro
    690                 695                 700

Ala Leu Glu Ser Ile Val Ala Gln Leu Ser Arg Pro Asp Pro Ala Leu
705                 710                 715                 720

Ala Ala Leu Thr Asn Asp His Leu Val Ala Leu Ala Cys Leu Gly Gly
                725                 730                 735

Arg Pro Ala Leu Asp Ala Val Lys Lys Gly Leu Pro His Ala Pro Ala
                740                 745                 750

Leu Ile Lys Arg Thr Asn Arg Arg Ile Pro Glu Arg Thr Ser His Arg
    755                 760                 765

Val Ala Asp His Ala Gln Val Val Arg Val Leu Gly Phe Phe Gln Cys
    770                 775                 780

His Ser His Pro Ala Gln Ala Phe Asp Asp Ala Met Thr Gln Phe Gly
785                 790                 795                 800

Met Ser Arg His Gly Leu Leu Gln Leu Phe Arg Arg Val Gly Val Thr
                805                 810                 815

Glu Leu Glu Ala Arg Ser Gly Thr Leu Pro Pro Ala Ser Gln Arg Trp
            820                 825                 830

Asp Arg Ile Leu Gln Ala Ser Gly Met Lys Arg Ala Lys Pro Ser Pro
    835                 840                 845

Thr Ser Thr Gln Thr Pro Asp Gln Ala Ser Leu His Ala Phe Ala Asp
    850                 855                 860
```

-continued

```
Ser Leu Glu Arg Asp Leu Asp Ala Pro Ser Pro Met His Glu Gly Asp
865                 870                 875                 880

Gln Thr Arg Ala Ser Ala Ser
                885

<210> SEQ ID NO 3
<211> LENGTH: 2661
<212> TYPE: DNA
<213> ORGANISM: Artificial Sequence
<220> FEATURE:
<223> OTHER INFORMATION: TALE_TERT-2
<220> FEATURE:
<221> NAME/KEY: CDS
<222> LOCATION: (1)..(2661)

<400> SEQUENCE: 3 atc cac gga gtc cca gca gcc gta gat ttg aga act ttg gga tat tca      48
Ile His Gly Val Pro Ala Ala Val Asp Leu Arg Thr Leu Gly Tyr Ser
1               5                   10                  15 cag cag cag cag gaa aag atc aag ccc aaa gtg agg tcg aca gtc gcg      96
Gln Gln Gln Gln Glu Lys Ile Lys Pro Lys Val Arg Ser Thr Val Ala
            20                  25                  30 cag cat cac gaa gcg ctg gtg ggt cat ggg ttt aca cat gcc cac atc     144
Gln His His Glu Ala Leu Val Gly His Gly Phe Thr His Ala His Ile
        35                  40                  45 gta gcc ttg tcg cag cac cct gca gcc ctt ggc acg gtc gcc gtc aag     192
Val Ala Leu Ser Gln His Pro Ala Ala Leu Gly Thr Val Ala Val Lys
    50                  55                  60 tac cag gac atg att gcg gcg ttg ccg gaa gcc aca cat gag gcg atc     240
Tyr Gln Asp Met Ile Ala Ala Leu Pro Glu Ala Thr His Glu Ala Ile
65                  70                  75                  80 gtc ggt gtg ggg aaa cag tgg agc gga gcc cga gcg ctt gag gcc ctg     288
Val Gly Val Gly Lys Gln Trp Ser Gly Ala Arg Ala Leu Glu Ala Leu
                85                  90                  95 ttg acg gtc gcg gga gag ctg aga ggg cct ccc ctt cag ctg gac acg     336
Leu Thr Val Ala Gly Glu Leu Arg Gly Pro Pro Leu Gln Leu Asp Thr
            100                 105                 110 ggc cag ttg ctg aag atc gcg aag cgg gga gga gtc acg gcg gtc gag     384
Gly Gln Leu Leu Lys Ile Ala Lys Arg Gly Gly Val Thr Ala Val Glu
        115                 120                 125 gcg gta cac gcg tgg cgc aat gcg ctc acg gga gca ccc ctc aac ctg     432
Ala Val His Ala Trp Arg Asn Ala Leu Thr Gly Ala Pro Leu Asn Leu
    130                 135                 140 acc ccg gac cag gtg gtt gca atc gcg tca cac gat ggg gga aag cag     480
Thr Pro Asp Gln Val Val Ala Ile Ala Ser His Asp Gly Gly Lys Gln
145                 150                 155                 160 gcc cta gaa acc gtt cag cga ctc ctg ccc gtc ctg tgc cag gac cac     528
Ala Leu Glu Thr Val Gln Arg Leu Leu Pro Val Leu Cys Gln Asp His
                165                 170                 175 ggc ctg acc ccg gaa cag gtg gtt gca atc gcg tca cac gat ggg gga     576
Gly Leu Thr Pro Glu Gln Val Val Ala Ile Ala Ser His Asp Gly Gly
            180                 185                 190 aag cag gcc cta gaa acc gtt cag cga ctc ctg ccc gtc ctg tgc cag     624
Lys Gln Ala Leu Glu Thr Val Gln Arg Leu Leu Pro Val Leu Cys Gln
        195                 200                 205 gcc cac ggc ctg acc ccg gac cag gtg gtt gca atc gcg tca cac gat     672
Ala His Gly Leu Thr Pro Asp Gln Val Val Ala Ile Ala Ser His Asp
    210                 215                 220 ggg gga aag cag gcc cta gaa acc gtt cag cga ctc ctg ccc gtc ctg     720
Gly Gly Lys Gln Ala Leu Glu Thr Val Gln Arg Leu Leu Pro Val Leu
225                 230                 235                 240
```

```
tgc cag gcc cac ggc ctg acc cca gcc cag gtt gtg gcc atc gcc agc      768
Cys Gln Ala His Gly Leu Thr Pro Ala Gln Val Val Ala Ile Ala Ser
            245                 250                 255 aac ata ggt ggc aag cag gcc ctc gaa acc gtc cag aga ctg tta ccg      816
Asn Ile Gly Gly Lys Gln Ala Leu Glu Thr Val Gln Arg Leu Leu Pro
            260                 265                 270 gtt ctc tgc cag gac cac ggc ctg acc ccg gac cag gtg gtt gca atc      864
Val Leu Cys Gln Asp His Gly Leu Thr Pro Asp Gln Val Val Ala Ile
            275                 280                 285 gcg tca cac gat ggg gga aag cag gcc cta gaa acc gtt cag cga ctc      912
Ala Ser His Asp Gly Gly Lys Gln Ala Leu Glu Thr Val Gln Arg Leu
            290                 295                 300 ctg ccc gtc ctg tgc cag gac cac ggc ctg acc cca gaa caa gtt gtc      960
Leu Pro Val Leu Cys Gln Asp His Gly Leu Thr Pro Glu Gln Val Val
305                 310                 315                 320 gcg att gca agc aac aac gga ggc aaa caa gcc tta gaa aca gtc cag     1008
Ala Ile Ala Ser Asn Asn Gly Gly Lys Gln Ala Leu Glu Thr Val Gln
                325                 330                 335 aga ttg ttg ccg gtg ctg tgc caa gcc cac ggc ctg acc ccc gac cag     1056
Arg Leu Leu Pro Val Leu Cys Gln Ala His Gly Leu Thr Pro Asp Gln
                340                 345                 350 gtt gtc gct att gct agt aac ggc gga ggc aaa cag gcg ctg gaa aca     1104
Val Val Ala Ile Ala Ser Asn Gly Gly Gly Lys Gln Ala Leu Glu Thr
                355                 360                 365 gtt cag cgc ctc ttg ccg gtc ttg tgt cag gcc cac ggc ctg acc cca     1152
Val Gln Arg Leu Leu Pro Val Leu Cys Gln Ala His Gly Leu Thr Pro
370                 375                 380 gcc caa gtt gtc gcg att gca agc aac aac gga ggc aaa caa gcc tta     1200
Ala Gln Val Val Ala Ile Ala Ser Asn Asn Gly Gly Lys Gln Ala Leu
385                 390                 395                 400 gaa aca gtc cag aga ttg ttg ccg gtg ctg tgc caa gac cac ggc ctg     1248
Glu Thr Val Gln Arg Leu Leu Pro Val Leu Cys Gln Asp His Gly Leu
                405                 410                 415 acc cca gac caa gtt gtc gcg att gca agc aac aac gga ggc aaa caa     1296
Thr Pro Asp Gln Val Val Ala Ile Ala Ser Asn Asn Gly Gly Lys Gln
            420                 425                 430 gcc tta gaa aca gtc cag aga ttg ttg ccg gtg ctg tgc caa gac cac     1344
Ala Leu Glu Thr Val Gln Arg Leu Leu Pro Val Leu Cys Gln Asp His
            435                 440                 445 ggc ctg acc ccg gaa cag gtg gtt gca atc gcg tca cac gat ggg gga     1392
Gly Leu Thr Pro Glu Gln Val Val Ala Ile Ala Ser His Asp Gly Gly
            450                 455                 460 aag cag gcc cta gaa acc gtt cag cga ctc ctg ccc gtc ctg tgc cag     1440
Lys Gln Ala Leu Glu Thr Val Gln Arg Leu Leu Pro Val Leu Cys Gln
465                 470                 475                 480 gcc cac ggc ctg acc cca gac caa gtt gtc gcg att gca agc aac aac     1488
Ala His Gly Leu Thr Pro Asp Gln Val Val Ala Ile Ala Ser Asn Asn
                485                 490                 495 gga ggc aaa caa gcc tta gaa aca gtc cag aga ttg ttg cct gtg ctg     1536
Gly Gly Lys Gln Ala Leu Glu Thr Val Gln Arg Leu Leu Pro Val Leu
            500                 505                 510 tgc caa gcc cac ggc ctg acc cca gcc caa gtt gtc gcg att gca agc     1584
Cys Gln Ala His Gly Leu Thr Pro Ala Gln Val Val Ala Ile Ala Ser
            515                 520                 525 aac aac gga ggc aaa caa gcc tta gaa aca gtc cag aga ttg ttg ccg     1632
Asn Asn Gly Gly Lys Gln Ala Leu Glu Thr Val Gln Arg Leu Leu Pro
            530                 535                 540 gtg ctg tgc caa gac cac ggc ctg acc cca gac cag gtt gtg gcc atc     1680
Val Leu Cys Gln Asp His Gly Leu Thr Pro Asp Gln Val Val Ala Ile
545                 550                 555                 560
```

-continued

```
gcc agc aac ata ggt ggc aag cag gcc ctc gaa acc gtc cag aga ctg       1728
Ala Ser Asn Ile Gly Gly Lys Gln Ala Leu Glu Thr Val Gln Arg Leu
            565                 570                 575 tta ccg gtt ctc tgc cag gac cac ggc ctg acc cca gaa caa gtt gtc       1776
Leu Pro Val Leu Cys Gln Asp His Gly Leu Thr Pro Glu Gln Val Val
        580                 585                 590 gcg att gca agc aac aac gga ggc aaa caa gcc tta gaa aca gtc cag       1824
Ala Ile Ala Ser Asn Asn Gly Gly Lys Gln Ala Leu Glu Thr Val Gln
    595                 600                 605 aga ttg ttg ccg gtg ctg tgc caa gcc cac ggc ctg acc cca gac caa       1872
Arg Leu Leu Pro Val Leu Cys Gln Ala His Gly Leu Thr Pro Asp Gln
610                 615                 620 gtt gtc gcg att gca agc aac aac gga ggc aaa caa gcc tta gaa aca       1920
Val Val Ala Ile Ala Ser Asn Asn Gly Gly Lys Gln Ala Leu Glu Thr
625                 630                 635                 640 gtc cag aga ttg ttg cct gtg ctg tgc caa gcc cac ggc ctg acc cca       1968
Val Gln Arg Leu Leu Pro Val Leu Cys Gln Ala His Gly Leu Thr Pro
            645                 650                 655 gcc caa gtt gtc gcg att gca agc aac aac gga ggc aaa caa gcc tta       2016
Ala Gln Val Val Ala Ile Ala Ser Asn Asn Gly Gly Lys Gln Ala Leu
        660                 665                 670 gaa aca gtc cag aga ttg ttg ccg gtg ctg tgc caa gac cac ggc ctg       2064
Glu Thr Val Gln Arg Leu Leu Pro Val Leu Cys Gln Asp His Gly Leu
    675                 680                 685 acc cct gag cag gta gtg gct att gca tcc cac gac ggg ggc aga ccc       2112
Thr Pro Glu Gln Val Val Ala Ile Ala Ser His Asp Gly Gly Arg Pro
690                 695                 700 gca ctg gag tca atc gtg gcc cag ctc tcg agg ccg gac ccc gcg ctg       2160
Ala Leu Glu Ser Ile Val Ala Gln Leu Ser Arg Pro Asp Pro Ala Leu
705                 710                 715                 720 gcc gca ctc act aat gat cat ctt gta gcg ctg gcc tgc ctc ggc gga       2208
Ala Ala Leu Thr Asn Asp His Leu Val Ala Leu Ala Cys Leu Gly Gly
            725                 730                 735 cga ccc gcc ttg gat gcg gtg aag aag ggg ctc ccg cac gcg cct gca       2256
Arg Pro Ala Leu Asp Ala Val Lys Lys Gly Leu Pro His Ala Pro Ala
        740                 745                 750 ttg att aag cgg acc aac aga agg atc ccc gag agg aca tca cat cga       2304
Leu Ile Lys Arg Thr Asn Arg Arg Ile Pro Glu Arg Thr Ser His Arg
    755                 760                 765 gtg gca gat cac gcg caa gtg gtc cgc gtg ctc gga ttc ttc cag tgt       2352
Val Ala Asp His Ala Gln Val Val Arg Val Leu Gly Phe Phe Gln Cys
770                 775                 780 cac tcc cac ccc gca caa gcg ttc gat gac gcc atg act caa ttt ggt       2400
His Ser His Pro Ala Gln Ala Phe Asp Asp Ala Met Thr Gln Phe Gly
785                 790                 795                 800 atg tcg aga cac gga ctg ctg cag ctc ttt cgt aga gtc ggt gtc aca       2448
Met Ser Arg His Gly Leu Leu Gln Leu Phe Arg Arg Val Gly Val Thr
            805                 810                 815 gaa ctg gag gcc cgc tcg ggc aca ctg cct ccc gcc tcc cag cgg tgg       2496
Glu Leu Glu Ala Arg Ser Gly Thr Leu Pro Pro Ala Ser Gln Arg Trp
        820                 825                 830 gac agg att ctc caa gcg agc ggt atg aaa cgc gcg aag cct tca cct       2544
Asp Arg Ile Leu Gln Ala Ser Gly Met Lys Arg Ala Lys Pro Ser Pro
    835                 840                 845 acg tca act cag aca cct gac cag gcg agc ctt cat gcg ttc gca gac       2592
Thr Ser Thr Gln Thr Pro Asp Gln Ala Ser Leu His Ala Phe Ala Asp
850                 855                 860 tcg ctg gag agg gat ttg gac gcg ccc tcg ccc atg cat gaa ggg gac       2640
Ser Leu Glu Arg Asp Leu Asp Ala Pro Ser Pro Met His Glu Gly Asp
```

```
                865         870         875         880
                caa act cgc gcg tca gcc agc                              2661
                Gln Thr Arg Ala Ser Ala Ser
                                    885

<210> SEQ ID NO 4
<211> LENGTH: 887
<212> TYPE: PRT
<213> ORGANISM: Artificial Sequence
<220> FEATURE:
<223> OTHER INFORMATION: Synthetic Construct

<400> SEQUENCE: 4

Ile His Gly Val Pro Ala Ala Val Asp Leu Arg Thr Leu Gly Tyr Ser
1               5                   10                  15

Gln Gln Gln Gln Glu Lys Ile Lys Pro Lys Val Arg Ser Thr Val Ala
                20                  25                  30

Gln His His Glu Ala Leu Val Gly His Gly Phe Thr His Ala His Ile
            35                  40                  45

Val Ala Leu Ser Gln His Pro Ala Ala Leu Gly Thr Val Ala Val Lys
    50                  55                  60

Tyr Gln Asp Met Ile Ala Ala Leu Pro Glu Ala Thr His Glu Ala Ile
65                  70                  75                  80

Val Gly Val Gly Lys Gln Trp Ser Gly Ala Arg Ala Leu Glu Ala Leu
                85                  90                  95

Leu Thr Val Ala Gly Glu Leu Arg Gly Pro Leu Gln Leu Asp Thr
                100                 105                 110

Gly Gln Leu Leu Lys Ile Ala Lys Arg Gly Gly Val Thr Ala Val Glu
            115                 120                 125

Ala Val His Ala Trp Arg Asn Ala Leu Thr Gly Ala Pro Leu Asn Leu
    130                 135                 140

Thr Pro Asp Gln Val Val Ala Ile Ala Ser His Asp Gly Gly Lys Gln
145                 150                 155                 160

Ala Leu Glu Thr Val Gln Arg Leu Leu Pro Val Leu Cys Gln Asp His
                165                 170                 175

Gly Leu Thr Pro Glu Gln Val Val Ala Ile Ala Ser His Asp Gly Gly
            180                 185                 190

Lys Gln Ala Leu Glu Thr Val Gln Arg Leu Leu Pro Val Leu Cys Gln
    195                 200                 205

Ala His Gly Leu Thr Pro Asp Gln Val Val Ala Ile Ala Ser His Asp
    210                 215                 220

Gly Gly Lys Gln Ala Leu Glu Thr Val Gln Arg Leu Leu Pro Val Leu
225                 230                 235                 240

Cys Gln Ala His Gly Leu Thr Pro Ala Gln Val Val Ala Ile Ala Ser
                245                 250                 255

Asn Ile Gly Gly Lys Gln Ala Leu Glu Thr Val Gln Arg Leu Leu Pro
                260                 265                 270

Val Leu Cys Gln Asp His Gly Leu Thr Pro Asp Gln Val Val Ala Ile
            275                 280                 285

Ala Ser His Asp Gly Gly Lys Gln Ala Leu Glu Thr Val Gln Arg Leu
    290                 295                 300

Leu Pro Val Leu Cys Gln Asp His Gly Leu Thr Pro Glu Gln Val Val
305                 310                 315                 320

Ala Ile Ala Ser Asn Asn Gly Gly Lys Gln Ala Leu Glu Thr Val Gln
                325                 330                 335
```

-continued

Arg Leu Leu Pro Val Leu Cys Gln Ala His Gly Leu Thr Pro Asp Gln
                340                 345                 350

Val Val Ala Ile Ala Ser Asn Gly Gly Lys Gln Ala Leu Glu Thr
                355             360                 365

Val Gln Arg Leu Leu Pro Val Leu Cys Gln Ala His Gly Leu Thr Pro
        370                 375                 380

Ala Gln Val Val Ala Ile Ala Ser Asn Asn Gly Gly Lys Gln Ala Leu
385                 390                 395                 400

Glu Thr Val Gln Arg Leu Leu Pro Val Leu Cys Gln Asp His Gly Leu
                405                 410                 415

Thr Pro Asp Gln Val Val Ala Ile Ala Ser Asn Asn Gly Gly Lys Gln
                420                 425                 430

Ala Leu Glu Thr Val Gln Arg Leu Leu Pro Val Leu Cys Gln Asp His
            435                 440                 445

Gly Leu Thr Pro Glu Gln Val Val Ala Ile Ala Ser His Asp Gly Gly
            450                 455                 460

Lys Gln Ala Leu Glu Thr Val Gln Arg Leu Leu Pro Val Leu Cys Gln
465                 470                 475                 480

Ala His Gly Leu Thr Pro Asp Gln Val Val Ala Ile Ala Ser Asn Asn
            485                 490                 495

Gly Gly Lys Gln Ala Leu Glu Thr Val Gln Arg Leu Leu Pro Val Leu
            500                 505                 510

Cys Gln Ala His Gly Leu Thr Pro Ala Gln Val Val Ala Ile Ala Ser
            515                 520                 525

Asn Asn Gly Gly Lys Gln Ala Leu Glu Thr Val Gln Arg Leu Leu Pro
530                 535                 540

Val Leu Cys Gln Asp His Gly Leu Thr Pro Asp Gln Val Val Ala Ile
545                 550                 555                 560

Ala Ser Asn Ile Gly Gly Lys Gln Ala Leu Glu Thr Val Gln Arg Leu
                565                 570                 575

Leu Pro Val Leu Cys Gln Asp His Gly Leu Thr Pro Glu Gln Val Val
                580                 585                 590

Ala Ile Ala Ser Asn Asn Gly Gly Lys Gln Ala Leu Glu Thr Val Gln
            595                 600                 605

Arg Leu Leu Pro Val Leu Cys Gln Ala His Gly Leu Thr Pro Asp Gln
            610                 615                 620

Val Val Ala Ile Ala Ser Asn Asn Gly Gly Lys Gln Ala Leu Glu Thr
625                 630                 635                 640

Val Gln Arg Leu Leu Pro Val Leu Cys Gln Ala His Gly Leu Thr Pro
                645                 650                 655

Ala Gln Val Val Ala Ile Ala Ser Asn Asn Gly Gly Lys Gln Ala Leu
                660                 665                 670

Glu Thr Val Gln Arg Leu Leu Pro Val Leu Cys Gln Asp His Gly Leu
            675                 680                 685

Thr Pro Glu Gln Val Val Ala Ile Ala Ser His Asp Gly Gly Arg Pro
            690                 695                 700

Ala Leu Glu Ser Ile Val Ala Gln Leu Ser Arg Pro Asp Pro Ala Leu
705                 710                 715                 720

Ala Ala Leu Thr Asn Asp His Leu Val Ala Leu Ala Cys Leu Gly Gly
                725                 730                 735

Arg Pro Ala Leu Asp Ala Val Lys Lys Gly Leu Pro His Ala Pro Ala
            740                 745                 750

Leu Ile Lys Arg Thr Asn Arg Arg Ile Pro Glu Arg Thr Ser His Arg

```
                755                 760                 765
Val Ala Asp His Ala Gln Val Val Arg Val Leu Gly Phe Phe Gln Cys
            770                 775                 780

His Ser His Pro Ala Gln Ala Phe Asp Asp Ala Met Thr Gln Phe Gly
785                 790                 795                 800

Met Ser Arg His Gly Leu Leu Gln Leu Phe Arg Arg Val Gly Val Thr
                805                 810                 815

Glu Leu Glu Ala Arg Ser Gly Thr Leu Pro Pro Ala Ser Gln Arg Trp
            820                 825                 830

Asp Arg Ile Leu Gln Ala Ser Gly Met Lys Arg Ala Lys Pro Ser Pro
            835                 840                 845

Thr Ser Thr Gln Thr Pro Asp Gln Ala Ser Leu His Ala Phe Ala Asp
            850                 855                 860

Ser Leu Glu Arg Asp Leu Asp Ala Pro Ser Pro Met His Glu Gly Asp
865                 870                 875                 880

Gln Thr Arg Ala Ser Ala Ser
                885

<210> SEQ ID NO 5
<211> LENGTH: 2661
<212> TYPE: DNA
<213> ORGANISM: Artificial Sequence
<220> FEATURE:
<223> OTHER INFORMATION: TALE_TERT-3
<220> FEATURE:
<221> NAME/KEY: CDS
<222> LOCATION: (1)..(2661)

<400> SEQUENCE: 5
```

| | | | | | | | | | | | | | | | | |
|---|---|---|---|---|---|---|---|---|---|---|---|---|---|---|---|---|
| atc | cac | gga | gtc | cca | gca | gcc | gta | gat | ttg | aga | act | ttg | gga | tat | tca | 48 |
| Ile | His | Gly | Val | Pro | Ala | Ala | Val | Asp | Leu | Arg | Thr | Leu | Gly | Tyr | Ser | |
| 1 | | | | 5 | | | | | 10 | | | | | 15 | | |
| cag | cag | cag | cag | gaa | aag | atc | aag | ccc | aaa | gtg | agg | tcg | aca | gtc | gcg | 96 |
| Gln | Gln | Gln | Gln | Glu | Lys | Ile | Lys | Pro | Lys | Val | Arg | Ser | Thr | Val | Ala | |
| | | 20 | | | | 25 | | | | 30 | | | | | | |
| cag | cat | cac | gaa | gcg | ctg | gtg | ggt | cat | ggg | ttt | aca | cat | gcc | cac | atc | 144 |
| Gln | His | His | Glu | Ala | Leu | Val | Gly | His | Gly | Phe | Thr | His | Ala | His | Ile | |
| | 35 | | | | | 40 | | | | | 45 | | | | | |
| gta | gcc | ttg | tcg | cag | cac | cct | gca | gcc | ctt | ggc | acg | gtc | gcc | gtc | aag | 192 |
| Val | Ala | Leu | Ser | Gln | His | Pro | Ala | Ala | Leu | Gly | Thr | Val | Ala | Val | Lys | |
| | 50 | | | | | 55 | | | | | 60 | | | | | |
| tac | cag | gac | atg | att | gcg | gcg | ttg | ccg | gaa | gcc | aca | cat | gag | gcg | atc | 240 |
| Tyr | Gln | Asp | Met | Ile | Ala | Ala | Leu | Pro | Glu | Ala | Thr | His | Glu | Ala | Ile | |
| 65 | | | | | 70 | | | | | 75 | | | | | 80 | |
| gtc | ggt | gtg | ggg | aaa | cag | tgg | agc | gga | gcc | cga | gcg | ctt | gag | gcc | ctg | 288 |
| Val | Gly | Val | Gly | Lys | Gln | Trp | Ser | Gly | Ala | Arg | Ala | Leu | Glu | Ala | Leu | |
| | | | | 85 | | | | | 90 | | | | | 95 | | |
| ttg | acg | gtc | gcg | gga | gag | ctg | aga | ggg | cct | ccc | ctt | cag | ctg | gac | acg | 336 |
| Leu | Thr | Val | Ala | Gly | Glu | Leu | Arg | Gly | Pro | Pro | Leu | Gln | Leu | Asp | Thr | |
| | | | 100 | | | | | 105 | | | | | 110 | | | |
| ggc | cag | ttg | ctg | aag | atc | gcg | aag | cgg | gga | gga | gtc | acg | gcg | gtc | gag | 384 |
| Gly | Gln | Leu | Leu | Lys | Ile | Ala | Lys | Arg | Gly | Gly | Val | Thr | Ala | Val | Glu | |
| | | 115 | | | | | 120 | | | | | 125 | | | | |
| gcg | gta | cac | gcg | tgg | cgc | aat | gcg | ctc | acg | gga | gca | ccc | ctc | aac | ctg | 432 |
| Ala | Val | His | Ala | Trp | Arg | Asn | Ala | Leu | Thr | Gly | Ala | Pro | Leu | Asn | Leu | |
| | 130 | | | | | 135 | | | | | 140 | | | | | |
| acc | cca | gac | cag | gtt | gtg | gcc | atc | gcc | agc | aac | ata | ggt | ggc | aag | cag | 480 |
| Thr | Pro | Asp | Gln | Val | Val | Ala | Ile | Ala | Ser | Asn | Ile | Gly | Gly | Lys | Gln | |
| 145 | | | | | 150 | | | | | 155 | | | | | 160 | |

-continued

| | |
|---|---|
| gcc ctc gaa acc gtc cag aga ctg tta ccg gtt ctc tgc cag gac cac<br>Ala Leu Glu Thr Val Gln Arg Leu Leu Pro Val Leu Cys Gln Asp His<br>                165                      170                  175 | 528 |
| ggc ctg acc cca gaa caa gtt gtc gcg att gca agc aac aac gga ggc<br>Gly Leu Thr Pro Glu Gln Val Val Ala Ile Ala Ser Asn Asn Gly Gly<br>              180                      185                      190 | 576 |
| aaa caa gcc tta gaa aca gtc cag aga ttg ttg ccg gtg ctg tgc caa<br>Lys Gln Ala Leu Glu Thr Val Gln Arg Leu Leu Pro Val Leu Cys Gln<br>              195                      200                      205 | 624 |
| gcc cac ggc ctg acc cca gac cag gtt gtc gcc atc gcc agc aac ata<br>Ala His Gly Leu Thr Pro Asp Gln Val Val Ala Ile Ala Ser Asn Ile<br>              210                      215                      220 | 672 |
| ggt ggc aag cag gcc ctc gaa acc gtc cag aga ctg tta ccg gtt ctc<br>Gly Gly Lys Gln Ala Leu Glu Thr Val Gln Arg Leu Leu Pro Val Leu<br>225                      230                      235                      240 | 720 |
| tgc cag gcc cac ggc ctg acc ccg gcc cag gtg gtt gca atc gcg tca<br>Cys Gln Ala His Gly Leu Thr Pro Ala Gln Val Val Ala Ile Ala Ser<br>                      245                      250                      255 | 768 |
| cac gat ggg gga aag cag gcc cta gaa acc gtt cag cga ctc ctg ccc<br>His Asp Gly Gly Lys Gln Ala Leu Glu Thr Val Gln Arg Leu Leu Pro<br>            260                      265                      270 | 816 |
| gtc ctg tgc cag gac cac ggc ctg acc ccg gac cag gtg gtt gca atc<br>Val Leu Cys Gln Asp His Gly Leu Thr Pro Asp Gln Val Val Ala Ile<br>              275                      280                      285 | 864 |
| gcg tca cac gat ggg gga aag cag gcc cta gaa acc gtt cag cga ctc<br>Ala Ser His Asp Gly Gly Lys Gln Ala Leu Glu Thr Val Gln Arg Leu<br>            290                      295                      300 | 912 |
| ctg ccc gtc ctg tgc cag gac cac ggc ctg acc ccg gaa cag gtg gtt<br>Leu Pro Val Leu Cys Gln Asp His Gly Leu Thr Pro Glu Gln Val Val<br>305                      310                      315                      320 | 960 |
| gca atc gcg tca cac gat ggg gga aag cag gcc cta gaa acc gtt cag<br>Ala Ile Ala Ser His Asp Gly Gly Lys Gln Ala Leu Glu Thr Val Gln<br>              325                      330                      335 | 1008 |
| cga ctc ctg ccc gtc ctg tgc cag gcc cac ggc ctg acc ccc gac cag<br>Arg Leu Leu Pro Val Leu Cys Gln Ala His Gly Leu Thr Pro Asp Gln<br>                  340                      345                      350 | 1056 |
| gtt gtc gct att gct agt aac ggc gga ggc aaa cag gcg ctg gaa aca<br>Val Val Ala Ile Ala Ser Asn Gly Gly Gly Lys Gln Ala Leu Glu Thr<br>              355                      360                      365 | 1104 |
| gtt cag cgc ctc ttg ccg gtc ttg tgt cag gcc cac ggc ctg acc cca<br>Val Gln Arg Leu Leu Pro Val Leu Cys Gln Ala His Gly Leu Thr Pro<br>            370                      375                      380 | 1152 |
| gcc caa gtt gtc gcg att gca agc aac aac gga ggc aaa caa gcc tta<br>Ala Gln Val Val Ala Ile Ala Ser Asn Asn Gly Gly Lys Gln Ala Leu<br>385                      390                      395                      400 | 1200 |
| gaa aca gtc cag aga ttg ttg ccg gtg ctg tgc caa gac cac ggc ctg<br>Glu Thr Val Gln Arg Leu Leu Pro Val Leu Cys Gln Asp His Gly Leu<br>                  405                      410                      415 | 1248 |
| acc cca gac caa gtt gtc gcg att gca agc aac aac gga ggc aaa caa<br>Thr Pro Asp Gln Val Val Ala Ile Ala Ser Asn Asn Gly Gly Lys Gln<br>              420                      425                      430 | 1296 |
| gcc tta gaa aca gtc cag aga ttg ttg ccg gtg ctg tgc caa gac cac<br>Ala Leu Glu Thr Val Gln Arg Leu Leu Pro Val Leu Cys Gln Asp His<br>                435                      440                      445 | 1344 |
| ggc ctg acc ccg gaa cag gtg gtt gca atc gcg tca cac gat ggg gga<br>Gly Leu Thr Pro Glu Gln Val Val Ala Ile Ala Ser His Asp Gly Gly<br>            450                      455                      460 | 1392 |
| aag cag gcc cta gaa acc gtt cag cga ctc ctg ccc gtc ctg tgc cag<br>Lys Gln Ala Leu Glu Thr Val Gln Arg Leu Leu Pro Val Leu Cys Gln<br>465                      470                      475                      480 | 1440 |

```
gcc cac ggc ctg acc cca gac cag gtt gtg gcc atc gcc agc aac ata    1488
Ala His Gly Leu Thr Pro Asp Gln Val Val Ala Ile Ala Ser Asn Ile
            485                 490                 495 ggt ggc aag cag gcc ctc gaa acc gtc cag aga ctg tta ccg gtt ctc    1536
Gly Gly Lys Gln Ala Leu Glu Thr Val Gln Arg Leu Leu Pro Val Leu
            500                 505                 510 tgc cag gcc cac ggc ctg acc cca gcc caa gtt gtc gcg att gca agc    1584
Cys Gln Ala His Gly Leu Thr Pro Ala Gln Val Val Ala Ile Ala Ser
            515                 520                 525 aac aac gga ggc aaa caa gcc tta gaa aca gtc cag aga ttg ttg ccg    1632
Asn Asn Gly Gly Lys Gln Ala Leu Glu Thr Val Gln Arg Leu Leu Pro
            530                 535                 540 gtg ctg tgc caa gac cac ggc ctg acc cca gac caa gtt gtc gcg att    1680
Val Leu Cys Gln Asp His Gly Leu Thr Pro Asp Gln Val Val Ala Ile
545                 550                 555                 560 gca agc aac aac gga ggc aaa caa gcc tta gaa aca gtc cag aga ttg    1728
Ala Ser Asn Asn Gly Gly Lys Gln Ala Leu Glu Thr Val Gln Arg Leu
                565                 570                 575 ttg ccg gtg ctg tgc caa gac cac ggc ctg acc ccg gaa cag gtg gtt    1776
Leu Pro Val Leu Cys Gln Asp His Gly Leu Thr Pro Glu Gln Val Val
            580                 585                 590 gca atc gcg tca cac gat ggg gga aag cag gcc cta gaa acc gtt cag    1824
Ala Ile Ala Ser His Asp Gly Gly Lys Gln Ala Leu Glu Thr Val Gln
            595                 600                 605 cga ctc ctg ccc gtc ctg tgc cag gcc cac ggc ctg acc cca gac cag    1872
Arg Leu Leu Pro Val Leu Cys Gln Ala His Gly Leu Thr Pro Asp Gln
            610                 615                 620 gtt gtg gcc atc gcc agc aac ata ggt ggc aag cag gcc ctc gaa acc    1920
Val Val Ala Ile Ala Ser Asn Ile Gly Gly Lys Gln Ala Leu Glu Thr
625                 630                 635                 640 gtc cag aga ctg tta ccg gtt ctc tgc cag gcc cac ggc ctg acc ccg    1968
Val Gln Arg Leu Leu Pro Val Leu Cys Gln Ala His Gly Leu Thr Pro
                645                 650                 655 gcc cag gtg gtt gca atc gcg tca cac gat ggg gga aag cag gcc cta    2016
Ala Gln Val Val Ala Ile Ala Ser His Asp Gly Gly Lys Gln Ala Leu
            660                 665                 670 gaa acc gtt cag cga ctc ctg ccc gtc ctg tgc cag gac cac ggc ctg    2064
Glu Thr Val Gln Arg Leu Leu Pro Val Leu Cys Gln Asp His Gly Leu
            675                 680                 685 acc cct gag cag gta gtg gct att gca tcc cac gac ggg gga aga ccc    2112
Thr Pro Glu Gln Val Val Ala Ile Ala Ser His Asp Gly Gly Arg Pro
            690                 695                 700 gca ctg gag tca atc gtg gcc cag ctc tcg agg ccg gac ccc gcg ctg    2160
Ala Leu Glu Ser Ile Val Ala Gln Leu Ser Arg Pro Asp Pro Ala Leu
705                 710                 715                 720 gcc gca ctc act aat gat cat ctt gta gcg ctg gcc tgc ctc ggc gga    2208
Ala Ala Leu Thr Asn Asp His Leu Val Ala Leu Ala Cys Leu Gly Gly
                725                 730                 735 cga ccc gcc ttg gat gcg gtg aag aag ggg ctc ccg cac gcg cct gca    2256
Arg Pro Ala Leu Asp Ala Val Lys Lys Gly Leu Pro His Ala Pro Ala
            740                 745                 750 ttg att aag cgg acc aac aga agg atc ccc gag agg aca tca cat cga    2304
Leu Ile Lys Arg Thr Asn Arg Arg Ile Pro Glu Arg Thr Ser His Arg
            755                 760                 765 gtg gca gat cac gcg caa gtg gtc cgc gtg ctc gga ttc ttc cag tgt    2352
Val Ala Asp His Ala Gln Val Val Arg Val Leu Gly Phe Phe Gln Cys
            770                 775                 780 cac tcc cac ccc gca caa gcg ttc gat gac gcc atg act caa ttt ggt    2400
His Ser His Pro Ala Gln Ala Phe Asp Asp Ala Met Thr Gln Phe Gly
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| 785 |     |     |     | 790 |     |     |     | 795 |     |     |     | 800 |     |     |     |      |
| atg | tcg | aga | cac | gga | ctg | ctg | cag | ctc | ttt | cgt | aga | gtc | ggt | gtc | aca | 2448 |
| Met | Ser | Arg | His | Gly | Leu | Leu | Gln | Leu | Phe | Arg | Arg | Val | Gly | Val | Thr |      |
|     |     |     |     | 805 |     |     |     |     | 810 |     |     |     |     | 815 |     |      |
| gaa | ctg | gag | gcc | cgc | tcg | ggc | aca | ctg | cct | ccc | gcc | tcc | cag | cgg | tgg | 2496 |
| Glu | Leu | Glu | Ala | Arg | Ser | Gly | Thr | Leu | Pro | Pro | Ala | Ser | Gln | Arg | Trp |      |
|     |     |     | 820 |     |     |     |     | 825 |     |     |     |     | 830 |     |     |      |
| gac | agg | att | ctc | caa | gcg | agc | ggt | atg | aaa | cgc | gcg | aag | cct | tca | cct | 2544 |
| Asp | Arg | Ile | Leu | Gln | Ala | Ser | Gly | Met | Lys | Arg | Ala | Lys | Pro | Ser | Pro |      |
|     |     | 835 |     |     |     |     | 840 |     |     |     |     | 845 |     |     |     |      |
| acg | tca | act | cag | aca | cct | gac | cag | gcg | agc | ctt | cat | gcg | ttc | gca | gac | 2592 |
| Thr | Ser | Thr | Gln | Thr | Pro | Asp | Gln | Ala | Ser | Leu | His | Ala | Phe | Ala | Asp |      |
| 850 |     |     |     |     | 855 |     |     |     |     | 860 |     |     |     |     |     |      |
| tcg | ctg | gag | agg | gat | ttg | gac | gcg | ccc | tcg | ccc | atg | cat | gaa | ggg | gac | 2640 |
| Ser | Leu | Glu | Arg | Asp | Leu | Asp | Ala | Pro | Ser | Pro | Met | His | Glu | Gly | Asp |      |
| 865 |     |     |     | 870 |     |     |     | 875 |     |     |     | 880 |     |     |     |      |
| caa | act | cgc | gcg | tca | gcc | agc |     |     |     |     |     |     |     |     |     | 2661 |
| Gln | Thr | Arg | Ala | Ser | Ala | Ser |     |     |     |     |     |     |     |     |     |      |
|     |     |     |     | 885 |     |     |     |     |     |     |     |     |     |     |     |      |

<210> SEQ ID NO 6
<211> LENGTH: 887
<212> TYPE: PRT
<213> ORGANISM: Artificial Sequence
<220> FEATURE:
<223> OTHER INFORMATION: Synthetic Construct

<400> SEQUENCE: 6

Ile His Gly Val Pro Ala Ala Val Asp Leu Arg Thr Leu Gly Tyr Ser
1               5                   10                  15

Gln Gln Gln Gln Glu Lys Ile Lys Pro Lys Val Arg Ser Thr Val Ala
            20                  25                  30

Gln His His Glu Ala Leu Val Gly His Gly Phe Thr His Ala His Ile
        35                  40                  45

Val Ala Leu Ser Gln His Pro Ala Ala Leu Gly Thr Val Ala Val Lys
    50                  55                  60

Tyr Gln Asp Met Ile Ala Ala Leu Pro Glu Ala Thr His Glu Ala Ile
65                  70                  75                  80

Val Gly Val Gly Lys Gln Trp Ser Gly Ala Arg Ala Leu Glu Ala Leu
                85                  90                  95

Leu Thr Val Ala Gly Glu Leu Arg Gly Pro Pro Leu Gln Leu Asp Thr
            100                 105                 110

Gly Gln Leu Leu Lys Ile Ala Lys Arg Gly Gly Val Thr Ala Val Glu
        115                 120                 125

Ala Val His Ala Trp Arg Asn Ala Leu Thr Gly Ala Pro Leu Asn Leu
    130                 135                 140

Thr Pro Asp Gln Val Val Ala Ile Ala Ser Asn Ile Gly Gly Lys Gln
145                 150                 155                 160

Ala Leu Glu Thr Val Gln Arg Leu Leu Pro Val Leu Cys Gln Asp His
                165                 170                 175

Gly Leu Thr Pro Glu Gln Val Val Ala Ile Ala Ser Asn Asn Gly Gly
            180                 185                 190

Lys Gln Ala Leu Glu Thr Val Gln Arg Leu Pro Val Leu Cys Gln
        195                 200                 205

Ala His Gly Leu Thr Pro Asp Gln Val Val Ala Ile Ala Ser Asn Ile
    210                 215                 220

Gly Gly Lys Gln Ala Leu Glu Thr Val Gln Arg Leu Leu Pro Val Leu

```
                225                 230                 235                 240
            Cys Gln Ala His Gly Leu Thr Pro Ala Gln Val Val Ala Ile Ala Ser
                                245                 250                 255
            His Asp Gly Gly Lys Gln Ala Leu Glu Thr Val Gln Arg Leu Leu Pro
                                260                 265                 270
            Val Leu Cys Gln Asp His Gly Leu Thr Pro Asp Gln Val Val Ala Ile
                                275                 280                 285
            Ala Ser His Asp Gly Gly Lys Gln Ala Leu Glu Thr Val Gln Arg Leu
                290                 295                 300
            Leu Pro Val Leu Cys Gln Asp His Gly Leu Thr Pro Glu Gln Val Val
            305                 310                 315                 320
            Ala Ile Ala Ser His Asp Gly Gly Lys Gln Ala Leu Glu Thr Val Gln
                                325                 330                 335
            Arg Leu Leu Pro Val Leu Cys Gln Ala His Gly Leu Thr Pro Asp Gln
                                340                 345                 350
            Val Val Ala Ile Ala Ser Asn Gly Gly Lys Gln Ala Leu Glu Thr
                            355                 360                 365
            Val Gln Arg Leu Leu Pro Val Leu Cys Gln Ala His Gly Leu Thr Pro
                370                 375                 380
            Ala Gln Val Val Ala Ile Ala Ser Asn Asn Gly Gly Lys Gln Ala Leu
            385                 390                 395                 400
            Glu Thr Val Gln Arg Leu Leu Pro Val Leu Cys Gln Asp His Gly Leu
                                405                 410                 415
            Thr Pro Asp Gln Val Val Ala Ile Ala Ser Asn Asn Gly Gly Lys Gln
                                420                 425                 430
            Ala Leu Glu Thr Val Gln Arg Leu Leu Pro Val Leu Cys Gln Asp His
                            435                 440                 445
            Gly Leu Thr Pro Glu Gln Val Val Ala Ile Ala Ser His Asp Gly Gly
                450                 455                 460
            Lys Gln Ala Leu Glu Thr Val Gln Arg Leu Leu Pro Val Leu Cys Gln
            465                 470                 475                 480
            Ala His Gly Leu Thr Pro Asp Gln Val Val Ala Ile Ala Ser Asn Ile
                                485                 490                 495
            Gly Gly Lys Gln Ala Leu Glu Thr Val Gln Arg Leu Leu Pro Val Leu
                            500                 505                 510
            Cys Gln Ala His Gly Leu Thr Pro Ala Gln Val Val Ala Ile Ala Ser
                            515                 520                 525
            Asn Asn Gly Gly Lys Gln Ala Leu Glu Thr Val Gln Arg Leu Leu Pro
                530                 535                 540
            Val Leu Cys Gln Asp His Gly Leu Thr Pro Asp Gln Val Val Ala Ile
            545                 550                 555                 560
            Ala Ser Asn Asn Gly Gly Lys Gln Ala Leu Glu Thr Val Gln Arg Leu
                            565                 570                 575
            Leu Pro Val Leu Cys Gln Asp His Gly Leu Thr Pro Glu Gln Val Val
                580                 585                 590
            Ala Ile Ala Ser His Asp Gly Gly Lys Gln Ala Leu Glu Thr Val Gln
                            595                 600                 605
            Arg Leu Leu Pro Val Leu Cys Gln Ala His Gly Leu Thr Pro Asp Gln
                            610                 615                 620
            Val Val Ala Ile Ala Ser Asn Ile Gly Gly Lys Gln Ala Leu Glu Thr
            625                 630                 635                 640
            Val Gln Arg Leu Leu Pro Val Leu Cys Gln Ala His Gly Leu Thr Pro
                            645                 650                 655
```

```
Ala Gln Val Val Ala Ile Ala Ser His Asp Gly Gly Lys Gln Ala Leu
            660                 665                 670

Glu Thr Val Gln Arg Leu Leu Pro Val Leu Cys Gln Asp His Gly Leu
        675                 680                 685

Thr Pro Glu Gln Val Val Ala Ile Ala Ser His Asp Gly Gly Arg Pro
    690                 695                 700

Ala Leu Glu Ser Ile Val Ala Gln Leu Ser Arg Pro Asp Pro Ala Leu
705                 710                 715                 720

Ala Ala Leu Thr Asn Asp His Leu Val Ala Leu Ala Cys Leu Gly Gly
                725                 730                 735

Arg Pro Ala Leu Asp Ala Val Lys Lys Gly Leu Pro His Ala Pro Ala
            740                 745                 750

Leu Ile Lys Arg Thr Asn Arg Arg Ile Pro Glu Arg Thr Ser His Arg
        755                 760                 765

Val Ala Asp His Ala Gln Val Val Arg Val Leu Gly Phe Phe Gln Cys
    770                 775                 780

His Ser His Pro Ala Gln Ala Phe Asp Asp Ala Met Thr Gln Phe Gly
785                 790                 795                 800

Met Ser Arg His Gly Leu Leu Gln Leu Phe Arg Arg Val Gly Val Thr
                805                 810                 815

Glu Leu Glu Ala Arg Ser Gly Thr Leu Pro Pro Ala Ser Gln Arg Trp
            820                 825                 830

Asp Arg Ile Leu Gln Ala Ser Gly Met Lys Arg Ala Lys Pro Ser Pro
        835                 840                 845

Thr Ser Thr Gln Thr Pro Asp Gln Ala Ser Leu His Ala Phe Ala Asp
    850                 855                 860

Ser Leu Glu Arg Asp Leu Asp Ala Pro Ser Pro Met His Glu Gly Asp
865                 870                 875                 880

Gln Thr Arg Ala Ser Ala Ser
                885

<210> SEQ ID NO 7
<211> LENGTH: 2661
<212> TYPE: DNA
<213> ORGANISM: Artificial Sequence
<220> FEATURE:
<223> OTHER INFORMATION: TALE_miR-346-1
<220> FEATURE:
<221> NAME/KEY: CDS
<222> LOCATION: (1)..(2661)

<400> SEQUENCE: 7 atc cac gga gtc cca gca gcc gta gat ttg aga act ttg gga tat tca    48
Ile His Gly Val Pro Ala Ala Val Asp Leu Arg Thr Leu Gly Tyr Ser
1               5                   10                  15 cag cag cag cag gaa aag atc aag ccc aaa gtg agg tcg aca gtc gcg    96
Gln Gln Gln Gln Glu Lys Ile Lys Pro Lys Val Arg Ser Thr Val Ala
                20                  25                  30 cag cat cac gaa gcg ctg gtg ggt cat ggg ttt aca cat gcc cac atc   144
Gln His His Glu Ala Leu Val Gly His Gly Phe Thr His Ala His Ile
            35                  40                  45 gta gcc ttg tcg cag cac cct gca gcc ctt ggc acg gtc gcc gtc aag   192
Val Ala Leu Ser Gln His Pro Ala Ala Leu Gly Thr Val Ala Val Lys
        50                  55                  60 tac cag gac atg att gcg gcg ttg ccg gaa gcc aca cat gag gcg atc   240
Tyr Gln Asp Met Ile Ala Ala Leu Pro Glu Ala Thr His Glu Ala Ile
65                  70                  75                  80
```

```
gtc ggt gtg ggg aaa cag tgg agc gga gcc cga gcg ctt gag gcc ctg        288
Val Gly Val Gly Lys Gln Trp Ser Gly Ala Arg Ala Leu Glu Ala Leu
                85                  90                  95 ttg acg gtc gcg gga gag ctg aga ggg cct ccc ctt cag ctg gac acg        336
Leu Thr Val Ala Gly Glu Leu Arg Gly Pro Pro Leu Gln Leu Asp Thr
            100                 105                 110 ggc cag ttg ctg aag atc gcg aag cgg gga gga gtc acg gcg gtc gag        384
Gly Gln Leu Leu Lys Ile Ala Lys Arg Gly Gly Val Thr Ala Val Glu
        115                 120                 125 gcg gta cac gcg tgg cgc aat gcg ctc acg gga gca ccc ctc aac ctg        432
Ala Val His Ala Trp Arg Asn Ala Leu Thr Gly Ala Pro Leu Asn Leu
    130                 135                 140 acc ccg gac cag gtg gtt gca atc gcg tca cac gat ggg gga aag cag        480
Thr Pro Asp Gln Val Val Ala Ile Ala Ser His Asp Gly Gly Lys Gln
145                 150                 155                 160 gcc cta gaa acc gtt cag cga ctc ctg ccc gtc ctg tgc cag gac cac        528
Ala Leu Glu Thr Val Gln Arg Leu Leu Pro Val Leu Cys Gln Asp His
                165                 170                 175 ggc ctg acc ccc gaa cag gtt gtc gct att gct agt aac ggc gga ggc        576
Gly Leu Thr Pro Glu Gln Val Val Ala Ile Ala Ser Asn Gly Gly Gly
            180                 185                 190 aaa cag gcg ctg gaa aca gtt cag cgc ctc ttg ccg gtc ttg tgt cag        624
Lys Gln Ala Leu Glu Thr Val Gln Arg Leu Leu Pro Val Leu Cys Gln
        195                 200                 205 gcc cac ggc ctg acc ccg gac cag gtg gtt gca atc gcg tca cac gat        672
Ala His Gly Leu Thr Pro Asp Gln Val Val Ala Ile Ala Ser His Asp
    210                 215                 220 ggg gga aag cag gcc cta gaa acc gtt cag cga ctc ctg ccc gtc ctg        720
Gly Gly Lys Gln Ala Leu Glu Thr Val Gln Arg Leu Leu Pro Val Leu
225                 230                 235                 240 tgc cag gcc cac ggc ctg acc ccg gcc cag gtg gtt gca atc gcg tca        768
Cys Gln Ala His Gly Leu Thr Pro Ala Gln Val Val Ala Ile Ala Ser
                245                 250                 255 cac gat ggg gga aag cag gcc cta gaa acc gtt cag cga ctc ctg ccc        816
His Asp Gly Gly Lys Gln Ala Leu Glu Thr Val Gln Arg Leu Leu Pro
            260                 265                 270 gtc ctg tgc cag gac cac ggc ctg acc ccc gac cag gtt gtc gct att        864
Val Leu Cys Gln Asp His Gly Leu Thr Pro Asp Gln Val Val Ala Ile
        275                 280                 285 gct agt aac ggc gga ggc aaa cag gcg ctg gaa aca gtt cag cgc ctc        912
Ala Ser Asn Gly Gly Gly Lys Gln Ala Leu Glu Thr Val Gln Arg Leu
    290                 295                 300 ttg ccg gtc ttg tgt cag gac cac ggc ctg acc ccg gaa cag gtg gtt        960
Leu Pro Val Leu Cys Gln Asp His Gly Leu Thr Pro Glu Gln Val Val
305                 310                 315                 320 gca atc gcg tca cac gat ggg gga aag cag gcc cta gaa acc gtt cag       1008
Ala Ile Ala Ser His Asp Gly Gly Lys Gln Ala Leu Glu Thr Val Gln
                325                 330                 335 cga ctc ctg ccc gtc ctg tgc cag gcc cac ggc ctg acc ccc gac cag       1056
Arg Leu Leu Pro Val Leu Cys Gln Ala His Gly Leu Thr Pro Asp Gln
            340                 345                 350 gtt gtc gct att gct agt aac ggc gga ggc aaa cag gcg ctg gaa aca       1104
Val Val Ala Ile Ala Ser Asn Gly Gly Gly Lys Gln Ala Leu Glu Thr
        355                 360                 365 gtt cag cgc ctc ttg ccg gtc ttg tgt cag gcc cac ggc ctg acc cca       1152
Val Gln Arg Leu Leu Pro Val Leu Cys Gln Ala His Gly Leu Thr Pro
    370                 375                 380 gcc cag gtt gtg gcc atc gcc agc aac ata ggt ggc aag cag gcc ctc       1200
Ala Gln Val Val Ala Ile Ala Ser Asn Ile Gly Gly Lys Gln Ala Leu
385                 390                 395                 400
```

```
gaa acc gtc cag aga ctg tta ccg gtt ctc tgc cag gac cac ggc ctg    1248
Glu Thr Val Gln Arg Leu Leu Pro Val Leu Cys Gln Asp His Gly Leu
            405                 410                 415 acc cca gac caa gtt gtc gcg att gca agc aac aac gga ggc aaa caa    1296
Thr Pro Asp Gln Val Val Ala Ile Ala Ser Asn Asn Gly Gly Lys Gln
        420                 425                 430 gcc tta gaa aca gtc cag aga ttg ttg ccg gtg ctg tgc caa gac cac    1344
Ala Leu Glu Thr Val Gln Arg Leu Leu Pro Val Leu Cys Gln Asp His
    435                 440                 445 ggc ctg acc cca gaa caa gtt gtc gcg att gca agc aac aac gga ggc    1392
Gly Leu Thr Pro Glu Gln Val Val Ala Ile Ala Ser Asn Asn Gly Gly
450                 455                 460 aaa caa gcc tta gaa aca gtc cag aga ttg ttg ccg gtg ctg tgc caa    1440
Lys Gln Ala Leu Glu Thr Val Gln Arg Leu Leu Pro Val Leu Cys Gln
465                 470                 475                 480 gcc cac ggc ctg acc cca gac cag gtt gtg gcc atc gcc agc aac ata    1488
Ala His Gly Leu Thr Pro Asp Gln Val Val Ala Ile Ala Ser Asn Ile
            485                 490                 495 ggt ggc aag cag gcc ctc gaa acc gtc cag aga ctg tta ccg gtt ctc    1536
Gly Gly Lys Gln Ala Leu Glu Thr Val Gln Arg Leu Leu Pro Val Leu
        500                 505                 510 tgc cag gcc cac ggc ctg acc cca gcc caa gtt gtc gcg att gca agc    1584
Cys Gln Ala His Gly Leu Thr Pro Ala Gln Val Val Ala Ile Ala Ser
    515                 520                 525 aac aac gga ggc aaa caa gcc tta gaa aca gtc cag aga ttg ttg ccg    1632
Asn Asn Gly Gly Lys Gln Ala Leu Glu Thr Val Gln Arg Leu Leu Pro
530                 535                 540 gtg ctg tgc caa gac cac ggc ctg acc ccg gac cag gtg gtt gca atc    1680
Val Leu Cys Gln Asp His Gly Leu Thr Pro Asp Gln Val Val Ala Ile
545                 550                 555                 560 gcg tca cac gat ggg gga aag cag gcc cta gaa acc gtt cag cga ctc    1728
Ala Ser His Asp Gly Gly Lys Gln Ala Leu Glu Thr Val Gln Arg Leu
            565                 570                 575 ctg ccc gtc ctg tgc cag gac cac ggc ctg acc ccg gaa cag gtg gtt    1776
Leu Pro Val Leu Cys Gln Asp His Gly Leu Thr Pro Glu Gln Val Val
        580                 585                 590 gca atc gcg tca cac gat ggg gga aag cag gcc cta gaa acc gtt cag    1824
Ala Ile Ala Ser His Asp Gly Gly Lys Gln Ala Leu Glu Thr Val Gln
    595                 600                 605 cga ctc ctg ccc gtc ctg tgc cag gcc cac ggc ctg acc ccc gac cag    1872
Arg Leu Leu Pro Val Leu Cys Gln Ala His Gly Leu Thr Pro Asp Gln
610                 615                 620 gtt gtc gct att gct agt aac ggc gga ggc aaa cag gcg ctg gaa aca    1920
Val Val Ala Ile Ala Ser Asn Gly Gly Gly Lys Gln Ala Leu Glu Thr
625                 630                 635                 640 gtt cag cgc ctc ttg ccg gtc ttg tgt cag gcc cac ggc ctg acc ccg    1968
Val Gln Arg Leu Leu Pro Val Leu Cys Gln Ala His Gly Leu Thr Pro
            645                 650                 655 gcc cag gtg gtt gca atc gcg tca cac gat ggg gga aag cag gcc cta    2016
Ala Gln Val Val Ala Ile Ala Ser His Asp Gly Gly Lys Gln Ala Leu
        660                 665                 670 gaa acc gtt cag cga ctc ctg ccc gtc ctg tgc cag gac cac ggc ctg    2064
Glu Thr Val Gln Arg Leu Leu Pro Val Leu Cys Gln Asp His Gly Leu
    675                 680                 685 acc cct gag cag gta gtg gct att gca tcc cac gac ggg ggc aga ccc    2112
Thr Pro Glu Gln Val Val Ala Ile Ala Ser His Asp Gly Gly Arg Pro
690                 695                 700 gca ctg gag tca atc gtg gcc cag ctc tcg agg ccg gac ccc gcg ctg    2160
Ala Leu Glu Ser Ile Val Ala Gln Leu Ser Arg Pro Asp Pro Ala Leu
```

|     |     |     |     |     |     |     |     |     |     |     |     |     |     |     |     |      |
|---|---|---|---|---|---|---|---|---|---|---|---|---|---|---|---|---|
| 705 | | | | | 710 | | | | | 715 | | | | | 720 | |
| gcc | gca | ctc | act | aat | gat | cat | ctt | gta | gcg | ctg | gcc | tgc | ctc | ggc | gga | 2208 |
| Ala | Ala | Leu | Thr | Asn | Asp | His | Leu | Val | Ala | Leu | Ala | Cys | Leu | Gly | Gly | |
| | | | | 725 | | | | | 730 | | | | | 735 | | |
| cga | ccc | gcc | ttg | gat | gcg | gtg | aag | aag | ggg | ctc | ccg | cac | gcg | cct | gca | 2256 |
| Arg | Pro | Ala | Leu | Asp | Ala | Val | Lys | Lys | Gly | Leu | Pro | His | Ala | Pro | Ala | |
| | | | 740 | | | | | 745 | | | | | 750 | | | |
| ttg | att | aag | cgg | acc | aac | aga | agg | atc | ccc | gag | agg | aca | tca | cat | cga | 2304 |
| Leu | Ile | Lys | Arg | Thr | Asn | Arg | Arg | Ile | Pro | Glu | Arg | Thr | Ser | His | Arg | |
| | | 755 | | | | | 760 | | | | | 765 | | | | |
| gtg | gca | gat | cac | gcg | caa | gtg | gtc | cgc | gtg | ctc | gga | ttc | ttc | cag | tgt | 2352 |
| Val | Ala | Asp | His | Ala | Gln | Val | Val | Arg | Val | Leu | Gly | Phe | Phe | Gln | Cys | |
| | 770 | | | | | 775 | | | | | 780 | | | | | |
| cac | tcc | cac | ccc | gca | caa | gcg | ttc | gat | gac | gcc | atg | act | caa | ttt | ggt | 2400 |
| His | Ser | His | Pro | Ala | Gln | Ala | Phe | Asp | Asp | Ala | Met | Thr | Gln | Phe | Gly | |
| 785 | | | | | 790 | | | | | 795 | | | | | 800 | |
| atg | tcg | aga | cac | gga | ctg | ctg | cag | ctc | ttt | cgt | aga | gtc | ggt | gtc | aca | 2448 |
| Met | Ser | Arg | His | Gly | Leu | Leu | Gln | Leu | Phe | Arg | Arg | Val | Gly | Val | Thr | |
| | | | | 805 | | | | | 810 | | | | | 815 | | |
| gaa | ctg | gag | gcc | cgc | tcg | ggc | aca | ctg | cct | ccc | gcc | tcc | cag | cgg | tgg | 2496 |
| Glu | Leu | Glu | Ala | Arg | Ser | Gly | Thr | Leu | Pro | Pro | Ala | Ser | Gln | Arg | Trp | |
| | | | 820 | | | | | 825 | | | | | 830 | | | |
| gac | agg | att | ctc | caa | gcg | agc | ggt | atg | aaa | cgc | gcg | aag | cct | tca | cct | 2544 |
| Asp | Arg | Ile | Leu | Gln | Ala | Ser | Gly | Met | Lys | Arg | Ala | Lys | Pro | Ser | Pro | |
| | | 835 | | | | | 840 | | | | | 845 | | | | |
| acg | tca | act | cag | aca | cct | gac | cag | gcg | agc | ctt | cat | gcg | ttc | gca | gac | 2592 |
| Thr | Ser | Thr | Gln | Thr | Pro | Asp | Gln | Ala | Ser | Leu | His | Ala | Phe | Ala | Asp | |
| | 850 | | | | | 855 | | | | | 860 | | | | | |
| tcg | ctg | gag | agg | gat | ttg | gac | gcg | ccc | tcg | ccc | atg | cat | gaa | ggg | gac | 2640 |
| Ser | Leu | Glu | Arg | Asp | Leu | Asp | Ala | Pro | Ser | Pro | Met | His | Glu | Gly | Asp | |
| 865 | | | | | 870 | | | | | 875 | | | | | 880 | |
| caa | act | cgc | gcg | tca | gcc | agc | | | | | | | | | | 2661 |
| Gln | Thr | Arg | Ala | Ser | Ala | Ser | | | | | | | | | | |
| | | | | 885 | | | | | | | | | | | | |

<210> SEQ ID NO 8
<211> LENGTH: 887
<212> TYPE: PRT
<213> ORGANISM: Artificial Sequence
<220> FEATURE:
<223> OTHER INFORMATION: Synthetic Construct

<400> SEQUENCE: 8

Ile His Gly Val Pro Ala Ala Val Asp Leu Arg Thr Leu Gly Tyr Ser
1               5                   10                  15

Gln Gln Gln Gln Glu Lys Ile Lys Pro Lys Val Arg Ser Thr Val Ala
            20                  25                  30

Gln His His Glu Ala Leu Val Gly His Gly Phe Thr His Ala His Ile
        35                  40                  45

Val Ala Leu Ser Gln His Pro Ala Ala Leu Gly Thr Val Ala Val Lys
    50                  55                  60

Tyr Gln Asp Met Ile Ala Ala Leu Pro Glu Ala Thr His Glu Ala Ile
65                  70                  75                  80

Val Gly Val Gly Lys Gln Trp Ser Gly Ala Arg Ala Leu Glu Ala Leu
                85                  90                  95

Leu Thr Val Ala Gly Glu Leu Arg Gly Pro Pro Leu Gln Leu Asp Thr
            100                 105                 110

Gly Gln Leu Leu Lys Ile Ala Lys Arg Gly Gly Val Thr Ala Val Glu
        115                 120                 125

```
Ala Val His Ala Trp Arg Asn Ala Leu Thr Gly Ala Pro Leu Asn Leu
130                 135                 140

Thr Pro Asp Gln Val Val Ala Ile Ala Ser His Asp Gly Gly Lys Gln
145                 150                 155                 160

Ala Leu Glu Thr Val Gln Arg Leu Leu Pro Val Leu Cys Gln Asp His
            165                 170                 175

Gly Leu Thr Pro Glu Gln Val Val Ala Ile Ala Ser Asn Gly Gly Gly
                180                 185                 190

Lys Gln Ala Leu Glu Thr Val Gln Arg Leu Leu Pro Val Leu Cys Gln
        195                 200                 205

Ala His Gly Leu Thr Pro Asp Gln Val Val Ala Ile Ala Ser His Asp
210                 215                 220

Gly Gly Lys Gln Ala Leu Glu Thr Val Gln Arg Leu Leu Pro Val Leu
225                 230                 235                 240

Cys Gln Ala His Gly Leu Thr Pro Ala Gln Val Val Ala Ile Ala Ser
                245                 250                 255

His Asp Gly Gly Lys Gln Ala Leu Glu Thr Val Gln Arg Leu Leu Pro
            260                 265                 270

Val Leu Cys Gln Asp His Gly Leu Thr Pro Asp Gln Val Val Ala Ile
        275                 280                 285

Ala Ser Asn Gly Gly Gly Lys Gln Ala Leu Glu Thr Val Gln Arg Leu
290                 295                 300

Leu Pro Val Leu Cys Gln Asp His Gly Leu Thr Pro Glu Gln Val Val
305                 310                 315                 320

Ala Ile Ala Ser His Asp Gly Gly Lys Gln Ala Leu Glu Thr Val Gln
                325                 330                 335

Arg Leu Leu Pro Val Leu Cys Gln Ala His Gly Leu Thr Pro Asp Gln
            340                 345                 350

Val Val Ala Ile Ala Ser Asn Gly Gly Gly Lys Gln Ala Leu Glu Thr
        355                 360                 365

Val Gln Arg Leu Leu Pro Val Leu Cys Gln Ala His Gly Leu Thr Pro
370                 375                 380

Ala Gln Val Val Ala Ile Ala Ser Asn Ile Gly Gly Lys Gln Ala Leu
385                 390                 395                 400

Glu Thr Val Gln Arg Leu Leu Pro Val Leu Cys Gln Asp His Gly Leu
                405                 410                 415

Thr Pro Asp Gln Val Val Ala Ile Ala Ser Asn Asn Gly Gly Lys Gln
            420                 425                 430

Ala Leu Glu Thr Val Gln Arg Leu Leu Pro Val Leu Cys Gln Asp His
        435                 440                 445

Gly Leu Thr Pro Glu Gln Val Val Ala Ile Ala Ser Asn Asn Gly Gly
450                 455                 460

Lys Gln Ala Leu Glu Thr Val Gln Arg Leu Leu Pro Val Leu Cys Gln
465                 470                 475                 480

Ala His Gly Leu Thr Pro Asp Gln Val Val Ala Ile Ala Ser Asn Ile
                485                 490                 495

Gly Gly Lys Gln Ala Leu Glu Thr Val Gln Arg Leu Leu Pro Val Leu
            500                 505                 510

Cys Gln Ala His Gly Leu Thr Pro Ala Gln Val Val Ala Ile Ala Ser
        515                 520                 525

Asn Asn Gly Gly Lys Gln Ala Leu Glu Thr Val Gln Arg Leu Leu Pro
530                 535                 540
```

Val Leu Cys Gln Asp His Gly Leu Thr Pro Asp Gln Val Val Ala Ile
545                 550                 555                 560

Ala Ser His Asp Gly Gly Lys Gln Ala Leu Glu Thr Val Gln Arg Leu
            565                 570                 575

Leu Pro Val Leu Cys Gln Asp His Gly Leu Thr Pro Glu Gln Val Val
        580                 585                 590

Ala Ile Ala Ser His Asp Gly Gly Lys Gln Ala Leu Glu Thr Val Gln
    595                 600                 605

Arg Leu Leu Pro Val Leu Cys Gln Ala His Gly Leu Thr Pro Asp Gln
610                 615                 620

Val Val Ala Ile Ala Ser Asn Gly Gly Lys Gln Ala Leu Glu Thr
625                 630                 635                 640

Val Gln Arg Leu Leu Pro Val Leu Cys Gln Ala His Gly Leu Thr Pro
            645                 650                 655

Ala Gln Val Val Ala Ile Ala Ser His Asp Gly Gly Lys Gln Ala Leu
        660                 665                 670

Glu Thr Val Gln Arg Leu Leu Pro Val Leu Cys Gln Asp His Gly Leu
    675                 680                 685

Thr Pro Glu Gln Val Val Ala Ile Ala Ser His Asp Gly Gly Arg Pro
690                 695                 700

Ala Leu Glu Ser Ile Val Ala Gln Leu Ser Arg Pro Asp Pro Ala Leu
705                 710                 715                 720

Ala Ala Leu Thr Asn Asp His Leu Val Ala Leu Ala Cys Leu Gly Gly
            725                 730                 735

Arg Pro Ala Leu Asp Ala Val Lys Lys Gly Leu Pro His Ala Pro Ala
        740                 745                 750

Leu Ile Lys Arg Thr Asn Arg Arg Ile Pro Glu Arg Thr Ser His Arg
    755                 760                 765

Val Ala Asp His Ala Gln Val Val Arg Val Leu Gly Phe Phe Gln Cys
770                 775                 780

His Ser His Pro Ala Gln Ala Phe Asp Asp Ala Met Thr Gln Phe Gly
785                 790                 795                 800

Met Ser Arg His Gly Leu Leu Gln Leu Phe Arg Arg Val Gly Val Thr
            805                 810                 815

Glu Leu Glu Ala Arg Ser Gly Thr Leu Pro Pro Ala Ser Gln Arg Trp
        820                 825                 830

Asp Arg Ile Leu Gln Ala Ser Gly Met Lys Arg Ala Lys Pro Ser Pro
    835                 840                 845

Thr Ser Thr Gln Thr Pro Asp Gln Ala Ser Leu His Ala Phe Ala Asp
850                 855                 860

Ser Leu Glu Arg Asp Leu Asp Ala Pro Ser Pro Met His Glu Gly Asp
865                 870                 875                 880

Gln Thr Arg Ala Ser Ala Ser
            885

<210> SEQ ID NO 9
<211> LENGTH: 2928
<212> TYPE: DNA
<213> ORGANISM: Artificial Sequence
<220> FEATURE:
<223> OTHER INFORMATION: NTP-TALE-TERT-1-VP64
<220> FEATURE:
<221> NAME/KEY: CDS
<222> LOCATION: (1)..(2928)

<400> SEQUENCE: 9

```
agg atc ttc atc cac ttc cgg atc ggc tgc gaa aac ctg tat ttc caa      48
Arg Ile Phe Ile His Phe Arg Ile Gly Cys Glu Asn Leu Tyr Phe Gln
1               5                   10                  15 tct ctc gag cgc gat cgc acc atg atc cac gga gtc cca gca gcc gta      96
Ser Leu Glu Arg Asp Arg Thr Met Ile His Gly Val Pro Ala Ala Val
                20                  25                  30 gat ttg aga act ttg gga tat tca cag cag cag cag gaa aag atc aag     144
Asp Leu Arg Thr Leu Gly Tyr Ser Gln Gln Gln Gln Glu Lys Ile Lys
            35                  40                  45 ccc aaa gtg agg tcg aca gtc gcg cag cat cac gaa gcg ctg gtg ggt     192
Pro Lys Val Arg Ser Thr Val Ala Gln His His Glu Ala Leu Val Gly
        50                  55                  60 cat ggg ttt aca cat gcc cac atc gta gcc ttg tcg cag cac cct gca     240
His Gly Phe Thr His Ala His Ile Val Ala Leu Ser Gln His Pro Ala
65                  70                  75                  80 gcc ctt ggc acg gtc gcc gtc aag tac cag gac atg att gcg gcg ttg     288
Ala Leu Gly Thr Val Ala Val Lys Tyr Gln Asp Met Ile Ala Ala Leu
                85                  90                  95 ccg gaa gcc aca cat gag gcg atc gtc ggt gtg ggg aaa cag tgg agc     336
Pro Glu Ala Thr His Glu Ala Ile Val Gly Val Gly Lys Gln Trp Ser
                100                 105                 110 gga gcc cga gcg ctt gag gcc ctg ttg acg gtc gcg gga gag ctg aga     384
Gly Ala Arg Ala Leu Glu Ala Leu Leu Thr Val Ala Gly Glu Leu Arg
            115                 120                 125 ggg cct ccc ctt cag ctg gac acg ggc cag ttg ctg aag atc gcg aag     432
Gly Pro Pro Leu Gln Leu Asp Thr Gly Gln Leu Leu Lys Ile Ala Lys
        130                 135                 140 cgg gga gga gtc acg gcg gtc gag gcg gta cac gcg tgg cgc aat gcg     480
Arg Gly Gly Val Thr Ala Val Glu Ala Val His Ala Trp Arg Asn Ala
145                 150                 155                 160 ctc acg gga gca ccc ctc aac ctg acc ccg gac cag gtg gtt gca atc     528
Leu Thr Gly Ala Pro Leu Asn Leu Thr Pro Asp Gln Val Val Ala Ile
                165                 170                 175 gcg tca cac gat ggg gga aag cag gcc cta gaa acc gtt cag cga ctc     576
Ala Ser His Asp Gly Gly Lys Gln Ala Leu Glu Thr Val Gln Arg Leu
                180                 185                 190 ctg ccc gtc ctg tgc cag gac cac ggc ctg acc cca gaa cag gtt gtg     624
Leu Pro Val Leu Cys Gln Asp His Gly Leu Thr Pro Glu Gln Val Val
            195                 200                 205 gcc atc gcc agc aac ata ggt ggc aag cag gcc ctc gaa acc gtc cag     672
Ala Ile Ala Ser Asn Ile Gly Gly Lys Gln Ala Leu Glu Thr Val Gln
        210                 215                 220 aga ctg tta ccg gtt ctc tgc cag gcc cac ggc ctg acc cca gac caa     720
Arg Leu Leu Pro Val Leu Cys Gln Ala His Gly Leu Thr Pro Asp Gln
225                 230                 235                 240 gtt gtc gcg att gca agc aac aac gga ggc aaa caa gcc tta gaa aca     768
Val Val Ala Ile Ala Ser Asn Asn Gly Gly Lys Gln Ala Leu Glu Thr
                245                 250                 255 gtc cag aga ttg ttg cct gtg ctg tgc caa gcc cac ggc ctg acc cca     816
Val Gln Arg Leu Leu Pro Val Leu Cys Gln Ala His Gly Leu Thr Pro
                260                 265                 270 gcc cag gtt gtg gcc atc gcc agc aac ata ggt ggc aag cag gcc ctc     864
Ala Gln Val Val Ala Ile Ala Ser Asn Ile Gly Gly Lys Gln Ala Leu
            275                 280                 285 gaa acc gtc cag aga ctg tta ccg gtt ctc tgc cag gac cac ggc ctg     912
Glu Thr Val Gln Arg Leu Leu Pro Val Leu Cys Gln Asp His Gly Leu
        290                 295                 300 acc cca gac caa gtt gtc gcg att gca agc aac aac gga ggc aaa caa     960
Thr Pro Asp Gln Val Val Ala Ile Ala Ser Asn Asn Gly Gly Lys Gln
305                 310                 315                 320
```

```
gcc tta gaa aca gtc cag aga ttg ttg ccg gtg ctg tgc caa gac cac        1008
Ala Leu Glu Thr Val Gln Arg Leu Leu Pro Val Leu Cys Gln Asp His
            325                 330                 335 ggc ctg acc cca gaa caa gtt gtc gcg att gca agc aac aac gga ggc        1056
Gly Leu Thr Pro Glu Gln Val Val Ala Ile Ala Ser Asn Asn Gly Gly
340                 345                 350 aaa caa gcc tta gaa aca gtc cag aga ttg ttg ccg gtg ctg tgc caa        1104
Lys Gln Ala Leu Glu Thr Val Gln Arg Leu Leu Pro Val Leu Cys Gln
        355                 360                 365 gcc cac ggc ctg acc cca gac caa gtt gtc gcg att gca agc aac aac        1152
Ala His Gly Leu Thr Pro Asp Gln Val Val Ala Ile Ala Ser Asn Asn
    370                 375                 380 gga ggc aaa caa gcc tta gaa aca gtc cag aga ttg ttg cct gtg ctg        1200
Gly Gly Lys Gln Ala Leu Glu Thr Val Gln Arg Leu Leu Pro Val Leu
385                 390                 395                 400 tgc caa gcc cac ggc ctg acc cca gcc cag gtt gtg gcc atc gcc agc        1248
Cys Gln Ala His Gly Leu Thr Pro Ala Gln Val Val Ala Ile Ala Ser
            405                 410                 415 aac ata ggt ggc aag cag gcc ctc gaa acc gtc cag aga ctg tta ccg        1296
Asn Ile Gly Gly Lys Gln Ala Leu Glu Thr Val Gln Arg Leu Leu Pro
        420                 425                 430 gtt ctc tgc cag gac cac ggc ctg acc ccg gac cag gtg gtt gca atc        1344
Val Leu Cys Gln Asp His Gly Leu Thr Pro Asp Gln Val Val Ala Ile
    435                 440                 445 gcg tca cac gat ggg gga aag cag gcc cta gaa acc gtc cag cga ctc        1392
Ala Ser His Asp Gly Gly Lys Gln Ala Leu Glu Thr Val Gln Arg Leu
450                 455                 460 ctg ccc gtc ctg tgc cag gac cac ggc ctg acc cca gaa caa gtt gtc        1440
Leu Pro Val Leu Cys Gln Asp His Gly Leu Thr Pro Glu Gln Val Val
465                 470                 475                 480 gcg att gca agc aac aac gga ggc aaa caa gcc tta gaa aca gtc cag        1488
Ala Ile Ala Ser Asn Asn Gly Gly Lys Gln Ala Leu Glu Thr Val Gln
            485                 490                 495 aga ttg ttg ccg gtg ctg tgc caa gcc cac ggc ctg acc ccg gac cag        1536
Arg Leu Leu Pro Val Leu Cys Gln Ala His Gly Leu Thr Pro Asp Gln
        500                 505                 510 gtg gtt gca atc gcg tca cac gat ggg gga aag cag gcc cta gaa acc        1584
Val Val Ala Ile Ala Ser His Asp Gly Gly Lys Gln Ala Leu Glu Thr
    515                 520                 525 gtt cag cga ctc ctg ccc gtc ctg tgc cag gcc cac ggc ctg acc cca        1632
Val Gln Arg Leu Leu Pro Val Leu Cys Gln Ala His Gly Leu Thr Pro
530                 535                 540 gcc cag gtt gtg gcc atc gcc agc aac ata ggt ggc aag cag gcc ctc        1680
Ala Gln Val Val Ala Ile Ala Ser Asn Ile Gly Gly Lys Gln Ala Leu
545                 550                 555                 560 gaa acc gtc cag aga ctg tta ccg gtt ctc tgc cag gac cac ggc ctg        1728
Glu Thr Val Gln Arg Leu Leu Pro Val Leu Cys Gln Asp His Gly Leu
            565                 570                 575 acc cca gac caa gtt gtc gcg att gca agc aac aac gga ggc aaa caa        1776
Thr Pro Asp Gln Val Val Ala Ile Ala Ser Asn Asn Gly Gly Lys Gln
        580                 585                 590 gcc tta gaa aca gtc cag aga ttg ttg ccg gtg ctg tgc caa gac cac        1824
Ala Leu Glu Thr Val Gln Arg Leu Leu Pro Val Leu Cys Gln Asp His
    595                 600                 605 ggc ctg acc ccc gaa cag gtt gtc gct att gct agt aac ggc gga ggc        1872
Gly Leu Thr Pro Glu Gln Val Val Ala Ile Ala Ser Asn Gly Gly Gly
610                 615                 620 aaa cag gcg ctg gaa aca gtt cag cgc ctc ttg ccg gtc ttg tgt cag        1920
Lys Gln Ala Leu Glu Thr Val Gln Arg Leu Leu Pro Val Leu Cys Gln
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 625 |     |     |     | 630 |     |     |     | 635 |     |     |     | 640 |     |     |      |
| gcc | cac | ggc | ctg | acc | ccg | gac | cag | gtg | gtt | gca | atc | gcg | tca | cac | gat | 1968 |
| Ala | His | Gly | Leu | Thr | Pro | Asp | Gln | Val | Val | Ala | Ile | Ala | Ser | His | Asp |      |
|     |     |     | 645 |     |     |     | 650 |     |     |     | 655 |     |     |     |     |      |
| ggg | gga | aag | cag | gcc | cta | gaa | acc | gtt | cag | cga | ctc | ctg | ccc | gtc | ctg | 2016 |
| Gly | Gly | Lys | Gln | Ala | Leu | Glu | Thr | Val | Gln | Arg | Leu | Leu | Pro | Val | Leu |      |
|     |     |     | 660 |     |     |     | 665 |     |     |     | 670 |     |     |     |     |      |
| tgc | cag | gcc | cac | ggc | ctg | acc | ccc | gcc | cag | gtt | gtc | gct | att | gct | agt | 2064 |
| Cys | Gln | Ala | His | Gly | Leu | Thr | Pro | Ala | Gln | Val | Val | Ala | Ile | Ala | Ser |      |
|     |     |     | 675 |     |     |     | 680 |     |     |     | 685 |     |     |     |     |      |
| aac | ggc | gga | ggc | aaa | cag | gcg | ctg | gaa | aca | gtt | cag | cgc | ctc | ttg | ccg | 2112 |
| Asn | Gly | Gly | Gly | Lys | Gln | Ala | Leu | Glu | Thr | Val | Gln | Arg | Leu | Leu | Pro |      |
|     |     |     | 690 |     |     |     | 695 |     |     |     | 700 |     |     |     |     |      |
| gtc | ttg | tgt | cag | gac | cac | ggc | ctg | acc | cct | gag | cag | gta | gtg | gct | att | 2160 |
| Val | Leu | Cys | Gln | Asp | His | Gly | Leu | Thr | Pro | Glu | Gln | Val | Val | Ala | Ile |      |
| 705 |     |     |     |     | 710 |     |     |     | 715 |     |     |     | 720 |     |     |      |
| gca | tcc | cac | gac | ggg | ggc | aga | ccc | gca | ctg | gag | tca | atc | gtg | gcc | cag | 2208 |
| Ala | Ser | His | Asp | Gly | Gly | Arg | Pro | Ala | Leu | Glu | Ser | Ile | Val | Ala | Gln |      |
|     |     |     |     | 725 |     |     |     | 730 |     |     |     | 735 |     |     |     |      |
| ctc | tcg | agg | ccg | gac | ccc | gcg | ctg | gcc | gca | ctc | act | aat | gat | cat | ctt | 2256 |
| Leu | Ser | Arg | Pro | Asp | Pro | Ala | Leu | Ala | Ala | Leu | Thr | Asn | Asp | His | Leu |      |
|     |     |     | 740 |     |     |     | 745 |     |     |     | 750 |     |     |     |     |      |
| gta | gcg | ctg | gcc | tgc | ctc | ggc | gga | cga | ccc | gcc | ttg | gat | gcg | gtg | aag | 2304 |
| Val | Ala | Leu | Ala | Cys | Leu | Gly | Gly | Arg | Pro | Ala | Leu | Asp | Ala | Val | Lys |      |
|     |     |     | 755 |     |     |     | 760 |     |     |     | 765 |     |     |     |     |      |
| aag | ggg | ctc | ccg | cac | gcg | cct | gca | ttg | att | aag | cgg | acc | aac | aga | agg | 2352 |
| Lys | Gly | Leu | Pro | His | Ala | Pro | Ala | Leu | Ile | Lys | Arg | Thr | Asn | Arg | Arg |      |
|     |     |     | 770 |     |     |     | 775 |     |     |     | 780 |     |     |     |     |      |
| atc | ccc | gag | agg | aca | tca | cat | cga | gtg | gca | gat | cac | gcg | caa | gtg | gtc | 2400 |
| Ile | Pro | Glu | Arg | Thr | Ser | His | Arg | Val | Ala | Asp | His | Ala | Gln | Val | Val |      |
| 785 |     |     |     |     | 790 |     |     |     | 795 |     |     |     | 800 |     |     |      |
| cgc | gtg | ctc | gga | ttc | ttc | cag | tgt | cac | tcc | cac | ccc | gca | caa | gcg | ttc | 2448 |
| Arg | Val | Leu | Gly | Phe | Phe | Gln | Cys | His | Ser | His | Pro | Ala | Gln | Ala | Phe |      |
|     |     |     |     | 805 |     |     |     | 810 |     |     |     | 815 |     |     |     |      |
| gat | gac | gcc | atg | act | caa | ttt | ggt | atg | tcg | aga | cac | gga | ctg | ctg | cag | 2496 |
| Asp | Asp | Ala | Met | Thr | Gln | Phe | Gly | Met | Ser | Arg | His | Gly | Leu | Leu | Gln |      |
|     |     |     | 820 |     |     |     | 825 |     |     |     | 830 |     |     |     |     |      |
| ctc | ttt | cgt | aga | gtc | ggt | gtc | aca | gaa | ctg | gag | gcc | cgc | tcg | ggc | aca | 2544 |
| Leu | Phe | Arg | Arg | Val | Gly | Val | Thr | Glu | Leu | Glu | Ala | Arg | Ser | Gly | Thr |      |
|     |     |     | 835 |     |     |     | 840 |     |     |     | 845 |     |     |     |     |      |
| ctg | cct | ccc | gcc | tcc | cag | cgg | tgg | gac | agg | att | ctc | caa | gcg | agc | ggt | 2592 |
| Leu | Pro | Pro | Ala | Ser | Gln | Arg | Trp | Asp | Arg | Ile | Leu | Gln | Ala | Ser | Gly |      |
|     | 850 |     |     |     |     | 855 |     |     |     | 860 |     |     |     |     |     |      |
| atg | aaa | cgc | gcg | aag | cct | tca | cct | acg | tca | act | cag | aca | cct | gac | cag | 2640 |
| Met | Lys | Arg | Ala | Lys | Pro | Ser | Pro | Thr | Ser | Thr | Gln | Thr | Pro | Asp | Gln |      |
| 865 |     |     |     |     | 870 |     |     |     | 875 |     |     |     | 880 |     |     |      |
| gcg | agc | ctt | cat | gcg | ttc | gca | gac | tcg | ctg | gag | agg | gat | ttg | gac | gcg | 2688 |
| Ala | Ser | Leu | His | Ala | Phe | Ala | Asp | Ser | Leu | Glu | Arg | Asp | Leu | Asp | Ala |      |
|     |     |     |     | 885 |     |     |     | 890 |     |     |     | 895 |     |     |     |      |
| ccc | tcg | ccc | atg | cat | gaa | ggg | gac | caa | act | cgc | gcg | tca | gcc | agc | ccc | 2736 |
| Pro | Ser | Pro | Met | His | Glu | Gly | Asp | Gln | Thr | Arg | Ala | Ser | Ala | Ser | Pro |      |
|     |     |     | 900 |     |     |     | 905 |     |     |     | 910 |     |     |     |     |      |
| aag | aag | aag | aga | aag | gtg | gag | gcc | agc | ggt | tcc | gga | cgg | gct | gac | gca | 2784 |
| Lys | Lys | Lys | Arg | Lys | Val | Glu | Ala | Ser | Gly | Ser | Gly | Arg | Ala | Asp | Ala |      |
|     |     |     | 915 |     |     |     | 920 |     |     |     | 925 |     |     |     |     |      |
| ttg | gac | gat | ttt | gat | ctg | gat | atg | ctg | gga | agt | gac | gcc | ctc | gat | gat | 2832 |
| Leu | Asp | Asp | Phe | Asp | Leu | Asp | Met | Leu | Gly | Ser | Asp | Ala | Leu | Asp | Asp |      |
|     |     |     | 930 |     |     |     | 935 |     |     |     | 940 |     |     |     |     |      |
| ttt | gac | ctt | gac | atg | ctt | ggt | tcg | gat | gcc | ctt | gat | gac | ttt | gac | ctc | 2880 |

```
Phe Asp Leu Asp Met Leu Gly Ser Asp Ala Leu Asp Phe Asp Leu
945                 950                 955                 960 gac atg ctc ggc agt gac gcc ctt gat gat ttc gac ctg gac atg ctg    2928
Asp Met Leu Gly Ser Asp Ala Leu Asp Asp Phe Asp Leu Asp Met Leu
                965                 970                 975
```

<210> SEQ ID NO 10
<211> LENGTH: 976
<212> TYPE: PRT
<213> ORGANISM: Artificial Sequence
<220> FEATURE:
<223> OTHER INFORMATION: Synthetic Construct

<400> SEQUENCE: 10

```
Arg Ile Phe Ile His Phe Arg Ile Gly Cys Glu Asn Leu Tyr Phe Gln
1               5                   10                  15

Ser Leu Glu Arg Asp Arg Thr Met Ile His Gly Val Pro Ala Ala Val
            20                  25                  30

Asp Leu Arg Thr Leu Gly Tyr Ser Gln Gln Gln Gln Glu Lys Ile Lys
        35                  40                  45

Pro Lys Val Arg Ser Thr Val Ala Gln His His Glu Ala Leu Val Gly
    50                  55                  60

His Gly Phe Thr His Ala His Ile Val Ala Leu Ser Gln His Pro Ala
65                  70                  75                  80

Ala Leu Gly Thr Val Ala Val Lys Tyr Gln Asp Met Ile Ala Ala Leu
                85                  90                  95

Pro Glu Ala Thr His Glu Ala Ile Val Gly Val Gly Lys Gln Trp Ser
            100                 105                 110

Gly Ala Arg Ala Leu Glu Ala Leu Leu Thr Val Ala Gly Glu Leu Arg
        115                 120                 125

Gly Pro Pro Leu Gln Leu Asp Thr Gly Gln Leu Leu Lys Ile Ala Lys
    130                 135                 140

Arg Gly Gly Val Thr Ala Val Glu Ala Val His Ala Trp Arg Asn Ala
145                 150                 155                 160

Leu Thr Gly Ala Pro Leu Asn Leu Thr Pro Asp Gln Val Val Ala Ile
                165                 170                 175

Ala Ser His Asp Gly Gly Lys Gln Ala Leu Glu Thr Val Gln Arg Leu
            180                 185                 190

Leu Pro Val Leu Cys Gln Asp His Gly Leu Thr Pro Glu Gln Val Val
        195                 200                 205

Ala Ile Ala Ser Asn Ile Gly Gly Lys Gln Ala Leu Glu Thr Val Gln
    210                 215                 220

Arg Leu Leu Pro Val Leu Cys Gln Ala His Gly Leu Thr Pro Asp Gln
225                 230                 235                 240

Val Val Ala Ile Ala Ser Asn Asn Gly Gly Lys Gln Ala Leu Glu Thr
                245                 250                 255

Val Gln Arg Leu Leu Pro Val Leu Cys Gln Ala His Gly Leu Thr Pro
            260                 265                 270

Ala Gln Val Val Ala Ile Ala Ser Asn Ile Gly Gly Lys Gln Ala Leu
        275                 280                 285

Glu Thr Val Gln Arg Leu Leu Pro Val Leu Cys Gln Asp His Gly Leu
    290                 295                 300

Thr Pro Asp Gln Val Val Ala Ile Ala Ser Asn Asn Gly Gly Lys Gln
305                 310                 315                 320

Ala Leu Glu Thr Val Gln Arg Leu Leu Pro Val Leu Cys Gln Asp His
                325                 330                 335
```

```
Gly Leu Thr Pro Glu Gln Val Ala Ile Ala Ser Asn Asn Gly Gly
            340                 345                 350

Lys Gln Ala Leu Glu Thr Val Gln Arg Leu Leu Pro Val Leu Cys Gln
            355                 360                 365

Ala His Gly Leu Thr Pro Asp Gln Val Val Ala Ile Ala Ser Asn Asn
            370                 375                 380

Gly Gly Lys Gln Ala Leu Glu Thr Val Gln Arg Leu Leu Pro Val Leu
385                 390                 395                 400

Cys Gln Ala His Gly Leu Thr Pro Ala Gln Val Val Ala Ile Ala Ser
                    405                 410                 415

Asn Ile Gly Gly Lys Gln Ala Leu Glu Thr Val Gln Arg Leu Leu Pro
            420                 425                 430

Val Leu Cys Gln Asp His Gly Leu Thr Pro Asp Gln Val Val Ala Ile
            435                 440                 445

Ala Ser His Asp Gly Gly Lys Gln Ala Leu Glu Thr Val Gln Arg Leu
            450                 455                 460

Leu Pro Val Leu Cys Gln Asp His Gly Leu Thr Pro Glu Gln Val Val
465                 470                 475                 480

Ala Ile Ala Ser Asn Asn Gly Gly Lys Gln Ala Leu Glu Thr Val Gln
                    485                 490                 495

Arg Leu Leu Pro Val Leu Cys Gln Ala His Gly Leu Thr Pro Asp Gln
                    500                 505                 510

Val Val Ala Ile Ala Ser His Asp Gly Gly Lys Gln Ala Leu Glu Thr
            515                 520                 525

Val Gln Arg Leu Leu Pro Val Leu Cys Gln Ala His Gly Leu Thr Pro
            530                 535                 540

Ala Gln Val Val Ala Ile Ala Ser Asn Ile Gly Gly Lys Gln Ala Leu
545                 550                 555                 560

Glu Thr Val Gln Arg Leu Leu Pro Val Leu Cys Gln Asp His Gly Leu
                    565                 570                 575

Thr Pro Asp Gln Val Val Ala Ile Ala Ser Asn Asn Gly Gly Lys Gln
            580                 585                 590

Ala Leu Glu Thr Val Gln Arg Leu Leu Pro Val Leu Cys Gln Asp His
            595                 600                 605

Gly Leu Thr Pro Glu Gln Val Val Ala Ile Ala Ser Asn Gly Gly Gly
            610                 615                 620

Lys Gln Ala Leu Glu Thr Val Gln Arg Leu Leu Pro Val Leu Cys Gln
625                 630                 635                 640

Ala His Gly Leu Thr Pro Asp Gln Val Val Ala Ile Ala Ser His Asp
                    645                 650                 655

Gly Gly Lys Gln Ala Leu Glu Thr Val Gln Arg Leu Leu Pro Val Leu
                    660                 665                 670

Cys Gln Ala His Gly Leu Thr Pro Ala Gln Val Val Ala Ile Ala Ser
            675                 680                 685

Asn Gly Gly Gly Lys Gln Ala Leu Glu Thr Val Gln Arg Leu Leu Pro
            690                 695                 700

Val Leu Cys Gln Asp His Gly Leu Thr Pro Glu Gln Val Val Ala Ile
705                 710                 715                 720

Ala Ser His Asp Gly Gly Arg Pro Ala Leu Glu Ser Ile Val Ala Gln
                    725                 730                 735

Leu Ser Arg Pro Asp Pro Ala Leu Ala Ala Leu Thr Asn Asp His Leu
            740                 745                 750
```

```
Val Ala Leu Ala Cys Leu Gly Arg Pro Ala Leu Asp Ala Val Lys
            755                 760                 765

Lys Gly Leu Pro His Ala Pro Ala Leu Ile Lys Arg Thr Asn Arg Arg
770                 775                 780

Ile Pro Glu Arg Thr Ser His Arg Val Ala Asp His Ala Gln Val Val
785                 790                 795                 800

Arg Val Leu Gly Phe Phe Gln Cys His Ser His Pro Ala Gln Ala Phe
                805                 810                 815

Asp Asp Ala Met Thr Gln Phe Gly Met Ser Arg His Gly Leu Leu Gln
            820                 825                 830

Leu Phe Arg Arg Val Gly Val Thr Glu Leu Glu Ala Arg Ser Gly Thr
        835                 840                 845

Leu Pro Pro Ala Ser Gln Arg Trp Asp Arg Ile Leu Gln Ala Ser Gly
    850                 855                 860

Met Lys Arg Ala Lys Pro Ser Pro Thr Ser Thr Gln Thr Pro Asp Gln
865                 870                 875                 880

Ala Ser Leu His Ala Phe Ala Asp Ser Leu Glu Arg Asp Leu Asp Ala
                885                 890                 895

Pro Ser Pro Met His Glu Gly Asp Gln Thr Arg Ala Ser Ala Ser Pro
            900                 905                 910

Lys Lys Lys Arg Lys Val Glu Ala Ser Gly Ser Gly Arg Ala Asp Ala
        915                 920                 925

Leu Asp Asp Phe Asp Leu Asp Met Leu Gly Ser Asp Ala Leu Asp Asp
    930                 935                 940

Phe Asp Leu Asp Met Leu Gly Ser Asp Ala Leu Asp Asp Phe Asp Leu
945                 950                 955                 960

Asp Met Leu Gly Ser Asp Ala Leu Asp Asp Phe Asp Leu Asp Met Leu
                965                 970                 975

<210> SEQ ID NO 11
<211> LENGTH: 4293
<212> TYPE: DNA
<213> ORGANISM: Artificial Sequence
<220> FEATURE:
<223> OTHER INFORMATION: NTP-TALE-TERT-1-VPR
<220> FEATURE:
<221> NAME/KEY: CDS
<222> LOCATION: (1)..(4293)

<400> SEQUENCE: 11 agg atc ttc atc cac ttc cgg atc ggc tgc gaa aac ctg tat ttc caa    48
Arg Ile Phe Ile His Phe Arg Ile Gly Cys Glu Asn Leu Tyr Phe Gln
1               5                   10                  15 tct ctc gag cgc gat cgc acc atg atc cac gga gtc cca gca gcc gta    96
Ser Leu Glu Arg Asp Arg Thr Met Ile His Gly Val Pro Ala Ala Val
            20                  25                  30 gat ttg aga act ttg gga tat tca cag cag cag cag gaa aag atc aag   144
Asp Leu Arg Thr Leu Gly Tyr Ser Gln Gln Gln Gln Glu Lys Ile Lys
        35                  40                  45 ccc aaa gtg agg tcg aca gtc gcg cag cat cac gaa gcg ctg gtg ggt   192
Pro Lys Val Arg Ser Thr Val Ala Gln His His Glu Ala Leu Val Gly
    50                  55                  60 cat ggg ttt aca cat gcc cac atc gta gcc ttg tcg cag cac cct gca   240
His Gly Phe Thr His Ala His Ile Val Ala Leu Ser Gln His Pro Ala
65                  70                  75                  80 gcc ctt ggc acg gtc gcc gtc aag tac cag gac atg att gcg gcg ttg   288
Ala Leu Gly Thr Val Ala Val Lys Tyr Gln Asp Met Ile Ala Ala Leu
                85                  90                  95
```

| | | | | | | | | | | | | | | | | |
|---|---|---|---|---|---|---|---|---|---|---|---|---|---|---|---|---|
| ccg | gaa | gcc | aca | cat | gag | gcg | atc | gtc | ggt | gtg | ggg | aaa | cag | tgg | agc | 336 |
| Pro | Glu | Ala | Thr | His | Glu | Ala | Ile | Val | Gly | Val | Gly | Lys | Gln | Trp | Ser | |
| | | | 100 | | | | 105 | | | | 110 | | | | | |
| gga | gcc | cga | gcg | ctt | gag | gcc | ctg | ttg | acg | gtc | gcg | gga | gag | ctg | aga | 384 |
| Gly | Ala | Arg | Ala | Leu | Glu | Ala | Leu | Leu | Thr | Val | Ala | Gly | Glu | Leu | Arg | |
| | | 115 | | | | | 120 | | | | | 125 | | | | |
| ggg | cct | ccc | ctt | cag | ctg | gac | acg | ggc | cag | ttg | ctg | aag | atc | gcg | aag | 432 |
| Gly | Pro | Pro | Leu | Gln | Leu | Asp | Thr | Gly | Gln | Leu | Leu | Lys | Ile | Ala | Lys | |
| | 130 | | | | | 135 | | | | | 140 | | | | | |
| cgg | gga | gga | gtc | acg | gcg | gtc | gag | gcg | gta | cac | gcg | tgg | cgc | aat | gcg | 480 |
| Arg | Gly | Gly | Val | Thr | Ala | Val | Glu | Ala | Val | His | Ala | Trp | Arg | Asn | Ala | |
| 145 | | | | 150 | | | | | 155 | | | | | 160 | | |
| ctc | acg | gga | gca | ccc | ctc | aac | ctg | acc | ccg | gac | cag | gtg | gtt | gca | atc | 528 |
| Leu | Thr | Gly | Ala | Pro | Leu | Asn | Leu | Thr | Pro | Asp | Gln | Val | Val | Ala | Ile | |
| | | | | 165 | | | | | 170 | | | | | 175 | | |
| gcg | tca | cac | gat | ggg | gga | aag | cag | gcc | cta | gaa | acc | gtt | cag | cga | ctc | 576 |
| Ala | Ser | His | Asp | Gly | Gly | Lys | Gln | Ala | Leu | Glu | Thr | Val | Gln | Arg | Leu | |
| | | | 180 | | | | | 185 | | | | | 190 | | | |
| ctg | ccc | gtc | ctg | tgc | cag | gac | cac | ggc | ctg | acc | cca | gaa | cag | gtt | gtg | 624 |
| Leu | Pro | Val | Leu | Cys | Gln | Asp | His | Gly | Leu | Thr | Pro | Glu | Gln | Val | Val | |
| | | | 195 | | | | | 200 | | | | | 205 | | | |
| gcc | atc | gcc | agc | aac | ata | ggt | ggc | aag | cag | gcc | ctc | gaa | acc | gtc | cag | 672 |
| Ala | Ile | Ala | Ser | Asn | Ile | Gly | Gly | Lys | Gln | Ala | Leu | Glu | Thr | Val | Gln | |
| | 210 | | | | | 215 | | | | | 220 | | | | | |
| aga | ctg | tta | ccg | gtt | ctc | tgc | cag | gcc | cac | ggc | ctg | acc | cca | gac | caa | 720 |
| Arg | Leu | Leu | Pro | Val | Leu | Cys | Gln | Ala | His | Gly | Leu | Thr | Pro | Asp | Gln | |
| 225 | | | | | 230 | | | | | 235 | | | | | 240 | |
| gtt | gtc | gcg | att | gca | agc | aac | aac | gga | ggc | aaa | caa | gcc | tta | gaa | aca | 768 |
| Val | Val | Ala | Ile | Ala | Ser | Asn | Asn | Gly | Gly | Lys | Gln | Ala | Leu | Glu | Thr | |
| | | | | 245 | | | | | 250 | | | | | 255 | | |
| gtc | cag | aga | ttg | ttg | cct | gtg | ctg | tgc | caa | gcc | cac | ggc | ctg | acc | cca | 816 |
| Val | Gln | Arg | Leu | Leu | Pro | Val | Leu | Cys | Gln | Ala | His | Gly | Leu | Thr | Pro | |
| | | 260 | | | | | 265 | | | | | 270 | | | | |
| gcc | cag | gtt | gtg | gcc | atc | gcc | agc | aac | ata | ggt | ggc | aag | cag | gcc | ctc | 864 |
| Ala | Gln | Val | Val | Ala | Ile | Ala | Ser | Asn | Ile | Gly | Gly | Lys | Gln | Ala | Leu | |
| | 275 | | | | | 280 | | | | | 285 | | | | | |
| gaa | acc | gtc | cag | aga | ctg | tta | ccg | gtt | ctc | tgc | cag | gac | cac | ggc | ctg | 912 |
| Glu | Thr | Val | Gln | Arg | Leu | Leu | Pro | Val | Leu | Cys | Gln | Asp | His | Gly | Leu | |
| 290 | | | | | 295 | | | | | 300 | | | | | | |
| acc | cca | gac | caa | gtt | gtc | gcg | att | gca | agc | aac | aac | gga | ggc | aaa | caa | 960 |
| Thr | Pro | Asp | Gln | Val | Val | Ala | Ile | Ala | Ser | Asn | Asn | Gly | Gly | Lys | Gln | |
| 305 | | | | 310 | | | | | 315 | | | | | 320 | | |
| gcc | tta | gaa | aca | gtc | cag | aga | ttg | ttg | ccg | gtg | ctg | tgc | caa | gac | cac | 1008 |
| Ala | Leu | Glu | Thr | Val | Gln | Arg | Leu | Leu | Pro | Val | Leu | Cys | Gln | Asp | His | |
| | | | 325 | | | | | 330 | | | | | 335 | | | |
| ggc | ctg | acc | cca | gaa | caa | gtt | gtc | gcg | att | gca | agc | aac | aac | gga | ggc | 1056 |
| Gly | Leu | Thr | Pro | Glu | Gln | Val | Val | Ala | Ile | Ala | Ser | Asn | Asn | Gly | Gly | |
| | | | 340 | | | | | 345 | | | | | 350 | | | |
| aaa | caa | gcc | tta | gaa | aca | gtc | cag | aga | ttg | ttg | ccg | gtg | ctg | tgc | caa | 1104 |
| Lys | Gln | Ala | Leu | Glu | Thr | Val | Gln | Arg | Leu | Leu | Pro | Val | Leu | Cys | Gln | |
| | | 355 | | | | | 360 | | | | | 365 | | | | |
| gcc | cac | ggc | ctg | acc | cca | gac | caa | gtt | gtc | gcg | att | gca | agc | aac | aac | 1152 |
| Ala | His | Gly | Leu | Thr | Pro | Asp | Gln | Val | Val | Ala | Ile | Ala | Ser | Asn | Asn | |
| | 370 | | | | | 375 | | | | | 380 | | | | | |
| gga | ggc | aaa | caa | gcc | tta | gaa | aca | gtc | cag | aga | ttg | ttg | cct | gtg | ctg | 1200 |
| Gly | Gly | Lys | Gln | Ala | Leu | Glu | Thr | Val | Gln | Arg | Leu | Leu | Pro | Val | Leu | |
| 385 | | | | | 390 | | | | | 395 | | | | | 400 | |
| tgc | caa | gcc | cac | ggc | ctg | acc | cca | gcc | cag | gtt | gtg | gcc | atc | gcc | agc | 1248 |
| Cys | Gln | Ala | His | Gly | Leu | Thr | Pro | Ala | Gln | Val | Val | Ala | Ile | Ala | Ser | |
| | | | | 405 | | | | | 410 | | | | | 415 | | |

-continued

```
aac ata ggt ggc aag cag gcc ctc gaa acc gtc cag aga ctg tta ccg      1296
Asn Ile Gly Gly Lys Gln Ala Leu Glu Thr Val Gln Arg Leu Leu Pro
        420                 425                 430 gtt ctc tgc cag gac cac ggc ctg acc ccg gac cag gtg gtt gca atc      1344
Val Leu Cys Gln Asp His Gly Leu Thr Pro Asp Gln Val Val Ala Ile
    435                 440                 445 gcg tca cac gat ggg gga aag cag gcc cta gaa acc gtt cag cga ctc      1392
Ala Ser His Asp Gly Gly Lys Gln Ala Leu Glu Thr Val Gln Arg Leu
450                 455                 460 ctg ccc gtc ctg tgc cag gac cac ggc ctg acc cca gaa caa gtt gtc      1440
Leu Pro Val Leu Cys Gln Asp His Gly Leu Thr Pro Glu Gln Val Val
465                 470                 475                 480 gcg att gca agc aac aac gga ggc aaa caa gcc tta gaa aca gtc cag      1488
Ala Ile Ala Ser Asn Asn Gly Gly Lys Gln Ala Leu Glu Thr Val Gln
                485                 490                 495 aga ttg ttg ccg gtg ctg tgc caa gcc cac ggc ctg acc ccg gac cag      1536
Arg Leu Leu Pro Val Leu Cys Gln Ala His Gly Leu Thr Pro Asp Gln
                500                 505                 510 gtg gtt gca atc gcg tca cac gat ggg gga aag cag gcc cta gaa acc      1584
Val Val Ala Ile Ala Ser His Asp Gly Gly Lys Gln Ala Leu Glu Thr
            515                 520                 525 gtt cag cga ctc ctg ccc gtc ctg tgc cag gcc cac ggc ctg acc cca      1632
Val Gln Arg Leu Leu Pro Val Leu Cys Gln Ala His Gly Leu Thr Pro
530                 535                 540 gcc cag gtt gtg gcc atc gcc agc aac ata ggt ggc aag cag gcc ctc      1680
Ala Gln Val Val Ala Ile Ala Ser Asn Ile Gly Gly Lys Gln Ala Leu
545                 550                 555                 560 gaa acc gtc cag aga ctg tta ccg gtt ctc tgc cag gac cac ggc ctg      1728
Glu Thr Val Gln Arg Leu Leu Pro Val Leu Cys Gln Asp His Gly Leu
                565                 570                 575 acc cca gac caa gtt gtc gcg att gca agc aac aac gga ggc aaa caa      1776
Thr Pro Asp Gln Val Val Ala Ile Ala Ser Asn Asn Gly Gly Lys Gln
                580                 585                 590 gcc tta gaa aca gtc cag aga ttg ttg ccg gtg ctg tgc caa gac cac      1824
Ala Leu Glu Thr Val Gln Arg Leu Leu Pro Val Leu Cys Gln Asp His
            595                 600                 605 ggc ctg acc ccc gaa cag gtt gtc gct att gct agt aac ggc gga ggc      1872
Gly Leu Thr Pro Glu Gln Val Val Ala Ile Ala Ser Asn Gly Gly Gly
        610                 615                 620 aaa cag gcg ctg gaa aca gtt cag cgc ctc ttg ccg gtc ttg tgt cag      1920
Lys Gln Ala Leu Glu Thr Val Gln Arg Leu Leu Pro Val Leu Cys Gln
625                 630                 635                 640 gcc cac ggc ctg acc ccg gac cag gtg gtt gca atc gcg tca cac gat      1968
Ala His Gly Leu Thr Pro Asp Gln Val Val Ala Ile Ala Ser His Asp
                645                 650                 655 ggg gga aag cag gcc cta gaa acc gtt cag cga ctc ctg ccc gtc ctg      2016
Gly Gly Lys Gln Ala Leu Glu Thr Val Gln Arg Leu Leu Pro Val Leu
            660                 665                 670 tgc cag gcc cac ggc ctg acc ccc gcc cag gtt gtc gct att gct agt      2064
Cys Gln Ala His Gly Leu Thr Pro Ala Gln Val Val Ala Ile Ala Ser
        675                 680                 685 aac ggc gga ggc aaa cag gcg ctg gaa aca gtt cag cgc ctc ttg ccg      2112
Asn Gly Gly Gly Lys Gln Ala Leu Glu Thr Val Gln Arg Leu Leu Pro
    690                 695                 700 gtc ttg tgt cag gac cac ggc ctg acc cct gag cag gta gtg gct att      2160
Val Leu Cys Gln Asp His Gly Leu Thr Pro Glu Gln Val Val Ala Ile
705                 710                 715                 720 gca tcc cac gac ggg ggc aga ccc gca ctg gag tca atc gtg gcc cag      2208
Ala Ser His Asp Gly Gly Arg Pro Ala Leu Glu Ser Ile Val Ala Gln
```

-continued

```
              725                 730                 735
ctc tcg agg ccg gac ccc gcg ctg gcc gca ctc act aat gat cat ctt    2256
Leu Ser Arg Pro Asp Pro Ala Leu Ala Ala Leu Thr Asn Asp His Leu
            740                 745                 750 gta gcg ctg gcc tgc ctc ggc gga cga ccc gcc ttg gat gcg gtg aag    2304
Val Ala Leu Ala Cys Leu Gly Gly Arg Pro Ala Leu Asp Ala Val Lys
            755                 760                 765 aag ggg ctc ccg cac gcg cct gca ttg att aag cgg acc aac aga agg    2352
Lys Gly Leu Pro His Ala Pro Ala Leu Ile Lys Arg Thr Asn Arg Arg
770                 775                 780 atc ccc gag agg aca tca cat cga gtg gca gat cac gcg caa gtg gtc    2400
Ile Pro Glu Arg Thr Ser His Arg Val Ala Asp His Ala Gln Val Val
785                 790                 795                 800 cgc gtg ctc gga ttc ttc cag tgt cac tcc cac ccc gca caa gcg ttc    2448
Arg Val Leu Gly Phe Phe Gln Cys His Ser His Pro Ala Gln Ala Phe
                805                 810                 815 gat gac gcc atg act caa ttt ggt atg tcg aga cac gga ctg ctg cag    2496
Asp Asp Ala Met Thr Gln Phe Gly Met Ser Arg His Gly Leu Leu Gln
                820                 825                 830 ctc ttt cgt aga gtc ggt gtc aca gaa ctg gag gcc cgc tcg ggc aca    2544
Leu Phe Arg Arg Val Gly Val Thr Glu Leu Glu Ala Arg Ser Gly Thr
            835                 840                 845 ctg cct ccc gcc tcc cag cgg tgg gac agg att ctc caa gcg agc ggt    2592
Leu Pro Pro Ala Ser Gln Arg Trp Asp Arg Ile Leu Gln Ala Ser Gly
850                 855                 860 atg aaa cgc gcg aag cct tca cct acg tca act cag aca cct gac cag    2640
Met Lys Arg Ala Lys Pro Ser Pro Thr Ser Thr Gln Thr Pro Asp Gln
865                 870                 875                 880 gcg agc ctt cat gcg ttc gca gac tcg ctg gag agg gat ttg gac gcg    2688
Ala Ser Leu His Ala Phe Ala Asp Ser Leu Glu Arg Asp Leu Asp Ala
                885                 890                 895 ccc tcg ccc atg cat gaa ggg gac caa act cgc gcg tca gcc agc gac    2736
Pro Ser Pro Met His Glu Gly Asp Gln Thr Arg Ala Ser Ala Ser Asp
                900                 905                 910 gca ttg gac gat ttt gat ctg gat atg ctg gga agt gac gcc ctc gat    2784
Ala Leu Asp Asp Phe Asp Leu Asp Met Leu Gly Ser Asp Ala Leu Asp
            915                 920                 925 gat ttt gac ctt gac atg ctt ggt tcg gat gcc ctt gat gac ttt gac    2832
Asp Phe Asp Leu Asp Met Leu Gly Ser Asp Ala Leu Asp Asp Phe Asp
930                 935                 940 ctc gac atg ctc ggc agt gac gcc ctt gat gat ttc gac ctg gac atg    2880
Leu Asp Met Leu Gly Ser Asp Ala Leu Asp Asp Phe Asp Leu Asp Met
945                 950                 955                 960 ctg agt tcc gga tct ccg aaa aag aaa cgc aaa gtt ggt agc cag tac    2928
Leu Ser Ser Gly Ser Pro Lys Lys Lys Arg Lys Val Gly Ser Gln Tyr
                965                 970                 975 ctg ccc gac acc gac gac cgg cac cgg atc gag gaa aag cgg aag cgg    2976
Leu Pro Asp Thr Asp Asp Arg His Arg Ile Glu Glu Lys Arg Lys Arg
            980                 985                 990 acc tac gag aca ttc aag agc atc atg aag aag tcc ccc ttc agc ggc    3024
Thr Tyr Glu Thr Phe Lys Ser Ile Met Lys Lys Ser Pro Phe Ser Gly
            995                 1000                1005 ccc acc gac cct aga cct cca cct aga aga atc gcc gtg ccc agc       3069
Pro Thr Asp Pro Arg Pro Pro Arg Arg Ile Ala Val Pro Ser
Pro Thr Asp Pro Arg Pro Pro Arg Arg Ile Ala Val Pro Ser
1010                1015                1020 aga tcc agc gcc agc gtg cca aaa cct gcc ccc cag cct tac ccc       3114
Arg Ser Ser Ala Ser Val Pro Lys Pro Ala Pro Gln Pro Tyr Pro
1025                1030                1035 ttc acc agc agc ctg agc acc atc aac tac gac gag ttc cct acc       3159
```

-continued

| | | | | | | | | | | | | |
|---|---|---|---|---|---|---|---|---|---|---|---|---|
| Phe | Thr | Ser | Ser | Leu | Ser | Thr | Ile | Asn | Tyr | Asp | Glu | Phe Pro Thr |
| | 1040 | | | | 1045 | | | | | 1050 | | |

| | | | | | | | | | | | | |
|---|---|---|---|---|---|---|---|---|---|---|---|---|
| atg | gtg | ttc | ccc | agc | ggc | cag | atc | tct | cag | gcc | tct | gct ctg gct | 3204 |
| Met | Val | Phe | Pro | Ser | Gly | Gln | Ile | Ser | Gln | Ala | Ser | Ala Leu Ala |
| | 1055 | | | | 1060 | | | | | 1065 | | |

| cca | gcc | cct | cct | cag | gtg | ctg | cct | cag | gct | cct | gct | cct gca cca | 3249 |
| Pro | Ala | Pro | Pro | Gln | Val | Leu | Pro | Gln | Ala | Pro | Ala | Pro Ala Pro |
| 1070 | | | | | 1075 | | | | | 1080 | | |

| gct | cca | gcc | atg | gtg | tct | gca | ctg | gct | cag | gca | cca | gca ccc gtg | 3294 |
| Ala | Pro | Ala | Met | Val | Ser | Ala | Leu | Ala | Gln | Ala | Pro | Ala Pro Val |
| 1085 | | | | | 1090 | | | | | 1095 | | |

| cct | gtg | ctg | gct | cct | gga | cct | cca | cag | gct | gtg | gct | cca cca gcc | 3339 |
| Pro | Val | Leu | Ala | Pro | Gly | Pro | Pro | Gln | Ala | Val | Ala | Pro Pro Ala |
| 1100 | | | | | 1105 | | | | | 1110 | | |

| cct | aaa | cct | aca | cag | gcc | ggc | gag | ggc | aca | ctg | tct | gaa gct ctg | 3384 |
| Pro | Lys | Pro | Thr | Gln | Ala | Gly | Glu | Gly | Thr | Leu | Ser | Glu Ala Leu |
| 1115 | | | | | 1120 | | | | | 1125 | | |

| ctg | cag | ctg | cag | ttc | gac | gac | gag | gat | ctg | gga | gcc | ctg ctg gga | 3429 |
| Leu | Gln | Leu | Gln | Phe | Asp | Asp | Glu | Asp | Leu | Gly | Ala | Leu Leu Gly |
| 1130 | | | | | 1135 | | | | | 1140 | | |

| aac | agc | acc | gat | cct | gcc | gtg | ttc | acc | gac | ctg | gcc | agc gtg gac | 3474 |
| Asn | Ser | Thr | Asp | Pro | Ala | Val | Phe | Thr | Asp | Leu | Ala | Ser Val Asp |
| 1145 | | | | | 1150 | | | | | 1155 | | |

| aac | agc | gag | ttc | cag | cag | ctg | ctg | aac | cag | ggc | atc | cct gtg gcc | 3519 |
| Asn | Ser | Glu | Phe | Gln | Gln | Leu | Leu | Asn | Gln | Gly | Ile | Pro Val Ala |
| 1160 | | | | | 1165 | | | | | 1170 | | |

| cct | cac | acc | acc | gag | ccc | atg | ctg | atg | gaa | tac | ccc | gag gcc atc | 3564 |
| Pro | His | Thr | Thr | Glu | Pro | Met | Leu | Met | Glu | Tyr | Pro | Glu Ala Ile |
| 1175 | | | | | 1180 | | | | | 1185 | | |

| acc | cgg | ctc | gtg | aca | ggc | gct | cag | agg | cct | cct | gat | cca gct cct | 3609 |
| Thr | Arg | Leu | Val | Thr | Gly | Ala | Gln | Arg | Pro | Pro | Asp | Pro Ala Pro |
| 1190 | | | | | 1195 | | | | | 1200 | | |

| gcc | cct | ctg | gga | gca | cca | ggc | ctg | cct | aat | gga | ctg | ctg tct ggc | 3654 |
| Ala | Pro | Leu | Gly | Ala | Pro | Gly | Leu | Pro | Asn | Gly | Leu | Leu Ser Gly |
| 1205 | | | | | 1210 | | | | | 1215 | | |

| gac | gag | gac | ttc | agc | tct | atc | gcc | gat | atg | gat | ttc | tca gcc ttg | 3699 |
| Asp | Glu | Asp | Phe | Ser | Ser | Ile | Ala | Asp | Met | Asp | Phe | Ser Ala Leu |
| 1220 | | | | | 1225 | | | | | 1230 | | |

| ctg | ggc | tct | ggc | agc | ggc | agc | cgg | gat | tcc | agg | gaa | ggg atg ttt | 3744 |
| Leu | Gly | Ser | Gly | Ser | Gly | Ser | Arg | Asp | Ser | Arg | Glu | Gly Met Phe |
| 1235 | | | | | 1240 | | | | | 1245 | | |

| ttg | ccg | aag | cct | gag | gcc | ggc | tcc | gct | att | agt | gac | gtg ttt gag | 3789 |
| Leu | Pro | Lys | Pro | Glu | Ala | Gly | Ser | Ala | Ile | Ser | Asp | Val Phe Glu |
| 1250 | | | | | 1255 | | | | | 1260 | | |

| ggc | cgc | gag | gtg | tgc | cag | cca | aaa | cga | atc | cgg | cca | ttt cat cct | 3834 |
| Gly | Arg | Glu | Val | Cys | Gln | Pro | Lys | Arg | Ile | Arg | Pro | Phe His Pro |
| 1265 | | | | | 1270 | | | | | 1275 | | |

| cca | gga | agt | cca | tgg | gcc | aac | cgc | cca | ctc | ccc | gcc | agc ctc gca | 3879 |
| Pro | Gly | Ser | Pro | Trp | Ala | Asn | Arg | Pro | Leu | Pro | Ala | Ser Leu Ala |
| 1280 | | | | | 1285 | | | | | 1290 | | |

| cca | aca | cca | acc | ggt | cca | gta | cat | gag | cca | gtc | ggg | tca ctg acc | 3924 |
| Pro | Thr | Pro | Thr | Gly | Pro | Val | His | Glu | Pro | Val | Gly | Ser Leu Thr |
| 1295 | | | | | 1300 | | | | | 1305 | | |

| ccg | gca | cca | gtc | cct | cag | cca | ctg | gat | cca | gcg | ccc | gca gtg act | 3969 |
| Pro | Ala | Pro | Val | Pro | Gln | Pro | Leu | Asp | Pro | Ala | Pro | Ala Val Thr |
| 1310 | | | | | 1315 | | | | | 1320 | | |

| ccc | gag | gcc | agt | cac | ctg | ttg | gag | gat | ccc | gat | gaa | gaa acg agc | 4014 |
| Pro | Glu | Ala | Ser | His | Leu | Leu | Glu | Asp | Pro | Asp | Glu | Glu Thr Ser |
| 1325 | | | | | 1330 | | | | | 1335 | | |

```
cag gct gtc aaa gcc ctt cgg gag atg gcc gat act gtg att ccc    4059
Gln Ala Val Lys Ala Leu Arg Glu Met Ala Asp Thr Val Ile Pro
    1340            1345                1350 cag aag gaa gag gct gca atc tgt ggc caa atg gac ctt tcc cat    4104
Gln Lys Glu Glu Ala Ala Ile Cys Gly Gln Met Asp Leu Ser His
1355                1360                1365 ccg ccc cca agg ggc cat ctg gat gag ctg aca acc aca ctt gag    4149
Pro Pro Pro Arg Gly His Leu Asp Glu Leu Thr Thr Thr Leu Glu
1370                1375                1380 tcc atg acc gag gat ctg aac ctg gac tca ccc ctg acc ccg gaa    4194
Ser Met Thr Glu Asp Leu Asn Leu Asp Ser Pro Leu Thr Pro Glu
    1385            1390                1395 ttg aac gag att ctg gat acc ttc ctg aac gac gag tgc ctc ttg    4239
Leu Asn Glu Ile Leu Asp Thr Phe Leu Asn Asp Glu Cys Leu Leu
    1400            1405                1410 cat gcc atg cat atc agc aca gga ctg tcc atc ttc gac aca tct    4284
His Ala Met His Ile Ser Thr Gly Leu Ser Ile Phe Asp Thr Ser
    1415            1420                1425 ctg ttt gtt                                                     4293
Leu Phe Val
    1430
```

<210> SEQ ID NO 12
<211> LENGTH: 1431
<212> TYPE: PRT
<213> ORGANISM: Artificial Sequence
<220> FEATURE:
<223> OTHER INFORMATION: Synthetic Construct

<400> SEQUENCE: 12

```
Arg Ile Phe Ile His Phe Arg Ile Gly Cys Glu Asn Leu Tyr Phe Gln
1               5                   10                  15

Ser Leu Glu Arg Asp Arg Thr Met Ile His Gly Val Pro Ala Ala Val
            20                  25                  30

Asp Leu Arg Thr Leu Gly Tyr Ser Gln Gln Gln Gln Glu Lys Ile Lys
        35                  40                  45

Pro Lys Val Arg Ser Thr Val Ala Gln His His Glu Ala Leu Val Gly
    50                  55                  60

His Gly Phe Thr His Ala His Ile Val Ala Leu Ser Gln His Pro Ala
65                  70                  75                  80

Ala Leu Gly Thr Val Ala Val Lys Tyr Gln Asp Met Ile Ala Ala Leu
                85                  90                  95

Pro Glu Ala Thr His Glu Ala Ile Val Gly Val Gly Lys Gln Trp Ser
            100                 105                 110

Gly Ala Arg Ala Leu Glu Ala Leu Leu Thr Val Ala Gly Glu Leu Arg
        115                 120                 125

Gly Pro Pro Leu Gln Leu Asp Thr Gly Gln Leu Leu Lys Ile Ala Lys
    130                 135                 140

Arg Gly Gly Val Thr Ala Val Glu Ala Val His Ala Trp Arg Asn Ala
145                 150                 155                 160

Leu Thr Gly Ala Pro Leu Asn Leu Thr Pro Asp Gln Val Val Ala Ile
                165                 170                 175

Ala Ser His Asp Gly Gly Lys Gln Ala Leu Glu Thr Val Gln Arg Leu
            180                 185                 190

Leu Pro Val Leu Cys Gln Asp His Gly Leu Thr Pro Glu Gln Val Val
        195                 200                 205

Ala Ile Ala Ser Asn Ile Gly Gly Lys Gln Ala Leu Glu Thr Val Gln
    210                 215                 220
```

-continued

```
Arg Leu Leu Pro Val Leu Cys Gln Ala His Gly Leu Thr Pro Asp Gln
225                 230                 235                 240

Val Val Ala Ile Ala Ser Asn Asn Gly Gly Lys Gln Ala Leu Glu Thr
            245                 250                 255

Val Gln Arg Leu Leu Pro Val Leu Cys Gln Ala His Gly Leu Thr Pro
        260                 265                 270

Ala Gln Val Val Ala Ile Ala Ser Asn Ile Gly Gly Lys Gln Ala Leu
    275                 280                 285

Glu Thr Val Gln Arg Leu Leu Pro Val Leu Cys Gln Asp His Gly Leu
290                 295                 300

Thr Pro Asp Gln Val Val Ala Ile Ala Ser Asn Asn Gly Gly Lys Gln
305                 310                 315                 320

Ala Leu Glu Thr Val Gln Arg Leu Leu Pro Val Leu Cys Gln Asp His
            325                 330                 335

Gly Leu Thr Pro Glu Gln Val Val Ala Ile Ala Ser Asn Asn Gly Gly
        340                 345                 350

Lys Gln Ala Leu Glu Thr Val Gln Arg Leu Leu Pro Val Leu Cys Gln
    355                 360                 365

Ala His Gly Leu Thr Pro Asp Gln Val Val Ala Ile Ala Ser Asn Asn
370                 375                 380

Gly Gly Lys Gln Ala Leu Glu Thr Val Gln Arg Leu Leu Pro Val Leu
385                 390                 395                 400

Cys Gln Ala His Gly Leu Thr Pro Ala Gln Val Val Ala Ile Ala Ser
            405                 410                 415

Asn Ile Gly Gly Lys Gln Ala Leu Glu Thr Val Gln Arg Leu Leu Pro
        420                 425                 430

Val Leu Cys Gln Asp His Gly Leu Thr Pro Asp Gln Val Val Ala Ile
    435                 440                 445

Ala Ser His Asp Gly Gly Lys Gln Ala Leu Glu Thr Val Gln Arg Leu
450                 455                 460

Leu Pro Val Leu Cys Gln Asp His Gly Leu Thr Pro Glu Gln Val Val
465                 470                 475                 480

Ala Ile Ala Ser Asn Asn Gly Gly Lys Gln Ala Leu Glu Thr Val Gln
            485                 490                 495

Arg Leu Leu Pro Val Leu Cys Gln Ala His Gly Leu Thr Pro Asp Gln
        500                 505                 510

Val Val Ala Ile Ala Ser His Asp Gly Gly Lys Gln Ala Leu Glu Thr
    515                 520                 525

Val Gln Arg Leu Leu Pro Val Leu Cys Gln Ala His Gly Leu Thr Pro
530                 535                 540

Ala Gln Val Val Ala Ile Ala Ser Asn Ile Gly Gly Lys Gln Ala Leu
545                 550                 555                 560

Glu Thr Val Gln Arg Leu Leu Pro Val Leu Cys Gln Asp His Gly Leu
            565                 570                 575

Thr Pro Asp Gln Val Val Ala Ile Ala Ser Asn Asn Gly Gly Lys Gln
        580                 585                 590

Ala Leu Glu Thr Val Gln Arg Leu Leu Pro Val Leu Cys Gln Asp His
    595                 600                 605

Gly Leu Thr Pro Glu Gln Val Val Ala Ile Ala Ser Asn Gly Gly Gly
610                 615                 620

Lys Gln Ala Leu Glu Thr Val Gln Arg Leu Leu Pro Val Leu Cys Gln
625                 630                 635                 640
```

```
Ala His Gly Leu Thr Pro Asp Gln Val Val Ala Ile Ala Ser His Asp
                645                 650                 655

Gly Gly Lys Gln Ala Leu Glu Thr Val Gln Arg Leu Leu Pro Val Leu
        660                 665                 670

Cys Gln Ala His Gly Leu Thr Pro Ala Gln Val Val Ala Ile Ala Ser
            675                 680                 685

Asn Gly Gly Lys Gln Ala Leu Glu Thr Val Gln Arg Leu Leu Pro
    690                 695                 700

Val Leu Cys Gln Asp His Gly Leu Thr Pro Glu Gln Val Val Ala Ile
705                 710                 715                 720

Ala Ser His Asp Gly Gly Arg Pro Ala Leu Glu Ser Ile Val Ala Gln
            725                 730                 735

Leu Ser Arg Pro Asp Pro Ala Leu Ala Ala Leu Thr Asn Asp His Leu
                740                 745                 750

Val Ala Leu Ala Cys Leu Gly Gly Arg Pro Ala Leu Asp Ala Val Lys
            755                 760                 765

Lys Gly Leu Pro His Ala Pro Ala Leu Ile Lys Arg Thr Asn Arg Arg
        770                 775                 780

Ile Pro Glu Arg Thr Ser His Arg Val Ala Asp His Ala Gln Val Val
785                 790                 795                 800

Arg Val Leu Gly Phe Phe Gln Cys His Ser His Pro Ala Gln Ala Phe
                805                 810                 815

Asp Asp Ala Met Thr Gln Phe Gly Met Ser Arg His Gly Leu Leu Gln
            820                 825                 830

Leu Phe Arg Arg Val Gly Val Thr Glu Leu Glu Ala Arg Ser Gly Thr
        835                 840                 845

Leu Pro Pro Ala Ser Gln Arg Trp Asp Arg Ile Leu Gln Ala Ser Gly
    850                 855                 860

Met Lys Arg Ala Lys Pro Ser Pro Thr Ser Thr Gln Thr Pro Asp Gln
865                 870                 875                 880

Ala Ser Leu His Ala Phe Ala Asp Ser Leu Glu Arg Asp Leu Asp Ala
            885                 890                 895

Pro Ser Pro Met His Glu Gly Asp Gln Thr Arg Ala Ser Ala Ser Asp
        900                 905                 910

Ala Leu Asp Asp Phe Asp Leu Asp Met Leu Gly Ser Asp Ala Leu Asp
    915                 920                 925

Asp Phe Asp Leu Asp Met Leu Gly Ser Asp Ala Leu Asp Asp Phe Asp
930                 935                 940

Leu Asp Met Leu Gly Ser Asp Ala Leu Asp Asp Phe Asp Leu Asp Met
945                 950                 955                 960

Leu Ser Ser Gly Ser Pro Lys Lys Lys Arg Lys Val Gly Ser Gln Tyr
            965                 970                 975

Leu Pro Asp Thr Asp Asp Arg His Arg Ile Glu Glu Lys Arg Lys Arg
        980                 985                 990

Thr Tyr Glu Thr Phe Lys Ser Ile Met Lys Lys Ser Pro Phe Ser Gly
        995                 1000                1005

Pro Thr Asp Pro Arg Pro Pro Arg Arg Ile Ala Val Pro Ser
    1010                1015                1020

Arg Ser Ser Ala Ser Val Pro Lys Pro Ala Pro Gln Pro Tyr Pro
    1025                1030                1035

Phe Thr Ser Ser Leu Ser Thr Ile Asn Tyr Asp Glu Phe Pro Thr
    1040                1045                1050

Met Val Phe Pro Ser Gly Gln Ile Ser Gln Ala Ser Ala Leu Ala
```

```
                        1055                1060                1065

Pro Ala Pro Pro Gln Val Leu Pro Gln Ala Pro Pro Ala Pro
                        1070                1075                1080

Ala Pro Ala Met Val Ser Ala Leu Ala Gln Ala Pro Ala Pro Val
            1085                1090                1095

Pro Val Leu Ala Pro Gly Pro Pro Gln Ala Val Ala Pro Pro Ala
            1100                1105                1110

Pro Lys Pro Thr Gln Ala Gly Glu Gly Thr Leu Ser Glu Ala Leu
            1115                1120                1125

Leu Gln Leu Gln Phe Asp Asp Glu Asp Leu Gly Ala Leu Leu Gly
            1130                1135                1140

Asn Ser Thr Asp Pro Ala Val Phe Thr Asp Leu Ala Ser Val Asp
            1145                1150                1155

Asn Ser Glu Phe Gln Gln Leu Leu Asn Gln Gly Ile Pro Val Ala
            1160                1165                1170

Pro His Thr Thr Glu Pro Met Leu Met Glu Tyr Pro Glu Ala Ile
            1175                1180                1185

Thr Arg Leu Val Thr Gly Ala Gln Arg Pro Pro Asp Pro Ala Pro
            1190                1195                1200

Ala Pro Leu Gly Ala Pro Gly Leu Pro Asn Gly Leu Leu Ser Gly
            1205                1210                1215

Asp Glu Asp Phe Ser Ser Ile Ala Asp Met Asp Phe Ser Ala Leu
            1220                1225                1230

Leu Gly Ser Gly Ser Gly Ser Arg Asp Ser Arg Glu Gly Met Phe
            1235                1240                1245

Leu Pro Lys Pro Glu Ala Gly Ser Ala Ile Ser Asp Val Phe Glu
            1250                1255                1260

Gly Arg Glu Val Cys Gln Pro Lys Arg Ile Arg Pro Phe His Pro
            1265                1270                1275

Pro Gly Ser Pro Trp Ala Asn Arg Pro Leu Pro Ala Ser Leu Ala
            1280                1285                1290

Pro Thr Pro Thr Gly Pro Val His Glu Pro Val Gly Ser Leu Thr
            1295                1300                1305

Pro Ala Pro Val Pro Gln Pro Leu Asp Pro Ala Pro Ala Val Thr
            1310                1315                1320

Pro Glu Ala Ser His Leu Leu Glu Asp Pro Asp Glu Glu Thr Ser
            1325                1330                1335

Gln Ala Val Lys Ala Leu Arg Glu Met Ala Asp Thr Val Ile Pro
            1340                1345                1350

Gln Lys Glu Glu Ala Ala Ile Cys Gly Gln Met Asp Leu Ser His
            1355                1360                1365

Pro Pro Pro Arg Gly His Leu Asp Glu Leu Thr Thr Thr Leu Glu
            1370                1375                1380

Ser Met Thr Glu Asp Leu Asn Leu Asp Ser Pro Leu Thr Pro Glu
            1385                1390                1395

Leu Asn Glu Ile Leu Asp Thr Phe Leu Asn Asp Glu Cys Leu Leu
            1400                1405                1410

His Ala Met His Ile Ser Thr Gly Leu Ser Ile Phe Asp Thr Ser
            1415                1420                1425

Leu Phe Val
            1430

<210> SEQ ID NO 13
```

```
<211> LENGTH: 4584
<212> TYPE: DNA
<213> ORGANISM: Artificial Sequence
<220> FEATURE:
<223> OTHER INFORMATION: NTP-TALE-TERT-1-p300CD
<220> FEATURE:
<221> NAME/KEY: CDS
<222> LOCATION: (1)..(4584)

<400> SEQUENCE: 13 agg atc ttc atc cac ttc cgg atc ggc tgc gaa aac ctg tat ttc caa      48
Arg Ile Phe Ile His Phe Arg Ile Gly Cys Glu Asn Leu Tyr Phe Gln
1               5                   10                  15 tct ctc gag cgc gat cgc acc atg atc cac gga gtc cca gca gcc gta      96
Ser Leu Glu Arg Asp Arg Thr Met Ile His Gly Val Pro Ala Ala Val
            20                  25                  30 gat ttg aga act ttg gga tat tca cag cag cag cag gaa aag atc aag     144
Asp Leu Arg Thr Leu Gly Tyr Ser Gln Gln Gln Gln Glu Lys Ile Lys
        35                  40                  45 ccc aaa gtg agg tcg aca gtc gcg cag cat cac gaa gcg ctg gtg ggt     192
Pro Lys Val Arg Ser Thr Val Ala Gln His His Glu Ala Leu Val Gly
    50                  55                  60 cat ggg ttt aca cat gcc cac atc gta gcc ttg tcg cag cac cct gca     240
His Gly Phe Thr His Ala His Ile Val Ala Leu Ser Gln His Pro Ala
65                  70                  75                  80 gcc ctt ggc acg gtc gcc gtc aag tac cag gac atg att gcg gcg ttg     288
Ala Leu Gly Thr Val Ala Val Lys Tyr Gln Asp Met Ile Ala Ala Leu
                85                  90                  95 ccg gaa gcc aca cat gag gcg atc gtc ggt gtg ggg aaa cag tgg agc     336
Pro Glu Ala Thr His Glu Ala Ile Val Gly Val Gly Lys Gln Trp Ser
            100                 105                 110 gga gcc cga gcg ctt gag gcc ctg ttg acg gtc gcg gga gag ctg aga     384
Gly Ala Arg Ala Leu Glu Ala Leu Leu Thr Val Ala Gly Glu Leu Arg
        115                 120                 125 ggg cct ccc ctt cag ctg gac acg ggc cag ttg ctg aag atc gcg aag     432
Gly Pro Pro Leu Gln Leu Asp Thr Gly Gln Leu Leu Lys Ile Ala Lys
    130                 135                 140 cgg gga gga gtc acg gcg gtc gag gcg gta cac gcg tgg cgc aat gcg     480
Arg Gly Gly Val Thr Ala Val Glu Ala Val His Ala Trp Arg Asn Ala
145                 150                 155                 160 ctc acg gga gca ccc ctc aac ctg acc ccg gac cag gtg gtt gca atc     528
Leu Thr Gly Ala Pro Leu Asn Leu Thr Pro Asp Gln Val Val Ala Ile
                165                 170                 175 gcg tca cac gat ggg gga aag cag gcc cta gaa acc gtt cag cga ctc     576
Ala Ser His Asp Gly Gly Lys Gln Ala Leu Glu Thr Val Gln Arg Leu
            180                 185                 190 ctg ccc gtc ctg tgc cag gac cac ggc ctg acc cca gaa cag gtt gtg     624
Leu Pro Val Leu Cys Gln Asp His Gly Leu Thr Pro Glu Gln Val Val
        195                 200                 205 gcc atc gcc agc aac ata ggt ggc aag cag gcc ctc gaa acc gtc cag     672
Ala Ile Ala Ser Asn Ile Gly Gly Lys Gln Ala Leu Glu Thr Val Gln
    210                 215                 220 aga ctg tta ccg gtt ctc tgc cag gcc cac ggc ctg acc cca gac caa     720
Arg Leu Leu Pro Val Leu Cys Gln Ala His Gly Leu Thr Pro Asp Gln
225                 230                 235                 240 gtt gtc gcg att gca agc aac aac gga ggc aaa caa gcc tta gaa aca     768
Val Val Ala Ile Ala Ser Asn Asn Gly Gly Lys Gln Ala Leu Glu Thr
                245                 250                 255 gtc cag aga ttg ttg cct gtg ctg tgc caa gcc cac ggc ctg acc cca     816
Val Gln Arg Leu Leu Pro Val Leu Cys Gln Ala His Gly Leu Thr Pro
            260                 265                 270
```

```
gcc cag gtt gtg gcc atc gcc agc aac ata ggt ggc aag cag gcc ctc      864
Ala Gln Val Val Ala Ile Ala Ser Asn Ile Gly Gly Lys Gln Ala Leu
        275                 280                 285 gaa acc gtc cag aga ctg tta ccg gtt ctc tgc cag gac cac ggc ctg      912
Glu Thr Val Gln Arg Leu Leu Pro Val Leu Cys Gln Asp His Gly Leu
    290                 295                 300 acc cca gac caa gtt gtc gcg att gca agc aac aac gga ggc aaa caa      960
Thr Pro Asp Gln Val Val Ala Ile Ala Ser Asn Asn Gly Gly Lys Gln
305                 310                 315                 320 gcc tta gaa aca gtc cag aga ttg ttg ccg gtg ctg tgc caa gac cac     1008
Ala Leu Glu Thr Val Gln Arg Leu Leu Pro Val Leu Cys Gln Asp His
            325                 330                 335 ggc ctg acc cca gaa caa gtt gtc gcg att gca agc aac aac gga ggc     1056
Gly Leu Thr Pro Glu Gln Val Val Ala Ile Ala Ser Asn Asn Gly Gly
                340                 345                 350 aaa caa gcc tta gaa aca gtc cag aga ttg ttg ccg gtg ctg tgc caa     1104
Lys Gln Ala Leu Glu Thr Val Gln Arg Leu Leu Pro Val Leu Cys Gln
                    355                 360                 365 gcc cac ggc ctg acc cca gac caa gtt gtc gcg att gca agc aac aac     1152
Ala His Gly Leu Thr Pro Asp Gln Val Val Ala Ile Ala Ser Asn Asn
            370                 375                 380 gga ggc aaa caa gcc tta gaa aca gtc cag aga ttg ttg cct gtg ctg     1200
Gly Gly Lys Gln Ala Leu Glu Thr Val Gln Arg Leu Leu Pro Val Leu
385                 390                 395                 400 tgc caa gcc cac ggc ctg acc cca gcc cag gtt gtg gcc atc gcc agc     1248
Cys Gln Ala His Gly Leu Thr Pro Ala Gln Val Val Ala Ile Ala Ser
                    405                 410                 415 aac ata ggt ggc aag cag gcc ctc gaa acc gtc cag aga ctg tta ccg     1296
Asn Ile Gly Gly Lys Gln Ala Leu Glu Thr Val Gln Arg Leu Leu Pro
                420                 425                 430 gtt ctc tgc cag gac cac ggc ctg acc ccg gac cag gtg gtt gca atc     1344
Val Leu Cys Gln Asp His Gly Leu Thr Pro Asp Gln Val Val Ala Ile
            435                 440                 445 gcg tca cac gat ggg gga aag cag gcc cta gaa acc gtt cag cga ctc     1392
Ala Ser His Asp Gly Gly Lys Gln Ala Leu Glu Thr Val Gln Arg Leu
    450                 455                 460 ctg ccc gtc ctg tgc cag gac cac ggc ctg acc cca gaa caa gtt gtc     1440
Leu Pro Val Leu Cys Gln Asp His Gly Leu Thr Pro Glu Gln Val Val
465                 470                 475                 480 gcg att gca agc aac aac gga ggc aaa caa gcc tta gaa aca gtc cag     1488
Ala Ile Ala Ser Asn Asn Gly Gly Lys Gln Ala Leu Glu Thr Val Gln
                    485                 490                 495 aga ttg ttg ccg gtg ctg tgc caa gcc cac ggc ctg acc ccg gac cag     1536
Arg Leu Leu Pro Val Leu Cys Gln Ala His Gly Leu Thr Pro Asp Gln
                500                 505                 510 gtg gtt gca atc gcg tca cac gat ggg gga aag cag gcc cta gaa acc     1584
Val Val Ala Ile Ala Ser His Asp Gly Gly Lys Gln Ala Leu Glu Thr
            515                 520                 525 gtt cag cga ctc ctg ccc gtc ctg tgc cag gcc cac ggc ctg acc cca     1632
Val Gln Arg Leu Leu Pro Val Leu Cys Gln Ala His Gly Leu Thr Pro
    530                 535                 540 gcc cag gtt gtg gcc atc gcc agc aac ata ggt ggc aag cag gcc ctc     1680
Ala Gln Val Val Ala Ile Ala Ser Asn Ile Gly Gly Lys Gln Ala Leu
545                 550                 555                 560 gaa acc gtc cag aga ctg tta ccg gtt ctc tgc cag gac cac ggc ctg     1728
Glu Thr Val Gln Arg Leu Leu Pro Val Leu Cys Gln Asp His Gly Leu
                    565                 570                 575 acc cca gac caa gtt gtc gcg att gca agc aac aac gga ggc aaa caa     1776
Thr Pro Asp Gln Val Val Ala Ile Ala Ser Asn Asn Gly Gly Lys Gln
            580                 585                 590
```

-continued

| | | |
|---|---|---|
| gcc tta gaa aca gtc cag aga ttg ttg ccg gtg ctg tgc caa gac cac<br>Ala Leu Glu Thr Val Gln Arg Leu Leu Pro Val Leu Cys Gln Asp His<br>595                         600                       605 | 1824 | |
| ggc ctg acc ccc gaa cag gtt gtc gct att gct agt aac ggc gga ggc<br>Gly Leu Thr Pro Glu Gln Val Val Ala Ile Ala Ser Asn Gly Gly Gly<br>610                       615                       620 | 1872 | |
| aaa cag gcg ctg gaa aca gtt cag cgc ctc ttg ccg gtc ttg tgt cag<br>Lys Gln Ala Leu Glu Thr Val Gln Arg Leu Leu Pro Val Leu Cys Gln<br>625                         630                       635                       640 | 1920 | |
| gcc cac ggc ctg acc ccg gac cag gtg gtt gca atc gcg tca cac gat<br>Ala His Gly Leu Thr Pro Asp Gln Val Val Ala Ile Ala Ser His Asp<br>                       645                       650                       655 | 1968 | |
| ggg gga aag cag gcc cta gaa acc gtt cag cga ctc ctg ccc gtc ctg<br>Gly Gly Lys Gln Ala Leu Glu Thr Val Gln Arg Leu Leu Pro Val Leu<br>         660                       665                       670 | 2016 | |
| tgc cag gcc cac ggc ctg acc ccc gcc cag gtt gtc gct att gct agt<br>Cys Gln Ala His Gly Leu Thr Pro Ala Gln Val Val Ala Ile Ala Ser<br>               675                       680                       685 | 2064 | |
| aac ggc gga ggc aaa cag gcg ctg gaa aca gtt cag cgc ctc ttg ccg<br>Asn Gly Gly Gly Lys Gln Ala Leu Glu Thr Val Gln Arg Leu Leu Pro<br>690                         695                       700 | 2112 | |
| gtc ttg tgt cag gac cac ggc ctg acc cct gag cag gta gtg gct att<br>Val Leu Cys Gln Asp His Gly Leu Thr Pro Glu Gln Val Val Ala Ile<br>705                         710                       715                       720 | 2160 | |
| gca tcc cac gac ggg ggc aga ccc gca ctg gag tca atc gtg gcc cag<br>Ala Ser His Asp Gly Gly Arg Pro Ala Leu Glu Ser Ile Val Ala Gln<br>                       725                       730                       735 | 2208 | |
| ctc tcg agg ccg gac ccc gcg ctg gcc gca ctc act aat gat cat ctt<br>Leu Ser Arg Pro Asp Pro Ala Leu Ala Ala Leu Thr Asn Asp His Leu<br>             740                       745                       750 | 2256 | |
| gta gcg ctg gcc tgc ctc ggc gga cga ccc gcc ttg gat gcg gtg aag<br>Val Ala Leu Ala Cys Leu Gly Gly Arg Pro Ala Leu Asp Ala Val Lys<br>         755                       760                       765 | 2304 | |
| aag ggg ctc ccg cac gcg cct gca ttg att aag cgg acc aac aga agg<br>Lys Gly Leu Pro His Ala Pro Ala Leu Ile Lys Arg Thr Asn Arg Arg<br>770                         775                       780 | 2352 | |
| atc ccc gag agg aca tca cat cga gtg gca gat cac gcg caa gtg gtc<br>Ile Pro Glu Arg Thr Ser His Arg Val Ala Asp His Ala Gln Val Val<br>785                         790                       795                       800 | 2400 | |
| cgc gtg ctc gga ttc ttc cag tgt cac tcc cac ccc gca caa gcg ttc<br>Arg Val Leu Gly Phe Phe Gln Cys His Ser His Pro Ala Gln Ala Phe<br>                       805                       810                       815 | 2448 | |
| gat gac gcc atg act caa ttt ggt atg tcg aga cac gga ctg ctg cag<br>Asp Asp Ala Met Thr Gln Phe Gly Met Ser Arg His Gly Leu Leu Gln<br>             820                       825                       830 | 2496 | |
| ctc ttt cgt aga gtc ggt gtc aca gaa ctg gag gcc cgc tcg ggc aca<br>Leu Phe Arg Arg Val Gly Val Thr Glu Leu Glu Ala Arg Ser Gly Thr<br>         835                       840                       845 | 2544 | |
| ctg cct ccc gcc tcc cag cgg tgg gac agg att ctc caa gcg agc ggt<br>Leu Pro Pro Ala Ser Gln Arg Trp Asp Arg Ile Leu Gln Ala Ser Gly<br>850                         855                       860 | 2592 | |
| atg aaa cgc gcg aag cct tca cct acg tca act cag aca cct gac cag<br>Met Lys Arg Ala Lys Pro Ser Pro Thr Ser Thr Gln Thr Pro Asp Gln<br>865                         870                       875                       880 | 2640 | |
| gcg agc ctt cat gcg ttc gca gac tcg ctg gag agg gat ttg gac gcg<br>Ala Ser Leu His Ala Phe Ala Asp Ser Leu Glu Arg Asp Leu Asp Ala<br>                       885                       890                       895 | 2688 | |
| ccc tcg ccc atg cat gaa ggg gac caa act cgc gcg tca gcc agc att<br>Pro Ser Pro Met His Glu Gly Asp Gln Thr Arg Ala Ser Ala Ser Ile | 2736 | |

-continued

```
                900             905             910
ttc aaa cca gaa gaa cta cga cag gca ctg atg cca act ttg gag gca    2784
Phe Lys Pro Glu Glu Leu Arg Gln Ala Leu Met Pro Thr Leu Glu Ala
        915                 920                 925 ctt tac cgt cag gat cca gaa tcc ctt ccc ttt cgt caa cct gtg gac    2832
Leu Tyr Arg Gln Asp Pro Glu Ser Leu Pro Phe Arg Gln Pro Val Asp
    930                 935                 940 cct cag ctt tta gga atc cct gat tac ttt gat att gtg aag agc ccc    2880
Pro Gln Leu Leu Gly Ile Pro Asp Tyr Phe Asp Ile Val Lys Ser Pro
945                 950                 955                 960 atg gat ctt tct acc att aag agg aag tta gac act gga cag tat cag    2928
Met Asp Leu Ser Thr Ile Lys Arg Lys Leu Asp Thr Gly Gln Tyr Gln
            965                 970                 975 gag ccc tgg cag tat gtc gat gat att tgg ctt atg ttc aat aat gcc    2976
Glu Pro Trp Gln Tyr Val Asp Asp Ile Trp Leu Met Phe Asn Asn Ala
        980                 985                 990 tgg tta tat aac cgg aaa aca tca cgg gta tac aaa tac tgc tcc aag    3024
Trp Leu Tyr Asn Arg Lys Thr Ser Arg Val Tyr Lys Tyr Cys Ser Lys
    995                 1000                1005 ctc tct gag gtc ttt gaa caa gaa att gac cca gtg atg caa agc       3069
Leu Ser Glu Val Phe Glu Gln Glu Ile Asp Pro Val Met Gln Ser
1010                1015                1020 ctt gga tac tgt tgt ggc aga aag ttg gag ttc tct cca cag aca       3114
Leu Gly Tyr Cys Cys Gly Arg Lys Leu Glu Phe Ser Pro Gln Thr
    1025                1030                1035 ctg tgt tgc tac ggc aaa cag ttg tgc aca ata cct cgt gat gcc       3159
Leu Cys Cys Tyr Gly Lys Gln Leu Cys Thr Ile Pro Arg Asp Ala
1040                1045                1050 act tat tac agt tac cag aac agg tat cat ttc tgt gag aag tgt       3204
Thr Tyr Tyr Ser Tyr Gln Asn Arg Tyr His Phe Cys Glu Lys Cys
    1055                1060                1065 ttc aat gag atc caa ggg gag agc gtt tct ttg ggg gat gac cct       3249
Phe Asn Glu Ile Gln Gly Glu Ser Val Ser Leu Gly Asp Asp Pro
1070                1075                1080 tcc cag cct caa act aca ata aat aaa gaa caa ttt tcc aag aga       3294
Ser Gln Pro Gln Thr Thr Ile Asn Lys Glu Gln Phe Ser Lys Arg
    1085                1090                1095 aaa aat gac aca ctg gat cct gaa ctg ttt gtt gaa tgt aca gag       3339
Lys Asn Asp Thr Leu Asp Pro Glu Leu Phe Val Glu Cys Thr Glu
1100                1105                1110 tgc gga aga aag atg cat cag atc tgt gtc ctt cac cat gag atc       3384
Cys Gly Arg Lys Met His Gln Ile Cys Val Leu His His Glu Ile
    1115                1120                1125 atc tgg cct gct gga ttc gtc tgt gat ggc tgt tta aag aaa agt       3429
Ile Trp Pro Ala Gly Phe Val Cys Asp Gly Cys Leu Lys Lys Ser
1130                1135                1140 gca cga act agg aaa gaa aat aag ttt tct gct aaa agg ttg cca       3474
Ala Arg Thr Arg Lys Glu Asn Lys Phe Ser Ala Lys Arg Leu Pro
    1145                1150                1155 tct acc aga ctt ggc acc ttt cta gag aat cgt gtg aat gac ttt       3519
Ser Thr Arg Leu Gly Thr Phe Leu Glu Asn Arg Val Asn Asp Phe
1160                1165                1170 ctg agg cga cag aat cac cct gag tca gga gag gtc act gtt aga       3564
Leu Arg Arg Gln Asn His Pro Glu Ser Gly Glu Val Thr Val Arg
    1175                1180                1185 gta gtt cat gct tct gac aaa acc gtg gaa gta aaa cca ggc atg       3609
Val Val His Ala Ser Asp Lys Thr Val Glu Val Lys Pro Gly Met
1190                1195                1200 aaa gca agg ttt gtg gac agt gga gag atg gca gaa tcc ttt cca       3654
Lys Ala Arg Phe Val Asp Ser Gly Glu Met Ala Glu Ser Phe Pro
```

|     |     |     |     |     |     |     |     |     |     |     |     |     |
| --- | --- | --- | --- | --- | --- | --- | --- | --- | --- | --- | --- | --- |
| Lys | Ala | Arg | Phe | Val | Asp | Ser | Gly | Glu | Met | Ala | Glu | Ser Phe Pro |
| 1205 |  |  |  | 1210 |  |  |  | 1215 |  |  |  |  |

| tac | cga | acc | aaa | gcc | ctc | ttt | gcc | ttt | gaa | gaa | att | gat ggt gtt | 3699 |
|---|---|---|---|---|---|---|---|---|---|---|---|---|---|
| Tyr | Arg | Thr | Lys | Ala | Leu | Phe | Ala | Phe | Glu | Glu | Ile | Asp Gly Val | |
| 1220 | | | | 1225 | | | | 1230 | | | | | |

| gac | ctg | tgc | ttc | ttt | ggc | atg | cat | gtt | caa | gag | tat | ggc tct gac | 3744 |
|---|---|---|---|---|---|---|---|---|---|---|---|---|---|
| Asp | Leu | Cys | Phe | Phe | Gly | Met | His | Val | Gln | Glu | Tyr | Gly Ser Asp | |
| 1235 | | | | 1240 | | | | 1245 | | | | | |

| tgc | cct | cca | ccc | aac | cag | agg | aga | gta | tac | ata | tct | tac ctc gat | 3789 |
|---|---|---|---|---|---|---|---|---|---|---|---|---|---|
| Cys | Pro | Pro | Pro | Asn | Gln | Arg | Arg | Val | Tyr | Ile | Ser | Tyr Leu Asp | |
| 1250 | | | | 1255 | | | | 1260 | | | | | |

| agt | gtt | cat | ttc | ttc | cgt | cct | aaa | tgc | ttg | agg | act | gca gtc tat | 3834 |
|---|---|---|---|---|---|---|---|---|---|---|---|---|---|
| Ser | Val | His | Phe | Phe | Arg | Pro | Lys | Cys | Leu | Arg | Thr | Ala Val Tyr | |
| 1265 | | | | 1270 | | | | 1275 | | | | | |

| cat | gaa | atc | cta | att | gga | tat | tta | gaa | tat | gtc | aag | aaa tta ggt | 3879 |
|---|---|---|---|---|---|---|---|---|---|---|---|---|---|
| His | Glu | Ile | Leu | Ile | Gly | Tyr | Leu | Glu | Tyr | Val | Lys | Lys Leu Gly | |
| 1280 | | | | 1285 | | | | 1290 | | | | | |

| tac | aca | aca | ggg | cat | att | tgg | gca | tgt | cca | cca | agt | gag gga gat | 3924 |
|---|---|---|---|---|---|---|---|---|---|---|---|---|---|
| Tyr | Thr | Thr | Gly | His | Ile | Trp | Ala | Cys | Pro | Pro | Ser | Glu Gly Asp | |
| 1295 | | | | 1300 | | | | 1305 | | | | | |

| gat | tat | atc | ttc | cat | tgc | cat | cct | cct | gac | cag | aag | ata ccc aag | 3969 |
|---|---|---|---|---|---|---|---|---|---|---|---|---|---|
| Asp | Tyr | Ile | Phe | His | Cys | His | Pro | Pro | Asp | Gln | Lys | Ile Pro Lys | |
| 1310 | | | | 1315 | | | | 1320 | | | | | |

| ccc | aag | cga | ctg | cag | gaa | tgg | tac | aaa | aaa | atg | ctt | gac aag gct | 4014 |
|---|---|---|---|---|---|---|---|---|---|---|---|---|---|
| Pro | Lys | Arg | Leu | Gln | Glu | Trp | Tyr | Lys | Lys | Met | Leu | Asp Lys Ala | |
| 1325 | | | | 1330 | | | | 1335 | | | | | |

| gta | tca | gag | cgt | att | gtc | cat | gac | tac | aag | gat | att | ttt aaa caa | 4059 |
|---|---|---|---|---|---|---|---|---|---|---|---|---|---|
| Val | Ser | Glu | Arg | Ile | Val | His | Asp | Tyr | Lys | Asp | Ile | Phe Lys Gln | |
| 1340 | | | | 1345 | | | | 1350 | | | | | |

| gct | act | gaa | gat | aga | tta | aca | agt | gca | aag | gaa | ttg | cct tat ttc | 4104 |
|---|---|---|---|---|---|---|---|---|---|---|---|---|---|
| Ala | Thr | Glu | Asp | Arg | Leu | Thr | Ser | Ala | Lys | Glu | Leu | Pro Tyr Phe | |
| 1355 | | | | 1360 | | | | 1365 | | | | | |

| gag | ggt | gat | ttc | tgg | ccc | aat | gtt | ctg | gaa | gaa | agc | att aag gaa | 4149 |
|---|---|---|---|---|---|---|---|---|---|---|---|---|---|
| Glu | Gly | Asp | Phe | Trp | Pro | Asn | Val | Leu | Glu | Glu | Ser | Ile Lys Glu | |
| 1370 | | | | 1375 | | | | 1380 | | | | | |

| ctg | gaa | cag | gag | gaa | gaa | gag | aga | aaa | cga | gag | gaa | aac acc agc | 4194 |
|---|---|---|---|---|---|---|---|---|---|---|---|---|---|
| Leu | Glu | Gln | Glu | Glu | Glu | Glu | Arg | Lys | Arg | Glu | Glu | Asn Thr Ser | |
| 1385 | | | | 1390 | | | | 1395 | | | | | |

| aat | gaa | agc | aca | gat | gtg | acc | aag | gga | gac | agc | aaa | aat gct aaa | 4239 |
|---|---|---|---|---|---|---|---|---|---|---|---|---|---|
| Asn | Glu | Ser | Thr | Asp | Val | Thr | Lys | Gly | Asp | Ser | Lys | Asn Ala Lys | |
| 1400 | | | | 1405 | | | | 1410 | | | | | |

| aag | aag | aat | aat | aag | aaa | acc | agc | aaa | aat | aag | agc | agc ctg agt | 4284 |
|---|---|---|---|---|---|---|---|---|---|---|---|---|---|
| Lys | Lys | Asn | Asn | Lys | Lys | Thr | Ser | Lys | Asn | Lys | Ser | Ser Leu Ser | |
| 1415 | | | | 1420 | | | | 1425 | | | | | |

| agg | ggc | aac | aag | aag | aaa | ccc | ggg | atg | ccc | aat | gta | tct aac gac | 4329 |
|---|---|---|---|---|---|---|---|---|---|---|---|---|---|
| Arg | Gly | Asn | Lys | Lys | Lys | Pro | Gly | Met | Pro | Asn | Val | Ser Asn Asp | |
| 1430 | | | | 1435 | | | | 1440 | | | | | |

| ctc | tca | cag | aaa | cta | tat | gcc | acc | atg | gag | aag | cat | aaa gag gtc | 4374 |
|---|---|---|---|---|---|---|---|---|---|---|---|---|---|
| Leu | Ser | Gln | Lys | Leu | Tyr | Ala | Thr | Met | Glu | Lys | His | Lys Glu Val | |
| 1445 | | | | 1450 | | | | 1455 | | | | | |

| ttc | ttt | gtg | atc | cgc | ctc | att | gct | ggc | cct | gct | gcc | aac tcc ctg | 4419 |
|---|---|---|---|---|---|---|---|---|---|---|---|---|---|
| Phe | Phe | Val | Ile | Arg | Leu | Ile | Ala | Gly | Pro | Ala | Ala | Asn Ser Leu | |
| 1460 | | | | 1465 | | | | 1470 | | | | | |

| cct | ccc | att | gtt | gat | cct | gat | cct | ctc | atc | ccc | tgc | gat ctg atg | 4464 |
|---|---|---|---|---|---|---|---|---|---|---|---|---|---|
| Pro | Pro | Ile | Val | Asp | Pro | Asp | Pro | Leu | Ile | Pro | Cys | Asp Leu Met | |
| 1475 | | | | 1480 | | | | 1485 | | | | | |

| gat | ggt | cgg | gat | gcg | ttt | ctc | acg | ctg | gca | agg | gac | aag cac ctg | 4509 |
|---|---|---|---|---|---|---|---|---|---|---|---|---|---|
| Asp | Gly | Arg | Asp | Ala | Phe | Leu | Thr | Leu | Ala | Arg | Asp | Lys His Leu | |
| 1490 | | | | 1495 | | | | 1500 | | | | | |

-continued

```
gag ttc tct tca ctc cga aga gcc cag tgg tcc acc atg tgc atg    4554
Glu Phe Ser Ser Leu Arg Arg Ala Gln Trp Ser Thr Met Cys Met
1505                1510                1515 ctg gtg gag ctg cac acg cag agc cag gac                          4584
Leu Val Glu Leu His Thr Gln Ser Gln Asp
1520                1525
```

<210> SEQ ID NO 14
<211> LENGTH: 1528
<212> TYPE: PRT
<213> ORGANISM: Artificial Sequence
<220> FEATURE:
<223> OTHER INFORMATION: Synthetic Construct

<400> SEQUENCE: 14

```
Arg Ile Phe Ile His Phe Arg Ile Gly Cys Glu Asn Leu Tyr Phe Gln
1               5                   10                  15

Ser Leu Glu Arg Asp Arg Thr Met Ile His Gly Val Pro Ala Ala Val
            20                  25                  30

Asp Leu Arg Thr Leu Gly Tyr Ser Gln Gln Gln Glu Lys Ile Lys
        35                  40                  45

Pro Lys Val Arg Ser Thr Val Ala Gln His His Glu Ala Leu Val Gly
50                  55                  60

His Gly Phe Thr His Ala His Ile Val Ala Leu Ser Gln His Pro Ala
65                  70                  75                  80

Ala Leu Gly Thr Val Ala Val Lys Tyr Gln Asp Met Ile Ala Ala Leu
                85                  90                  95

Pro Glu Ala Thr His Glu Ala Ile Val Gly Val Gly Lys Gln Trp Ser
            100                 105                 110

Gly Ala Arg Ala Leu Glu Ala Leu Leu Thr Val Ala Gly Glu Leu Arg
        115                 120                 125

Gly Pro Pro Leu Gln Leu Asp Thr Gly Gln Leu Leu Lys Ile Ala Lys
130                 135                 140

Arg Gly Gly Val Thr Ala Val Glu Ala Val His Ala Trp Arg Asn Ala
145                 150                 155                 160

Leu Thr Gly Ala Pro Leu Asn Leu Thr Pro Asp Gln Val Val Ala Ile
                165                 170                 175

Ala Ser His Asp Gly Gly Lys Gln Ala Leu Glu Thr Val Gln Arg Leu
            180                 185                 190

Leu Pro Val Leu Cys Gln Asp His Gly Leu Thr Pro Glu Gln Val Val
        195                 200                 205

Ala Ile Ala Ser Asn Ile Gly Gly Lys Gln Ala Leu Glu Thr Val Gln
210                 215                 220

Arg Leu Leu Pro Val Leu Cys Gln Ala His Gly Leu Thr Pro Asp Gln
225                 230                 235                 240

Val Val Ala Ile Ala Ser Asn Gly Gly Lys Gln Ala Leu Glu Thr
                245                 250                 255

Val Gln Arg Leu Leu Pro Val Leu Cys Gln Ala His Gly Leu Thr Pro
            260                 265                 270

Ala Gln Val Val Ala Ile Ala Ser Asn Ile Gly Gly Lys Gln Ala Leu
        275                 280                 285

Glu Thr Val Gln Arg Leu Leu Pro Val Leu Cys Gln Asp His Gly Leu
            290                 295                 300

Thr Pro Asp Gln Val Val Ala Ile Ala Ser Asn Asn Gly Gly Lys Gln
305                 310                 315                 320

Ala Leu Glu Thr Val Gln Arg Leu Leu Pro Val Leu Cys Gln Asp His
```

-continued

```
            325                 330                 335
Gly Leu Thr Pro Glu Gln Val Ala Ile Ala Ser Asn Asn Gly Gly
            340                 345                 350

Lys Gln Ala Leu Glu Thr Val Gln Arg Leu Leu Pro Val Leu Cys Gln
355                 360                 365

Ala His Gly Leu Thr Pro Asp Gln Val Val Ala Ile Ala Ser Asn Asn
            370                 375                 380

Gly Gly Lys Gln Ala Leu Glu Thr Val Gln Arg Leu Leu Pro Val Leu
385                 390                 395                 400

Cys Gln Ala His Gly Leu Thr Pro Ala Gln Val Val Ala Ile Ala Ser
                405                 410                 415

Asn Ile Gly Gly Lys Gln Ala Leu Glu Thr Val Gln Arg Leu Leu Pro
            420                 425                 430

Val Leu Cys Gln Asp His Gly Leu Thr Pro Asp Gln Val Val Ala Ile
            435                 440                 445

Ala Ser His Asp Gly Gly Lys Gln Ala Leu Glu Thr Val Gln Arg Leu
450                 455                 460

Leu Pro Val Leu Cys Gln Asp His Gly Leu Thr Pro Glu Gln Val Val
465                 470                 475                 480

Ala Ile Ala Ser Asn Asn Gly Gly Lys Gln Ala Leu Glu Thr Val Gln
                485                 490                 495

Arg Leu Leu Pro Val Leu Cys Gln Ala His Gly Leu Thr Pro Asp Gln
            500                 505                 510

Val Val Ala Ile Ala Ser His Asp Gly Gly Lys Gln Ala Leu Glu Thr
            515                 520                 525

Val Gln Arg Leu Leu Pro Val Leu Cys Gln Ala His Gly Leu Thr Pro
            530                 535                 540

Ala Gln Val Val Ala Ile Ala Ser Asn Ile Gly Gly Lys Gln Ala Leu
545                 550                 555                 560

Glu Thr Val Gln Arg Leu Leu Pro Val Leu Cys Gln Asp His Gly Leu
                565                 570                 575

Thr Pro Asp Gln Val Val Ala Ile Ala Ser Asn Asn Gly Gly Lys Gln
            580                 585                 590

Ala Leu Glu Thr Val Gln Arg Leu Leu Pro Val Leu Cys Gln Asp His
            595                 600                 605

Gly Leu Thr Pro Glu Gln Val Ala Ile Ala Ser Asn Gly Gly Gly
            610                 615                 620

Lys Gln Ala Leu Glu Thr Val Gln Arg Leu Leu Pro Val Leu Cys Gln
625                 630                 635                 640

Ala His Gly Leu Thr Pro Asp Gln Val Val Ala Ile Ala Ser His Asp
                645                 650                 655

Gly Gly Lys Gln Ala Leu Glu Thr Val Gln Arg Leu Leu Pro Val Leu
            660                 665                 670

Cys Gln Ala His Gly Leu Thr Pro Ala Gln Val Val Ala Ile Ala Ser
            675                 680                 685

Asn Gly Gly Gly Lys Gln Ala Leu Glu Thr Val Gln Arg Leu Leu Pro
            690                 695                 700

Val Leu Cys Gln Asp His Gly Leu Thr Pro Glu Gln Val Val Ala Ile
705                 710                 715                 720

Ala Ser His Asp Gly Gly Arg Pro Ala Leu Glu Ser Ile Val Ala Gln
                725                 730                 735

Leu Ser Arg Pro Asp Pro Ala Leu Ala Ala Leu Thr Asn Asp His Leu
            740                 745                 750
```

-continued

Val Ala Leu Ala Cys Leu Gly Gly Arg Pro Ala Leu Asp Ala Val Lys
        755                 760                 765

Lys Gly Leu Pro His Ala Pro Ala Leu Ile Lys Arg Thr Asn Arg Arg
    770                 775                 780

Ile Pro Glu Arg Thr Ser His Arg Val Ala Asp His Ala Gln Val Val
785                 790                 795                 800

Arg Val Leu Gly Phe Phe Gln Cys His Ser His Pro Ala Gln Ala Phe
                805                 810                 815

Asp Asp Ala Met Thr Gln Phe Gly Met Ser Arg His Gly Leu Leu Gln
            820                 825                 830

Leu Phe Arg Arg Val Gly Val Thr Glu Leu Glu Ala Arg Ser Gly Thr
        835                 840                 845

Leu Pro Pro Ala Ser Gln Arg Trp Asp Arg Ile Leu Gln Ala Ser Gly
    850                 855                 860

Met Lys Arg Ala Lys Pro Ser Pro Thr Ser Thr Gln Thr Pro Asp Gln
865                 870                 875                 880

Ala Ser Leu His Ala Phe Ala Asp Ser Leu Glu Arg Asp Leu Asp Ala
                885                 890                 895

Pro Ser Pro Met His Glu Gly Asp Gln Thr Arg Ala Ser Ala Ser Ile
            900                 905                 910

Phe Lys Pro Glu Glu Leu Arg Gln Ala Leu Met Pro Thr Leu Glu Ala
        915                 920                 925

Leu Tyr Arg Gln Asp Pro Glu Ser Leu Pro Phe Arg Gln Pro Val Asp
    930                 935                 940

Pro Gln Leu Leu Gly Ile Pro Asp Tyr Phe Asp Ile Val Lys Ser Pro
945                 950                 955                 960

Met Asp Leu Ser Thr Ile Lys Arg Lys Leu Asp Thr Gly Gln Tyr Gln
                965                 970                 975

Glu Pro Trp Gln Tyr Val Asp Asp Ile Trp Leu Met Phe Asn Asn Ala
            980                 985                 990

Trp Leu Tyr Asn Arg Lys Thr Ser Arg Val Tyr Lys Tyr Cys Ser Lys
        995                 1000                1005

Leu Ser Glu Val Phe Glu Gln Glu Ile Asp Pro Val Met Gln Ser
    1010                1015                1020

Leu Gly Tyr Cys Cys Gly Arg Lys Leu Glu Phe Ser Pro Gln Thr
    1025                1030                1035

Leu Cys Cys Tyr Gly Lys Gln Leu Cys Thr Ile Pro Arg Asp Ala
    1040                1045                1050

Thr Tyr Tyr Ser Tyr Gln Asn Arg Tyr His Phe Cys Glu Lys Cys
    1055                1060                1065

Phe Asn Glu Ile Gln Gly Glu Ser Val Ser Leu Gly Asp Asp Pro
    1070                1075                1080

Ser Gln Pro Gln Thr Thr Ile Asn Lys Glu Gln Phe Ser Lys Arg
    1085                1090                1095

Lys Asn Asp Thr Leu Asp Pro Glu Leu Phe Val Glu Cys Thr Glu
    1100                1105                1110

Cys Gly Arg Lys Met His Gln Ile Cys Val Leu His His Glu Ile
    1115                1120                1125

Ile Trp Pro Ala Gly Phe Val Cys Asp Gly Cys Leu Lys Lys Ser
    1130                1135                1140

Ala Arg Thr Arg Lys Glu Asn Lys Phe Ser Ala Lys Arg Leu Pro
    1145                1150                1155

```
Ser Thr Arg Leu Gly Thr Phe Leu Glu Asn Arg Val Asn Asp Phe
    1160                1165                1170

Leu Arg Arg Gln Asn His Pro Glu Ser Gly Glu Val Thr Val Arg
    1175                1180                1185

Val Val His Ala Ser Asp Lys Thr Val Glu Val Lys Pro Gly Met
    1190                1195                1200

Lys Ala Arg Phe Val Asp Ser Gly Glu Met Ala Glu Ser Phe Pro
    1205                1210                1215

Tyr Arg Thr Lys Ala Leu Phe Ala Phe Glu Glu Ile Asp Gly Val
    1220                1225                1230

Asp Leu Cys Phe Phe Gly Met His Val Gln Glu Tyr Gly Ser Asp
    1235                1240                1245

Cys Pro Pro Pro Asn Gln Arg Arg Val Tyr Ile Ser Tyr Leu Asp
    1250                1255                1260

Ser Val His Phe Phe Arg Pro Lys Cys Leu Arg Thr Ala Val Tyr
    1265                1270                1275

His Glu Ile Leu Ile Gly Tyr Leu Glu Tyr Val Lys Lys Leu Gly
    1280                1285                1290

Tyr Thr Thr Gly His Ile Trp Ala Cys Pro Pro Ser Glu Gly Asp
    1295                1300                1305

Asp Tyr Ile Phe His Cys His Pro Pro Asp Gln Lys Ile Pro Lys
    1310                1315                1320

Pro Lys Arg Leu Gln Glu Trp Tyr Lys Lys Met Leu Asp Lys Ala
    1325                1330                1335

Val Ser Glu Arg Ile Val His Asp Tyr Lys Asp Ile Phe Lys Gln
    1340                1345                1350

Ala Thr Glu Asp Arg Leu Thr Ser Ala Lys Glu Leu Pro Tyr Phe
    1355                1360                1365

Glu Gly Asp Phe Trp Pro Asn Val Leu Glu Glu Ser Ile Lys Glu
    1370                1375                1380

Leu Glu Gln Glu Glu Glu Arg Lys Arg Glu Glu Asn Thr Ser
    1385                1390                1395

Asn Glu Ser Thr Asp Val Thr Lys Gly Asp Ser Lys Asn Ala Lys
    1400                1405                1410

Lys Lys Asn Asn Lys Lys Thr Ser Lys Asn Lys Ser Ser Leu Ser
    1415                1420                1425

Arg Gly Asn Lys Lys Lys Pro Gly Met Pro Asn Val Ser Asn Asp
    1430                1435                1440

Leu Ser Gln Lys Leu Tyr Ala Thr Met Glu Lys His Lys Glu Val
    1445                1450                1455

Phe Phe Val Ile Arg Leu Ile Ala Gly Pro Ala Ala Asn Ser Leu
    1460                1465                1470

Pro Pro Ile Val Asp Pro Asp Pro Leu Ile Pro Cys Asp Leu Met
    1475                1480                1485

Asp Gly Arg Asp Ala Phe Leu Thr Leu Ala Arg Asp Lys His Leu
    1490                1495                1500

Glu Phe Ser Ser Leu Arg Arg Ala Gln Trp Ser Thr Met Cys Met
    1505                1510                1515

Leu Val Glu Leu His Thr Gln Ser Gln Asp
    1520                1525

<210> SEQ ID NO 15
<211> LENGTH: 3756
<212> TYPE: DNA
```

<213> ORGANISM: Artificial Sequence
<220> FEATURE:
<223> OTHER INFORMATION: NTP-TALE-TERT-1-GCN5CD
<220> FEATURE:
<221> NAME/KEY: CDS
<222> LOCATION: (1)..(3756)

<400> SEQUENCE: 15

```
agg atc ttc atc cac ttc cgg atc ggc tgc gaa aac ctg tat ttc caa       48
Arg Ile Phe Ile His Phe Arg Ile Gly Cys Glu Asn Leu Tyr Phe Gln
1               5                   10                  15 tct ctc gag cgc gat cgc acc atg atc cac gga gtc cca gca gcc gta       96
Ser Leu Glu Arg Asp Arg Thr Met Ile His Gly Val Pro Ala Ala Val
            20                  25                  30 gat ttg aga act ttg gga tat tca cag cag cag cag gaa aag atc aag      144
Asp Leu Arg Thr Leu Gly Tyr Ser Gln Gln Gln Gln Glu Lys Ile Lys
        35                  40                  45 ccc aaa gtg agg tcg aca gtc gcg cag cat cac gaa gcg ctg gtg ggt      192
Pro Lys Val Arg Ser Thr Val Ala Gln His His Glu Ala Leu Val Gly
50                  55                  60 cat ggg ttt aca cat gcc cac atc gta gcc ttg tcg cag cac cct gca      240
His Gly Phe Thr His Ala His Ile Val Ala Leu Ser Gln His Pro Ala
65                  70                  75                  80 gcc ctt ggc acg gtc gcc gtc aag tac cag gac atg att gcg gcg ttg      288
Ala Leu Gly Thr Val Ala Val Lys Tyr Gln Asp Met Ile Ala Ala Leu
            85                  90                  95 ccg gaa gcc aca cat gag gcg atc gtc ggt gtg ggg aaa cag tgg agc      336
Pro Glu Ala Thr His Glu Ala Ile Val Gly Val Gly Lys Gln Trp Ser
            100                 105                 110 gga gcc cga gcg ctt gag gcc ctg ttg acg gtc gcg gga gag ctg aga      384
Gly Ala Arg Ala Leu Glu Ala Leu Leu Thr Val Ala Gly Glu Leu Arg
        115                 120                 125 ggg cct ccc ctt cag ctg gac acg ggc cag ttg ctg aag atc gcg aag      432
Gly Pro Pro Leu Gln Leu Asp Thr Gly Gln Leu Leu Lys Ile Ala Lys
    130                 135                 140 cgg gga gga gtc acg gcg gtc gag gcg gta cac gcg tgg cgc aat gcg      480
Arg Gly Gly Val Thr Ala Val Glu Ala Val His Ala Trp Arg Asn Ala
145                 150                 155                 160 ctc acg gga gca ccc ctc aac ctg acc ccg gac cag gtg gtt gca atc      528
Leu Thr Gly Ala Pro Leu Asn Leu Thr Pro Asp Gln Val Val Ala Ile
            165                 170                 175 gcg tca cac gat ggg gga aag cag gcc cta gaa acc gtt cag cga ctc      576
Ala Ser His Asp Gly Gly Lys Gln Ala Leu Glu Thr Val Gln Arg Leu
            180                 185                 190 ctg ccc gtc ctg tgc cag gac cac ggc ctg acc cca gaa cag gtt gtg      624
Leu Pro Val Leu Cys Gln Asp His Gly Leu Thr Pro Glu Gln Val Val
        195                 200                 205 gcc atc gcc agc aac ata ggt ggc aag cag gcc ctc gaa acc gtc cag      672
Ala Ile Ala Ser Asn Ile Gly Gly Lys Gln Ala Leu Glu Thr Val Gln
    210                 215                 220 aga ctg tta ccg gtt ctc tgc cag gcc cac ggc ctg acc cca gac caa      720
Arg Leu Leu Pro Val Leu Cys Gln Ala His Gly Leu Thr Pro Asp Gln
225                 230                 235                 240 gtt gtc gcg att gca agc aac aac gga ggc aaa caa gcc tta gaa aca      768
Val Val Ala Ile Ala Ser Asn Asn Gly Gly Lys Gln Ala Leu Glu Thr
            245                 250                 255 gtc cag aga ttg ttg cct gtg ctg tgc caa gcc cac ggc ctg acc cca      816
Val Gln Arg Leu Leu Pro Val Leu Cys Gln Ala His Gly Leu Thr Pro
            260                 265                 270 gcc cag gtt gtg gcc atc gcc agc aac ata ggt ggc aag cag gcc ctc      864
Ala Gln Val Val Ala Ile Ala Ser Asn Ile Gly Gly Lys Gln Ala Leu
```

-continued

|  | 275 | | | | 280 | | | | | 285 | | | | | |
|---|---|---|---|---|---|---|---|---|---|---|---|---|---|---|---|
| gaa | acc | gtc | cag | aga | ctg | tta | ccg | gtt | ctc | tgc | cag | gac | cac | ggc | ctg | 912 |
| Glu | Thr | Val | Gln | Arg | Leu | Leu | Pro | Val | Leu | Cys | Gln | Asp | His | Gly | Leu |
| 290 | | | | | 295 | | | | | 300 | | | | | | acc cca gac caa gtt gtc gcg att gca agc aac aac gga ggc aaa caa   960
Thr Pro Asp Gln Val Val Ala Ile Ala Ser Asn Asn Gly Gly Lys Gln
305                 310                 315                 320 gcc tta gaa aca gtc cag aga ttg ttg ccg gtg ctg tgc caa gac cac  1008
Ala Leu Glu Thr Val Gln Arg Leu Leu Pro Val Leu Cys Gln Asp His
            325                 330                 335 ggc ctg acc cca gaa caa gtt gtc gcg att gca agc aac aac gga ggc  1056
Gly Leu Thr Pro Glu Gln Val Val Ala Ile Ala Ser Asn Asn Gly Gly
                340                 345                 350 aaa caa gcc tta gaa aca gtc cag aga ttg ttg ccg gtg ctg tgc caa  1104
Lys Gln Ala Leu Glu Thr Val Gln Arg Leu Leu Pro Val Leu Cys Gln
                    355                 360                 365 gcc cac ggc ctg acc cca gac caa gtt gtc gcg att gca agc aac aac  1152
Ala His Gly Leu Thr Pro Asp Gln Val Val Ala Ile Ala Ser Asn Asn
370                 375                 380 gga ggc aaa caa gcc tta gaa aca gtc cag aga ttg ttg cct gtg ctg  1200
Gly Gly Lys Gln Ala Leu Glu Thr Val Gln Arg Leu Leu Pro Val Leu
385                 390                 395                 400 tgc caa gcc cac ggc ctg acc cca gcc cag gtt gtg gcc atc gcc agc  1248
Cys Gln Ala His Gly Leu Thr Pro Ala Gln Val Val Ala Ile Ala Ser
            405                 410                 415 aac ata ggt ggc aag cag gcc ctc gaa acc gtc cag aga ctg tta ccg  1296
Asn Ile Gly Gly Lys Gln Ala Leu Glu Thr Val Gln Arg Leu Leu Pro
            420                 425                 430 gtt ctc tgc cag gac cac ggc ctg acc ccg gac cag gtg gtt gca atc  1344
Val Leu Cys Gln Asp His Gly Leu Thr Pro Asp Gln Val Val Ala Ile
            435                 440                 445 gcg tca cac gat ggg gga aag cag gcc cta gaa acc gtt cag cga ctc  1392
Ala Ser His Asp Gly Gly Lys Gln Ala Leu Glu Thr Val Gln Arg Leu
450                 455                 460 ctg ccc gtc ctg tgc cag gac cac ggc ctg acc cca gaa caa gtt gtc  1440
Leu Pro Val Leu Cys Gln Asp His Gly Leu Thr Pro Glu Gln Val Val
465                 470                 475                 480 gcg att gca agc aac aac gga ggc aaa caa gcc tta gaa aca gtc cag  1488
Ala Ile Ala Ser Asn Asn Gly Gly Lys Gln Ala Leu Glu Thr Val Gln
                485                 490                 495 aga ttg ttg ccg gtg ctg tgc caa gcc cac ggc ctg acc ccg gac cag  1536
Arg Leu Leu Pro Val Leu Cys Gln Ala His Gly Leu Thr Pro Asp Gln
            500                 505                 510 gtg gtt gca atc gcg tca cac gat ggg gga aag cag gcc cta gaa acc  1584
Val Val Ala Ile Ala Ser His Asp Gly Gly Lys Gln Ala Leu Glu Thr
            515                 520                 525 gtt cag cga ctc ctg ccc gtc ctg tgc cag gcc cac ggc ctg acc cca  1632
Val Gln Arg Leu Leu Pro Val Leu Cys Gln Ala His Gly Leu Thr Pro
530                 535                 540 gcc cag gtt gtg gcc atc gcc agc aac ata ggt ggc aag cag gcc ctc  1680
Ala Gln Val Val Ala Ile Ala Ser Asn Ile Gly Gly Lys Gln Ala Leu
545                 550                 555                 560 gaa acc gtc cag aga ctg tta ccg gtt ctc tgc cag gac cac ggc ctg  1728
Glu Thr Val Gln Arg Leu Leu Pro Val Leu Cys Gln Asp His Gly Leu
            565                 570                 575 acc cca gac caa gtt gtc gcg att gca agc aac aac gga ggc aaa caa  1776
Thr Pro Asp Gln Val Val Ala Ile Ala Ser Asn Asn Gly Gly Lys Gln
                580                 585                 590 gcc tta gaa aca gtc cag aga ttg ttg ccg gtg ctg tgc caa gac cac  1824

-continued

```
              Ala Leu Glu Thr Val Gln Arg Leu Leu Pro Val Leu Cys Gln Asp His
                      595                 600                 605 ggc ctg acc ccc gaa cag gtt gtc gct att gct agt aac ggc gga ggc        1872
Gly Leu Thr Pro Glu Gln Val Val Ala Ile Ala Ser Asn Gly Gly Gly
610                 615                 620 aaa cag gcg ctg gaa aca gtt cag cgc ctc ttg ccg gtc ttg tgt cag        1920
Lys Gln Ala Leu Glu Thr Val Gln Arg Leu Leu Pro Val Leu Cys Gln
625                 630                 635                 640 gcc cac ggc ctg acc ccg gac cag gtg gtt gca atc gcg tca cac gat        1968
Ala His Gly Leu Thr Pro Asp Gln Val Val Ala Ile Ala Ser His Asp
                645                 650                 655 ggg gga aag cag gcc cta gaa acc gtt cag cga ctc ctg ccc gtc ctg        2016
Gly Gly Lys Gln Ala Leu Glu Thr Val Gln Arg Leu Leu Pro Val Leu
            660                 665                 670 tgc cag gcc cac ggc ctg acc ccc gcc cag gtt gtc gct att gct agt        2064
Cys Gln Ala His Gly Leu Thr Pro Ala Gln Val Val Ala Ile Ala Ser
        675                 680                 685 aac ggc gga ggc aaa cag gcg ctg gaa aca gtt cag cgc ctc ttg ccg        2112
Asn Gly Gly Gly Lys Gln Ala Leu Glu Thr Val Gln Arg Leu Leu Pro
690                 695                 700 gtc ttg tgt cag gac cac ggc ctg acc cct gag cag gta gtg gct att        2160
Val Leu Cys Gln Asp His Gly Leu Thr Pro Glu Gln Val Val Ala Ile
705                 710                 715                 720 gca tcc cac gac ggg ggc aga ccc gca ctg gag tca atc gtg gcc cag        2208
Ala Ser His Asp Gly Gly Arg Pro Ala Leu Glu Ser Ile Val Ala Gln
                725                 730                 735 ctc tcg agg ccg gac ccc gcg ctg gcc gca ctc act aat gat cat ctt        2256
Leu Ser Arg Pro Asp Pro Ala Leu Ala Ala Leu Thr Asn Asp His Leu
            740                 745                 750 gta gcg ctg gcc tgc ctc ggc gga cga ccc gcc ttg gat gcg gtg aag        2304
Val Ala Leu Ala Cys Leu Gly Gly Arg Pro Ala Leu Asp Ala Val Lys
        755                 760                 765 aag ggg ctc ccg cac gcg cct gca ttg att aag cgg acc aac aga agg        2352
Lys Gly Leu Pro His Ala Pro Ala Leu Ile Lys Arg Thr Asn Arg Arg
770                 775                 780 atc ccc gag agg aca tca cat cga gtg gca gat cac gcg caa gtg gtc        2400
Ile Pro Glu Arg Thr Ser His Arg Val Ala Asp His Ala Gln Val Val
785                 790                 795                 800 cgc gtg ctc gga ttc ttc cag tgt cac tcc cac ccc gca caa gcg ttc        2448
Arg Val Leu Gly Phe Phe Gln Cys His Ser His Pro Ala Gln Ala Phe
                805                 810                 815 gat gac gcc atg act caa ttt ggt atg tcg aga cac gga ctg ctg cag        2496
Asp Asp Ala Met Thr Gln Phe Gly Met Ser Arg His Gly Leu Leu Gln
            820                 825                 830 ctc ttt cgt aga gtc ggt gtc aca gaa ctg gag gcc cgc tcg ggc aca        2544
Leu Phe Arg Arg Val Gly Val Thr Glu Leu Glu Ala Arg Ser Gly Thr
        835                 840                 845 ctg cct ccc gcc tcc cag cgg tgg gac agg att ctc caa gcg agc ggt        2592
Leu Pro Pro Ala Ser Gln Arg Trp Asp Arg Ile Leu Gln Ala Ser Gly
850                 855                 860 atg aaa cgc gcg aag cct tca cct acg tca act cag aca cct gac cag        2640
Met Lys Arg Ala Lys Pro Ser Pro Thr Ser Thr Gln Thr Pro Asp Gln
865                 870                 875                 880 gcg agc ctt cat gcg ttc gca gac tcg ctg gag agg gat ttg gac gcg        2688
Ala Ser Leu His Ala Phe Ala Asp Ser Leu Glu Arg Asp Leu Asp Ala
                885                 890                 895 ccc tcg ccc atg cat gaa ggg gac caa act cgc gcg tca gcc agc ggc        2736
Pro Ser Pro Met His Glu Gly Asp Gln Thr Arg Ala Ser Ala Ser Gly
            900                 905                 910
```

-continued

| | |
|---|---|
| atc atc gag ttc cat gtc atc ggc aac tca ctg acg ccc aag gcc aac<br>Ile Ile Glu Phe His Val Ile Gly Asn Ser Leu Thr Pro Lys Ala Asn<br>              915                    920                  925 | 2784 |
| cgg cgg gtg ttg ctg tgg ctc gtg ggg ctg cag aat gtc ttt tcc cac<br>Arg Arg Val Leu Leu Trp Leu Val Gly Leu Gln Asn Val Phe Ser His<br>930                    935                    940 | 2832 |
| cag ctg ccg cgc atg cct aag gag tat atc gcc cgc ctc gtc ttt gac<br>Gln Leu Pro Arg Met Pro Lys Glu Tyr Ile Ala Arg Leu Val Phe Asp<br>945                    950                    955                  960 | 2880 |
| ccg aag cac aag act ctg gcc ttg atc aag gat ggg cgg gtc atc ggt<br>Pro Lys His Lys Thr Leu Ala Leu Ile Lys Asp Gly Arg Val Ile Gly<br>              965                    970                    975 | 2928 |
| ggc atc tgc ttc cgc atg ttt ccc acc cag ggc ttc acg gag att gtc<br>Gly Ile Cys Phe Arg Met Phe Pro Thr Gln Gly Phe Thr Glu Ile Val<br>                980                    985                    990 | 2976 |
| ttc tgt gct gtc acc tcg aat gag cag gtc aag ggt tat ggg acc cac<br>Phe Cys Ala Val Thr Ser Asn Glu Gln Val Lys Gly Tyr Gly Thr His<br>              995                    1000                1005 | 3024 |
| ctg atg aac cac ctg aag gag tat cac atc aag cac aac att ctc<br>Leu Met Asn His Leu Lys Glu Tyr His Ile Lys His Asn Ile Leu<br>1010                    1015                    1020 | 3069 |
| tac ttc ctc acc tac gcc gac gag tac gcc atc ggc tac ttc aaa<br>Tyr Phe Leu Thr Tyr Ala Asp Glu Tyr Ala Ile Gly Tyr Phe Lys<br>1025                    1030                    1035 | 3114 |
| aag cag ggt ttc tcc aag gac atc aag gtg ccc aag agc cgc tac<br>Lys Gln Gly Phe Ser Lys Asp Ile Lys Val Pro Lys Ser Arg Tyr<br>1040                    1045                    1050 | 3159 |
| ctg ggc tac atc aag gac tac gag gga gcg acg ctg atg gag tgt<br>Leu Gly Tyr Ile Lys Asp Tyr Glu Gly Ala Thr Leu Met Glu Cys<br>1055                    1060                    1065 | 3204 |
| gag ctg aat ccc cgc atc ccc tac acg gag ctg tcc cac atc atc<br>Glu Leu Asn Pro Arg Ile Pro Tyr Thr Glu Leu Ser His Ile Ile<br>1070                    1075                    1080 | 3249 |
| aag aag cag aaa gag atc atc aag aag ctg att gag cgc aaa cag<br>Lys Lys Gln Lys Glu Ile Ile Lys Lys Leu Ile Glu Arg Lys Gln<br>1085                    1090                    1095 | 3294 |
| gcc cag atc cgc aag gtc tac ccg ggg ctc agc tgc ttc aag gag<br>Ala Gln Ile Arg Lys Val Tyr Pro Gly Leu Ser Cys Phe Lys Glu<br>1100                    1105                    1110 | 3339 |
| ggc gtg agg cag atc cct gtg gag agc gtt cct ggc att cga gag<br>Gly Val Arg Gln Ile Pro Val Glu Ser Val Pro Gly Ile Arg Glu<br>1115                    1120                    1125 | 3384 |
| aca ggc tgg aag cca ttg ggg aag gag aag ggg aag gag ctg aag<br>Thr Gly Trp Lys Pro Leu Gly Lys Glu Lys Gly Lys Glu Leu Lys<br>1130                    1135                    1140 | 3429 |
| gac ccc gac cag ctc tac aca acc ctc aaa aac ctg ctg gcc caa<br>Asp Pro Asp Gln Leu Tyr Thr Thr Leu Lys Asn Leu Leu Ala Gln<br>1145                    1150                    1155 | 3474 |
| atc aag tct cac ccc agt gcc tgg ccc ttc atg gag cct gtg aag<br>Ile Lys Ser His Pro Ser Ala Trp Pro Phe Met Glu Pro Val Lys<br>1160                    1165                    1170 | 3519 |
| aag tcg gag gcc cct gac tac tac gag gtc atc cgc ttc ccc att<br>Lys Ser Glu Ala Pro Asp Tyr Tyr Glu Val Ile Arg Phe Pro Ile<br>1175                    1180                    1185 | 3564 |
| gac ctg aag acc atg act gag cgg ctg cga agc cgc tac tac gtg<br>Asp Leu Lys Thr Met Thr Glu Arg Leu Arg Ser Arg Tyr Tyr Val<br>1190                    1195                    1200 | 3609 |
| acc cgg aag ctc ttt gtg gcc gac ctg cag cgg gtc atc gcc aac<br>Thr Arg Lys Leu Phe Val Ala Asp Leu Gln Arg Val Ile Ala Asn<br>1205                    1210                    1215 | 3654 |

```
tgt cgc gag tac aac ccc ccg gac agc gag tac tgc cgc tgt gcc       3699
Cys Arg Glu Tyr Asn Pro Pro Asp Ser Glu Tyr Cys Arg Cys Ala
    1220                1225                1230 agc gcc ctg gag aag ttc ttc tac ttc aag ctc aag gag gga ggc       3744
Ser Ala Leu Glu Lys Phe Phe Tyr Phe Lys Leu Lys Glu Gly Gly
1235                1240                1245 ctc att gac aag                                                    3756
Leu Ile Asp Lys
    1250

<210> SEQ ID NO 16
<211> LENGTH: 1252
<212> TYPE: PRT
<213> ORGANISM: Artificial Sequence
<220> FEATURE:
<223> OTHER INFORMATION: Synthetic Construct

<400> SEQUENCE: 16

Arg Ile Phe Ile His Phe Arg Ile Gly Cys Glu Asn Leu Tyr Phe Gln
1               5                   10                  15

Ser Leu Glu Arg Asp Arg Thr Met Ile His Gly Val Pro Ala Ala Val
            20                  25                  30

Asp Leu Arg Thr Leu Gly Tyr Ser Gln Gln Gln Gln Glu Lys Ile Lys
        35                  40                  45

Pro Lys Val Arg Ser Thr Val Ala Gln His His Glu Ala Leu Val Gly
    50                  55                  60

His Gly Phe Thr His Ala His Ile Val Ala Leu Ser Gln His Pro Ala
65                  70                  75                  80

Ala Leu Gly Thr Val Ala Val Lys Tyr Gln Asp Met Ile Ala Ala Leu
                85                  90                  95

Pro Glu Ala Thr His Glu Ala Ile Val Gly Val Gly Lys Gln Trp Ser
            100                 105                 110

Gly Ala Arg Ala Leu Glu Ala Leu Leu Thr Val Ala Gly Glu Leu Arg
        115                 120                 125

Gly Pro Pro Leu Gln Leu Asp Thr Gly Gln Leu Leu Lys Ile Ala Lys
    130                 135                 140

Arg Gly Gly Val Thr Ala Val Glu Ala Val His Ala Trp Arg Asn Ala
145                 150                 155                 160

Leu Thr Gly Ala Pro Leu Asn Leu Thr Pro Asp Gln Val Val Ala Ile
                165                 170                 175

Ala Ser His Asp Gly Gly Lys Gln Ala Leu Glu Thr Val Gln Arg Leu
            180                 185                 190

Leu Pro Val Leu Cys Gln Asp His Gly Leu Thr Pro Glu Gln Val Val
        195                 200                 205

Ala Ile Ala Ser Asn Ile Gly Gly Lys Gln Ala Leu Glu Thr Val Gln
    210                 215                 220

Arg Leu Leu Pro Val Leu Cys Gln Ala His Gly Leu Thr Pro Asp Gln
225                 230                 235                 240

Val Val Ala Ile Ala Ser Asn Gly Gly Lys Gln Ala Leu Glu Thr
                245                 250                 255

Val Gln Arg Leu Leu Pro Val Leu Cys Gln Ala His Gly Leu Thr Pro
            260                 265                 270

Ala Gln Val Val Ala Ile Ala Ser Asn Ile Gly Gly Lys Gln Ala Leu
        275                 280                 285

Glu Thr Val Gln Arg Leu Leu Pro Val Leu Cys Gln Asp His Gly Leu
    290                 295                 300
```

```
Thr Pro Asp Gln Val Val Ala Ile Ala Ser Asn Asn Gly Gly Lys Gln
305                 310                 315                 320

Ala Leu Glu Thr Val Gln Arg Leu Leu Pro Val Leu Cys Gln Asp His
            325                 330                 335

Gly Leu Thr Pro Glu Gln Val Val Ala Ile Ala Ser Asn Asn Gly Gly
                340                 345                 350

Lys Gln Ala Leu Glu Thr Val Gln Arg Leu Leu Pro Val Leu Cys Gln
            355                 360                 365

Ala His Gly Leu Thr Pro Asp Gln Val Val Ala Ile Ala Ser Asn Asn
370                 375                 380

Gly Gly Lys Gln Ala Leu Glu Thr Val Gln Arg Leu Leu Pro Val Leu
385                 390                 395                 400

Cys Gln Ala His Gly Leu Thr Pro Ala Gln Val Val Ala Ile Ala Ser
                405                 410                 415

Asn Ile Gly Gly Lys Gln Ala Leu Glu Thr Val Gln Arg Leu Leu Pro
                420                 425                 430

Val Leu Cys Gln Asp His Gly Leu Thr Pro Asp Gln Val Val Ala Ile
            435                 440                 445

Ala Ser His Asp Gly Gly Lys Gln Ala Leu Glu Thr Val Gln Arg Leu
450                 455                 460

Leu Pro Val Leu Cys Gln Asp His Gly Leu Thr Pro Glu Gln Val Val
465                 470                 475                 480

Ala Ile Ala Ser Asn Asn Gly Gly Lys Gln Ala Leu Glu Thr Val Gln
                485                 490                 495

Arg Leu Leu Pro Val Leu Cys Gln Ala His Gly Leu Thr Pro Asp Gln
                500                 505                 510

Val Val Ala Ile Ala Ser His Asp Gly Gly Lys Gln Ala Leu Glu Thr
            515                 520                 525

Val Gln Arg Leu Leu Pro Val Leu Cys Gln Ala His Gly Leu Thr Pro
            530                 535                 540

Ala Gln Val Val Ala Ile Ala Ser Asn Ile Gly Gly Lys Gln Ala Leu
545                 550                 555                 560

Glu Thr Val Gln Arg Leu Leu Pro Val Leu Cys Gln Asp His Gly Leu
                565                 570                 575

Thr Pro Asp Gln Val Val Ala Ile Ala Ser Asn Asn Gly Gly Lys Gln
            580                 585                 590

Ala Leu Glu Thr Val Gln Arg Leu Leu Pro Val Leu Cys Gln Asp His
            595                 600                 605

Gly Leu Thr Pro Glu Gln Val Val Ala Ile Ala Ser Asn Gly Gly Gly
            610                 615                 620

Lys Gln Ala Leu Glu Thr Val Gln Arg Leu Leu Pro Val Leu Cys Gln
625                 630                 635                 640

Ala His Gly Leu Thr Pro Asp Gln Val Val Ala Ile Ala Ser His Asp
                645                 650                 655

Gly Gly Lys Gln Ala Leu Glu Thr Val Gln Arg Leu Leu Pro Val Leu
                660                 665                 670

Cys Gln Ala His Gly Leu Thr Pro Ala Gln Val Val Ala Ile Ala Ser
            675                 680                 685

Asn Gly Gly Gly Lys Gln Ala Leu Glu Thr Val Gln Arg Leu Leu Pro
            690                 695                 700

Val Leu Cys Gln Asp His Gly Leu Thr Pro Glu Gln Val Val Ala Ile
705                 710                 715                 720
```

```
Ala Ser His Asp Gly Gly Arg Pro Ala Leu Glu Ser Ile Val Ala Gln
                725                 730                 735

Leu Ser Arg Pro Asp Pro Ala Leu Ala Ala Leu Thr Asn Asp His Leu
        740                 745                 750

Val Ala Leu Ala Cys Leu Gly Gly Arg Pro Ala Leu Asp Ala Val Lys
            755                 760                 765

Lys Gly Leu Pro His Ala Pro Ala Leu Ile Lys Arg Thr Asn Arg Arg
        770                 775                 780

Ile Pro Glu Arg Thr Ser His Arg Val Ala Asp His Ala Gln Val Val
785                 790                 795                 800

Arg Val Leu Gly Phe Phe Gln Cys His Ser His Pro Ala Gln Ala Phe
                805                 810                 815

Asp Asp Ala Met Thr Gln Phe Gly Met Ser Arg His Gly Leu Leu Gln
            820                 825                 830

Leu Phe Arg Arg Val Gly Val Thr Glu Leu Glu Ala Arg Ser Gly Thr
        835                 840                 845

Leu Pro Pro Ala Ser Gln Arg Trp Asp Arg Ile Leu Gln Ala Ser Gly
    850                 855                 860

Met Lys Arg Ala Lys Pro Ser Pro Thr Ser Thr Gln Thr Pro Asp Gln
865                 870                 875                 880

Ala Ser Leu His Ala Phe Ala Asp Ser Leu Glu Arg Asp Leu Asp Ala
                885                 890                 895

Pro Ser Pro Met His Glu Gly Asp Gln Thr Arg Ala Ser Ala Ser Gly
            900                 905                 910

Ile Ile Glu Phe His Val Ile Gly Asn Ser Leu Thr Pro Lys Ala Asn
        915                 920                 925

Arg Arg Val Leu Leu Trp Leu Val Gly Leu Gln Asn Val Phe Ser His
    930                 935                 940

Gln Leu Pro Arg Met Pro Lys Glu Tyr Ile Ala Arg Leu Val Phe Asp
945                 950                 955                 960

Pro Lys His Lys Thr Leu Ala Leu Ile Lys Asp Gly Arg Val Ile Gly
                965                 970                 975

Gly Ile Cys Phe Arg Met Phe Pro Thr Gln Gly Phe Thr Glu Ile Val
            980                 985                 990

Phe Cys Ala Val Thr Ser Asn Glu  Gln Val Lys Gly Tyr  Gly Thr His
        995                 1000                1005

Leu Met  Asn His Leu Lys Glu  Tyr His Ile Lys His  Asn Ile Leu
    1010                1015                1020

Tyr Phe  Leu Thr Tyr Ala Asp  Glu Tyr Ala Ile Gly  Tyr Phe Lys
    1025                1030                1035

Lys Gln  Gly Phe Ser Lys Asp  Ile Lys Val Pro Lys  Ser Arg Tyr
    1040                1045                1050

Leu Gly  Tyr Ile Lys Asp Tyr  Glu Gly Ala Thr Leu  Met Glu Cys
    1055                1060                1065

Glu Leu  Asn Pro Arg Ile Pro  Tyr Thr Glu Leu Ser  His Ile Ile
    1070                1075                1080

Lys Lys  Gln Lys Glu Ile Ile  Lys Lys Leu Ile Glu  Arg Lys Gln
    1085                1090                1095

Ala Gln  Ile Arg Lys Val Tyr  Pro Gly Leu Ser Cys  Phe Lys Glu
    1100                1105                1110

Gly Val  Arg Gln Ile Pro Val  Glu Ser Val Pro Gly  Ile Arg Glu
    1115                1120                1125

Thr Gly  Trp Lys Pro Leu Gly  Lys Glu Lys Gly Lys  Glu Leu Lys
```

```
                      1130                    1135                   1140
Asp Pro Asp Gln Leu Tyr Thr Thr Leu Lys Asn Leu Leu Ala Gln
    1145                    1150                  1155

Ile Lys Ser His Pro Ser Ala Trp Pro Phe Met Glu Pro Val Lys
    1160                    1165                  1170

Lys Ser Glu Ala Pro Asp Tyr Tyr Glu Val Ile Arg Phe Pro Ile
    1175                    1180                  1185

Asp Leu Lys Thr Met Thr Glu Arg Leu Arg Ser Arg Tyr Tyr Val
    1190                    1195                  1200

Thr Arg Lys Leu Phe Val Ala Asp Leu Gln Arg Val Ile Ala Asn
    1205                    1210                  1215

Cys Arg Glu Tyr Asn Pro Pro Asp Ser Glu Tyr Cys Arg Cys Ala
    1220                    1225                  1230

Ser Ala Leu Glu Lys Phe Phe Tyr Phe Leu Lys Leu Glu Gly Gly
    1235                    1240                  1245

Leu Ile Asp Lys
    1250

<210> SEQ ID NO 17
<211> LENGTH: 4584
<212> TYPE: DNA
<213> ORGANISM: Artificial Sequence
<220> FEATURE:
<223> OTHER INFORMATION: NTP-TALE-TERT-2-p300CD
<220> FEATURE:
<221> NAME/KEY: CDS
<222> LOCATION: (1)..(4584)

<400> SEQUENCE: 17 agg atc ttc atc cac ttc cgg atc ggc tgc gaa aac ctg tat ttc caa      48
Arg Ile Phe Ile His Phe Arg Ile Gly Cys Glu Asn Leu Tyr Phe Gln
1               5                   10                  15 tct ctc gag cgc gat cgc acc atg atc cac gga gtc cca gca gcc gta      96
Ser Leu Glu Arg Asp Arg Thr Met Ile His Gly Val Pro Ala Ala Val
            20                  25                  30 gat ttg aga act ttg gga tat tca cag cag cag cag gaa aag atc aag     144
Asp Leu Arg Thr Leu Gly Tyr Ser Gln Gln Gln Gln Glu Lys Ile Lys
        35                  40                  45 ccc aaa gtg agg tcg aca gtc gcg cag cat cac gaa gcg ctg gtg ggt     192
Pro Lys Val Arg Ser Thr Val Ala Gln His His Glu Ala Leu Val Gly
    50                  55                  60 cat ggg ttt aca cat gcc cac atc gta gcc ttg tcg cag cac cct gca     240
His Gly Phe Thr His Ala His Ile Val Ala Leu Ser Gln His Pro Ala
65                  70                  75                  80 gcc ctt ggc acg gtc gcc gtc aag tac cag gac atg att gcg gcg ttg     288
Ala Leu Gly Thr Val Ala Val Lys Tyr Gln Asp Met Ile Ala Ala Leu
                85                  90                  95 ccg gaa gcc aca cat gag gcg atc gtc ggt gtg ggg aaa cag tgg agc     336
Pro Glu Ala Thr His Glu Ala Ile Val Gly Val Gly Lys Gln Trp Ser
            100                 105                 110 gga gcc cga gcg ctt gag gcc ctg ttg acg gtc gcg gga gag ctg aga     384
Gly Ala Arg Ala Leu Glu Ala Leu Leu Thr Val Ala Gly Glu Leu Arg
        115                 120                 125 ggg cct ccc ctt cag ctg gac acg ggc cag ttg ctg aag atc gcg aag     432
Gly Pro Pro Leu Gln Leu Asp Thr Gly Gln Leu Leu Lys Ile Ala Lys
    130                 135                 140 cgg gga gga gtc acg gcg gtc gag gcg gta cac gcg tgg cgc aat gcg     480
Arg Gly Gly Val Thr Ala Val Glu Ala Val His Ala Trp Arg Asn Ala
145                 150                 155                 160
```

```
ctc acg gga gca ccc ctc aac ctg acc ccg gac cag gtg gtt gca atc        528
Leu Thr Gly Ala Pro Leu Asn Leu Thr Pro Asp Gln Val Val Ala Ile
            165                 170                 175 gcg tca cac gat ggg gga aag cag gcc cta gaa acc gtt cag cga ctc        576
Ala Ser His Asp Gly Gly Lys Gln Ala Leu Glu Thr Val Gln Arg Leu
            180                 185                 190 ctg ccc gtc ctg tgc cag gac cac ggc ctg acc ccg gaa cag gtg gtt        624
Leu Pro Val Leu Cys Gln Asp His Gly Leu Thr Pro Glu Gln Val Val
            195                 200                 205 gca atc gcg tca cac gat ggg gga aag cag gcc cta gaa acc gtt cag        672
Ala Ile Ala Ser His Asp Gly Gly Lys Gln Ala Leu Glu Thr Val Gln
            210                 215                 220 cga ctc ctg ccc gtc ctg tgc cag gcc cac ggc ctg acc ccg gac cag        720
Arg Leu Leu Pro Val Leu Cys Gln Ala His Gly Leu Thr Pro Asp Gln
225                 230                 235                 240 gtg gtt gca atc gcg tca cac gat ggg gga aag cag gcc cta gaa acc        768
Val Val Ala Ile Ala Ser His Asp Gly Gly Lys Gln Ala Leu Glu Thr
                245                 250                 255 gtt cag cga ctc ctg ccc gtc ctg tgc cag gcc cac ggc ctg acc cca        816
Val Gln Arg Leu Leu Pro Val Leu Cys Gln Ala His Gly Leu Thr Pro
            260                 265                 270 gcc cag gtt gtg gcc atc gcc agc aac ata ggt ggc aag cag gcc ctc        864
Ala Gln Val Val Ala Ile Ala Ser Asn Ile Gly Gly Lys Gln Ala Leu
            275                 280                 285 gaa acc gtc cag aga ctg tta ccg gtt ctc tgc cag gac cac ggc ctg        912
Glu Thr Val Gln Arg Leu Leu Pro Val Leu Cys Gln Asp His Gly Leu
            290                 295                 300 acc ccg gac cag gtg gtt gca atc gcg tca cac gat ggg gga aag cag        960
Thr Pro Asp Gln Val Val Ala Ile Ala Ser His Asp Gly Gly Lys Gln
305                 310                 315                 320 gcc cta gaa acc gtt cag cga ctc ctg ccc gtc ctg tgc cag gac cac       1008
Ala Leu Glu Thr Val Gln Arg Leu Leu Pro Val Leu Cys Gln Asp His
                325                 330                 335 ggc ctg acc cca gaa caa gtt gtc gcg att gca agc aac aac gga ggc       1056
Gly Leu Thr Pro Glu Gln Val Val Ala Ile Ala Ser Asn Asn Gly Gly
            340                 345                 350 aaa caa gcc tta gaa aca gtc cag aga ttg ttg ccg gtg ctg tgc caa       1104
Lys Gln Ala Leu Glu Thr Val Gln Arg Leu Leu Pro Val Leu Cys Gln
            355                 360                 365 gcc cac ggc ctg acc ccc gac cag gtt gtc gct att gct agt aac ggc       1152
Ala His Gly Leu Thr Pro Asp Gln Val Val Ala Ile Ala Ser Asn Gly
            370                 375                 380 gga ggc aaa cag gcg ctg gaa aca gtt cag cgc ctc ttg ccg gtc ttg       1200
Gly Gly Lys Gln Ala Leu Glu Thr Val Gln Arg Leu Leu Pro Val Leu
385                 390                 395                 400 tgt cag gcc cac ggc ctg acc cca gcc caa gtt gtc gcg att gca agc       1248
Cys Gln Ala His Gly Leu Thr Pro Ala Gln Val Val Ala Ile Ala Ser
                405                 410                 415 aac aac gga ggc aaa caa gcc tta gaa aca gtc cag aga ttg ttg ccg       1296
Asn Asn Gly Gly Lys Gln Ala Leu Glu Thr Val Gln Arg Leu Leu Pro
            420                 425                 430 gtg ctg tgc caa gac cac ggc ctg acc cca gac caa gtt gtc gcg att       1344
Val Leu Cys Gln Asp His Gly Leu Thr Pro Asp Gln Val Val Ala Ile
            435                 440                 445 gca agc aac aac gga ggc aaa caa gcc tta gaa aca gtc cag aga ttg       1392
Ala Ser Asn Asn Gly Gly Lys Gln Ala Leu Glu Thr Val Gln Arg Leu
            450                 455                 460 ttg ccg gtg ctg tgc caa gac cac ggc ctg acc ccg gaa cag gtg gtt       1440
Leu Pro Val Leu Cys Gln Asp His Gly Leu Thr Pro Glu Gln Val Val
465                 470                 475                 480
```

```
gca atc gcg tca cac gat ggg gga aag cag gcc cta gaa acc gtt cag      1488
Ala Ile Ala Ser His Asp Gly Gly Lys Gln Ala Leu Glu Thr Val Gln
            485                 490                 495 cga ctc ctg ccc gtc ctg tgc cag gcc cac ggc ctg acc cca gac caa      1536
Arg Leu Leu Pro Val Leu Cys Gln Ala His Gly Leu Thr Pro Asp Gln
            500                 505                 510 gtt gtc gcg att gca agc aac aac gga ggc aaa caa gcc tta gaa aca      1584
Val Val Ala Ile Ala Ser Asn Asn Gly Gly Lys Gln Ala Leu Glu Thr
            515                 520                 525 gtc cag aga ttg ttg cct gtg ctg tgc caa gcc cac ggc ctg acc cca      1632
Val Gln Arg Leu Leu Pro Val Leu Cys Gln Ala His Gly Leu Thr Pro
    530                 535                 540 gcc caa gtt gtc gcg att gca agc aac aac gga ggc aaa caa gcc tta      1680
Ala Gln Val Val Ala Ile Ala Ser Asn Asn Gly Gly Lys Gln Ala Leu
545                 550                 555                 560 gaa aca gtc cag aga ttg ttg ccg gtg ctg tgc caa gac cac ggc ctg      1728
Glu Thr Val Gln Arg Leu Leu Pro Val Leu Cys Gln Asp His Gly Leu
                565                 570                 575 acc cca gac cag gtt gtg gcc atc gcc agc aac ata ggt ggc aag cag      1776
Thr Pro Asp Gln Val Val Ala Ile Ala Ser Asn Ile Gly Gly Lys Gln
            580                 585                 590 gcc ctc gaa acc gtc cag aga ctg tta ccg gtt ctc tgc cag gac cac      1824
Ala Leu Glu Thr Val Gln Arg Leu Leu Pro Val Leu Cys Gln Asp His
            595                 600                 605 ggc ctg acc cca gaa caa gtt gtc gcg att gca agc aac aac gga ggc      1872
Gly Leu Thr Pro Glu Gln Val Val Ala Ile Ala Ser Asn Asn Gly Gly
            610                 615                 620 aaa caa gcc tta gaa aca gtc cag aga ttg ttg ccg gtg ctg tgc caa      1920
Lys Gln Ala Leu Glu Thr Val Gln Arg Leu Leu Pro Val Leu Cys Gln
625                 630                 635                 640 gcc cac ggc ctg acc cca gac caa gtt gtc gcg att gca agc aac aac      1968
Ala His Gly Leu Thr Pro Asp Gln Val Val Ala Ile Ala Ser Asn Asn
                645                 650                 655 gga ggc aaa caa gcc tta gaa aca gtc cag aga ttg ttg cct gtg ctg      2016
Gly Gly Lys Gln Ala Leu Glu Thr Val Gln Arg Leu Leu Pro Val Leu
            660                 665                 670 tgc caa gcc cac ggc ctg acc cca gcc caa gtt gtc gcg att gca agc      2064
Cys Gln Ala His Gly Leu Thr Pro Ala Gln Val Val Ala Ile Ala Ser
            675                 680                 685 aac aac gga ggc aaa caa gcc tta gaa aca gtc cag aga ttg ttg ccg      2112
Asn Asn Gly Gly Lys Gln Ala Leu Glu Thr Val Gln Arg Leu Leu Pro
690                 695                 700 gtg ctg tgc caa gac cac ggc ctg acc cct gag cag gta gtg gct att      2160
Val Leu Cys Gln Asp His Gly Leu Thr Pro Glu Gln Val Val Ala Ile
705                 710                 715                 720 gca tcc cac gac ggg ggc aga ccc gca ctg gag tca atc gtg gcc cag      2208
Ala Ser His Asp Gly Gly Arg Pro Ala Leu Glu Ser Ile Val Ala Gln
                725                 730                 735 ctc tcg agg ccg gac ccc gcg ctg gcc gca ctc act aat gat cat ctt      2256
Leu Ser Arg Pro Asp Pro Ala Leu Ala Ala Leu Thr Asn Asp His Leu
            740                 745                 750 gta gcg ctg gcc tgc ctc ggc gga cga ccc gcc ttg gat gcg gtg aag      2304
Val Ala Leu Ala Cys Leu Gly Gly Arg Pro Ala Leu Asp Ala Val Lys
            755                 760                 765 aag ggg ctc ccg cac gcg cct gca ttg att aag cgg acc aac aga agg      2352
Lys Gly Leu Pro His Ala Pro Ala Leu Ile Lys Arg Thr Asn Arg Arg
            770                 775                 780 atc ccc gag agg aca tca cat cga gtg gca gat cac gcg caa gtg gtc      2400
Ile Pro Glu Arg Thr Ser His Arg Val Ala Asp His Ala Gln Val Val
```

-continued

| | | | |
|---|---|---|---|
| 785 | 790 | 795 | 800 | cgc gtg ctc gga ttc ttc cag tgt cac tcc cac ccc gca caa gcg ttc    2448
Arg Val Leu Gly Phe Phe Gln Cys His Ser His Pro Ala Gln Ala Phe
            805                 810                 815 gat gac gcc atg act caa ttt ggt atg tcg aga cac gga ctg ctg cag    2496
Asp Asp Ala Met Thr Gln Phe Gly Met Ser Arg His Gly Leu Leu Gln
            820                 825                 830 ctc ttt cgt aga gtc ggt gtc aca gaa ctg gag gcc cgc tcg ggc aca    2544
Leu Phe Arg Arg Val Gly Val Thr Glu Leu Glu Ala Arg Ser Gly Thr
            835                 840                 845 ctg cct ccc gcc tcc cag cgg tgg gac agg att ctc caa gcg agc ggt    2592
Leu Pro Pro Ala Ser Gln Arg Trp Asp Arg Ile Leu Gln Ala Ser Gly
    850                 855                 860 atg aaa cgc gcg aag cct tca cct acg tca act cag aca cct gac cag    2640
Met Lys Arg Ala Lys Pro Ser Pro Thr Ser Thr Gln Thr Pro Asp Gln
865                 870                 875                 880 gcg agc ctt cat gcg ttc gca gac tcg ctg gag agg gat ttg gac gcg    2688
Ala Ser Leu His Ala Phe Ala Asp Ser Leu Glu Arg Asp Leu Asp Ala
                    885                 890                 895 ccc tcg ccc atg cat gaa ggg gac caa act cgc gcg tca gcc agc att    2736
Pro Ser Pro Met His Glu Gly Asp Gln Thr Arg Ala Ser Ala Ser Ile
            900                 905                 910 ttc aaa cca gaa gaa cta cga cag gca ctg atg cca act ttg gag gca    2784
Phe Lys Pro Glu Glu Leu Arg Gln Ala Leu Met Pro Thr Leu Glu Ala
            915                 920                 925 ctt tac cgt cag gat cca gaa tcc ctt ccc ttt cgt caa cct gtg gac    2832
Leu Tyr Arg Gln Asp Pro Glu Ser Leu Pro Phe Arg Gln Pro Val Asp
    930                 935                 940 cct cag ctt tta gga atc cct gat tac ttt gat att gtg aag agc ccc    2880
Pro Gln Leu Leu Gly Ile Pro Asp Tyr Phe Asp Ile Val Lys Ser Pro
945                 950                 955                 960 atg gat ctt tct acc att aag agg aag tta gac act gga cag tat cag    2928
Met Asp Leu Ser Thr Ile Lys Arg Lys Leu Asp Thr Gly Gln Tyr Gln
                    965                 970                 975 gag ccc tgg cag tat gtc gat gat att tgg ctt atg ttc aat aat gcc    2976
Glu Pro Trp Gln Tyr Val Asp Asp Ile Trp Leu Met Phe Asn Asn Ala
            980                 985                 990 tgg tta tat aac cgg aaa aca tca cgg gta tac aaa tac tgc tcc aag    3024
Trp Leu Tyr Asn Arg Lys Thr Ser Arg Val Tyr Lys Tyr Cys Ser Lys
            995                 1000                1005 ctc tct gag gtc ttt gaa caa gaa att gac cca gtg atg caa agc       3069
Leu Ser Glu Val Phe Glu Gln Glu Ile Asp Pro Val Met Gln Ser
    1010                1015                1020 ctt gga tac tgt tgt ggc aga aag ttg gag ttc tct cca cag aca       3114
Leu Gly Tyr Cys Cys Gly Arg Lys Leu Glu Phe Ser Pro Gln Thr
    1025                1030                1035 ctg tgt tgc tac ggc aaa cag ttg tgc aca ata cct cgt gat gcc       3159
Leu Cys Cys Tyr Gly Lys Gln Leu Cys Thr Ile Pro Arg Asp Ala
    1040                1045                1050 act tat tac agt tac cag aac agg tat cat ttc tgt gag aag tgt       3204
Thr Tyr Tyr Ser Tyr Gln Asn Arg Tyr His Phe Cys Glu Lys Cys
    1055                1060                1065 ttc aat gag atc caa ggg gag agc gtt tct ttg ggg gat gac cct       3249
Phe Asn Glu Ile Gln Gly Glu Ser Val Ser Leu Gly Asp Asp Pro
    1070                1075                1080 tcc cag cct caa act aca ata aat aaa gaa caa ttt tcc aag aga       3294
Ser Gln Pro Gln Thr Thr Ile Asn Lys Glu Gln Phe Ser Lys Arg
    1085                1090                1095 aaa aat gac aca ctg gat cct gaa ctg ttt gtt gaa tgt aca gag       3339

|   |   |   |   |   |   |   |   |   |   |   |   |   |   |   |      |
|---|---|---|---|---|---|---|---|---|---|---|---|---|---|---|------|
| Lys | Asn | Asp | Thr | Leu | Asp | Pro | Glu | Leu | Phe | Val | Glu | Cys | Thr | Glu |  |
|  | 1100 |  |  |  | 1105 |  |  |  | 1110 |  |  |  |  |  |  |

```
tgc gga aga aag atg cat cag atc tgt gtc ctt cac cat gag atc       3384
Cys Gly Arg Lys Met His Gln Ile Cys Val Leu His His Glu Ile
    1115                1120                1125 atc tgg cct gct gga ttc gtc tgt gat ggc tgt tta aag aaa agt       3429
Ile Trp Pro Ala Gly Phe Val Cys Asp Gly Cys Leu Lys Lys Ser
    1130                1135                1140 gca cga act agg aaa gaa aat aag ttt tct gct aaa agg ttg cca       3474
Ala Arg Thr Arg Lys Glu Asn Lys Phe Ser Ala Lys Arg Leu Pro
    1145                1150                1155 tct acc aga ctt ggc acc ttt cta gag aat cgt gtg aat gac ttt       3519
Ser Thr Arg Leu Gly Thr Phe Leu Glu Asn Arg Val Asn Asp Phe
    1160                1165                1170 ctg agg cga cag aat cac cct gag tca gga gag gtc act gtt aga       3564
Leu Arg Arg Gln Asn His Pro Glu Ser Gly Glu Val Thr Val Arg
    1175                1180                1185 gta gtt cat gct tct gac aaa acc gtg gaa gta aaa cca ggc atg       3609
Val Val His Ala Ser Asp Lys Thr Val Glu Val Lys Pro Gly Met
    1190                1195                1200 aaa gca agg ttt gtg gac agt gga gag atg gca gaa tcc ttt cca       3654
Lys Ala Arg Phe Val Asp Ser Gly Glu Met Ala Glu Ser Phe Pro
    1205                1210                1215 tac cga acc aaa gcc ctc ttt gcc ttt gaa gaa att gat ggt gtt       3699
Tyr Arg Thr Lys Ala Leu Phe Ala Phe Glu Glu Ile Asp Gly Val
    1220                1225                1230 gac ctg tgc ttc ttt ggc atg cat gtt caa gag tat ggc tct gac       3744
Asp Leu Cys Phe Phe Gly Met His Val Gln Glu Tyr Gly Ser Asp
    1235                1240                1245 tgc cct cca ccc aac cag agg aga gta tac ata tct tac ctc gat       3789
Cys Pro Pro Pro Asn Gln Arg Arg Val Tyr Ile Ser Tyr Leu Asp
    1250                1255                1260 agt gtt cat ttc ttc cgt cct aaa tgc ttg agg act gca gtc tat       3834
Ser Val His Phe Phe Arg Pro Lys Cys Leu Arg Thr Ala Val Tyr
    1265                1270                1275 cat gaa atc cta att gga tat tta gaa tat gtc aag aaa tta ggt       3879
His Glu Ile Leu Ile Gly Tyr Leu Glu Tyr Val Lys Lys Leu Gly
    1280                1285                1290 tac aca aca ggg cat att tgg gca tgt cca cca agt gag gga gat       3924
Tyr Thr Thr Gly His Ile Trp Ala Cys Pro Pro Ser Glu Gly Asp
    1295                1300                1305 gat tat atc ttc cat tgc cat cct cct gac cag aag ata ccc aag       3969
Asp Tyr Ile Phe His Cys His Pro Pro Asp Gln Lys Ile Pro Lys
    1310                1315                1320 ccc aag cga ctg cag gaa tgg tac aaa aaa atg ctt gac aag gct       4014
Pro Lys Arg Leu Gln Glu Trp Tyr Lys Lys Met Leu Asp Lys Ala
    1325                1330                1335 gta tca gag cgt att gtc cat gac tac aag gat att ttt aaa caa       4059
Val Ser Glu Arg Ile Val His Asp Tyr Lys Asp Ile Phe Lys Gln
    1340                1345                1350 gct act gaa gat aga tta aca agt gca aag gaa ttg cct tat ttc       4104
Ala Thr Glu Asp Arg Leu Thr Ser Ala Lys Glu Leu Pro Tyr Phe
    1355                1360                1365 gag ggt gat ttc tgg ccc aat gtt ctg gaa gaa agc att aag gaa       4149
Glu Gly Asp Phe Trp Pro Asn Val Leu Glu Glu Ser Ile Lys Glu
    1370                1375                1380 ctg gaa cag gag gaa gaa gag aga aaa cga gag gaa aac acc agc       4194
Leu Glu Gln Glu Glu Glu Glu Arg Lys Arg Glu Glu Asn Thr Ser
    1385                1390                1395
```

| | | | | | | | | | | | | | | |
|---|---|---|---|---|---|---|---|---|---|---|---|---|---|---|
| aat | gaa | agc | aca | gat | gtg | acc | aag | gga | gac | agc | aaa | aat | gct | aaa | 4239
| Asn | Glu | Ser | Thr | Asp | Val | Thr | Lys | Gly | Asp | Ser | Lys | Asn | Ala | Lys |
| | 1400 | | | | 1405 | | | | | 1410 | | | | |

```
aat gaa agc aca gat gtg acc aag gga gac agc aaa aat gct aaa     4239
Asn Glu Ser Thr Asp Val Thr Lys Gly Asp Ser Lys Asn Ala Lys
        1400                1405                1410 aag aag aat aat aag aaa acc agc aaa aat aag agc agc ctg agt     4284
Lys Lys Asn Asn Lys Lys Thr Ser Lys Asn Lys Ser Ser Leu Ser
        1415                1420                1425 agg ggc aac aag aag aaa ccc ggg atg ccc aat gta tct aac gac     4329
Arg Gly Asn Lys Lys Lys Pro Gly Met Pro Asn Val Ser Asn Asp
        1430                1435                1440 ctc tca cag aaa cta tat gcc acc atg gag aag cat aaa gag gtc     4374
Leu Ser Gln Lys Leu Tyr Ala Thr Met Glu Lys His Lys Glu Val
        1445                1450                1455 ttc ttt gtg atc cgc ctc att gct ggc cct gct gcc aac tcc ctg     4419
Phe Phe Val Ile Arg Leu Ile Ala Gly Pro Ala Ala Asn Ser Leu
        1460                1465                1470 cct ccc att gtt gat cct gat cct ctc atc ccc tgc gat ctg atg     4464
Pro Pro Ile Val Asp Pro Asp Pro Leu Ile Pro Cys Asp Leu Met
        1475                1480                1485 gat ggt cgg gat gcg ttt ctc acg ctg gca agg gac aag cac ctg     4509
Asp Gly Arg Asp Ala Phe Leu Thr Leu Ala Arg Asp Lys His Leu
        1490                1495                1500 gag ttc tct tca ctc cga aga gcc cag tgg tcc acc atg tgc atg     4554
Glu Phe Ser Ser Leu Arg Arg Ala Gln Trp Ser Thr Met Cys Met
        1505                1510                1515 ctg gtg gag ctg cac acg cag agc cag gac                         4584
Leu Val Glu Leu His Thr Gln Ser Gln Asp
        1520                1525

<210> SEQ ID NO 18
<211> LENGTH: 1528
<212> TYPE: PRT
<213> ORGANISM: Artificial Sequence
<220> FEATURE:
<223> OTHER INFORMATION: Synthetic Construct

<400> SEQUENCE: 18

Arg Ile Phe Ile His Phe Arg Ile Gly Cys Glu Asn Leu Tyr Phe Gln
1               5                   10                  15

Ser Leu Glu Arg Asp Arg Thr Met Ile His Gly Val Pro Ala Ala Val
            20                  25                  30

Asp Leu Arg Thr Leu Gly Tyr Ser Gln Gln Gln Gln Glu Lys Ile Lys
        35                  40                  45

Pro Lys Val Arg Ser Thr Val Ala Gln His His Glu Ala Leu Val Gly
    50                  55                  60

His Gly Phe Thr His Ala His Ile Val Ala Leu Ser Gln His Pro Ala
65                  70                  75                  80

Ala Leu Gly Thr Val Ala Val Lys Tyr Gln Asp Met Ile Ala Ala Leu
                85                  90                  95

Pro Glu Ala Thr His Glu Ala Ile Val Gly Val Gly Lys Gln Trp Ser
            100                 105                 110

Gly Ala Arg Ala Leu Glu Ala Leu Leu Thr Val Ala Gly Glu Leu Arg
        115                 120                 125

Gly Pro Pro Leu Gln Leu Asp Thr Gly Gln Leu Leu Lys Ile Ala Lys
    130                 135                 140

Arg Gly Gly Val Thr Ala Val Glu Ala Val His Ala Trp Arg Asn Ala
145                 150                 155                 160

Leu Thr Gly Ala Pro Leu Asn Leu Thr Pro Asp Gln Val Val Ala Ile
                165                 170                 175
```

```
Ala Ser His Asp Gly Gly Lys Gln Ala Leu Glu Thr Val Gln Arg Leu
            180                 185                 190

Leu Pro Val Leu Cys Gln Asp His Gly Leu Thr Pro Glu Gln Val Val
        195                 200                 205

Ala Ile Ala Ser His Asp Gly Gly Lys Gln Ala Leu Glu Thr Val Gln
    210                 215                 220

Arg Leu Leu Pro Val Leu Cys Gln Ala His Gly Leu Thr Pro Asp Gln
225                 230                 235                 240

Val Val Ala Ile Ala Ser His Asp Gly Gly Lys Gln Ala Leu Glu Thr
                245                 250                 255

Val Gln Arg Leu Leu Pro Val Leu Cys Gln Ala His Gly Leu Thr Pro
            260                 265                 270

Ala Gln Val Val Ala Ile Ala Ser Asn Ile Gly Gly Lys Gln Ala Leu
        275                 280                 285

Glu Thr Val Gln Arg Leu Leu Pro Val Leu Cys Gln Asp His Gly Leu
    290                 295                 300

Thr Pro Asp Gln Val Val Ala Ile Ala Ser His Asp Gly Gly Lys Gln
305                 310                 315                 320

Ala Leu Glu Thr Val Gln Arg Leu Leu Pro Val Leu Cys Gln Asp His
                325                 330                 335

Gly Leu Thr Pro Glu Gln Val Val Ala Ile Ala Ser Asn Asn Gly Gly
            340                 345                 350

Lys Gln Ala Leu Glu Thr Val Gln Arg Leu Leu Pro Val Leu Cys Gln
        355                 360                 365

Ala His Gly Leu Thr Pro Asp Gln Val Val Ala Ile Ala Ser Asn Gly
    370                 375                 380

Gly Gly Lys Gln Ala Leu Glu Thr Val Gln Arg Leu Leu Pro Val Leu
385                 390                 395                 400

Cys Gln Ala His Gly Leu Thr Pro Ala Gln Val Val Ala Ile Ala Ser
                405                 410                 415

Asn Asn Gly Gly Lys Gln Ala Leu Glu Thr Val Gln Arg Leu Leu Pro
            420                 425                 430

Val Leu Cys Gln Asp His Gly Leu Thr Pro Asp Gln Val Val Ala Ile
        435                 440                 445

Ala Ser Asn Asn Gly Gly Lys Gln Ala Leu Glu Thr Val Gln Arg Leu
    450                 455                 460

Leu Pro Val Leu Cys Gln Asp His Gly Leu Thr Pro Glu Gln Val Val
465                 470                 475                 480

Ala Ile Ala Ser His Asp Gly Gly Lys Gln Ala Leu Glu Thr Val Gln
                485                 490                 495

Arg Leu Leu Pro Val Leu Cys Gln Ala His Gly Leu Thr Pro Asp Gln
            500                 505                 510

Val Val Ala Ile Ala Ser Asn Asn Gly Gly Lys Gln Ala Leu Glu Thr
        515                 520                 525

Val Gln Arg Leu Leu Pro Val Leu Cys Gln Ala His Gly Leu Thr Pro
    530                 535                 540

Ala Gln Val Val Ala Ile Ala Ser Asn Asn Gly Gly Lys Gln Ala Leu
545                 550                 555                 560

Glu Thr Val Gln Arg Leu Leu Pro Val Leu Cys Gln Asp His Gly Leu
                565                 570                 575

Thr Pro Asp Gln Val Val Ala Ile Ala Ser Asn Ile Gly Gly Lys Gln
            580                 585                 590

Ala Leu Glu Thr Val Gln Arg Leu Leu Pro Val Leu Cys Gln Asp His
```

```
                  595                 600                 605
Gly Leu Thr Pro Glu Gln Val Ala Ile Ala Ser Asn Asn Gly Gly
    610                 615                 620

Lys Gln Ala Leu Glu Thr Val Gln Arg Leu Leu Pro Val Leu Cys Gln
625                 630                 635                 640

Ala His Gly Leu Thr Pro Asp Gln Val Val Ala Ile Ala Ser Asn Asn
                    645                 650                 655

Gly Gly Lys Gln Ala Leu Glu Thr Val Gln Arg Leu Leu Pro Val Leu
            660                 665                 670

Cys Gln Ala His Gly Leu Thr Pro Ala Gln Val Val Ala Ile Ala Ser
        675                 680                 685

Asn Asn Gly Gly Lys Gln Ala Leu Glu Thr Val Gln Arg Leu Leu Pro
690                 695                 700

Val Leu Cys Gln Asp His Gly Leu Thr Pro Glu Gln Val Val Ala Ile
705                 710                 715                 720

Ala Ser His Asp Gly Gly Arg Pro Ala Leu Glu Ser Ile Val Ala Gln
                    725                 730                 735

Leu Ser Arg Pro Asp Pro Ala Leu Ala Ala Leu Thr Asn Asp His Leu
            740                 745                 750

Val Ala Leu Ala Cys Leu Gly Gly Arg Pro Ala Leu Asp Ala Val Lys
        755                 760                 765

Lys Gly Leu Pro His Ala Pro Ala Leu Ile Lys Arg Thr Asn Arg Arg
770                 775                 780

Ile Pro Glu Arg Thr Ser His Arg Val Ala Asp His Ala Gln Val Val
785                 790                 795                 800

Arg Val Leu Gly Phe Phe Gln Cys His Ser His Pro Ala Gln Ala Phe
                    805                 810                 815

Asp Asp Ala Met Thr Gln Phe Gly Met Ser Arg His Gly Leu Leu Gln
            820                 825                 830

Leu Phe Arg Arg Val Gly Val Thr Glu Leu Glu Ala Arg Ser Gly Thr
        835                 840                 845

Leu Pro Pro Ala Ser Gln Arg Trp Asp Arg Ile Leu Gln Ala Ser Gly
        850                 855                 860

Met Lys Arg Ala Lys Pro Ser Pro Thr Ser Thr Gln Thr Pro Asp Gln
865                 870                 875                 880

Ala Ser Leu His Ala Phe Ala Asp Ser Leu Glu Arg Asp Leu Asp Ala
                    885                 890                 895

Pro Ser Pro Met His Glu Gly Asp Gln Thr Arg Ala Ser Ala Ser Ile
            900                 905                 910

Phe Lys Pro Glu Glu Leu Arg Gln Ala Leu Met Pro Thr Leu Glu Ala
        915                 920                 925

Leu Tyr Arg Gln Asp Pro Glu Ser Leu Pro Phe Arg Gln Pro Val Asp
        930                 935                 940

Pro Gln Leu Leu Gly Ile Pro Asp Tyr Phe Asp Ile Val Lys Ser Pro
945                 950                 955                 960

Met Asp Leu Ser Thr Ile Lys Arg Lys Leu Asp Thr Gly Gln Tyr Gln
                    965                 970                 975

Glu Pro Trp Gln Tyr Val Asp Asp Ile Trp Leu Met Phe Asn Asn Ala
            980                 985                 990

Trp Leu Tyr Asn Arg Lys Thr Ser Arg Val Tyr Lys Tyr Cys Ser Lys
        995                 1000                1005

Leu Ser Glu Val Phe Glu Gln Glu Ile Asp Pro Val Met Gln Ser
        1010                1015                1020
```

```
Leu Gly Tyr Cys Cys Gly Arg Lys Leu Glu Phe Ser Pro Gln Thr
1025                1030                1035

Leu Cys Cys Tyr Gly Lys Gln Leu Cys Thr Ile Pro Arg Asp Ala
1040                1045                1050

Thr Tyr Tyr Ser Tyr Gln Asn Arg Tyr His Phe Cys Glu Lys Cys
1055                1060                1065

Phe Asn Glu Ile Gln Gly Glu Ser Val Ser Leu Gly Asp Asp Pro
1070                1075                1080

Ser Gln Pro Gln Thr Thr Ile Asn Lys Glu Gln Phe Ser Lys Arg
1085                1090                1095

Lys Asn Asp Thr Leu Asp Pro Glu Leu Phe Val Glu Cys Thr Glu
1100                1105                1110

Cys Gly Arg Lys Met His Gln Ile Cys Val Leu His His Glu Ile
1115                1120                1125

Ile Trp Pro Ala Gly Phe Val Cys Asp Gly Cys Leu Lys Lys Ser
1130                1135                1140

Ala Arg Thr Arg Lys Glu Asn Lys Phe Ser Ala Lys Arg Leu Pro
1145                1150                1155

Ser Thr Arg Leu Gly Thr Phe Leu Glu Asn Arg Val Asn Asp Phe
1160                1165                1170

Leu Arg Arg Gln Asn His Pro Glu Ser Gly Glu Val Thr Val Arg
1175                1180                1185

Val Val His Ala Ser Asp Lys Thr Val Glu Val Lys Pro Gly Met
1190                1195                1200

Lys Ala Arg Phe Val Asp Ser Gly Glu Met Ala Glu Ser Phe Pro
1205                1210                1215

Tyr Arg Thr Lys Ala Leu Phe Ala Phe Glu Glu Ile Asp Gly Val
1220                1225                1230

Asp Leu Cys Phe Phe Gly Met His Val Gln Glu Tyr Gly Ser Asp
1235                1240                1245

Cys Pro Pro Pro Asn Gln Arg Arg Val Tyr Ile Ser Tyr Leu Asp
1250                1255                1260

Ser Val His Phe Phe Arg Pro Lys Cys Leu Arg Thr Ala Val Tyr
1265                1270                1275

His Glu Ile Leu Ile Gly Tyr Leu Glu Tyr Val Lys Lys Leu Gly
1280                1285                1290

Tyr Thr Thr Gly His Ile Trp Ala Cys Pro Pro Ser Glu Gly Asp
1295                1300                1305

Asp Tyr Ile Phe His Cys His Pro Pro Asp Gln Lys Ile Pro Lys
1310                1315                1320

Pro Lys Arg Leu Gln Glu Trp Tyr Lys Lys Met Leu Asp Lys Ala
1325                1330                1335

Val Ser Glu Arg Ile Val His Asp Tyr Lys Asp Ile Phe Lys Gln
1340                1345                1350

Ala Thr Glu Asp Arg Leu Thr Ser Ala Lys Glu Leu Pro Tyr Phe
1355                1360                1365

Glu Gly Asp Phe Trp Pro Asn Val Leu Glu Glu Ser Ile Lys Glu
1370                1375                1380

Leu Glu Gln Glu Glu Glu Glu Arg Lys Arg Glu Glu Asn Thr Ser
1385                1390                1395

Asn Glu Ser Thr Asp Val Thr Lys Gly Asp Ser Lys Asn Ala Lys
1400                1405                1410
```

-continued

```
Lys Lys Asn Asn Lys Lys Thr Ser Lys Asn Lys Ser Ser Leu Ser
    1415                1420                1425

Arg Gly Asn Lys Lys Pro Gly Met Pro Asn Val Ser Asn Asp
    1430                1435                1440

Leu Ser Gln Lys Leu Tyr Ala Thr Met Glu Lys His Lys Glu Val
    1445                1450                1455

Phe Phe Val Ile Arg Leu Ile Ala Gly Pro Ala Ala Asn Ser Leu
    1460                1465                1470

Pro Pro Ile Val Asp Pro Asp Pro Leu Ile Pro Cys Asp Leu Met
    1475                1480                1485

Asp Gly Arg Asp Ala Phe Leu Thr Leu Ala Arg Asp Lys His Leu
    1490                1495                1500

Glu Phe Ser Ser Leu Arg Arg Ala Gln Trp Ser Thr Met Cys Met
    1505                1510                1515

Leu Val Glu Leu His Thr Gln Ser Gln Asp
    1520                1525

<210> SEQ ID NO 19
<211> LENGTH: 4584
<212> TYPE: DNA
<213> ORGANISM: Artificial Sequence
<220> FEATURE:
<223> OTHER INFORMATION: NTP-TALE-TERT-3-p300CD
<220> FEATURE:
<221> NAME/KEY: CDS
<222> LOCATION: (1)..(4584)

<400> SEQUENCE: 19 agg atc ttc atc cac ttc cgg atc ggc tgc gaa aac ctg tat ttc caa      48
Arg Ile Phe Ile His Phe Arg Ile Gly Cys Glu Asn Leu Tyr Phe Gln
1               5                   10                  15 tct ctc gag cgc gat cgc acc atg atc cac gga gtc cca gca gcc gta      96
Ser Leu Glu Arg Asp Arg Thr Met Ile His Gly Val Pro Ala Ala Val
            20                  25                  30 gat ttg aga act ttg gga tat tca cag cag cag cag gaa aag atc aag     144
Asp Leu Arg Thr Leu Gly Tyr Ser Gln Gln Gln Gln Glu Lys Ile Lys
        35                  40                  45 ccc aaa gtg agg tcg aca gtc gcg cag cat cac gaa gcg ctg gtg ggt     192
Pro Lys Val Arg Ser Thr Val Ala Gln His His Glu Ala Leu Val Gly
    50                  55                  60 cat ggg ttt aca cat gcc cac atc gta gcc ttg tcg cag cac cct gca     240
His Gly Phe Thr His Ala His Ile Val Ala Leu Ser Gln His Pro Ala
65                  70                  75                  80 gcc ctt ggc acg gtc gcc gtc aag tac cag gac atg att gcg gcg ttg     288
Ala Leu Gly Thr Val Ala Val Lys Tyr Gln Asp Met Ile Ala Ala Leu
                85                  90                  95 ccg gaa gcc aca cat gag gcg atc gtc ggt gtg ggg aaa cag tgg agc     336
Pro Glu Ala Thr His Glu Ala Ile Val Gly Val Gly Lys Gln Trp Ser
            100                 105                 110 gga gcc cga gcg ctt gag gcc ctg ttg acg gtc gcg gga gag ctg aga     384
Gly Ala Arg Ala Leu Glu Ala Leu Leu Thr Val Ala Gly Glu Leu Arg
        115                 120                 125 ggg cct ccc ctt cag ctg gac acg ggc cag ttg ctg aag atc gcg aag     432
Gly Pro Pro Leu Gln Leu Asp Thr Gly Gln Leu Leu Lys Ile Ala Lys
    130                 135                 140 cgg gga gga gtc acg gcg gtc gag gcg gta cac gcg tgg cgc aat gcg     480
Arg Gly Gly Val Thr Ala Val Glu Ala Val His Ala Trp Arg Asn Ala
145                 150                 155                 160 ctc acg gga gca ccc ctc aac ctg acc cca gac cag gtt gtg gcc atc     528
Leu Thr Gly Ala Pro Leu Asn Leu Thr Pro Asp Gln Val Val Ala Ile
```

|  |  |
|---|---:|
| ```
                   165                 170                 175
gcc agc aac ata ggt ggc aag cag gcc ctc gaa acc gtc cag aga ctg
Ala Ser Asn Ile Gly Gly Lys Gln Ala Leu Glu Thr Val Gln Arg Leu
            180                 185                 190 tta ccg gtt ctc tgc cag gac cac ggc ctg acc cca gaa caa gtt gtc
Leu Pro Val Leu Cys Gln Asp His Gly Leu Thr Pro Glu Gln Val Val
        195                 200                 205 gcg att gca agc aac aac gga ggc aaa caa gcc tta gaa aca gtc cag
Ala Ile Ala Ser Asn Asn Gly Gly Lys Gln Ala Leu Glu Thr Val Gln
    210                 215                 220 aga ttg ttg ccg gtg ctg tgc caa gcc cac ggc ctg acc cca gac cag
Arg Leu Leu Pro Val Leu Cys Gln Ala His Gly Leu Thr Pro Asp Gln
225                 230                 235                 240 gtt gtg gcc atc gcc agc aac ata ggt ggc aag cag gcc ctc gaa acc
Val Val Ala Ile Ala Ser Asn Ile Gly Gly Lys Gln Ala Leu Glu Thr
                245                 250                 255 gtc cag aga ctg tta ccg gtt ctc tgc cag gcc cac ggc ctg acc ccg
Val Gln Arg Leu Leu Pro Val Leu Cys Gln Ala His Gly Leu Thr Pro
            260                 265                 270 gcc cag gtg gtt gca atc gcg tca cac gat ggg gga aag cag gcc cta
Ala Gln Val Val Ala Ile Ala Ser His Asp Gly Gly Lys Gln Ala Leu
        275                 280                 285 gaa acc gtt cag cga ctc ctc ccc gtc ctg tgc cag gac cac ggc ctg
Glu Thr Val Gln Arg Leu Leu Pro Val Leu Cys Gln Asp His Gly Leu
    290                 295                 300 acc ccg gac cag gtg gtt gca atc gcg tca cac gat ggg gga aag cag
Thr Pro Asp Gln Val Val Ala Ile Ala Ser His Asp Gly Gly Lys Gln
305                 310                 315                 320 gcc cta gaa acc gtt cag cga ctc ctc ccc gtc ctg tgc cag gac cac
Ala Leu Glu Thr Val Gln Arg Leu Leu Pro Val Leu Cys Gln Asp His
                325                 330                 335 ggc ctg acc ccg gaa cag gtg gtt gca atc gcg tca cac gat ggg gga
Gly Leu Thr Pro Glu Gln Val Val Ala Ile Ala Ser His Asp Gly Gly
            340                 345                 350 aag cag gcc cta gaa acc gtt cag cga ctc ctc ccc gtc ctg tgc cag
Lys Gln Ala Leu Glu Thr Val Gln Arg Leu Leu Pro Val Leu Cys Gln
        355                 360                 365 gcc cac ggc ctg acc ccc gac cag gtt gtc gct att gct agt aac ggc
Ala His Gly Leu Thr Pro Asp Gln Val Val Ala Ile Ala Ser Asn Gly
    370                 375                 380 gga ggc aaa cag gcg ctg gaa aca gtt cag cgc ctc ttg ccg gtc ttg
Gly Gly Lys Gln Ala Leu Glu Thr Val Gln Arg Leu Leu Pro Val Leu
385                 390                 395                 400 tgt cag gcc cac ggc ctg acc cca gcc caa gtt gtc gcg att gca agc
Cys Gln Ala His Gly Leu Thr Pro Ala Gln Val Val Ala Ile Ala Ser
                405                 410                 415 aac aac gga ggc aaa caa gcc tta gaa aca gtc cag aga ttg ttg ccg
Asn Asn Gly Gly Lys Gln Ala Leu Glu Thr Val Gln Arg Leu Leu Pro
            420                 425                 430 gtg ctg tgc caa gac cac ggc ctg acc cca gac caa gtt gtc gcg att
Val Leu Cys Gln Asp His Gly Leu Thr Pro Asp Gln Val Val Ala Ile
        435                 440                 445 gca agc aac aac gga ggc aaa caa gcc tta gaa aca gtc cag aga ttg
Ala Ser Asn Asn Gly Gly Lys Gln Ala Leu Glu Thr Val Gln Arg Leu
    450                 455                 460 ttg ccg gtg ctg tgc caa gac cac ggc ctg acc ccg gaa cag gtg gtt
Leu Pro Val Leu Cys Gln Asp His Gly Leu Thr Pro Glu Gln Val Val
465                 470                 475                 480 gca atc gcg tca cac gat ggg gga aag cag gcc cta gaa acc gtt cag
Ala Ile Ala Ser His Asp Gly Gly Lys Gln Ala Leu Glu Thr Val Gln
``` | 576<br><br><br>624<br><br><br>672<br><br><br>720<br><br><br>768<br><br><br>816<br><br><br>864<br><br><br>912<br><br><br>960<br><br><br>1008<br><br><br>1056<br><br><br>1104<br><br><br>1152<br><br><br>1200<br><br><br>1248<br><br><br>1296<br><br><br>1344<br><br><br>1392<br><br><br>1440<br><br><br>1488 |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Ala | Ile | Ala | Ser | His | Asp | Gly | Gly | Lys | Gln | Ala | Leu | Glu | Thr | Val | Gln | |
|     |     |     |     | 485 |     |     |     | 490 |     |     |     | 495 |     |     |     | |

| cga | ctc | ctg | ccc | gtc | ctg | tgc | cag | gcc | cac | ggc | ctg | acc | cca | gac | cag | 1536 |
| --- | --- | --- | --- | --- | --- | --- | --- | --- | --- | --- | --- | --- | --- | --- | --- | --- |
| Arg | Leu | Leu | Pro | Val | Leu | Cys | Gln | Ala | His | Gly | Leu | Thr | Pro | Asp | Gln | |
|     |     |     | 500 |     |     |     |     | 505 |     |     |     |     | 510 |     |     | |

| gtt | gtg | gcc | atc | gcc | agc | aac | ata | ggt | ggc | aag | cag | gcc | ctc | gaa | acc | 1584 |
| --- | --- | --- | --- | --- | --- | --- | --- | --- | --- | --- | --- | --- | --- | --- | --- | --- |
| Val | Val | Ala | Ile | Ala | Ser | Asn | Ile | Gly | Gly | Lys | Gln | Ala | Leu | Glu | Thr | |
|     |     |     | 515 |     |     |     |     | 520 |     |     |     |     | 525 |     |     | |

| gtc | cag | aga | ctg | tta | ccg | gtt | ctc | tgc | cag | gcc | cac | ggc | ctg | acc | cca | 1632 |
| --- | --- | --- | --- | --- | --- | --- | --- | --- | --- | --- | --- | --- | --- | --- | --- | --- |
| Val | Gln | Arg | Leu | Leu | Pro | Val | Leu | Cys | Gln | Ala | His | Gly | Leu | Thr | Pro | |
|     |     | 530 |     |     |     |     | 535 |     |     |     |     | 540 |     |     |     | |

| gcc | caa | gtt | gtc | gcg | att | gca | agc | aac | aac | gga | ggc | aaa | caa | gcc | tta | 1680 |
| --- | --- | --- | --- | --- | --- | --- | --- | --- | --- | --- | --- | --- | --- | --- | --- | --- |
| Ala | Gln | Val | Val | Ala | Ile | Ala | Ser | Asn | Asn | Gly | Gly | Lys | Gln | Ala | Leu | |
| 545 |     |     |     |     | 550 |     |     |     |     | 555 |     |     |     |     | 560 | |

| gaa | aca | gtc | cag | aga | ttg | ttg | ccg | gtg | ctg | tgc | caa | gac | cac | ggc | ctg | 1728 |
| --- | --- | --- | --- | --- | --- | --- | --- | --- | --- | --- | --- | --- | --- | --- | --- | --- |
| Glu | Thr | Val | Gln | Arg | Leu | Leu | Pro | Val | Leu | Cys | Gln | Asp | His | Gly | Leu | |
|     |     |     | 565 |     |     |     |     | 570 |     |     |     |     | 575 |     |     | |

| acc | cca | gac | caa | gtt | gtc | gcg | att | gca | agc | aac | aac | gga | ggc | aaa | caa | 1776 |
| --- | --- | --- | --- | --- | --- | --- | --- | --- | --- | --- | --- | --- | --- | --- | --- | --- |
| Thr | Pro | Asp | Gln | Val | Val | Ala | Ile | Ala | Ser | Asn | Asn | Gly | Gly | Lys | Gln | |
|     |     | 580 |     |     |     |     | 585 |     |     |     |     | 590 |     |     |     | |

| gcc | tta | gaa | aca | gtc | cag | aga | ttg | ttg | ccg | gtg | ctg | tgc | caa | gac | cac | 1824 |
| --- | --- | --- | --- | --- | --- | --- | --- | --- | --- | --- | --- | --- | --- | --- | --- | --- |
| Ala | Leu | Glu | Thr | Val | Gln | Arg | Leu | Leu | Pro | Val | Leu | Cys | Gln | Asp | His | |
|     |     | 595 |     |     |     |     | 600 |     |     |     |     | 605 |     |     |     | |

| ggc | ctg | acc | ccg | gaa | cag | gtg | gtt | gca | atc | gcg | tca | cac | gat | ggg | gga | 1872 |
| --- | --- | --- | --- | --- | --- | --- | --- | --- | --- | --- | --- | --- | --- | --- | --- | --- |
| Gly | Leu | Thr | Pro | Glu | Gln | Val | Val | Ala | Ile | Ala | Ser | His | Asp | Gly | Gly | |
|     | 610 |     |     |     |     | 615 |     |     |     |     | 620 |     |     |     |     | |

| aag | cag | gcc | cta | gaa | acc | gtt | cag | cga | ctc | ctg | ccc | gtc | ctg | tgc | cag | 1920 |
| --- | --- | --- | --- | --- | --- | --- | --- | --- | --- | --- | --- | --- | --- | --- | --- | --- |
| Lys | Gln | Ala | Leu | Glu | Thr | Val | Gln | Arg | Leu | Leu | Pro | Val | Leu | Cys | Gln | |
| 625 |     |     |     |     | 630 |     |     |     |     | 635 |     |     |     |     | 640 | |

| gcc | cac | ggc | ctg | acc | cca | gac | cag | gtt | gtg | gcc | atc | gcc | agc | aac | ata | 1968 |
| --- | --- | --- | --- | --- | --- | --- | --- | --- | --- | --- | --- | --- | --- | --- | --- | --- |
| Ala | His | Gly | Leu | Thr | Pro | Asp | Gln | Val | Val | Ala | Ile | Ala | Ser | Asn | Ile | |
|     |     |     |     | 645 |     |     |     |     | 650 |     |     |     |     | 655 |     | |

| ggt | ggc | aag | cag | gcc | ctc | gaa | acc | gtc | cag | aga | ctg | tta | ccg | gtt | ctc | 2016 |
| --- | --- | --- | --- | --- | --- | --- | --- | --- | --- | --- | --- | --- | --- | --- | --- | --- |
| Gly | Gly | Lys | Gln | Ala | Leu | Glu | Thr | Val | Gln | Arg | Leu | Leu | Pro | Val | Leu | |
|     |     |     | 660 |     |     |     |     | 665 |     |     |     |     | 670 |     |     | |

| tgc | cag | gcc | cac | ggc | ctg | acc | ccg | gcc | cag | gtg | gtt | gca | atc | gcg | tca | 2064 |
| --- | --- | --- | --- | --- | --- | --- | --- | --- | --- | --- | --- | --- | --- | --- | --- | --- |
| Cys | Gln | Ala | His | Gly | Leu | Thr | Pro | Ala | Gln | Val | Val | Ala | Ile | Ala | Ser | |
|     |     | 675 |     |     |     |     | 680 |     |     |     |     | 685 |     |     |     | |

| cac | gat | ggg | gga | aag | cag | gcc | cta | gaa | acc | gtt | cag | cga | ctc | ctg | ccc | 2112 |
| --- | --- | --- | --- | --- | --- | --- | --- | --- | --- | --- | --- | --- | --- | --- | --- | --- |
| His | Asp | Gly | Gly | Lys | Gln | Ala | Leu | Glu | Thr | Val | Gln | Arg | Leu | Leu | Pro | |
|     |     | 690 |     |     |     |     | 695 |     |     |     |     | 700 |     |     |     | |

| gtc | ctg | tgc | cag | gac | cac | ggc | ctg | acc | cct | gag | cag | gta | gtg | gct | att | 2160 |
| --- | --- | --- | --- | --- | --- | --- | --- | --- | --- | --- | --- | --- | --- | --- | --- | --- |
| Val | Leu | Cys | Gln | Asp | His | Gly | Leu | Thr | Pro | Glu | Gln | Val | Val | Ala | Ile | |
| 705 |     |     |     |     | 710 |     |     |     |     | 715 |     |     |     |     | 720 | |

| gca | tcc | cac | gac | ggg | ggc | aga | ccc | gca | ctg | gag | tca | atc | gtg | gcc | cag | 2208 |
| --- | --- | --- | --- | --- | --- | --- | --- | --- | --- | --- | --- | --- | --- | --- | --- | --- |
| Ala | Ser | His | Asp | Gly | Gly | Arg | Pro | Ala | Leu | Glu | Ser | Ile | Val | Ala | Gln | |
|     |     |     |     | 725 |     |     |     |     | 730 |     |     |     |     | 735 |     | |

| ctc | tcg | agg | ccg | gac | ccc | gcg | ctg | gcc | gca | ctc | act | aat | gat | cat | ctt | 2256 |
| --- | --- | --- | --- | --- | --- | --- | --- | --- | --- | --- | --- | --- | --- | --- | --- | --- |
| Leu | Ser | Arg | Pro | Asp | Pro | Ala | Leu | Ala | Ala | Leu | Thr | Asn | Asp | His | Leu | |
|     |     |     | 740 |     |     |     |     | 745 |     |     |     |     | 750 |     |     | |

| gta | gcg | ctg | gcc | tgc | ctc | ggc | gga | cga | ccc | gcc | ttg | gat | gcg | gtg | aag | 2304 |
| --- | --- | --- | --- | --- | --- | --- | --- | --- | --- | --- | --- | --- | --- | --- | --- | --- |
| Val | Ala | Leu | Ala | Cys | Leu | Gly | Gly | Arg | Pro | Ala | Leu | Asp | Ala | Val | Lys | |
|     |     |     | 755 |     |     |     |     | 760 |     |     |     |     | 765 |     |     | |

| aag | ggg | ctc | ccg | cac | gcg | cct | gca | ttg | att | aag | cgg | acc | aac | aga | agg | 2352 |
| --- | --- | --- | --- | --- | --- | --- | --- | --- | --- | --- | --- | --- | --- | --- | --- | --- |
| Lys | Gly | Leu | Pro | His | Ala | Pro | Ala | Leu | Ile | Lys | Arg | Thr | Asn | Arg | Arg | |
|     |     |     | 770 |     |     |     |     | 775 |     |     |     |     | 780 |     |     | |

| atc | ccc | gag | agg | aca | tca | cat | cga | gtg | gca | gat | cac | gcg | caa | gtg | gtc | 2400 |
| --- | --- | --- | --- | --- | --- | --- | --- | --- | --- | --- | --- | --- | --- | --- | --- | --- |
| Ile | Pro | Glu | Arg | Thr | Ser | His | Arg | Val | Ala | Asp | His | Ala | Gln | Val | Val | |
| 785 |     |     |     |     | 790 |     |     |     |     | 795 |     |     |     |     | 800 | |

-continued

| | |
|---|---|
| cgc gtg ctc gga ttc ttc cag tgt cac tcc cac ccc gca caa gcg ttc<br>Arg Val Leu Gly Phe Phe Gln Cys His Ser His Pro Ala Gln Ala Phe<br>805 810 815 | 2448 |
| gat gac gcc atg act caa ttt ggt atg tcg aga cac gga ctg ctg cag<br>Asp Asp Ala Met Thr Gln Phe Gly Met Ser Arg His Gly Leu Leu Gln<br>820 825 830 | 2496 |
| ctc ttt cgt aga gtc ggt gtc aca gaa ctg gag gcc cgc tcg ggc aca<br>Leu Phe Arg Arg Val Gly Val Thr Glu Leu Glu Ala Arg Ser Gly Thr<br>835 840 845 | 2544 |
| ctg cct ccc gcc tcc cag cgg tgg gac agg att ctc caa gcg agc ggt<br>Leu Pro Pro Ala Ser Gln Arg Trp Asp Arg Ile Leu Gln Ala Ser Gly<br>850 855 860 | 2592 |
| atg aaa cgc gcg aag cct tca cct acg tca act cag aca cct gac cag<br>Met Lys Arg Ala Lys Pro Ser Pro Thr Ser Thr Gln Thr Pro Asp Gln<br>865 870 875 880 | 2640 |
| gcg agc ctt cat gcg ttc gca gac tcg ctg gag agg gat ttg gac gcg<br>Ala Ser Leu His Ala Phe Ala Asp Ser Leu Glu Arg Asp Leu Asp Ala<br>885 890 895 | 2688 |
| ccc tcg ccc atg cat gaa ggg gac caa act cgc gcg tca gcc agc att<br>Pro Ser Pro Met His Glu Gly Asp Gln Thr Arg Ala Ser Ala Ser Ile<br>900 905 910 | 2736 |
| ttc aaa cca gaa gaa cta cga cag gca ctg atg cca act ttg gag gca<br>Phe Lys Pro Glu Glu Leu Arg Gln Ala Leu Met Pro Thr Leu Glu Ala<br>915 920 925 | 2784 |
| ctt tac cgt cag gat cca gaa tcc ctt ccc ttt cgt caa cct gtg gac<br>Leu Tyr Arg Gln Asp Pro Glu Ser Leu Pro Phe Arg Gln Pro Val Asp<br>930 935 940 | 2832 |
| cct cag ctt tta gga atc cct gat tac ttt gat att gtg aag agc ccc<br>Pro Gln Leu Leu Gly Ile Pro Asp Tyr Phe Asp Ile Val Lys Ser Pro<br>945 950 955 960 | 2880 |
| atg gat ctt tct acc att aag agg aag tta gac act gga cag tat cag<br>Met Asp Leu Ser Thr Ile Lys Arg Lys Leu Asp Thr Gly Gln Tyr Gln<br>965 970 975 | 2928 |
| gag ccc tgg cag tat gtc gat gat att tgg ctt atg ttc aat aat gcc<br>Glu Pro Trp Gln Tyr Val Asp Asp Ile Trp Leu Met Phe Asn Asn Ala<br>980 985 990 | 2976 |
| tgg tta tat aac cgg aaa aca tca cgg gta tac aaa tac tgc tcc aag<br>Trp Leu Tyr Asn Arg Lys Thr Ser Arg Val Tyr Lys Tyr Cys Ser Lys<br>995 1000 1005 | 3024 |
| ctc tct gag gtc ttt gaa caa gaa att gac cca gtg atg caa agc<br>Leu Ser Glu Val Phe Glu Gln Glu Ile Asp Pro Val Met Gln Ser<br>1010 1015 1020 | 3069 |
| ctt gga tac tgt tgt ggc aga aag ttg gag ttc tct cca cag aca<br>Leu Gly Tyr Cys Cys Gly Arg Lys Leu Glu Phe Ser Pro Gln Thr<br>1025 1030 1035 | 3114 |
| ctg tgt tgc tac ggc aaa cag ttg tgc aca ata cct cgt gat gcc<br>Leu Cys Cys Tyr Gly Lys Gln Leu Cys Thr Ile Pro Arg Asp Ala<br>1040 1045 1050 | 3159 |
| act tat tac agt tac cag aac agg tat cat ttc tgt gag aag tgt<br>Thr Tyr Tyr Ser Tyr Gln Asn Arg Tyr His Phe Cys Glu Lys Cys<br>1055 1060 1065 | 3204 |
| ttc aat gag atc caa ggg gag agc gtt tct ttg ggg gat gac cct<br>Phe Asn Glu Ile Gln Gly Glu Ser Val Ser Leu Gly Asp Asp Pro<br>1070 1075 1080 | 3249 |
| tcc cag cct caa act aca ata aat aaa gaa caa ttt tcc aag aga<br>Ser Gln Pro Gln Thr Thr Ile Asn Lys Glu Gln Phe Ser Lys Arg<br>1085 1090 1095 | 3294 |
| aaa aat gac aca ctg gat cct gaa ctg ttt gtt gaa tgt aca gag<br>Lys Asn Asp Thr Leu Asp Pro Glu Leu Phe Val Glu Cys Thr Glu<br>1100 1105 1110 | 3339 |

```
tgc gga aga aag atg cat cag atc tgt gtc ctt cac cat gag atc     3384
Cys Gly Arg Lys Met His Gln Ile Cys Val Leu His His Glu Ile
    1115            1120                1125 atc tgg cct gct gga ttc gtc tgt gat ggc tgt tta aag aaa agt     3429
Ile Trp Pro Ala Gly Phe Val Cys Asp Gly Cys Leu Lys Lys Ser
    1130            1135                1140 gca cga act agg aaa gaa aat aag ttt tct gct aaa agg ttg cca     3474
Ala Arg Thr Arg Lys Glu Asn Lys Phe Ser Ala Lys Arg Leu Pro
    1145            1150                1155 tct acc aga ctt ggc acc ttt cta gag aat cgt gtg aat gac ttt     3519
Ser Thr Arg Leu Gly Thr Phe Leu Glu Asn Arg Val Asn Asp Phe
    1160            1165                1170 ctg agg cga cag aat cac cct gag tca gga gag gtc act gtt aga     3564
Leu Arg Arg Gln Asn His Pro Glu Ser Gly Glu Val Thr Val Arg
    1175            1180                1185 gta gtt cat gct tct gac aaa acc gtg gaa gta aaa cca ggc atg     3609
Val Val His Ala Ser Asp Lys Thr Val Glu Val Lys Pro Gly Met
    1190            1195                1200 aaa gca agg ttt gtg gac agt gga gag atg gca gaa tcc ttt cca     3654
Lys Ala Arg Phe Val Asp Ser Gly Glu Met Ala Glu Ser Phe Pro
    1205            1210                1215 tac cga acc aaa gcc ctc ttt gcc ttt gaa gaa att gat ggt gtt     3699
Tyr Arg Thr Lys Ala Leu Phe Ala Phe Glu Glu Ile Asp Gly Val
    1220            1225                1230 gac ctg tgc ttc ttt ggc atg cat gtt caa gag tat ggc tct gac     3744
Asp Leu Cys Phe Phe Gly Met His Val Gln Glu Tyr Gly Ser Asp
    1235            1240                1245 tgc cct cca ccc aac cag agg aga gta tac ata tct tac ctc gat     3789
Cys Pro Pro Pro Asn Gln Arg Arg Val Tyr Ile Ser Tyr Leu Asp
    1250            1255                1260 agt gtt cat ttc ttc cgt cct aaa tgc ttg agg act gca gtc tat     3834
Ser Val His Phe Phe Arg Pro Lys Cys Leu Arg Thr Ala Val Tyr
    1265            1270                1275 cat gaa atc cta att gga tat tta gaa tat gtc aag aaa tta ggt     3879
His Glu Ile Leu Ile Gly Tyr Leu Glu Tyr Val Lys Lys Leu Gly
    1280            1285                1290 tac aca aca ggg cat att tgg gca tgt cca cca agt gag gga gat     3924
Tyr Thr Thr Gly His Ile Trp Ala Cys Pro Pro Ser Glu Gly Asp
    1295            1300                1305 gat tat atc ttc cat tgc cat cct cct gac cag aag ata ccc aag     3969
Asp Tyr Ile Phe His Cys His Pro Pro Asp Gln Lys Ile Pro Lys
    1310            1315                1320 ccc aag cga ctg cag gaa tgg tac aaa aaa atg ctt gac aag gct     4014
Pro Lys Arg Leu Gln Glu Trp Tyr Lys Lys Met Leu Asp Lys Ala
    1325            1330                1335 gta tca gag cgt att gtc cat gac tac aag gat att ttt aaa caa     4059
Val Ser Glu Arg Ile Val His Asp Tyr Lys Asp Ile Phe Lys Gln
    1340            1345                1350 gct act gaa gat aga tta aca agt gca aag gaa ttg cct tat ttc     4104
Ala Thr Glu Asp Arg Leu Thr Ser Ala Lys Glu Leu Pro Tyr Phe
    1355            1360                1365 gag ggt gat ttc tgg ccc aat gtt ctg gaa gaa agc att aag gaa     4149
Glu Gly Asp Phe Trp Pro Asn Val Leu Glu Glu Ser Ile Lys Glu
    1370            1375                1380 ctg gaa cag gag gaa gaa gag aga aaa cga gag gaa aac acc agc     4194
Leu Glu Gln Glu Glu Glu Glu Arg Lys Arg Glu Glu Asn Thr Ser
    1385            1390                1395 aat gaa agc aca gat gtg acc aag gga gac agc aaa aat gct aaa     4239
Asn Glu Ser Thr Asp Val Thr Lys Gly Asp Ser Lys Asn Ala Lys
```

```
aag aag aat aat aag aaa acc agc aaa aat aag agc agc ctg agt    4284
Lys Lys Asn Asn Lys Lys Thr Ser Lys Asn Lys Ser Ser Leu Ser
    1415                1420                1425 agg ggc aac aag aag aaa ccc ggg atg ccc aat gta tct aac gac    4329
Arg Gly Asn Lys Lys Lys Pro Gly Met Pro Asn Val Ser Asn Asp
1430                1435                1440 ctc tca cag aaa cta tat gcc acc atg gag aag cat aaa gag gtc    4374
Leu Ser Gln Lys Leu Tyr Ala Thr Met Glu Lys His Lys Glu Val
    1445                1450                1455 ttc ttt gtg atc cgc ctc att gct ggc cct gct gcc aac tcc ctg    4419
Phe Phe Val Ile Arg Leu Ile Ala Gly Pro Ala Ala Asn Ser Leu
1460                1465                1470 cct ccc att gtt gat cct gat cct ctc atc ccc tgc gat ctg atg    4464
Pro Pro Ile Val Asp Pro Asp Pro Leu Ile Pro Cys Asp Leu Met
    1475                1480                1485 gat ggt cgg gat gcg ttt ctc acg ctg gca agg gac aag cac ctg    4509
Asp Gly Arg Asp Ala Phe Leu Thr Leu Ala Arg Asp Lys His Leu
1490                1495                1500 gag ttc tct tca ctc cga aga gcc cag tgg tcc acc atg tgc atg    4554
Glu Phe Ser Ser Leu Arg Arg Ala Gln Trp Ser Thr Met Cys Met
    1505                1510                1515 ctg gtg gag ctg cac acg cag agc cag gac                        4584
Leu Val Glu Leu His Thr Gln Ser Gln Asp
1520                1525
```

<210> SEQ ID NO 20
<211> LENGTH: 1528
<212> TYPE: PRT
<213> ORGANISM: Artificial Sequence
<220> FEATURE:
<223> OTHER INFORMATION: Synthetic Construct

<400> SEQUENCE: 20

```
Arg Ile Phe Ile His Phe Arg Ile Gly Cys Glu Asn Leu Tyr Phe Gln
1               5                   10                  15

Ser Leu Glu Arg Asp Arg Thr Met Ile His Gly Val Pro Ala Ala Val
            20                  25                  30

Asp Leu Arg Thr Leu Gly Tyr Ser Gln Gln Gln Gln Glu Lys Ile Lys
        35                  40                  45

Pro Lys Val Arg Ser Thr Val Ala Gln His His Glu Ala Leu Val Gly
    50                  55                  60

His Gly Phe Thr His Ala His Ile Val Ala Leu Ser Gln His Pro Ala
65                  70                  75                  80

Ala Leu Gly Thr Val Ala Val Lys Tyr Gln Asp Met Ile Ala Ala Leu
                85                  90                  95

Pro Glu Ala Thr His Glu Ala Ile Val Gly Val Gly Lys Gln Trp Ser
            100                 105                 110

Gly Ala Arg Ala Leu Glu Ala Leu Leu Thr Val Ala Gly Glu Leu Arg
        115                 120                 125

Gly Pro Pro Leu Gln Leu Asp Thr Gly Gln Leu Leu Lys Ile Ala Lys
    130                 135                 140

Arg Gly Gly Val Thr Ala Val Glu Ala Val His Ala Trp Arg Asn Ala
145                 150                 155                 160

Leu Thr Gly Ala Pro Leu Asn Leu Thr Pro Asp Gln Val Val Ala Ile
                165                 170                 175

Ala Ser Asn Ile Gly Gly Lys Gln Ala Leu Glu Thr Val Gln Arg Leu
            180                 185                 190
```

```
Leu Pro Val Leu Cys Gln Asp His Gly Leu Thr Pro Glu Gln Val Val
        195                 200                 205

Ala Ile Ala Ser Asn Asn Gly Gly Lys Gln Ala Leu Glu Thr Val Gln
        210                 215                 220

Arg Leu Leu Pro Val Leu Cys Gln Ala His Gly Leu Thr Pro Asp Gln
225                 230                 235                 240

Val Val Ala Ile Ala Ser Asn Ile Gly Gly Lys Gln Ala Leu Glu Thr
                245                 250                 255

Val Gln Arg Leu Leu Pro Val Leu Cys Gln Ala His Gly Leu Thr Pro
            260                 265                 270

Ala Gln Val Val Ala Ile Ala Ser His Asp Gly Gly Lys Gln Ala Leu
            275                 280                 285

Glu Thr Val Gln Arg Leu Leu Pro Val Leu Cys Gln Asp His Gly Leu
            290                 295                 300

Thr Pro Asp Gln Val Val Ala Ile Ala Ser His Asp Gly Gly Lys Gln
305                 310                 315                 320

Ala Leu Glu Thr Val Gln Arg Leu Leu Pro Val Leu Cys Gln Asp His
                325                 330                 335

Gly Leu Thr Pro Glu Gln Val Val Ala Ile Ala Ser His Asp Gly Gly
            340                 345                 350

Lys Gln Ala Leu Glu Thr Val Gln Arg Leu Leu Pro Val Leu Cys Gln
            355                 360                 365

Ala His Gly Leu Thr Pro Asp Gln Val Val Ala Ile Ala Ser Asn Gly
            370                 375                 380

Gly Gly Lys Gln Ala Leu Glu Thr Val Gln Arg Leu Leu Pro Val Leu
385                 390                 395                 400

Cys Gln Ala His Gly Leu Thr Pro Ala Gln Val Val Ala Ile Ala Ser
                405                 410                 415

Asn Asn Gly Gly Lys Gln Ala Leu Glu Thr Val Gln Arg Leu Leu Pro
            420                 425                 430

Val Leu Cys Gln Asp His Gly Leu Thr Pro Asp Gln Val Val Ala Ile
            435                 440                 445

Ala Ser Asn Asn Gly Gly Lys Gln Ala Leu Glu Thr Val Gln Arg Leu
            450                 455                 460

Leu Pro Val Leu Cys Gln Asp His Gly Leu Thr Pro Glu Gln Val Val
465                 470                 475                 480

Ala Ile Ala Ser His Asp Gly Gly Lys Gln Ala Leu Glu Thr Val Gln
                485                 490                 495

Arg Leu Leu Pro Val Leu Cys Gln Ala His Gly Leu Thr Pro Asp Gln
            500                 505                 510

Val Val Ala Ile Ala Ser Asn Ile Gly Gly Lys Gln Ala Leu Glu Thr
            515                 520                 525

Val Gln Arg Leu Leu Pro Val Leu Cys Gln Ala His Gly Leu Thr Pro
            530                 535                 540

Ala Gln Val Val Ala Ile Ala Ser Asn Asn Gly Gly Lys Gln Ala Leu
545                 550                 555                 560

Glu Thr Val Gln Arg Leu Leu Pro Val Leu Cys Gln Asp His Gly Leu
                565                 570                 575

Thr Pro Asp Gln Val Val Ala Ile Ala Ser Asn Asn Gly Gly Lys Gln
            580                 585                 590

Ala Leu Glu Thr Val Gln Arg Leu Leu Pro Val Leu Cys Gln Asp His
            595                 600                 605
```

-continued

```
Gly Leu Thr Pro Glu Gln Val Val Ala Ile Ala Ser His Asp Gly
610                 615                 620

Lys Gln Ala Leu Glu Thr Val Gln Arg Leu Leu Pro Val Leu Cys Gln
625                 630                 635                 640

Ala His Gly Leu Thr Pro Asp Gln Val Val Ala Ile Ala Ser Asn Ile
            645                 650                 655

Gly Gly Lys Gln Ala Leu Glu Thr Val Gln Arg Leu Leu Pro Val Leu
                660                 665                 670

Cys Gln Ala His Gly Leu Thr Pro Ala Gln Val Val Ala Ile Ala Ser
            675                 680                 685

His Asp Gly Gly Lys Gln Ala Leu Glu Thr Val Gln Arg Leu Leu Pro
690                 695                 700

Val Leu Cys Gln Asp His Gly Leu Thr Pro Glu Gln Val Val Ala Ile
705                 710                 715                 720

Ala Ser His Asp Gly Gly Arg Pro Ala Leu Glu Ser Ile Val Ala Gln
                725                 730                 735

Leu Ser Arg Pro Asp Pro Ala Leu Ala Ala Leu Thr Asn Asp His Leu
            740                 745                 750

Val Ala Leu Ala Cys Leu Gly Gly Arg Pro Ala Leu Asp Ala Val Lys
755                 760                 765

Lys Gly Leu Pro His Ala Pro Ala Leu Ile Lys Arg Thr Asn Arg Arg
770                 775                 780

Ile Pro Glu Arg Thr Ser His Arg Val Ala Asp His Ala Gln Val Val
785                 790                 795                 800

Arg Val Leu Gly Phe Phe Gln Cys His Ser His Pro Ala Gln Ala Phe
                805                 810                 815

Asp Asp Ala Met Thr Gln Phe Gly Met Ser Arg His Gly Leu Leu Gln
            820                 825                 830

Leu Phe Arg Arg Val Gly Val Thr Glu Leu Glu Ala Arg Ser Gly Thr
            835                 840                 845

Leu Pro Pro Ala Ser Gln Arg Trp Asp Arg Ile Leu Gln Ala Ser Gly
850                 855                 860

Met Lys Arg Ala Lys Pro Ser Pro Thr Ser Thr Gln Thr Pro Asp Gln
865                 870                 875                 880

Ala Ser Leu His Ala Phe Ala Asp Ser Leu Glu Arg Asp Leu Asp Ala
            885                 890                 895

Pro Ser Pro Met His Glu Gly Asp Gln Thr Arg Ala Ser Ala Ser Ile
            900                 905                 910

Phe Lys Pro Glu Glu Leu Arg Gln Ala Leu Met Pro Thr Leu Glu Ala
            915                 920                 925

Leu Tyr Arg Gln Asp Pro Glu Ser Leu Pro Phe Arg Gln Pro Val Asp
930                 935                 940

Pro Gln Leu Leu Gly Ile Pro Asp Tyr Phe Asp Ile Val Lys Ser Pro
945                 950                 955                 960

Met Asp Leu Ser Thr Ile Lys Arg Lys Leu Asp Thr Gly Gln Tyr Gln
            965                 970                 975

Glu Pro Trp Gln Tyr Val Asp Asp Ile Trp Leu Met Phe Asn Asn Ala
            980                 985                 990

Trp Leu Tyr Asn Arg Lys Thr Ser  Arg Val Tyr Lys Tyr Cys Ser Lys
            995                 1000                1005

Leu Ser Glu Val Phe Glu Gln  Glu Ile Asp Pro Val  Met Gln Ser
    1010                1015                1020

Leu Gly Tyr Cys Cys Gly Arg  Lys Leu Glu Phe Ser  Pro Gln Thr
```

-continued

```
                1025                1030                1035
Leu Cys Cys Tyr Gly Lys Gln Leu Cys Thr Ile Pro Arg Asp Ala
       1040                1045                1050

Thr Tyr Tyr Ser Tyr Gln Asn Arg Tyr His Phe Cys Glu Lys Cys
       1055                1060                1065

Phe Asn Glu Ile Gln Gly Glu Ser Val Ser Leu Gly Asp Asp Pro
       1070                1075                1080

Ser Gln Pro Gln Thr Thr Ile Asn Lys Glu Gln Phe Ser Lys Arg
       1085                1090                1095

Lys Asn Asp Thr Leu Asp Pro Glu Leu Phe Val Glu Cys Thr Glu
       1100                1105                1110

Cys Gly Arg Lys Met His Gln Ile Cys Val Leu His His Glu Ile
       1115                1120                1125

Ile Trp Pro Ala Gly Phe Val Cys Asp Gly Cys Leu Lys Lys Ser
       1130                1135                1140

Ala Arg Thr Arg Lys Glu Asn Lys Phe Ser Ala Lys Arg Leu Pro
       1145                1150                1155

Ser Thr Arg Leu Gly Thr Phe Leu Glu Asn Arg Val Asn Asp Phe
       1160                1165                1170

Leu Arg Arg Gln Asn His Pro Glu Ser Gly Glu Val Thr Val Arg
       1175                1180                1185

Val Val His Ala Ser Asp Lys Thr Val Glu Val Lys Pro Gly Met
       1190                1195                1200

Lys Ala Arg Phe Val Asp Ser Gly Glu Met Ala Glu Ser Phe Pro
       1205                1210                1215

Tyr Arg Thr Lys Ala Leu Phe Ala Phe Glu Glu Ile Asp Gly Val
       1220                1225                1230

Asp Leu Cys Phe Phe Gly Met His Val Gln Glu Tyr Gly Ser Asp
       1235                1240                1245

Cys Pro Pro Pro Asn Gln Arg Arg Val Tyr Ile Ser Tyr Leu Asp
       1250                1255                1260

Ser Val His Phe Phe Arg Pro Lys Cys Leu Arg Thr Ala Val Tyr
       1265                1270                1275

His Glu Ile Leu Ile Gly Tyr Leu Glu Tyr Val Lys Lys Leu Gly
       1280                1285                1290

Tyr Thr Thr Gly His Ile Trp Ala Cys Pro Pro Ser Glu Gly Asp
       1295                1300                1305

Asp Tyr Ile Phe His Cys His Pro Pro Asp Gln Lys Ile Pro Lys
       1310                1315                1320

Pro Lys Arg Leu Gln Glu Trp Tyr Lys Lys Met Leu Asp Lys Ala
       1325                1330                1335

Val Ser Glu Arg Ile Val His Asp Tyr Lys Asp Ile Phe Lys Gln
       1340                1345                1350

Ala Thr Glu Asp Arg Leu Thr Ser Ala Lys Glu Leu Pro Tyr Phe
       1355                1360                1365

Glu Gly Asp Phe Trp Pro Asn Val Leu Glu Glu Ser Ile Lys Glu
       1370                1375                1380

Leu Glu Gln Glu Glu Glu Glu Arg Lys Arg Glu Glu Asn Thr Ser
       1385                1390                1395

Asn Glu Ser Thr Asp Val Thr Lys Gly Asp Ser Lys Asn Ala Lys
       1400                1405                1410

Lys Lys Asn Asn Lys Lys Thr Ser Lys Asn Lys Ser Ser Leu Ser
       1415                1420                1425
```

```
Arg Gly Asn Lys Lys Lys Pro Gly Met Pro Asn Val Ser Asn Asp
    1430                1435                1440

Leu Ser Gln Lys Leu Tyr Ala Thr Met Glu Lys His Lys Glu Val
    1445                1450                1455

Phe Phe Val Ile Arg Leu Ile Ala Gly Pro Ala Ala Asn Ser Leu
    1460                1465                1470

Pro Pro Ile Val Asp Pro Asp Pro Leu Ile Pro Cys Asp Leu Met
    1475                1480                1485

Asp Gly Arg Asp Ala Phe Leu Thr Leu Ala Arg Asp Lys His Leu
    1490                1495                1500

Glu Phe Ser Ser Leu Arg Arg Ala Gln Trp Ser Thr Met Cys Met
    1505                1510                1515

Leu Val Glu Leu His Thr Gln Ser Gln Asp
    1520                1525

<210> SEQ ID NO 21
<211> LENGTH: 2928
<212> TYPE: DNA
<213> ORGANISM: Artificial Sequence
<220> FEATURE:
<223> OTHER INFORMATION: NTP-TALE-miR-346-1-VP64
<220> FEATURE:
<221> NAME/KEY: CDS
<222> LOCATION: (1)..(2928)

<400> SEQUENCE: 21 agg atc ttc atc cac ttc cgg atc ggc tgc gaa aac ctg tat ttc caa     48
Arg Ile Phe Ile His Phe Arg Ile Gly Cys Glu Asn Leu Tyr Phe Gln
1               5                   10                  15 tct ctc gag cgc gat cgc acc atg atc cac gga gtc cca gca gcc gta     96
Ser Leu Glu Arg Asp Arg Thr Met Ile His Gly Val Pro Ala Ala Val
            20                  25                  30 gat ttg aga act ttg gga tat tca cag cag cag cag gaa aag atc aag    144
Asp Leu Arg Thr Leu Gly Tyr Ser Gln Gln Gln Gln Glu Lys Ile Lys
        35                  40                  45 ccc aaa gtg agg tcg aca gtc gcg cag cat cac gaa gcg ctg gtg ggt    192
Pro Lys Val Arg Ser Thr Val Ala Gln His His Glu Ala Leu Val Gly
    50                  55                  60 cat ggg ttt aca cat gcc cac atc gta gcc ttg tcg cag cac cct gca    240
His Gly Phe Thr His Ala His Ile Val Ala Leu Ser Gln His Pro Ala
65                  70                  75                  80 gcc ctt ggc acg gtc gcc gtc aag tac cag gac atg att gcg gcg ttg    288
Ala Leu Gly Thr Val Ala Val Lys Tyr Gln Asp Met Ile Ala Ala Leu
                85                  90                  95 ccg gaa gcc aca cat gag gcg atc gtc ggt gtg ggg aaa cag tgg agc    336
Pro Glu Ala Thr His Glu Ala Ile Val Gly Val Gly Lys Gln Trp Ser
            100                 105                 110 gga gcc cga gcg ctt gag gcc ctg ttg acg gtc gcg gga gag ctg aga    384
Gly Ala Arg Ala Leu Glu Ala Leu Leu Thr Val Ala Gly Glu Leu Arg
        115                 120                 125 ggg cct ccc ctt cag ctg gac acg ggc cag ttg ctg aag atc gcg aag    432
Gly Pro Pro Leu Gln Leu Asp Thr Gly Gln Leu Leu Lys Ile Ala Lys
    130                 135                 140 cgg gga gga gtc acg gcg gtc gag gcg gta cac gcg tgg cgc aat gcg    480
Arg Gly Gly Val Thr Ala Val Glu Ala Val His Ala Trp Arg Asn Ala
145                 150                 155                 160 ctc acg gga gca ccc ctc aac ctg acc ccg gac cag gtg gtt gca atc    528
Leu Thr Gly Ala Pro Leu Asn Leu Thr Pro Asp Gln Val Val Ala Ile
                165                 170                 175
```

```
gcg tca cac gat ggg gga aag cag gcc cta gaa acc gtt cag cga ctc      576
Ala Ser His Asp Gly Gly Lys Gln Ala Leu Glu Thr Val Gln Arg Leu
            180                 185                 190 ctg ccc gtc ctg tgc cag gac cac ggc ctg acc ccc gaa cag gtt gtc      624
Leu Pro Val Leu Cys Gln Asp His Gly Leu Thr Pro Glu Gln Val Val
        195                 200                 205 gct att gct agt aac ggc gga ggc aaa cag gcg ctg gaa aca gtt cag      672
Ala Ile Ala Ser Asn Gly Gly Gly Lys Gln Ala Leu Glu Thr Val Gln
    210                 215                 220 cgc ctc ttg ccg gtc ttg tgt cag gcc cac ggc ctg acc ccg gac cag      720
Arg Leu Leu Pro Val Leu Cys Gln Ala His Gly Leu Thr Pro Asp Gln
225                 230                 235                 240 gtg gtt gca atc gcg tca cac gat ggg gga aag cag gcc cta gaa acc      768
Val Val Ala Ile Ala Ser His Asp Gly Gly Lys Gln Ala Leu Glu Thr
                245                 250                 255 gtt cag cga ctc ctg ccc gtc ctg tgc cag gcc cac ggc ctg acc ccg      816
Val Gln Arg Leu Leu Pro Val Leu Cys Gln Ala His Gly Leu Thr Pro
            260                 265                 270 gcc cag gtg gtt gca atc gcg tca cac gat ggg gga aag cag gcc cta      864
Ala Gln Val Val Ala Ile Ala Ser His Asp Gly Gly Lys Gln Ala Leu
        275                 280                 285 gaa acc gtt cag cga ctc ctg ccc gtc ctg tgc cag gac cac ggc ctg      912
Glu Thr Val Gln Arg Leu Leu Pro Val Leu Cys Gln Asp His Gly Leu
    290                 295                 300 acc ccc gac cag gtt gtc gct att gct agt aac ggc gga ggc aaa cag      960
Thr Pro Asp Gln Val Val Ala Ile Ala Ser Asn Gly Gly Gly Lys Gln
305                 310                 315                 320 gcg ctg gaa aca gtt cag cgc ctc ttg ccg gtc ttg tgt cag gac cac     1008
Ala Leu Glu Thr Val Gln Arg Leu Leu Pro Val Leu Cys Gln Asp His
                325                 330                 335 ggc ctg acc ccg gaa cag gtg gtt gca atc gcg tca cac gat ggg gga     1056
Gly Leu Thr Pro Glu Gln Val Val Ala Ile Ala Ser His Asp Gly Gly
            340                 345                 350 aag cag gcc cta gaa acc gtt cag cga ctc ctg ccc gtc ctg tgc cag     1104
Lys Gln Ala Leu Glu Thr Val Gln Arg Leu Leu Pro Val Leu Cys Gln
        355                 360                 365 gcc cac ggc ctg acc ccc gac cag gtt gtc gct att gct agt aac ggc     1152
Ala His Gly Leu Thr Pro Asp Gln Val Val Ala Ile Ala Ser Asn Gly
    370                 375                 380 gga ggc aaa cag gcg ctg gaa aca gtt cag cgc ctc ttg ccg gtc ttg     1200
Gly Gly Lys Gln Ala Leu Glu Thr Val Gln Arg Leu Leu Pro Val Leu
385                 390                 395                 400 tgt cag gcc cac ggc ctg acc cca gcc cag gtt gtg gcc atc gcc agc     1248
Cys Gln Ala His Gly Leu Thr Pro Ala Gln Val Val Ala Ile Ala Ser
                405                 410                 415 aac ata ggt ggc aag cag gcc ctc gaa acc gtc cag aga ctg tta ccg     1296
Asn Ile Gly Gly Lys Gln Ala Leu Glu Thr Val Gln Arg Leu Leu Pro
            420                 425                 430 gtt ctc tgc cag gac cac ggc ctg acc cca gac caa gtt gtc gcg att     1344
Val Leu Cys Gln Asp His Gly Leu Thr Pro Asp Gln Val Val Ala Ile
        435                 440                 445 gca agc aac aac gga ggc aaa caa gcc tta gaa aca gtc cag aga ttg     1392
Ala Ser Asn Asn Gly Gly Lys Gln Ala Leu Glu Thr Val Gln Arg Leu
    450                 455                 460 ttg ccg gtg ctg tgc caa gac cac ggc ctg acc cca gaa caa gtt gtc     1440
Leu Pro Val Leu Cys Gln Asp His Gly Leu Thr Pro Glu Gln Val Val
465                 470                 475                 480 gcg att gca agc aac aac gga ggc aaa caa gcc tta gaa aca gtc cag     1488
Ala Ile Ala Ser Asn Asn Gly Gly Lys Gln Ala Leu Glu Thr Val Gln
                485                 490                 495
```

```
aga ttg ttg ccg gtg ctg tgc caa gcc cac ggc ctg acc cca gac cag    1536
Arg Leu Leu Pro Val Leu Cys Gln Ala His Gly Leu Thr Pro Asp Gln
            500                 505                 510 gtt gtg gcc atc gcc agc aac ata ggt ggc aag cag gcc ctc gaa acc    1584
Val Val Ala Ile Ala Ser Asn Ile Gly Gly Lys Gln Ala Leu Glu Thr
        515                 520                 525 gtc cag aga ctg tta ccg gtt ctc tgc cag gcc cac ggc ctg acc cca    1632
Val Gln Arg Leu Leu Pro Val Leu Cys Gln Ala His Gly Leu Thr Pro
    530                 535                 540 gcc caa gtt gtc gcg att gca agc aac aac gga ggc aaa caa gcc tta    1680
Ala Gln Val Val Ala Ile Ala Ser Asn Asn Gly Gly Lys Gln Ala Leu
545                 550                 555                 560 gaa aca gtc cag aga ttg ttg ccg gtg ctg tgc caa gac cac ggc ctg    1728
Glu Thr Val Gln Arg Leu Leu Pro Val Leu Cys Gln Asp His Gly Leu
                565                 570                 575 acc ccg gac cag gtg gtt gca atc gcg tca cac gat ggg gga aag cag    1776
Thr Pro Asp Gln Val Val Ala Ile Ala Ser His Asp Gly Gly Lys Gln
            580                 585                 590 gcc cta gaa acc gtt cag cga ctc ctg ccc gtc ctg tgc cag gac cac    1824
Ala Leu Glu Thr Val Gln Arg Leu Leu Pro Val Leu Cys Gln Asp His
        595                 600                 605 ggc ctg acc ccg gaa cag gtg gtt gca atc gcg tca cac gat ggg gga    1872
Gly Leu Thr Pro Glu Gln Val Val Ala Ile Ala Ser His Asp Gly Gly
    610                 615                 620 aag cag gcc cta gaa acc gtt cag cga ctc ctg ccc gtc ctg tgc cag    1920
Lys Gln Ala Leu Glu Thr Val Gln Arg Leu Leu Pro Val Leu Cys Gln
625                 630                 635                 640 gcc cac ggc ctg acc ccc gac cag gtt gtc gct att gct agt aac ggc    1968
Ala His Gly Leu Thr Pro Asp Gln Val Val Ala Ile Ala Ser Asn Gly
                645                 650                 655 gga ggc aaa cag gcg ctg gaa aca gtt cag cgc ctc ttg ccg gtc ttg    2016
Gly Gly Lys Gln Ala Leu Glu Thr Val Gln Arg Leu Leu Pro Val Leu
            660                 665                 670 tgt cag gcc cac ggc ctg acc ccg gcc cag gtg gtt gca atc gcg tca    2064
Cys Gln Ala His Gly Leu Thr Pro Ala Gln Val Val Ala Ile Ala Ser
        675                 680                 685 cac gat ggg gga aag cag gcc cta gaa acc gtt cag cga ctc ctg ccc    2112
His Asp Gly Gly Lys Gln Ala Leu Glu Thr Val Gln Arg Leu Leu Pro
    690                 695                 700 gtc ctg tgc cag gac cac ggc ctg acc cct gag cag gta gtg gct att    2160
Val Leu Cys Gln Asp His Gly Leu Thr Pro Glu Gln Val Val Ala Ile
705                 710                 715                 720 gca tcc cac gac ggg ggc aga ccc gca ctg gag tca atc gtg gcc cag    2208
Ala Ser His Asp Gly Gly Arg Pro Ala Leu Glu Ser Ile Val Ala Gln
                725                 730                 735 ctc tcg agg ccg gac ccc gcg ctg gcc gca ctc act aat gat cat ctt    2256
Leu Ser Arg Pro Asp Pro Ala Leu Ala Ala Leu Thr Asn Asp His Leu
            740                 745                 750 gta gcg ctg gcc tgc ctc ggc gga cga ccc gcc ttg gat gcg gtg aag    2304
Val Ala Leu Ala Cys Leu Gly Gly Arg Pro Ala Leu Asp Ala Val Lys
        755                 760                 765 aag ggg ctc ccg cac gcg cct gca ttg att aag cgg acc aac aga agg    2352
Lys Gly Leu Pro His Ala Pro Ala Leu Ile Lys Arg Thr Asn Arg Arg
    770                 775                 780 atc ccc gag agg aca tca cat cga gtg gca gat cac gcg caa gtg gtc    2400
Ile Pro Glu Arg Thr Ser His Arg Val Ala Asp His Ala Gln Val Val
785                 790                 795                 800 cgc gtg ctc gga ttc ttc cag tgt cac tcc cac ccc gca caa gcg ttc    2448
Arg Val Leu Gly Phe Phe Gln Cys His Ser His Pro Ala Gln Ala Phe
```

```
                    805                 810                 815
gat gac gcc atg act caa ttt ggt atg tcg aga cac gga ctg ctg cag    2496
Asp Asp Ala Met Thr Gln Phe Gly Met Ser Arg His Gly Leu Leu Gln
        820                 825                 830 ctc ttt cgt aga gtc ggt gtc aca gaa ctg gag gcc cgc tcg ggc aca    2544
Leu Phe Arg Arg Val Gly Val Thr Glu Leu Glu Ala Arg Ser Gly Thr
            835                 840                 845 ctg cct ccc gcc tcc cag cgg tgg gac agg att ctc caa gcg agc ggt    2592
Leu Pro Pro Ala Ser Gln Arg Trp Asp Arg Ile Leu Gln Ala Ser Gly
850                 855                 860 atg aaa cgc gcg aag cct tca cct acg tca act cag aca cct gac cag    2640
Met Lys Arg Ala Lys Pro Ser Pro Thr Ser Thr Gln Thr Pro Asp Gln
865                 870                 875                 880 gcg agc ctt cat gcg ttc gca gac tcg ctg gag agg gat ttg gac gcg    2688
Ala Ser Leu His Ala Phe Ala Asp Ser Leu Glu Arg Asp Leu Asp Ala
            885                 890                 895 ccc tcg ccc atg cat gaa ggg gac caa act cgc gcg tca gcc agc ccc    2736
Pro Ser Pro Met His Glu Gly Asp Gln Thr Arg Ala Ser Ala Ser Pro
        900                 905                 910 aag aag aag aga aag gtg gag gcc agc ggt tcc gga cgg gct gac gca    2784
Lys Lys Lys Arg Lys Val Glu Ala Ser Gly Ser Gly Arg Ala Asp Ala
    915                 920                 925 ttg gac gat ttt gat ctg gat atg ctg gga agt gac gcc ctc gat gat    2832
Leu Asp Asp Phe Asp Leu Asp Met Leu Gly Ser Asp Ala Leu Asp Asp
930                 935                 940 ttt gac ctt gac atg ctt ggt tcg gat gcc ctt gat gac ttt gac ctc    2880
Phe Asp Leu Asp Met Leu Gly Ser Asp Ala Leu Asp Asp Phe Asp Leu
945                 950                 955                 960 gac atg ctc ggc agt gac gcc ctt gat gat ttc gac ctg gac atg ctg    2928
Asp Met Leu Gly Ser Asp Ala Leu Asp Asp Phe Asp Leu Asp Met Leu
            965                 970                 975

<210> SEQ ID NO 22
<211> LENGTH: 976
<212> TYPE: PRT
<213> ORGANISM: Artificial Sequence
<220> FEATURE:
<223> OTHER INFORMATION: Synthetic Construct

<400> SEQUENCE: 22

Arg Ile Phe Ile His Phe Arg Ile Gly Cys Glu Asn Leu Tyr Phe Gln
1               5                   10                  15

Ser Leu Glu Arg Asp Arg Thr Met Ile His Gly Val Pro Ala Ala Val
            20                  25                  30

Asp Leu Arg Thr Leu Gly Tyr Ser Gln Gln Gln Gln Glu Lys Ile Lys
        35                  40                  45

Pro Lys Val Arg Ser Thr Val Ala Gln His His Glu Ala Leu Val Gly
    50                  55                  60

His Gly Phe Thr His Ala His Ile Val Ala Leu Ser Gln His Pro Ala
65                  70                  75                  80

Ala Leu Gly Thr Val Ala Val Lys Tyr Gln Asp Met Ile Ala Ala Leu
                85                  90                  95

Pro Glu Ala Thr His Glu Ala Ile Val Gly Val Gly Lys Gln Trp Ser
            100                 105                 110

Gly Ala Arg Ala Leu Glu Ala Leu Leu Thr Val Ala Gly Glu Leu Arg
        115                 120                 125

Gly Pro Pro Leu Gln Leu Asp Thr Gly Gln Leu Leu Lys Ile Ala Lys
    130                 135                 140
```

```
Arg Gly Gly Val Thr Ala Val Glu Ala Val His Ala Trp Arg Asn Ala
145                 150                 155                 160

Leu Thr Gly Ala Pro Leu Asn Leu Thr Pro Asp Gln Val Val Ala Ile
            165                 170                 175

Ala Ser His Asp Gly Gly Lys Gln Ala Leu Glu Thr Val Gln Arg Leu
        180                 185                 190

Leu Pro Val Leu Cys Gln Asp His Gly Leu Thr Pro Glu Gln Val Val
    195                 200                 205

Ala Ile Ala Ser Asn Gly Gly Lys Gln Ala Leu Glu Thr Val Gln
    210                 215                 220

Arg Leu Leu Pro Val Leu Cys Gln Ala His Gly Leu Thr Pro Asp Gln
225                 230                 235                 240

Val Val Ala Ile Ala Ser His Asp Gly Gly Lys Gln Ala Leu Glu Thr
            245                 250                 255

Val Gln Arg Leu Leu Pro Val Leu Cys Gln Ala His Gly Leu Thr Pro
        260                 265                 270

Ala Gln Val Val Ala Ile Ala Ser His Asp Gly Gly Lys Gln Ala Leu
    275                 280                 285

Glu Thr Val Gln Arg Leu Leu Pro Val Leu Cys Gln Asp His Gly Leu
290                 295                 300

Thr Pro Asp Gln Val Val Ala Ile Ala Ser Asn Gly Gly Lys Gln
305                 310                 315                 320

Ala Leu Glu Thr Val Gln Arg Leu Leu Pro Val Leu Cys Gln Asp His
            325                 330                 335

Gly Leu Thr Pro Glu Gln Val Val Ala Ile Ala Ser His Asp Gly Gly
        340                 345                 350

Lys Gln Ala Leu Glu Thr Val Gln Arg Leu Leu Pro Val Leu Cys Gln
    355                 360                 365

Ala His Gly Leu Thr Pro Asp Gln Val Val Ala Ile Ala Ser Asn Gly
    370                 375                 380

Gly Gly Lys Gln Ala Leu Glu Thr Val Gln Arg Leu Leu Pro Val Leu
385                 390                 395                 400

Cys Gln Ala His Gly Leu Thr Pro Ala Gln Val Val Ala Ile Ala Ser
            405                 410                 415

Asn Ile Gly Gly Lys Gln Ala Leu Glu Thr Val Gln Arg Leu Leu Pro
        420                 425                 430

Val Leu Cys Gln Asp His Gly Leu Thr Pro Asp Gln Val Val Ala Ile
    435                 440                 445

Ala Ser Asn Asn Gly Gly Lys Gln Ala Leu Glu Thr Val Gln Arg Leu
450                 455                 460

Leu Pro Val Leu Cys Gln Asp His Gly Leu Thr Pro Glu Gln Val Val
465                 470                 475                 480

Ala Ile Ala Ser Asn Asn Gly Gly Lys Gln Ala Leu Glu Thr Val Gln
            485                 490                 495

Arg Leu Leu Pro Val Leu Cys Gln Ala His Gly Leu Thr Pro Asp Gln
        500                 505                 510

Val Val Ala Ile Ala Ser Asn Ile Gly Gly Lys Gln Ala Leu Glu Thr
    515                 520                 525

Val Gln Arg Leu Leu Pro Val Leu Cys Gln Ala His Gly Leu Thr Pro
    530                 535                 540

Ala Gln Val Val Ala Ile Ala Ser Asn Asn Gly Gly Lys Gln Ala Leu
545                 550                 555                 560

Glu Thr Val Gln Arg Leu Leu Pro Val Leu Cys Gln Asp His Gly Leu
```

```
                565                 570                 575
Thr Pro Asp Gln Val Ala Ile Ala Ser His Asp Gly Lys Gln
            580                 585                 590

Ala Leu Glu Thr Val Gln Arg Leu Leu Pro Val Leu Cys Gln Asp His
            595                 600                 605

Gly Leu Thr Pro Glu Gln Val Ala Ile Ala Ser His Asp Gly Gly
            610                 615                 620

Lys Gln Ala Leu Glu Thr Val Gln Arg Leu Leu Pro Val Leu Cys Gln
625                 630                 635                 640

Ala His Gly Leu Thr Pro Asp Gln Val Ala Ile Ala Ser Asn Gly
            645                 650                 655

Gly Gly Lys Gln Ala Leu Glu Thr Val Gln Arg Leu Leu Pro Val Leu
            660                 665                 670

Cys Gln Ala His Gly Leu Thr Pro Ala Gln Val Ala Ile Ala Ser
            675                 680                 685

His Asp Gly Gly Lys Gln Ala Leu Glu Thr Val Gln Arg Leu Leu Pro
            690                 695                 700

Val Leu Cys Gln Asp His Gly Leu Thr Pro Glu Gln Val Val Ala Ile
705                 710                 715                 720

Ala Ser His Asp Gly Gly Arg Pro Ala Leu Glu Ser Ile Val Ala Gln
            725                 730                 735

Leu Ser Arg Pro Asp Pro Ala Leu Ala Ala Leu Thr Asn Asp His Leu
            740                 745                 750

Val Ala Leu Ala Cys Leu Gly Gly Arg Pro Ala Leu Asp Ala Val Lys
            755                 760                 765

Lys Gly Leu Pro His Ala Pro Ala Leu Ile Lys Arg Thr Asn Arg Arg
            770                 775                 780

Ile Pro Glu Arg Thr Ser His Arg Val Ala Asp His Ala Gln Val Val
785                 790                 795                 800

Arg Val Leu Gly Phe Phe Gln Cys His Ser His Pro Ala Gln Ala Phe
            805                 810                 815

Asp Asp Ala Met Thr Gln Phe Gly Met Ser Arg His Gly Leu Leu Gln
            820                 825                 830

Leu Phe Arg Arg Val Gly Val Thr Glu Leu Glu Ala Arg Ser Gly Thr
            835                 840                 845

Leu Pro Pro Ala Ser Gln Arg Trp Asp Arg Ile Leu Gln Ala Ser Gly
            850                 855                 860

Met Lys Arg Ala Lys Pro Ser Pro Thr Ser Thr Gln Thr Pro Asp Gln
865                 870                 875                 880

Ala Ser Leu His Ala Phe Ala Asp Ser Leu Glu Arg Asp Leu Asp Ala
            885                 890                 895

Pro Ser Pro Met His Glu Gly Asp Gln Thr Arg Ala Ser Ala Ser Pro
            900                 905                 910

Lys Lys Lys Arg Lys Val Glu Ala Ser Gly Ser Gly Arg Ala Asp Ala
            915                 920                 925

Leu Asp Asp Phe Asp Leu Asp Met Leu Gly Ser Asp Ala Leu Asp Asp
            930                 935                 940

Phe Asp Leu Asp Met Leu Gly Ser Asp Ala Leu Asp Asp Phe Asp Leu
945                 950                 955                 960

Asp Met Leu Gly Ser Asp Ala Leu Asp Asp Phe Asp Leu Asp Met Leu
            965                 970                 975

<210> SEQ ID NO 23
```

```
<211> LENGTH: 30
<212> TYPE: DNA
<213> ORGANISM: Artificial Sequence
<220> FEATURE:
<223> OTHER INFORMATION: NTP

<400> SEQUENCE: 23
aggatcttca tccacttccg gatcggctgc                                    30

<210> SEQ ID NO 24
<211> LENGTH: 687
<212> TYPE: DNA
<213> ORGANISM: Schistosoma japonicum

<400> SEQUENCE: 24 atgtcccta tactaggtta ttggaaaatt aagggccttg tgcaacccac tcgacttctt    60
ttggaatatc ttgaagaaaa atatgaagag catttgtatg agcgcgatga aggtgataaa   120
tggcgaaaca aaaagtttga attgggtttg gagtttccca atcttcctta ttatattgat   180
ggtgatgtta aattaacaca gtctatggcc atcatacgtt atatagctga caagcacaac   240
atgttgggtg gttgtccaaa agagcgtgca gagatttcaa tgcttgaagg agcggttttg   300
gatattagat acggtgtttc gagaattgca tatagtaaag actttgaaac tctcaaagtt   360
gattttctta gcaagctacc tgaaatgctg aaaatgttcg aagatcgttt atgtcataaa   420
acatatttaa atggtgatca tgtaacccat cctgacttca tgttgtatga cgctcttgat   480
gttgttttat acatggaccc aatgtgcctg gatgcgttcc caaaattagt ttgttttaaa   540
aaacgtattg aagctatccc acaaattgat aagtacttga atccagcaa  gtatatagca   600 tggcctttgc agggctggca agccacgttt ggtggtggcg accatcctcc aaaatcggat   660
ctggaagttc tgttccaggg gcccctg                                      687

<210> SEQ ID NO 25
<211> LENGTH: 21
<212> TYPE: DNA
<213> ORGANISM: Artificial Sequence
<220> FEATURE:
<223> OTHER INFORMATION: TEV

<400> SEQUENCE: 25
gaaaacctgt atttccaatc t                                             21

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
gtcacagctt gtctgtaagc g                                             21

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
aaagggcctc gtgatacgcc t                                             21
```

<210> SEQ ID NO 28
<211> LENGTH: 1687
<212> TYPE: DNA
<213> ORGANISM: Artificial Sequence
<220> FEATURE:
<223> OTHER INFORMATION: deltaTALE-VP64

<400> SEQUENCE: 28

```
accatgatcc acggagtccc agcagccgta gatttgagaa ctttgggata ttcacagcag      60
cagcaggaaa agatcaagcc caaagtgagg tcgacagtcg cgcagcatca cgaagcgctg     120
gtgggtcatg ggtttacaca tgcccacatc gtagccttgt cgcagcaccc tgcagcCCtt     180
ggcacggtcg ccgtcaagta ccaggacatg attgcggcgt tgccggaagc cacacatgag     240
gcgatcgtcg gtgtggggaa acagtggagc ggagcccgag cgcttgaggc cctgttgacg     300
gtcgcgggag agctgagagg gcctcccctt cagctggaca cgggccagtt gctgaagatc     360
gcgaagcggg gaggagtcac ggcggtcgag gcggtacacg cgtggcgcaa tgcgctcacg     420
ggagcacccc tcaaggagac gggcgccgct acagggcgcg tcccattcgc cattcaggct     480
gcgcaactgt tgggaagggc gatcggtgcg ggcctcttcg ctattacgcc agctggcgaa     540
agggggatgt gctgcaaggc gattaagttg ggtaacgcca gggttttccc agtcacgacg     600
ttgtaaaacg acggccagtg agcgcgcgta atacgactca ctataggcg aattgggtac     660
cgggcccccc ctcgaggtcc tccagctttt gttcccttta gtgagggtta attgcgcgct     720
tggcgtaatc atggtcatag ctgtttcctg tgtgaaattg ttatccgctc acaattccac     780
acaacatacg agccggaagc ataaagtgta aagcctgggg tgcctaatga gtgagctaac     840
tcacattaat tgcgttgcgc tcactgcccg ctttccaccg tcgtctcca ccctgagca      900
ggtagtggct attgcatccc acgacggggg cagacccgca ctggagtcaa tcgtggccca     960
gctctcgagg ccggaccccg cgctggccgc actcactaat gatcatcttg tagcgctggc    1020
ctgcctcggc ggacgacccg ccttggatgc ggtgaagaag gggctcccgc acgcgcctgc    1080
attgattaag cggaccaaca gaaggatccc cgagaggaca tcacatcgag tggcagatca    1140
cgcgcaagtg gtccgcgtgc tcggattctt ccagtgtcac tcccaccccg cacaagcgtt    1200
cgatgacgcc atgactcaat ttggtatgtc gagacacgga ctgctgcagc tctttcgtag    1260
agtcggtgtc acagaactgg aggcccgctc gggcacactg cctcccgcct cccagcggtg    1320
ggacaggatt ctccaagcga gcggtatgaa acgcgcgaag ccttcaccta cgtcaactca    1380
gacacctgac caggcgagcc ttcatgcgtt cgcagactcg ctggagaggg atttggacgc    1440
gccctcgccc atgcatgaag gggaccaaac tcgcgcgtca gccagcccca agaagaagag    1500
aaaggtggag gccagcggtt ccggacgggc tgacgcattg gacgattttg atctggatat    1560
gctgggaagt gacgccctcg atgatttgat ccttgacatg cttggttcgg atgcccttga    1620
tgactttgac ctcgacatgc tcggcagtga cgccctttgat gatttcgacc tggacatgct    1680
ggtttaa                                                              1687
```

<210> SEQ ID NO 29
<211> LENGTH: 50
<212> TYPE: PRT
<213> ORGANISM: Artificial Sequence
<220> FEATURE:
<223> OTHER INFORMATION: VP64

<400> SEQUENCE: 29

```
Asp Ala Leu Asp Asp Phe Asp Leu Asp Met Leu Gly Ser Asp Ala Leu
1               5                   10                  15
```

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45

Met Leu
    50

<210> SEQ ID NO 30
<211> LENGTH: 38
<212> TYPE: DNA
<213> ORGANISM: Artificial Sequence
<220> FEATURE:
<223> OTHER INFORMATION: Primer

<400> SEQUENCE: 30
cccgcgatcg caccatgatc cacggagtcc cagcagcc                              38

<210> SEQ ID NO 31
<211> LENGTH: 35
<212> TYPE: DNA
<213> ORGANISM: Artificial Sequence
<220> FEATURE:
<223> OTHER INFORMATION: Primer

<400> SEQUENCE: 31
gatttcgacc tggacatgct gtaagcggcc gcggg                                 35

<210> SEQ ID NO 32
<211> LENGTH: 36
<212> TYPE: DNA
<213> ORGANISM: Artificial Sequence
<220> FEATURE:
<223> OTHER INFORMATION: Primer

<400> SEQUENCE: 32
cgcgcgtcag ccagcgacgc attggacgat tttgat                                36

<210> SEQ ID NO 33
<211> LENGTH: 36
<212> TYPE: DNA
<213> ORGANISM: Artificial Sequence
<220> FEATURE:
<223> OTHER INFORMATION: Primer

<400> SEQUENCE: 33
ggccgcagtt taaacaaaca gagatgtgtc gaagat                                36

<210> SEQ ID NO 34
<211> LENGTH: 520
<212> TYPE: PRT
<213> ORGANISM: Artificial Sequence
<220> FEATURE:
<223> OTHER INFORMATION: VPR

<400> SEQUENCE: 34

Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45

Met Leu Ser Ser Gly Ser Pro Lys Lys Lys Arg Lys Val Gly Ser Gln
    50                  55                  60

-continued

```
Tyr Leu Pro Asp Thr Asp Arg His Arg Ile Glu Glu Lys Arg Lys
 65                  70                  75                  80

Arg Thr Tyr Glu Thr Phe Lys Ser Ile Met Lys Lys Ser Pro Phe Ser
                 85                  90                  95

Gly Pro Thr Asp Pro Arg Pro Pro Arg Arg Ile Ala Val Pro Ser
            100                 105                 110

Arg Ser Ser Ala Ser Val Pro Lys Pro Ala Pro Gln Pro Tyr Pro Phe
            115                 120                 125

Thr Ser Ser Leu Ser Thr Ile Asn Tyr Asp Glu Phe Pro Thr Met Val
130                 135                 140

Phe Pro Ser Gly Gln Ile Ser Gln Ala Ser Ala Leu Ala Pro Ala Pro
145                 150                 155                 160

Pro Gln Val Leu Pro Gln Ala Pro Ala Pro Ala Pro Ala Pro Ala Met
                165                 170                 175

Val Ser Ala Leu Ala Gln Ala Pro Ala Pro Val Pro Val Leu Ala Pro
            180                 185                 190

Gly Pro Pro Gln Ala Val Ala Pro Pro Ala Pro Lys Pro Thr Gln Ala
            195                 200                 205

Gly Glu Gly Thr Leu Ser Glu Ala Leu Leu Gln Leu Gln Phe Asp Asp
210                 215                 220

Glu Asp Leu Gly Ala Leu Leu Gly Asn Ser Thr Asp Pro Ala Val Phe
225                 230                 235                 240

Thr Asp Leu Ala Ser Val Asp Asn Ser Glu Phe Gln Gln Leu Leu Asn
                245                 250                 255

Gln Gly Ile Pro Val Ala Pro His Thr Thr Glu Pro Met Leu Met Glu
            260                 265                 270

Tyr Pro Glu Ala Ile Thr Arg Leu Val Thr Gly Ala Gln Arg Pro Pro
            275                 280                 285

Asp Pro Ala Pro Ala Pro Leu Gly Ala Pro Gly Leu Pro Asn Gly Leu
            290                 295                 300

Leu Ser Gly Asp Glu Asp Phe Ser Ser Ile Ala Asp Met Asp Phe Ser
305                 310                 315                 320

Ala Leu Leu Gly Ser Gly Ser Gly Ser Arg Asp Ser Arg Glu Gly Met
                325                 330                 335

Phe Leu Pro Lys Pro Glu Ala Gly Ser Ala Ile Ser Asp Val Phe Glu
            340                 345                 350

Gly Arg Glu Val Cys Gln Pro Lys Arg Ile Arg Pro Phe His Pro Pro
            355                 360                 365

Gly Ser Pro Trp Ala Asn Arg Pro Leu Pro Ala Ser Leu Ala Pro Thr
            370                 375                 380

Pro Thr Gly Pro Val His Glu Pro Val Gly Ser Leu Thr Pro Ala Pro
385                 390                 395                 400

Val Pro Gln Pro Leu Asp Pro Ala Pro Ala Val Thr Pro Glu Ala Ser
                405                 410                 415

His Leu Leu Glu Asp Pro Asp Glu Glu Thr Ser Gln Ala Val Lys Ala
            420                 425                 430

Leu Arg Glu Met Ala Asp Thr Val Ile Pro Gln Lys Glu Glu Ala Ala
            435                 440                 445

Ile Cys Gly Gln Met Asp Leu Ser His Pro Pro Pro Arg Gly His Leu
            450                 455                 460

Asp Glu Leu Thr Thr Thr Leu Glu Ser Met Thr Glu Asp Leu Asn Leu
465                 470                 475                 480
```

-continued

```
Asp Ser Pro Leu Thr Pro Glu Leu Asn Glu Ile Leu Asp Thr Phe Leu
            485                 490                 495

Asn Asp Glu Cys Leu Leu His Ala Met His Ile Ser Thr Gly Leu Ser
        500                 505                 510

Ile Phe Asp Thr Ser Leu Phe Val
        515             520

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
gtttaaactg cggccgcgtc g                                              21

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
gctggctgac gcgcgagttt g                                              21

<210> SEQ ID NO 37
<211> LENGTH: 36
<212> TYPE: DNA
<213> ORGANISM: Artificial Sequence
<220> FEATURE:
<223> OTHER INFORMATION: Primer

<400> SEQUENCE: 37
cgcgcgtcag ccagcatttt caaaccagaa gaacta                              36

<210> SEQ ID NO 38
<211> LENGTH: 36
<212> TYPE: DNA
<213> ORGANISM: Artificial Sequence
<220> FEATURE:
<223> OTHER INFORMATION: Primer

<400> SEQUENCE: 38
ggccgcagtt taaactcctg gctctgcgtg tgcagc                              36

<210> SEQ ID NO 39
<211> LENGTH: 617
<212> TYPE: PRT
<213> ORGANISM: Homo sapiens

<400> SEQUENCE: 39

Ile Phe Lys Pro Glu Glu Leu Arg Gln Ala Leu Met Pro Thr Leu Glu
1               5                   10                  15

Ala Leu Tyr Arg Gln Asp Pro Glu Ser Leu Pro Phe Arg Gln Pro Val
            20                  25                  30

Asp Pro Gln Leu Leu Gly Ile Pro Asp Tyr Phe Asp Ile Val Lys Ser
        35                  40                  45

Pro Met Asp Leu Ser Thr Ile Lys Arg Lys Leu Asp Thr Gly Gln Tyr
    50                  55                  60

Gln Glu Pro Trp Gln Tyr Val Asp Asp Ile Trp Leu Met Phe Asn Asn
65                  70                  75                  80
```

```
Ala Trp Leu Tyr Asn Arg Lys Thr Ser Arg Val Tyr Lys Tyr Cys Ser
                85                  90                  95

Lys Leu Ser Glu Val Phe Glu Gln Glu Ile Asp Pro Val Met Gln Ser
            100                 105                 110

Leu Gly Tyr Cys Cys Gly Arg Lys Leu Glu Phe Ser Pro Gln Thr Leu
        115                 120                 125

Cys Cys Tyr Gly Lys Gln Leu Cys Thr Ile Pro Arg Asp Ala Thr Tyr
    130                 135                 140

Tyr Ser Tyr Gln Asn Arg Tyr His Phe Cys Glu Lys Cys Phe Asn Glu
145                 150                 155                 160

Ile Gln Gly Glu Ser Val Ser Leu Gly Asp Asp Pro Ser Gln Pro Gln
                165                 170                 175

Thr Thr Ile Asn Lys Glu Gln Phe Ser Lys Arg Lys Asn Asp Thr Leu
            180                 185                 190

Asp Pro Glu Leu Phe Val Glu Cys Thr Glu Cys Gly Arg Lys Met His
        195                 200                 205

Gln Ile Cys Val Leu His His Glu Ile Ile Trp Pro Ala Gly Phe Val
    210                 215                 220

Cys Asp Gly Cys Leu Lys Lys Ser Ala Arg Thr Arg Lys Glu Asn Lys
225                 230                 235                 240

Phe Ser Ala Lys Arg Leu Pro Ser Thr Arg Leu Gly Thr Phe Leu Glu
                245                 250                 255

Asn Arg Val Asn Asp Phe Leu Arg Arg Gln Asn His Pro Glu Ser Gly
            260                 265                 270

Glu Val Thr Val Arg Val Val His Ala Ser Asp Lys Thr Val Glu Val
        275                 280                 285

Lys Pro Gly Met Lys Ala Arg Phe Val Asp Ser Gly Glu Met Ala Glu
    290                 295                 300

Ser Phe Pro Tyr Arg Thr Lys Ala Leu Phe Ala Phe Glu Glu Ile Asp
305                 310                 315                 320

Gly Val Asp Leu Cys Phe Phe Gly Met His Val Gln Glu Tyr Gly Ser
                325                 330                 335

Asp Cys Pro Pro Pro Asn Gln Arg Arg Val Tyr Ile Ser Tyr Leu Asp
            340                 345                 350

Ser Val His Phe Phe Arg Pro Lys Cys Leu Arg Thr Ala Val Tyr His
        355                 360                 365

Glu Ile Leu Ile Gly Tyr Leu Glu Tyr Val Lys Lys Leu Gly Tyr Thr
    370                 375                 380

Thr Gly His Ile Trp Ala Cys Pro Pro Ser Glu Gly Asp Asp Tyr Ile
385                 390                 395                 400

Phe His Cys His Pro Pro Asp Gln Lys Ile Pro Lys Pro Lys Arg Leu
                405                 410                 415

Gln Glu Trp Tyr Lys Lys Met Leu Asp Lys Ala Val Ser Glu Arg Ile
            420                 425                 430

Val His Asp Tyr Lys Asp Ile Phe Lys Gln Ala Thr Glu Asp Arg Leu
        435                 440                 445

Thr Ser Ala Lys Glu Leu Pro Tyr Phe Glu Gly Asp Phe Trp Pro Asn
    450                 455                 460

Val Leu Glu Glu Ser Ile Lys Glu Leu Glu Gln Glu Glu Glu Glu Arg
465                 470                 475                 480

Lys Arg Glu Glu Asn Thr Ser Asn Glu Ser Thr Asp Val Thr Lys Gly
                485                 490                 495
```

```
Asp Ser Lys Asn Ala Lys Lys Asn Asn Lys Lys Thr Ser Lys Asn
            500                 505                 510

Lys Ser Ser Leu Ser Arg Gly Asn Lys Lys Pro Gly Met Pro Asn
    515                 520                 525

Val Ser Asn Asp Leu Ser Gln Lys Leu Tyr Ala Thr Met Glu Lys His
    530                 535                 540

Lys Glu Val Phe Phe Val Ile Arg Leu Ile Ala Gly Pro Ala Ala Asn
545                 550                 555                 560

Ser Leu Pro Pro Ile Val Asp Pro Asp Leu Ile Pro Cys Asp Leu
                565                 570                 575

Met Asp Gly Arg Asp Ala Phe Leu Thr Leu Ala Arg Asp Lys His Leu
            580                 585                 590

Glu Phe Ser Ser Leu Arg Arg Ala Gln Trp Ser Thr Met Cys Met Leu
            595                 600                 605

Val Glu Leu His Thr Gln Ser Gln Asp
    610                 615

<210> SEQ ID NO 40
<211> LENGTH: 36
<212> TYPE: DNA
<213> ORGANISM: Artificial Sequence
<220> FEATURE:
<223> OTHER INFORMATION: Primer

<400> SEQUENCE: 40
cgcgcgtcag ccagcggcat catcgagttc catgtc                          36

<210> SEQ ID NO 41
<211> LENGTH: 36
<212> TYPE: DNA
<213> ORGANISM: Artificial Sequence
<220> FEATURE:
<223> OTHER INFORMATION: Primer

<400> SEQUENCE: 41
ggccgcagtt taaaccttgt caatgaggcc tccctc                          36

<210> SEQ ID NO 42
<211> LENGTH: 341
<212> TYPE: PRT
<213> ORGANISM: Homo sapiens

<400> SEQUENCE: 42

Gly Ile Ile Glu Phe His Val Ile Gly Asn Ser Leu Thr Pro Lys Ala
1               5                   10                  15

Asn Arg Arg Val Leu Leu Trp Leu Val Gly Leu Gln Asn Val Phe Ser
            20                  25                  30

His Gln Leu Pro Arg Met Pro Lys Glu Tyr Ile Ala Arg Leu Val Phe
        35                  40                  45

Asp Pro Lys His Lys Thr Leu Ala Leu Ile Lys Asp Gly Arg Val Ile
    50                  55                  60

Gly Gly Ile Cys Phe Arg Met Phe Pro Thr Gln Gly Phe Thr Glu Ile
65                  70                  75                  80

Val Phe Cys Ala Val Thr Ser Asn Glu Gln Val Lys Gly Tyr Gly Thr
                85                  90                  95

His Leu Met Asn His Leu Lys Glu Tyr His Ile Lys His Asn Ile Leu
            100                 105                 110

Tyr Phe Leu Thr Tyr Ala Asp Glu Tyr Ala Ile Gly Tyr Phe Lys Lys
        115                 120                 125
```

```
Gln Gly Phe Ser Lys Asp Ile Lys Val Pro Lys Ser Arg Tyr Leu Gly
    130                 135                 140
Tyr Ile Lys Asp Tyr Glu Gly Ala Thr Leu Met Glu Cys Glu Leu Asn
145                 150                 155                 160
Pro Arg Ile Pro Tyr Thr Glu Leu Ser His Ile Ile Lys Gln Lys
            165                 170                 175
Glu Ile Ile Lys Lys Leu Ile Glu Arg Lys Gln Ala Gln Ile Arg Lys
            180                 185                 190
Val Tyr Pro Gly Leu Ser Cys Phe Lys Glu Gly Val Arg Gln Ile Pro
            195                 200                 205
Val Glu Ser Val Pro Gly Ile Arg Glu Thr Gly Trp Lys Pro Leu Gly
    210                 215                 220
Lys Glu Lys Gly Lys Glu Leu Lys Asp Pro Asp Gln Leu Tyr Thr Thr
225                 230                 235                 240
Leu Lys Asn Leu Leu Ala Gln Ile Lys Ser His Pro Ser Ala Trp Pro
            245                 250                 255
Phe Met Glu Pro Val Lys Lys Ser Glu Ala Pro Asp Tyr Tyr Glu Val
            260                 265                 270
Ile Arg Phe Pro Ile Asp Leu Lys Thr Met Thr Glu Arg Leu Arg Ser
            275                 280                 285
Arg Tyr Tyr Val Thr Arg Lys Leu Phe Val Ala Asp Leu Gln Arg Val
    290                 295                 300
Ile Ala Asn Cys Arg Glu Tyr Asn Pro Pro Asp Ser Glu Tyr Cys Arg
305                 310                 315                 320
Cys Ala Ser Ala Leu Glu Lys Phe Phe Tyr Phe Lys Leu Lys Glu Gly
            325                 330                 335
Gly Leu Ile Asp Lys
            340

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
ggagcaagtt gcaaagcatt g                                             21

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
tgggagcagc tactggatct t                                             21

<210> SEQ ID NO 45
<211> LENGTH: 19
<212> TYPE: DNA
<213> ORGANISM: Artificial Sequence
<220> FEATURE:
<223> OTHER INFORMATION: Primer

<400> SEQUENCE: 45
gatcggcggc tccatcctg                                                19
```

```
<210> SEQ ID NO 46
<211> LENGTH: 22
<212> TYPE: DNA
<213> ORGANISM: Artificial Sequence
<220> FEATURE:
<223> OTHER INFORMATION: Primer

<400> SEQUENCE: 46
gactcgtcat actcctgctt gc                                              22

<210> SEQ ID NO 47
<211> LENGTH: 23
<212> TYPE: DNA
<213> ORGANISM: Artificial Sequence
<220> FEATURE:
<223> OTHER INFORMATION: Primer

<400> SEQUENCE: 47
tgtctgcccg catgcctgcc tct                                             23

<210> SEQ ID NO 48
<211> LENGTH: 22
<212> TYPE: DNA
<213> ORGANISM: Artificial Sequence
<220> FEATURE:
<223> OTHER INFORMATION: Primer

<400> SEQUENCE: 48
gtgctcgctt cggcagcaca ta                                              22

<210> SEQ ID NO 49
<211> LENGTH: 18
<212> TYPE: DNA
<213> ORGANISM: Homo sapiens

<400> SEQUENCE: 49
tcagagggac gcagtctt                                                   18

<210> SEQ ID NO 50
<211> LENGTH: 18
<212> TYPE: DNA
<213> ORGANISM: Homo sapiens

<400> SEQUENCE: 50
ccccacgtgg cggaggga                                                   18

<210> SEQ ID NO 51
<211> LENGTH: 18
<212> TYPE: DNA
<213> ORGANISM: Homo sapiens

<400> SEQUENCE: 51
tagaccctgg caggcact                                                   18

<210> SEQ ID NO 52
<211> LENGTH: 18
<212> TYPE: DNA
<213> ORGANISM: Homo sapiens

<400> SEQUENCE: 52
agaggctcct agaggaga                                                   18

<210> SEQ ID NO 53
<211> LENGTH: 20
```

```
<212> TYPE: PRT
<213> ORGANISM: Artificial Sequence
<220> FEATURE:
<223> OTHER INFORMATION: Cell Penetrating Peptide

<400> SEQUENCE: 53

Arg Ile Leu Gln Gln Leu Leu Phe Ile His Phe Arg Ile Gly Cys Arg
1               5                   10                  15

His Ser Arg Ile
            20

<210> SEQ ID NO 54
<211> LENGTH: 17
<212> TYPE: PRT
<213> ORGANISM: Artificial Sequence
<220> FEATURE:
<223> OTHER INFORMATION: Cell Penetrating Peptide

<400> SEQUENCE: 54

Arg Ile Leu Gln Gln Leu Leu Phe Ile His Phe Arg Ile Gly Cys Arg
1               5                   10                  15

His

<210> SEQ ID NO 55
<211> LENGTH: 15
<212> TYPE: PRT
<213> ORGANISM: Artificial Sequence
<220> FEATURE:
<223> OTHER INFORMATION: Cell Penetrating Peptide

<400> SEQUENCE: 55

Arg Ile Leu Gln Gln Leu Leu Phe Ile His Phe Arg Ile Gly Cys
1               5                   10                  15

<210> SEQ ID NO 56
<211> LENGTH: 10
<212> TYPE: PRT
<213> ORGANISM: Artificial Sequence
<220> FEATURE:
<223> OTHER INFORMATION: Cell Penetrating Peptide

<400> SEQUENCE: 56

Arg Ile Phe Ile His Phe Arg Ile Gly Cys
1               5                   10

<210> SEQ ID NO 57
<211> LENGTH: 8
<212> TYPE: PRT
<213> ORGANISM: Artificial Sequence
<220> FEATURE:
<223> OTHER INFORMATION: Cell Penetrating Peptide

<400> SEQUENCE: 57

Arg Ile Phe Ile Arg Ile Gly Cys
1               5

<210> SEQ ID NO 58
<211> LENGTH: 15
<212> TYPE: DNA
<213> ORGANISM: Artificial Sequence
<220> FEATURE:
<223> OTHER INFORMATION: VPR-PCR 5'-terminal

<400> SEQUENCE: 58
cgcgcgtcag ccagc                                                    15
```

```
<210> SEQ ID NO 59
<211> LENGTH: 15
<212> TYPE: DNA
<213> ORGANISM: Artificial Sequence
<220> FEATURE:
<223> OTHER INFORMATION: VPR-PCR 3'-terminal

<400> SEQUENCE: 59
gtttaaactg cggcc                                                        15

<210> SEQ ID NO 60
<211> LENGTH: 10
<212> TYPE: PRT
<213> ORGANISM: Artificial Sequence
<220> FEATURE:
<223> OTHER INFORMATION: Cell Penetrating Peptide

<400> SEQUENCE: 60

Arg Ile Phe Ile His Phe Arg Gln Gly Gln
1               5                   10

<210> SEQ ID NO 61
<211> LENGTH: 4293
<212> TYPE: DNA
<213> ORGANISM: Artificial Sequence
<220> FEATURE:
<223> OTHER INFORMATION: ICQ2-TALE-TERT-1-VPR
<220> FEATURE:
<221> NAME/KEY: CDS
<222> LOCATION: (1)..(4293)

<400> SEQUENCE: 61
agg atc ttc atc cac ttc cgg cag ggc cag gaa aac ctg tat ttc caa      48
Arg Ile Phe Ile His Phe Arg Gln Gly Gln Glu Asn Leu Tyr Phe Gln
1               5                   10                  15 tct ctc gag cgc gat cgc acc atg atc cac gga gtc cca gca gcc gta      96
Ser Leu Glu Arg Asp Arg Thr Met Ile His Gly Val Pro Ala Ala Val
            20                  25                  30 gat ttg aga act ttg gga tat tca cag cag cag cag gaa aag atc aag     144
Asp Leu Arg Thr Leu Gly Tyr Ser Gln Gln Gln Gln Glu Lys Ile Lys
        35                  40                  45 ccc aaa gtg agg tcg aca gtc gcg cag cat cac gaa gcg ctg gtg ggt     192
Pro Lys Val Arg Ser Thr Val Ala Gln His His Glu Ala Leu Val Gly
    50                  55                  60 cat ggg ttt aca cat gcc cac atc gta gcc ttg tcg cag cac cct gca     240
His Gly Phe Thr His Ala His Ile Val Ala Leu Ser Gln His Pro Ala
65                  70                  75                  80 gcc ctt ggc acg gtc gcc gtc aag tac cag gac atg att gcg gcg ttg     288
Ala Leu Gly Thr Val Ala Val Lys Tyr Gln Asp Met Ile Ala Ala Leu
                85                  90                  95 ccg gaa gcc aca cat gag gcg atc gtc ggt gtg ggg aaa cag tgg agc     336
Pro Glu Ala Thr His Glu Ala Ile Val Gly Val Gly Lys Gln Trp Ser
            100                 105                 110 gga gcc cga gcg ctt gag gcc ctg ttg acg gtc gcg gga gag ctg aga     384
Gly Ala Arg Ala Leu Glu Ala Leu Leu Thr Val Ala Gly Glu Leu Arg
        115                 120                 125 ggg cct ccc ctt cag ctg gac acg ggc cag ttg ctg aag atc gcg aag     432
Gly Pro Pro Leu Gln Leu Asp Thr Gly Gln Leu Leu Lys Ile Ala Lys
    130                 135                 140 cgg gga gga gtc acg gcg gtc gag gcg gta cac gcg tgg cgc aat gcg     480
Arg Gly Gly Val Thr Ala Val Glu Ala Val His Ala Trp Arg Asn Ala
145                 150                 155                 160 ctc acg gga gca ccc ctc aac ctg acc ccg gac cag gtg gtt gca atc     528
Leu Thr Gly Ala Pro Leu Asn Leu Thr Pro Asp Gln Val Val Ala Ile
```

-continued

```
                165                 170                  175
gcg tca cac gat ggg gga aag cag gcc cta gaa acc gtt cag cga ctc    576
Ala Ser His Asp Gly Gly Lys Gln Ala Leu Glu Thr Val Gln Arg Leu
            180                 185                 190 ctg ccc gtc ctg tgc cag gac cac ggc ctg acc cca gaa cag gtt gtg    624
Leu Pro Val Leu Cys Gln Asp His Gly Leu Thr Pro Glu Gln Val Val
        195                 200                 205 gcc atc gcc agc aac ata ggt ggc aag cag gcc ctc gaa acc gtc cag    672
Ala Ile Ala Ser Asn Ile Gly Gly Lys Gln Ala Leu Glu Thr Val Gln
    210                 215                 220 aga ctg tta ccg gtt ctc tgc cag gcc cac ggc ctg acc cca gac caa    720
Arg Leu Leu Pro Val Leu Cys Gln Ala His Gly Leu Thr Pro Asp Gln
225                 230                 235                 240 gtt gtc gcg att gca agc aac aac gga ggc aaa caa gcc tta gaa aca    768
Val Val Ala Ile Ala Ser Asn Asn Gly Gly Lys Gln Ala Leu Glu Thr
                245                 250                 255 gtc cag aga ttg ttg cct gtg ctg tgc caa gcc cac ggc ctg acc cca    816
Val Gln Arg Leu Leu Pro Val Leu Cys Gln Ala His Gly Leu Thr Pro
            260                 265                 270 gcc cag gtt gtg gcc atc gcc agc aac ata ggt ggc aag cag gcc ctc    864
Ala Gln Val Val Ala Ile Ala Ser Asn Ile Gly Gly Lys Gln Ala Leu
        275                 280                 285 gaa acc gtc cag aga ctg tta ccg gtt ctc tgc cag gac cac ggc ctg    912
Glu Thr Val Gln Arg Leu Leu Pro Val Leu Cys Gln Asp His Gly Leu
    290                 295                 300 acc cca gac caa gtt gtc gcg att gca agc aac aac gga ggc aaa caa    960
Thr Pro Asp Gln Val Val Ala Ile Ala Ser Asn Asn Gly Gly Lys Gln
305                 310                 315                 320 gcc tta gaa aca gtc cag aga ttg ttg ccg gtg ctg tgc caa gac cac   1008
Ala Leu Glu Thr Val Gln Arg Leu Leu Pro Val Leu Cys Gln Asp His
                325                 330                 335 ggc ctg acc cca gaa caa gtt gtc gcg att gca agc aac aac gga ggc   1056
Gly Leu Thr Pro Glu Gln Val Val Ala Ile Ala Ser Asn Asn Gly Gly
            340                 345                 350 aaa caa gcc tta gaa aca gtc cag aga ttg ttg ccg gtg ctg tgc caa   1104
Lys Gln Ala Leu Glu Thr Val Gln Arg Leu Leu Pro Val Leu Cys Gln
        355                 360                 365 gcc cac ggc ctg acc cca gac caa gtt gtc gcg att gca agc aac aac   1152
Ala His Gly Leu Thr Pro Asp Gln Val Val Ala Ile Ala Ser Asn Asn
    370                 375                 380 gga ggc aaa caa gcc tta gaa aca gtc cag aga ttg ttg cct gtg ctg   1200
Gly Gly Lys Gln Ala Leu Glu Thr Val Gln Arg Leu Leu Pro Val Leu
385                 390                 395                 400 tgc caa gcc cac ggc ctg acc cca gcc cag gtt gtg gcc atc gcc agc   1248
Cys Gln Ala His Gly Leu Thr Pro Ala Gln Val Val Ala Ile Ala Ser
                405                 410                 415 aac ata ggt ggc aag cag gcc ctc gaa acc gtc cag aga ctg tta ccg   1296
Asn Ile Gly Gly Lys Gln Ala Leu Glu Thr Val Gln Arg Leu Leu Pro
            420                 425                 430 gtt ctc tgc cag gac cac ggc ctg acc ccg gac cag gtg gtt gca atc   1344
Val Leu Cys Gln Asp His Gly Leu Thr Pro Asp Gln Val Val Ala Ile
        435                 440                 445 gcg tca cac gat ggg gga aag cag gcc cta gaa acc gtt cag cga ctc   1392
Ala Ser His Asp Gly Gly Lys Gln Ala Leu Glu Thr Val Gln Arg Leu
    450                 455                 460 ctg ccc gtc ctg tgc cag gac cac ggc ctg acc cca gaa caa gtt gtc   1440
Leu Pro Val Leu Cys Gln Asp His Gly Leu Thr Pro Glu Gln Val Val
465                 470                 475                 480 gcg att gca agc aac aac gga ggc aaa caa gcc tta gaa aca gtc cag   1488
```

```
           Ala Ile Ala Ser Asn Asn Gly Gly Lys Gln Ala Leu Glu Thr Val Gln
                       485                 490                 495 aga ttg ttg ccg gtg ctg tgc caa gcc cac ggc ctg acc ccg gac cag          1536
Arg Leu Leu Pro Val Leu Cys Gln Ala His Gly Leu Thr Pro Asp Gln
            500                 505                 510 gtg gtt gca atc gcg tca cac gat ggg gga aag cag gcc cta gaa acc          1584
Val Val Ala Ile Ala Ser His Asp Gly Gly Lys Gln Ala Leu Glu Thr
            515                 520                 525 gtt cag cga ctc ctg ccc gtc ctg tgc cag gcc cac ggc ctg acc cca          1632
Val Gln Arg Leu Leu Pro Val Leu Cys Gln Ala His Gly Leu Thr Pro
            530                 535                 540 gcc cag gtt gtg gcc atc gcc agc aac ata ggt ggc aag cag gcc ctc          1680
Ala Gln Val Val Ala Ile Ala Ser Asn Ile Gly Gly Lys Gln Ala Leu
545                 550                 555                 560 gaa acc gtc cag aga ctg tta ccg gtt ctc tgc cag gac cac ggc ctg          1728
Glu Thr Val Gln Arg Leu Leu Pro Val Leu Cys Gln Asp His Gly Leu
                565                 570                 575 acc cca gac caa gtt gtc gcg att gca agc aac aac gga ggc aaa caa          1776
Thr Pro Asp Gln Val Val Ala Ile Ala Ser Asn Asn Gly Gly Lys Gln
            580                 585                 590 gcc tta gaa aca gtc cag aga ttg ttg ccg gtg ctg tgc caa gac cac          1824
Ala Leu Glu Thr Val Gln Arg Leu Leu Pro Val Leu Cys Gln Asp His
            595                 600                 605 ggc ctg acc ccc gaa cag gtt gtc gct att gct agt aac ggc gga ggc          1872
Gly Leu Thr Pro Glu Gln Val Val Ala Ile Ala Ser Asn Gly Gly Gly
            610                 615                 620 aaa cag gcg ctg gaa aca gtt cag cgc ctc ttg ccg gtc ttg tgt cag          1920
Lys Gln Ala Leu Glu Thr Val Gln Arg Leu Leu Pro Val Leu Cys Gln
625                 630                 635                 640 gcc cac ggc ctg acc ccg gac cag gtg gtt gca atc gcg tca cac gat          1968
Ala His Gly Leu Thr Pro Asp Gln Val Val Ala Ile Ala Ser His Asp
                645                 650                 655 ggg gga aag cag gcc cta gaa acc gtt cag cga ctc ctg ccc gtc ctg          2016
Gly Gly Lys Gln Ala Leu Glu Thr Val Gln Arg Leu Leu Pro Val Leu
            660                 665                 670 tgc cag gcc cac ggc ctg acc ccc gcc cag gtt gtc gct att gct agt          2064
Cys Gln Ala His Gly Leu Thr Pro Ala Gln Val Val Ala Ile Ala Ser
            675                 680                 685 aac ggc gga ggc aaa cag gcg ctg gaa aca gtt cag cgc ctc ttg ccg          2112
Asn Gly Gly Gly Lys Gln Ala Leu Glu Thr Val Gln Arg Leu Leu Pro
            690                 695                 700 gtc ttg tgt cag gac cac ggc ctg acc cct gag cag gta gtg gct att          2160
Val Leu Cys Gln Asp His Gly Leu Thr Pro Glu Gln Val Val Ala Ile
705                 710                 715                 720 gca tcc cac gac ggg ggc aga ccc gca ctg gag tca atc gtg gcc cag          2208
Ala Ser His Asp Gly Gly Arg Pro Ala Leu Glu Ser Ile Val Ala Gln
                725                 730                 735 ctc tcg agg ccg gac ccc gcg ctg gcc gca ctc act aat gat cat ctt          2256
Leu Ser Arg Pro Asp Pro Ala Leu Ala Ala Leu Thr Asn Asp His Leu
            740                 745                 750 gta gcg ctg gcc tgc ctc ggc gga cga ccc gcc ttg gat gcg gtg aag          2304
Val Ala Leu Ala Cys Leu Gly Gly Arg Pro Ala Leu Asp Ala Val Lys
            755                 760                 765 aag ggg ctc ccg cac gcg cct gca ttg att aag cgg acc aac aga agg          2352
Lys Gly Leu Pro His Ala Pro Ala Leu Ile Lys Arg Thr Asn Arg Arg
            770                 775                 780 atc ccc gag agg aca tca cat cga gtg gca gat cac gcg caa gtg gtc          2400
Ile Pro Glu Arg Thr Ser His Arg Val Ala Asp His Ala Gln Val Val
785                 790                 795                 800
```

| | |
|---|---|
| cgc gtg ctc gga ttc ttc cag tgt cac tcc cac ccc gca caa gcg ttc<br>Arg Val Leu Gly Phe Phe Gln Cys His Ser His Pro Ala Gln Ala Phe<br>                  805                         810               815 | 2448 |
| gat gac gcc atg act caa ttt ggt atg tcg aga cac gga ctg ctg cag<br>Asp Asp Ala Met Thr Gln Phe Gly Met Ser Arg His Gly Leu Leu Gln<br>820                   825                     830 | 2496 |
| ctc ttt cgt aga gtc ggt gtc aca gaa ctg gag gcc cgc tcg ggc aca<br>Leu Phe Arg Arg Val Gly Val Thr Glu Leu Glu Ala Arg Ser Gly Thr<br>         835                    840                 845 | 2544 |
| ctg cct ccc gcc tcc cag cgg tgg gac agg att ctc caa gcg agc ggt<br>Leu Pro Pro Ala Ser Gln Arg Trp Asp Arg Ile Leu Gln Ala Ser Gly<br>850                   855                   860 | 2592 |
| atg aaa cgc gcg aag cct tca cct acg tca act cag aca cct gac cag<br>Met Lys Arg Ala Lys Pro Ser Pro Thr Ser Thr Gln Thr Pro Asp Gln<br>865                   870                   875               880 | 2640 |
| gcg agc ctt cat gcg ttc gca gac tcg ctg gag agg gat ttg gac gcg<br>Ala Ser Leu His Ala Phe Ala Asp Ser Leu Glu Arg Asp Leu Asp Ala<br>                  885                     890               895 | 2688 |
| ccc tcg ccc atg cat gaa ggg gac caa act cgc gcg tca gcc agc gac<br>Pro Ser Pro Met His Glu Gly Asp Gln Thr Arg Ala Ser Ala Ser Asp<br>             900                    905                 910 | 2736 |
| gca ttg gac gat ttt gat ctg gat atg ctg gga agt gac gcc ctc gat<br>Ala Leu Asp Asp Phe Asp Leu Asp Met Leu Gly Ser Asp Ala Leu Asp<br>         915                    920                 925 | 2784 |
| gat ttt gac ctt gac atg ctt ggt tcg gat gcc ctt gat gac ttt gac<br>Asp Phe Asp Leu Asp Met Leu Gly Ser Asp Ala Leu Asp Asp Phe Asp<br>930                   935                     940 | 2832 |
| ctc gac atg ctc ggc agt gac gcc ctt gat gat ttc gac ctg gac atg<br>Leu Asp Met Leu Gly Ser Asp Ala Leu Asp Asp Phe Asp Leu Asp Met<br>945                   950                   955               960 | 2880 |
| ctg agt tcc gga tct ccg aaa aag aaa cgc aaa gtt ggt agc cag tac<br>Leu Ser Ser Gly Ser Pro Lys Lys Lys Arg Lys Val Gly Ser Gln Tyr<br>                  965                    970               975 | 2928 |
| ctg ccc gac acc gac gac cgg cac cgg atc gag gaa aag cgg aag cgg<br>Leu Pro Asp Thr Asp Asp Arg His Arg Ile Glu Glu Lys Arg Lys Arg<br>             980                    985                 990 | 2976 |
| acc tac gag aca ttc aag agc atc atg aag aag tcc ccc ttc agc ggc<br>Thr Tyr Glu Thr Phe Lys Ser Ile Met Lys Lys Ser Pro Phe Ser Gly<br>               995                  1000               1005 | 3024 |
| ccc acc gac cct aga cct cca cct aga aga atc gcc gtg ccc agc<br>Pro Thr Asp Pro Arg Pro Pro Arg Arg Ile Ala Val Pro Ser<br>1010                    1015                  1020 | 3069 |
| aga tcc agc gcc agc gtg cca aaa cct gcc ccc cag cct tac ccc<br>Arg Ser Ser Ala Ser Val Pro Lys Pro Ala Pro Gln Pro Tyr Pro<br>        1025                  1030                  1035 | 3114 |
| ttc acc agc agc ctg agc acc atc aac tac gac gag ttc cct acc<br>Phe Thr Ser Ser Leu Ser Thr Ile Asn Tyr Asp Glu Phe Pro Thr<br>        1040                  1045                  1050 | 3159 |
| atg gtg ttc ccc agc ggc cag atc tct cag gcc tct gct ctg gct<br>Met Val Phe Pro Ser Gly Gln Ile Ser Gln Ala Ser Ala Leu Ala<br>        1055                  1060                  1065 | 3204 |
| cca gcc cct cct cag gtg ctg cct cag gct cct gct cct gca cca<br>Pro Ala Pro Pro Gln Val Leu Pro Gln Ala Pro Ala Pro Ala Pro<br>        1070                  1075                  1080 | 3249 |
| gct cca gcc atg gtg tct gca ctg gct cag gca cca gca ccc gtg<br>Ala Pro Ala Met Val Ser Ala Leu Ala Gln Ala Pro Ala Pro Val<br>        1085                  1090                  1095 | 3294 |
| cct gtg ctg gct cct gga cct cca cag gct gtg gct cca cca gcc<br>Pro Val Leu Ala Pro Gly Pro Pro Gln Ala Val Ala Pro Pro Ala<br>        1100                  1105                  1110 | 3339 |

-continued

| | | |
|---|---|---|
| cct aaa cct aca cag gcc ggc gag ggc aca ctg tct gaa gct ctg<br>Pro Lys Pro Thr Gln Ala Gly Glu Gly Thr Leu Ser Glu Ala Leu<br>1115                    1120                       1125 | 3384 |
| ctg cag ctg cag ttc gac gac gag gat ctg gga gcc ctg ctg gga<br>Leu Gln Leu Gln Phe Asp Asp Glu Asp Leu Gly Ala Leu Leu Gly<br>1130                    1135                       1140 | 3429 |
| aac agc acc gat cct gcc gtg ttc acc gac ctg gcc agc gtg gac<br>Asn Ser Thr Asp Pro Ala Val Phe Thr Asp Leu Ala Ser Val Asp<br>1145                    1150                       1155 | 3474 |
| aac agc gag ttc cag cag ctg ctg aac cag ggc atc cct gtg gcc<br>Asn Ser Glu Phe Gln Gln Leu Leu Asn Gln Gly Ile Pro Val Ala<br>1160                    1165                       1170 | 3519 |
| cct cac acc acc gag ccc atg ctg atg gaa tac ccc gag gcc atc<br>Pro His Thr Thr Glu Pro Met Leu Met Glu Tyr Pro Glu Ala Ile<br>1175                    1180                       1185 | 3564 |
| acc cgg ctc gtg aca ggc gct cag agg cct cct gat cca gct cct<br>Thr Arg Leu Val Thr Gly Ala Gln Arg Pro Pro Asp Pro Ala Pro<br>1190                    1195                       1200 | 3609 |
| gcc cct ctg gga gca cca ggc ctg cct aat gga ctg ctg tct ggc<br>Ala Pro Leu Gly Ala Pro Gly Leu Pro Asn Gly Leu Leu Ser Gly<br>1205                    1210                       1215 | 3654 |
| gac gag gac ttc agc tct atc gcc gat atg gat ttc tca gcc ttg<br>Asp Glu Asp Phe Ser Ser Ile Ala Asp Met Asp Phe Ser Ala Leu<br>1220                    1225                       1230 | 3699 |
| ctg ggc tct ggc agc ggc agc cgg gat tcc agg gaa ggg atg ttt<br>Leu Gly Ser Gly Ser Gly Ser Arg Asp Ser Arg Glu Gly Met Phe<br>1235                    1240                       1245 | 3744 |
| ttg ccg aag cct gag gcc ggc tcc gct att agt gac gtg ttt gag<br>Leu Pro Lys Pro Glu Ala Gly Ser Ala Ile Ser Asp Val Phe Glu<br>1250                    1255                       1260 | 3789 |
| ggc cgc gag gtg tgc cag cca aaa cga atc cgg cca ttt cat cct<br>Gly Arg Glu Val Cys Gln Pro Lys Arg Ile Arg Pro Phe His Pro<br>1265                    1270                       1275 | 3834 |
| cca gga agt cca tgg gcc aac cgc cca ctc ccc gcc agc ctc gca<br>Pro Gly Ser Pro Trp Ala Asn Arg Pro Leu Pro Ala Ser Leu Ala<br>1280                    1285                       1290 | 3879 |
| cca aca cca acc ggt cca gta cat gag cca gtc ggg tca ctg acc<br>Pro Thr Pro Thr Gly Pro Val His Glu Pro Val Gly Ser Leu Thr<br>1295                    1300                       1305 | 3924 |
| ccg gca cca gtc cct cag cca ctg gat cca gcg ccc gca gtg act<br>Pro Ala Pro Val Pro Gln Pro Leu Asp Pro Ala Pro Ala Val Thr<br>1310                    1315                       1320 | 3969 |
| ccc gag gcc agt cac ctg ttg gag gat ccc gat gaa gaa acg agc<br>Pro Glu Ala Ser His Leu Leu Glu Asp Pro Asp Glu Glu Thr Ser<br>1325                    1330                       1335 | 4014 |
| cag gct gtc aaa gcc ctt cgg gag atg gcc gat act gtg att ccc<br>Gln Ala Val Lys Ala Leu Arg Glu Met Ala Asp Thr Val Ile Pro<br>1340                    1345                       1350 | 4059 |
| cag aag gaa gag gct gca atc tgt ggc caa atg gac ctt tcc cat<br>Gln Lys Glu Glu Ala Ala Ile Cys Gly Gln Met Asp Leu Ser His<br>1355                    1360                       1365 | 4104 |
| ccg ccc cca agg ggc cat ctg gat gag ctg aca acc aca ctt gag<br>Pro Pro Pro Arg Gly His Leu Asp Glu Leu Thr Thr Thr Leu Glu<br>1370                    1375                       1380 | 4149 |
| tcc atg acc gag gat ctg aac ctg gac tca ccc ctg acc ccg gaa<br>Ser Met Thr Glu Asp Leu Asn Leu Asp Ser Pro Leu Thr Pro Glu<br>1385                    1390                       1395 | 4194 |
| ttg aac gag att ctg gat acc ttc ctg aac gac gag tgc ctc ttg<br>Leu Asn Glu Ile Leu Asp Thr Phe Leu Asn Asp Glu Cys Leu Leu | 4239 |

-continued

```
            1400                1405                1410
cat gcc atg cat atc agc aca gga ctg tcc atc ttc gac aca tct        4284
His Ala Met His Ile Ser Thr Gly Leu Ser Ile Phe Asp Thr Ser
    1415                1420                1425 ctg ttt gtt                                                        4293
Leu Phe Val
    1430
```

<210> SEQ ID NO 62
<211> LENGTH: 1431
<212> TYPE: PRT
<213> ORGANISM: Artificial Sequence
<220> FEATURE:
<223> OTHER INFORMATION: Synthetic Construct

<400> SEQUENCE: 62

Arg Ile Phe Ile His Phe Arg Gln Gly Gln Glu Asn Leu Tyr Phe Gln
1               5                   10                  15

Ser Leu Glu Arg Asp Arg Thr Met Ile His Gly Val Pro Ala Ala Val
            20                  25                  30

Asp Leu Arg Thr Leu Gly Tyr Ser Gln Gln Gln Gln Glu Lys Ile Lys
        35                  40                  45

Pro Lys Val Arg Ser Thr Val Ala Gln His His Glu Ala Leu Val Gly
    50                  55                  60

His Gly Phe Thr His Ala His Ile Val Ala Leu Ser Gln His Pro Ala
65                  70                  75                  80

Ala Leu Gly Thr Val Ala Val Lys Tyr Gln Asp Met Ile Ala Ala Leu
                85                  90                  95

Pro Glu Ala Thr His Glu Ala Ile Val Gly Val Gly Lys Gln Trp Ser
            100                 105                 110

Gly Ala Arg Ala Leu Glu Ala Leu Leu Thr Val Ala Gly Glu Leu Arg
        115                 120                 125

Gly Pro Pro Leu Gln Leu Asp Thr Gly Gln Leu Leu Lys Ile Ala Lys
    130                 135                 140

Arg Gly Gly Val Thr Ala Val Glu Ala Val His Ala Trp Arg Asn Ala
145                 150                 155                 160

Leu Thr Gly Ala Pro Leu Asn Leu Thr Pro Asp Gln Val Val Ala Ile
                165                 170                 175

Ala Ser His Asp Gly Gly Lys Gln Ala Leu Glu Thr Val Gln Arg Leu
            180                 185                 190

Leu Pro Val Leu Cys Gln Asp His Gly Leu Thr Pro Glu Gln Val Val
        195                 200                 205

Ala Ile Ala Ser Asn Ile Gly Gly Lys Gln Ala Leu Glu Thr Val Gln
    210                 215                 220

Arg Leu Leu Pro Val Leu Cys Gln Ala His Gly Leu Thr Pro Asp Gln
225                 230                 235                 240

Val Val Ala Ile Ala Ser Asn Asn Gly Gly Lys Gln Ala Leu Glu Thr
                245                 250                 255

Val Gln Arg Leu Leu Pro Val Leu Cys Gln Ala His Gly Leu Thr Pro
            260                 265                 270

Ala Gln Val Val Ala Ile Ala Ser Asn Ile Gly Gly Lys Gln Ala Leu
        275                 280                 285

Glu Thr Val Gln Arg Leu Leu Pro Val Leu Cys Gln Asp His Gly Leu
    290                 295                 300

Thr Pro Asp Gln Val Val Ala Ile Ala Ser Asn Asn Gly Gly Lys Gln
305                 310                 315                 320

Ala Leu Glu Thr Val Gln Arg Leu Leu Pro Val Leu Cys Gln Asp His
              325                 330                 335

Gly Leu Thr Pro Glu Gln Val Val Ala Ile Ala Ser Asn Asn Gly Gly
              340                 345                 350

Lys Gln Ala Leu Glu Thr Val Gln Arg Leu Leu Pro Val Leu Cys Gln
              355                 360                 365

Ala His Gly Leu Thr Pro Asp Gln Val Val Ala Ile Ala Ser Asn Asn
              370                 375                 380

Gly Gly Lys Gln Ala Leu Glu Thr Val Gln Arg Leu Leu Pro Val Leu
385                 390                 395                 400

Cys Gln Ala His Gly Leu Thr Pro Ala Gln Val Val Ala Ile Ala Ser
              405                 410                 415

Asn Ile Gly Gly Lys Gln Ala Leu Glu Thr Val Gln Arg Leu Leu Pro
              420                 425                 430

Val Leu Cys Gln Asp His Gly Leu Thr Pro Asp Gln Val Val Ala Ile
              435                 440                 445

Ala Ser His Asp Gly Gly Lys Gln Ala Leu Glu Thr Val Gln Arg Leu
              450                 455                 460

Leu Pro Val Leu Cys Gln Asp His Gly Leu Thr Pro Glu Gln Val Val
465                 470                 475                 480

Ala Ile Ala Ser Asn Asn Gly Gly Lys Gln Ala Leu Glu Thr Val Gln
              485                 490                 495

Arg Leu Leu Pro Val Leu Cys Gln Ala His Gly Leu Thr Pro Asp Gln
              500                 505                 510

Val Val Ala Ile Ala Ser His Asp Gly Gly Lys Gln Ala Leu Glu Thr
              515                 520                 525

Val Gln Arg Leu Leu Pro Val Leu Cys Gln Ala His Gly Leu Thr Pro
              530                 535                 540

Ala Gln Val Val Ala Ile Ala Ser Asn Ile Gly Gly Lys Gln Ala Leu
545                 550                 555                 560

Glu Thr Val Gln Arg Leu Leu Pro Val Leu Cys Gln Asp His Gly Leu
              565                 570                 575

Thr Pro Asp Gln Val Val Ala Ile Ala Ser Asn Asn Gly Gly Lys Gln
              580                 585                 590

Ala Leu Glu Thr Val Gln Arg Leu Leu Pro Val Leu Cys Gln Asp His
              595                 600                 605

Gly Leu Thr Pro Glu Gln Val Val Ala Ile Ala Ser Asn Gly Gly Gly
              610                 615                 620

Lys Gln Ala Leu Glu Thr Val Gln Arg Leu Leu Pro Val Leu Cys Gln
625                 630                 635                 640

Ala His Gly Leu Thr Pro Asp Gln Val Val Ala Ile Ala Ser His Asp
              645                 650                 655

Gly Gly Lys Gln Ala Leu Glu Thr Val Gln Arg Leu Leu Pro Val Leu
              660                 665                 670

Cys Gln Ala His Gly Leu Thr Pro Ala Gln Val Val Ala Ile Ala Ser
              675                 680                 685

Asn Gly Gly Gly Lys Gln Ala Leu Glu Thr Val Gln Arg Leu Leu Pro
              690                 695                 700

Val Leu Cys Gln Asp His Gly Leu Thr Pro Glu Gln Val Val Ala Ile
705                 710                 715                 720

Ala Ser His Asp Gly Gly Arg Pro Ala Leu Glu Ser Ile Val Ala Gln
              725                 730                 735

```
Leu Ser Arg Pro Asp Pro Ala Leu Ala Ala Leu Thr Asn Asp His Leu
            740                 745                 750

Val Ala Leu Ala Cys Leu Gly Gly Arg Pro Ala Leu Asp Ala Val Lys
            755                 760                 765

Lys Gly Leu Pro His Ala Pro Ala Leu Ile Lys Arg Thr Asn Arg Arg
    770                 775                 780

Ile Pro Glu Arg Thr Ser His Arg Val Ala Asp His Ala Gln Val Val
785                 790                 795                 800

Arg Val Leu Gly Phe Phe Gln Cys His Ser His Pro Ala Gln Ala Phe
                805                 810                 815

Asp Asp Ala Met Thr Gln Phe Gly Met Ser Arg His Gly Leu Leu Gln
            820                 825                 830

Leu Phe Arg Arg Val Gly Val Thr Glu Leu Glu Ala Arg Ser Gly Thr
        835                 840                 845

Leu Pro Pro Ala Ser Gln Arg Trp Asp Arg Ile Leu Gln Ala Ser Gly
    850                 855                 860

Met Lys Arg Ala Lys Pro Ser Pro Thr Ser Thr Gln Thr Pro Asp Gln
865                 870                 875                 880

Ala Ser Leu His Ala Phe Ala Asp Ser Leu Glu Arg Asp Leu Asp Ala
                885                 890                 895

Pro Ser Pro Met His Glu Gly Asp Gln Thr Arg Ala Ser Ala Ser Asp
            900                 905                 910

Ala Leu Asp Asp Phe Asp Leu Asp Met Leu Gly Ser Asp Ala Leu Asp
        915                 920                 925

Asp Phe Asp Leu Asp Met Leu Gly Ser Asp Ala Leu Asp Asp Phe Asp
    930                 935                 940

Leu Asp Met Leu Gly Ser Asp Ala Leu Asp Asp Phe Asp Leu Asp Met
945                 950                 955                 960

Leu Ser Ser Gly Ser Pro Lys Lys Arg Lys Val Gly Ser Gln Tyr
                965                 970                 975

Leu Pro Asp Thr Asp Asp Arg His Arg Ile Glu Glu Lys Arg Lys Arg
            980                 985                 990

Thr Tyr Glu Thr Phe Lys Ser Ile Met Lys Lys Ser Pro Phe Ser Gly
        995                 1000                1005

Pro Thr Asp Pro Arg Pro Pro Arg Arg Ile Ala Val Pro Ser
    1010                1015                1020

Arg Ser Ser Ala Ser Val Pro Lys Pro Ala Pro Gln Pro Tyr Pro
    1025                1030                1035

Phe Thr Ser Ser Leu Ser Thr Ile Asn Tyr Asp Glu Phe Pro Thr
    1040                1045                1050

Met Val Phe Pro Ser Gly Gln Ile Ser Gln Ala Ser Ala Leu Ala
    1055                1060                1065

Pro Ala Pro Pro Gln Val Leu Pro Gln Ala Pro Ala Pro Ala Pro
    1070                1075                1080

Ala Pro Ala Met Val Ser Ala Leu Ala Gln Ala Pro Ala Pro Val
    1085                1090                1095

Pro Val Leu Ala Pro Gly Pro Pro Gln Ala Val Ala Pro Pro Ala
    1100                1105                1110

Pro Lys Pro Thr Gln Ala Gly Glu Gly Thr Leu Ser Glu Ala Leu
    1115                1120                1125

Leu Gln Leu Gln Phe Asp Asp Glu Asp Leu Gly Ala Leu Leu Gly
    1130                1135                1140

Asn Ser Thr Asp Pro Ala Val Phe Thr Asp Leu Ala Ser Val Asp
```

-continued

```
                1145                1150                1155
Asn Ser Glu Phe Gln Gln Leu Leu Asn Gln Gly Ile Pro Val Ala
    1160                1165                1170

Pro His Thr Thr Glu Pro Met Leu Met Glu Tyr Pro Glu Ala Ile
    1175                1180                1185

Thr Arg Leu Val Thr Gly Ala Gln Arg Pro Pro Asp Pro Ala Pro
    1190                1195                1200

Ala Pro Leu Gly Ala Pro Gly Leu Pro Asn Gly Leu Leu Ser Gly
    1205                1210                1215

Asp Glu Asp Phe Ser Ser Ile Ala Asp Met Asp Phe Ser Ala Leu
    1220                1225                1230

Leu Gly Ser Gly Ser Gly Ser Arg Asp Ser Arg Glu Gly Met Phe
    1235                1240                1245

Leu Pro Lys Pro Glu Ala Gly Ser Ala Ile Ser Asp Val Phe Glu
    1250                1255                1260

Gly Arg Glu Val Cys Gln Pro Lys Arg Ile Arg Pro Phe His Pro
    1265                1270                1275

Pro Gly Ser Pro Trp Ala Asn Arg Pro Leu Pro Ala Ser Leu Ala
    1280                1285                1290

Pro Thr Pro Thr Gly Pro Val His Glu Pro Val Gly Ser Leu Thr
    1295                1300                1305

Pro Ala Pro Val Pro Gln Pro Leu Asp Pro Ala Pro Ala Val Thr
    1310                1315                1320

Pro Glu Ala Ser His Leu Leu Glu Asp Pro Asp Glu Glu Thr Ser
    1325                1330                1335

Gln Ala Val Lys Ala Leu Arg Glu Met Ala Asp Thr Val Ile Pro
    1340                1345                1350

Gln Lys Glu Glu Ala Ala Ile Cys Gly Gln Met Asp Leu Ser His
    1355                1360                1365

Pro Pro Pro Arg Gly His Leu Asp Glu Leu Thr Thr Thr Leu Glu
    1370                1375                1380

Ser Met Thr Glu Asp Leu Asn Leu Asp Ser Pro Leu Thr Pro Glu
    1385                1390                1395

Leu Asn Glu Ile Leu Asp Thr Phe Leu Asn Asp Glu Cys Leu Leu
    1400                1405                1410

His Ala Met His Ile Ser Thr Gly Leu Ser Ile Phe Asp Thr Ser
    1415                1420                1425

Leu Phe Val
    1430

<210> SEQ ID NO 63
<211> LENGTH: 2415
<212> TYPE: DNA
<213> ORGANISM: Artificial Sequence
<220> FEATURE:
<223> OTHER INFORMATION: polynucleotide fragment
<220> FEATURE:
<221> NAME/KEY: CDS
<222> LOCATION: (1)..(2415)

<400> SEQUENCE: 63 atg gct tcc tcc cct cca aag aaa aag aga aag gtt gcg gcc gct gac      48
Met Ala Ser Ser Pro Pro Lys Lys Lys Arg Lys Val Ala Ala Ala Asp
1               5                   10                  15 tac aag gat gac gac gat aaa agt tgg aag gac gca agt ggt tgg tct      96
Tyr Lys Asp Asp Asp Asp Lys Ser Trp Lys Asp Ala Ser Gly Trp Ser
            20                  25                  30
```

-continued

| | | |
|---|---|---|
| aga atg cat gcg gcc ccg cga cgg cgt gct gcg caa ccc tcc gac gct<br>Arg Met His Ala Ala Pro Arg Arg Arg Ala Ala Gln Pro Ser Asp Ala<br>35                    40                    45 | 144 |
| tcg ccg gcc gcg cag gtg gat cta cgc acg ctc ggc tac agt cag cag<br>Ser Pro Ala Ala Gln Val Asp Leu Arg Thr Leu Gly Tyr Ser Gln Gln<br>50                    55                    60 | 192 |
| cag caa gag aag atc aaa ccg aag gtg cgt tcg aca gtg gcg cag cac<br>Gln Gln Glu Lys Ile Lys Pro Lys Val Arg Ser Thr Val Ala Gln His<br>65                    70                    75                    80 | 240 |
| cac gag gca ctg gtg ggc cat ggg ttt aca cac gcg cac atc gtt gcg<br>His Glu Ala Leu Val Gly His Gly Phe Thr His Ala His Ile Val Ala<br>                    85                    90                    95 | 288 |
| ctc agc caa cac ccg gca gcg tta ggg acc gtc gct gtc acg tat cag<br>Leu Ser Gln His Pro Ala Ala Leu Gly Thr Val Ala Val Thr Tyr Gln<br>                  100                  105                  110 | 336 |
| cac ata atc acg gcg ttg cca gag gcg aca cac gaa gac atc gtt ggc<br>His Ile Ile Thr Ala Leu Pro Glu Ala Thr His Glu Asp Ile Val Gly<br>                  115                  120                  125 | 384 |
| gtc ggc aaa cag tgg tcc ggc gca cgc gcc ctg gag gcc ttg ctc acg<br>Val Gly Lys Gln Trp Ser Gly Ala Arg Ala Leu Glu Ala Leu Leu Thr<br>130                    135                  140 | 432 |
| gat gcg ggg gag ttg aga ggt ccg ccg tta cag ttg gac aca ggc caa<br>Asp Ala Gly Glu Leu Arg Gly Pro Pro Leu Gln Leu Asp Thr Gly Gln<br>145                    150                  155                  160 | 480 |
| ctt gtg aag att gca aaa cgt ggc ggc gtg acc gca atg gag gca gtg<br>Leu Val Lys Ile Ala Lys Arg Gly Gly Val Thr Ala Met Glu Ala Val<br>                  165                  170                  175 | 528 |
| cat gca tcg cgc aat gcg ctc acg gga gca ccc ctc aac ctg acc cca<br>His Ala Ser Arg Asn Ala Leu Thr Gly Ala Pro Leu Asn Leu Thr Pro<br>                  180                  185                  190 | 576 |
| gac caa gtt gtc gcg att gca agc aac aac gga ggc aaa caa gcc tta<br>Asp Gln Val Val Ala Ile Ala Ser Asn Asn Gly Gly Lys Gln Ala Leu<br>                  195                  200                  205 | 624 |
| gaa aca gtc cag aga ttg ttg ccg gtg ctg tgc caa gac cac ggc ctg<br>Glu Thr Val Gln Arg Leu Leu Pro Val Leu Cys Gln Asp His Gly Leu<br>210                    215                  220 | 672 |
| acc ccg gaa cag gtg gtt gca atc gcg tca cac gat ggg gga aag cag<br>Thr Pro Glu Gln Val Val Ala Ile Ala Ser His Asp Gly Gly Lys Gln<br>225                    230                  235                  240 | 720 |
| gcc cta gaa acc gtt cag cga ctc ctg ccc gtc ctg tgc cag gcc cac<br>Ala Leu Glu Thr Val Gln Arg Leu Leu Pro Val Leu Cys Gln Ala His<br>                  245                  250                  255 | 768 |
| ggc ctg acc cca gac caa gtt gtc gcg att gca agc aac aac gga ggc<br>Gly Leu Thr Pro Asp Gln Val Val Ala Ile Ala Ser Asn Asn Gly Gly<br>                  260                  265                  270 | 816 |
| aaa caa gcc tta gaa aca gtc cag aga ttg ttg cct gtg ctg tgc caa<br>Lys Gln Ala Leu Glu Thr Val Gln Arg Leu Leu Pro Val Leu Cys Gln<br>275                    280                  285 | 864 |
| gcc cac ggc ctg acc ccc gcc cag gtt gtc gct att gct agt aac ggc<br>Ala His Gly Leu Thr Pro Ala Gln Val Val Ala Ile Ala Ser Asn Gly<br>290                    295                  300 | 912 |
| gga ggc aaa cag gcg ctg gaa aca gtt cag cgc ctc ttg ccg gtc ttg<br>Gly Gly Lys Gln Ala Leu Glu Thr Val Gln Arg Leu Leu Pro Val Leu<br>305                    310                  315                  320 | 960 |
| tgt cag gac cac ggc ctg acc cca gac cag gtt gtg gcc atc gcc agc<br>Cys Gln Asp His Gly Leu Thr Pro Asp Gln Val Val Ala Ile Ala Ser<br>                  325                  330                  335 | 1008 |
| aac ata ggt ggc aag cag gcc ctc gaa acc gtc cag aga ctg tta ccg<br>Asn Ile Gly Gly Lys Gln Ala Leu Glu Thr Val Gln Arg Leu Leu Pro | 1056 |

-continued

| | |
|---|---|
| gtt ctc tgc cag gac cac ggc ctg acc ccg gaa cag gtg gtt gca atc<br>Val Leu Cys Gln Asp His Gly Leu Thr Pro Glu Gln Val Val Ala Ile<br>355                       360                     365 | 1104 |
| gcg tca cac gat ggg gga aag cag gcc cta gaa acc gtt cag cga ctc<br>Ala Ser His Asp Gly Gly Lys Gln Ala Leu Glu Thr Val Gln Arg Leu<br>370                       375                     380 | 1152 |
| ctg ccc gtc ctg tgc cag gcc cac ggc ctg acc cca gac cag gtt gtg<br>Leu Pro Val Leu Cys Gln Ala His Gly Leu Thr Pro Asp Gln Val Val<br>385                     390                     395                     400 | 1200 |
| gcc atc gcc agc aac ata ggt ggc aag cag gcc ctc gaa acc gtc cag<br>Ala Ile Ala Ser Asn Ile Gly Gly Lys Gln Ala Leu Glu Thr Val Gln<br>                  405                     410                     415 | 1248 |
| aga ctg tta ccg gtt ctc tgc cag gcc cac ggc ctg acc cca gcc cag<br>Arg Leu Leu Pro Val Leu Cys Gln Ala His Gly Leu Thr Pro Ala Gln<br>                  420                     425                     430 | 1296 |
| gtt gtg gcc atc gcc agc aac ata ggt ggc aag cag gcc ctc gaa acc<br>Val Val Ala Ile Ala Ser Asn Ile Gly Gly Lys Gln Ala Leu Glu Thr<br>             435                     440                     445 | 1344 |
| gtc cag aga ctg tta ccg gtt ctc tgc cag gac cac ggc ctg acc cca<br>Val Gln Arg Leu Leu Pro Val Leu Cys Gln Asp His Gly Leu Thr Pro<br>450                       455                     460 | 1392 |
| gac cag gtt gtg gcc atc gcc agc aac ata ggt ggc aag cag gcc ctc<br>Asp Gln Val Val Ala Ile Ala Ser Asn Ile Gly Gly Lys Gln Ala Leu<br>465                       470                     475                     480 | 1440 |
| gaa acc gtc cag aga ctg tta ccg gtt ctc tgc cag gac cac ggc ctg<br>Glu Thr Val Gln Arg Leu Leu Pro Val Leu Cys Gln Asp His Gly Leu<br>                  485                     490                     495 | 1488 |
| acc cca gaa caa gtt gtc gcg att gca agc aac aac gga ggc aaa caa<br>Thr Pro Glu Gln Val Val Ala Ile Ala Ser Asn Asn Gly Gly Lys Gln<br>            500                     505                     510 | 1536 |
| gcc tta gaa aca gtc cag aga ttg ttg ccg gtg ctg tgc caa gcc cac<br>Ala Leu Glu Thr Val Gln Arg Leu Leu Pro Val Leu Cys Gln Ala His<br>             515                     520                     525 | 1584 |
| ggc ctg acc ccc gac cag gtt gtc gct att gct agt aac ggc gga ggc<br>Gly Leu Thr Pro Asp Gln Val Val Ala Ile Ala Ser Asn Gly Gly Gly<br>530                       535                     540 | 1632 |
| aaa cag gcg ctg gaa aca gtt cag cgc ctc ttg ccg gtc ttg tgt cag<br>Lys Gln Ala Leu Glu Thr Val Gln Arg Leu Leu Pro Val Leu Cys Gln<br>545                       550                     555                     560 | 1680 |
| gcc cac ggc ctg acc cca gcc cag gtt gtg gcc atc gcc agc aac ata<br>Ala His Gly Leu Thr Pro Ala Gln Val Val Ala Ile Ala Ser Asn Ile<br>                  565                     570                     575 | 1728 |
| ggt ggc aag cag gcc ctc gaa acc gtc cag aga ctg tta ccg gtt ctc<br>Gly Gly Lys Gln Ala Leu Glu Thr Val Gln Arg Leu Leu Pro Val Leu<br>            580                     585                     590 | 1776 |
| tgc cag gac cac ggc ctg acc ccc gac cag gtt gtc gct att gct agt<br>Cys Gln Asp His Gly Leu Thr Pro Asp Gln Val Val Ala Ile Ala Ser<br>       595                     600                     605 | 1824 |
| aac ggc gga ggc aaa cag gcg ctg gaa aca gtt cag cgc ctc ttg ccg<br>Asn Gly Gly Gly Lys Gln Ala Leu Glu Thr Val Gln Arg Leu Leu Pro<br>610                       615                     620 | 1872 |
| gtc ttg tgt cag gac cac ggc ctg acc cca gaa cag gtt gtg gcc atc<br>Val Leu Cys Gln Asp His Gly Leu Thr Pro Glu Gln Val Val Ala Ile<br>625                       630                     635                     640 | 1920 |
| gcc agc aac ata ggt ggc aag cag gcc ctc gaa acc gtc cag aga ctg<br>Ala Ser Asn Ile Gly Gly Lys Gln Ala Leu Glu Thr Val Gln Arg Leu<br>                  645                     650                     655 | 1968 |
| tta ccg gtt ctc tgc cag gcc cac ggc ctg acc ccg gac cag gtg gtt | 2016 |

```
Leu Pro Val Leu Cys Gln Ala His Gly Leu Thr Pro Asp Gln Val Val
            660                 665                 670 gca atc gcg tca cac gat ggg gga aag cag gcc cta gaa acc gtt cag        2064
Ala Ile Ala Ser His Asp Gly Gly Lys Gln Ala Leu Glu Thr Val Gln
            675                 680                 685 cga ctc ctg ccc gtc ctg tgc cag gcc cac ggc ctg acc cca gcc cag        2112
Arg Leu Leu Pro Val Leu Cys Gln Ala His Gly Leu Thr Pro Ala Gln
            690                 695                 700 gtt gtg gcc atc gcc agc aac ata ggt ggc aag cag gcc ctc gaa acc        2160
Val Val Ala Ile Ala Ser Asn Ile Gly Gly Lys Gln Ala Leu Glu Thr
705                 710                 715                 720 gtc cag aga ctg tta ccg gtt ctc tgc cag gac cac ggc ctg acg cct        2208
Val Gln Arg Leu Leu Pro Val Leu Cys Gln Asp His Gly Leu Thr Pro
            725                 730                 735 gag cag gta gtg gct att gca tcc aac gga ggg ggc aga ccc gca ctg        2256
Glu Gln Val Val Ala Ile Ala Ser Asn Gly Gly Gly Arg Pro Ala Leu
            740                 745                 750 gag tca atc gtg gcc cag ctt tcg agg ccg gac ccc gcg ctg gcc gca        2304
Glu Ser Ile Val Ala Gln Leu Ser Arg Pro Asp Pro Ala Leu Ala Ala
            755                 760                 765 ctc act aat gat cat ctt gta gcg ctg gcc tgc ctc ggc gga cgt cct        2352
Leu Thr Asn Asp His Leu Val Ala Leu Ala Cys Leu Gly Gly Arg Pro
            770                 775                 780 gcc atg gat gca gtg aaa aag gga ttg ccg cac gcg ccg gaa ttg atc        2400
Ala Met Asp Ala Val Lys Lys Gly Leu Pro His Ala Pro Glu Leu Ile
785                 790                 795                 800 aga tcc cgg atc cgc                                                    2415
Arg Ser Arg Ile Arg
            805

<210> SEQ ID NO 64
<211> LENGTH: 805
<212> TYPE: PRT
<213> ORGANISM: Artificial Sequence
<220> FEATURE:
<223> OTHER INFORMATION: Synthetic Construct

<400> SEQUENCE: 64

Met Ala Ser Ser Pro Lys Lys Lys Arg Lys Val Ala Ala Asp
1               5                   10                  15

Tyr Lys Asp Asp Asp Lys Ser Trp Lys Asp Ala Ser Gly Trp Ser
            20                  25                  30

Arg Met His Ala Ala Pro Arg Arg Ala Ala Gln Pro Ser Asp Ala
            35                  40                  45

Ser Pro Ala Ala Gln Val Asp Leu Arg Thr Leu Gly Tyr Ser Gln Gln
    50                  55                  60

Gln Gln Glu Lys Ile Lys Pro Lys Val Arg Ser Thr Val Ala Gln His
65                  70                  75                  80

His Glu Ala Leu Val Gly His Gly Phe Thr His Ala His Ile Val Ala
            85                  90                  95

Leu Ser Gln His Pro Ala Ala Leu Gly Thr Val Ala Val Thr Tyr Gln
            100                 105                 110

His Ile Ile Thr Ala Leu Pro Glu Ala Thr His Glu Asp Ile Val Gly
            115                 120                 125

Val Gly Lys Gln Trp Ser Gly Ala Arg Ala Leu Glu Ala Leu Leu Thr
            130                 135                 140

Asp Ala Gly Glu Leu Arg Gly Pro Pro Leu Gln Leu Asp Thr Gly Gln
145                 150                 155                 160
```

```
Leu Val Lys Ile Ala Lys Arg Gly Gly Val Thr Ala Met Glu Ala Val
            165                 170                 175

His Ala Ser Arg Asn Ala Leu Thr Gly Ala Pro Leu Asn Leu Thr Pro
            180                 185                 190

Asp Gln Val Val Ala Ile Ala Ser Asn Asn Gly Gly Lys Gln Ala Leu
            195                 200                 205

Glu Thr Val Gln Arg Leu Leu Pro Val Leu Cys Gln Asp His Gly Leu
            210                 215                 220

Thr Pro Glu Gln Val Val Ala Ile Ala Ser His Asp Gly Gly Lys Gln
225                 230                 235                 240

Ala Leu Glu Thr Val Gln Arg Leu Leu Pro Val Leu Cys Gln Ala His
            245                 250                 255

Gly Leu Thr Pro Asp Gln Val Val Ala Ile Ala Ser Asn Asn Gly Gly
            260                 265                 270

Lys Gln Ala Leu Glu Thr Val Gln Arg Leu Leu Pro Val Leu Cys Gln
            275                 280                 285

Ala His Gly Leu Thr Pro Ala Gln Val Val Ala Ile Ala Ser Asn Gly
            290                 295                 300

Gly Gly Lys Gln Ala Leu Glu Thr Val Gln Arg Leu Leu Pro Val Leu
305                 310                 315                 320

Cys Gln Asp His Gly Leu Thr Pro Asp Gln Val Val Ala Ile Ala Ser
            325                 330                 335

Asn Ile Gly Gly Lys Gln Ala Leu Glu Thr Val Gln Arg Leu Leu Pro
            340                 345                 350

Val Leu Cys Gln Asp His Gly Leu Thr Pro Glu Gln Val Val Ala Ile
            355                 360                 365

Ala Ser His Asp Gly Gly Lys Gln Ala Leu Glu Thr Val Gln Arg Leu
            370                 375                 380

Leu Pro Val Leu Cys Gln Ala His Gly Leu Thr Pro Asp Gln Val Val
385                 390                 395                 400

Ala Ile Ala Ser Asn Ile Gly Gly Lys Gln Ala Leu Glu Thr Val Gln
            405                 410                 415

Arg Leu Leu Pro Val Leu Cys Gln Ala His Gly Leu Thr Pro Ala Gln
            420                 425                 430

Val Val Ala Ile Ala Ser Asn Ile Gly Gly Lys Gln Ala Leu Glu Thr
            435                 440                 445

Val Gln Arg Leu Leu Pro Val Leu Cys Gln Asp His Gly Leu Thr Pro
            450                 455                 460

Asp Gln Val Val Ala Ile Ala Ser Asn Ile Gly Gly Lys Gln Ala Leu
465                 470                 475                 480

Glu Thr Val Gln Arg Leu Leu Pro Val Leu Cys Gln Asp His Gly Leu
            485                 490                 495

Thr Pro Glu Gln Val Val Ala Ile Ala Ser Asn Asn Gly Gly Lys Gln
            500                 505                 510

Ala Leu Glu Thr Val Gln Arg Leu Leu Pro Val Leu Cys Gln Ala His
            515                 520                 525

Gly Leu Thr Pro Asp Gln Val Val Ala Ile Ala Ser Asn Gly Gly Gly
            530                 535                 540

Lys Gln Ala Leu Glu Thr Val Gln Arg Leu Leu Pro Val Leu Cys Gln
545                 550                 555                 560

Ala His Gly Leu Thr Pro Ala Gln Val Val Ala Ile Ala Ser Asn Ile
            565                 570                 575

Gly Gly Lys Gln Ala Leu Glu Thr Val Gln Arg Leu Leu Pro Val Leu
```

```
                580             585             590
Cys Gln Asp His Gly Leu Thr Pro Asp Gln Val Val Ala Ile Ala Ser
            595                 600                 605

Asn Gly Gly Gly Lys Gln Ala Leu Glu Thr Val Gln Arg Leu Leu Pro
        610                 615                 620

Val Leu Cys Gln Asp His Gly Leu Thr Pro Glu Gln Val Val Ala Ile
625                 630                 635                 640

Ala Ser Asn Ile Gly Gly Lys Gln Ala Leu Glu Thr Val Gln Arg Leu
                645                 650                 655

Leu Pro Val Leu Cys Gln Ala His Gly Leu Thr Pro Asp Gln Val Val
            660                 665                 670

Ala Ile Ala Ser His Asp Gly Gly Lys Gln Ala Leu Glu Thr Val Gln
        675                 680                 685

Arg Leu Leu Pro Val Leu Cys Gln Ala His Gly Leu Thr Pro Ala Gln
        690                 695                 700

Val Val Ala Ile Ala Ser Asn Ile Gly Gly Lys Gln Ala Leu Glu Thr
705                 710                 715                 720

Val Gln Arg Leu Leu Pro Val Leu Cys Gln Asp His Gly Leu Thr Pro
                725                 730                 735

Glu Gln Val Val Ala Ile Ala Ser Asn Gly Gly Arg Pro Ala Leu
            740                 745                 750

Glu Ser Ile Val Ala Gln Leu Ser Arg Pro Asp Pro Ala Leu Ala Ala
        755                 760                 765

Leu Thr Asn Asp His Leu Val Ala Leu Ala Cys Leu Gly Gly Arg Pro
    770                 775                 780

Ala Met Asp Ala Val Lys Lys Gly Leu Pro His Ala Pro Glu Leu Ile
785                 790                 795                 800

Arg Ser Arg Ile Arg
                805

<210> SEQ ID NO 65
<211> LENGTH: 1445
<212> TYPE: DNA
<213> ORGANISM: Artificial Sequence
<220> FEATURE:
<223> OTHER INFORMATION: EGFP polynucleotide

<400> SEQUENCE: 65
ctcgagatgc ggatcttcat ccacttccgg atcggctgct cccctatact aggttattgg    60
aaaattaagg ccttgtgca  acccactcga cttcttttgg aatatcttga agaaaaatat   120
gaagagcatt tgtatgagcg cgatgaaggt gataaatggc gaaacaaaaa gtttgaattg   180
ggtttggagt tcccaatctt tccttattat attgatggtg atgttaaatt aacacagtct   240
atggccatca tacgttatat agctgacaag cacaacatgt gggtggttg  tccaaaagag   300 cgtgcagaga tttcaatgct gaaggagcg  gttttggata ttagatacgg tgtttcgaga   360
attgcatata gtaaagactt tgaaactctc aaagttgatt tcttagcaa  gctacctgaa   420 atgctgaaaa tgttcgaaga tcgtttatgt cataaaacat atttaaatgg tgatcatgta   480
acccatcctg acttcatgtt gtatgacgct cttgatgttg ttttatacat ggacccaatg   540
tgcctggatg cgttcccaaa attagtttgt tttaaaaaac gtattgaagc tatcccacaa   600
attgataagt acttgaaatc cagcaagtat atagcatggc ctttgcaggg ctggcaagcc   660
acgtttggtg gtggcgacca tcctccaaaa tcgatctgg  aagttctgtt ccaggggccc   720
gtgtccaagg gcgaggaact gttcacaggc gtggtgccca tcctggtgga actggacggg   780
```

```
gatgtgaacg gccacaagtt cagcgtgtcc ggcgagggcg aaggcgacgc cacatatggc    840
aagctgaccc tgaagttcat ctgcaccacc ggcaagctgc ccgtgccttg gcctaccctc    900
gtgaccacac tgacctacgg cgtgcagtgc ttcagcagat accccgacca tatgaagcag    960
cacgacttct tcaagagcgc catgcccgag ggctacgtgc aggaacggac catcttcttt   1020
aaggacgacg gcaactacaa gaccagggcc gaagtgaagt tcgagggcga caccctcgtg   1080
aaccggatcg agctgaaggg catcgacttc aaagaggacg gcaacatcct gggccacaag   1140
ctggagtaca actacaacag ccacaacgtg tacatcatgg ccgacaagca gaaaaacggc   1200
atcaaagtga acttcaagat ccggcacaac atcgaggacg gctccgtgca gctggccgac   1260
cactaccagc agaacacccc catcggagat ggccccgtgc tgctgcccga caaccactac   1320
ctgagcacac agagcgccct gagcaaggac cccaacgaga gcgggacca catggtgctg    1380 ctggaattcg tgaccgccgc tggcatcacc ctgggcatgg acgagctgta caagtgagcg   1440
gccgc                                                                1445

<210> SEQ ID NO 66
<211> LENGTH: 341
<212> TYPE: DNA
<213> ORGANISM: Artificial Sequence
<220> FEATURE:
<223> OTHER INFORMATION: polynucleotide comprising polynucleotide
      encoding ICQ2

<400> SEQUENCE: 66
acatatttaa atggtgatca tgtaacccat cctgacttca tgttgtatga cgctcttgat     60
gttgttttat acatggaccc aatgtgcctg gatgcgttcc caaaattagt ttgttttaaa    120
aaacgtattg aagctatccc acaaattgat aagtacttga atccagcaa gtatatagca     180 tggcctttgc agggctggca agccacgttt ggtggtggcg accatcctcc aaaatcggat    240
ctggaagttc tgttccaggg gccctggga tccaggatct tcatccactt ccggcagggc     300
caggaaaacc tgtatttcca atctctcgag cgcgatcgca c                        341

<210> SEQ ID NO 67
<211> LENGTH: 30
<212> TYPE: DNA
<213> ORGANISM: Artificial Sequence
<220> FEATURE:
<223> OTHER INFORMATION: ICQ2

<400> SEQUENCE: 67
aggatcttca tccacttccg gcagggccag                                      30

<210> SEQ ID NO 68
<211> LENGTH: 17
<212> TYPE: DNA
<213> ORGANISM: Artificial Sequence
<220> FEATURE:
<223> OTHER INFORMATION: oligonucleotide

<400> SEQUENCE: 68
gatatcatga gcccaat                                                    17

<210> SEQ ID NO 69
<211> LENGTH: 78
<212> TYPE: DNA
<213> ORGANISM: Artificial Sequence
<220> FEATURE:
<223> OTHER INFORMATION: polynucleotide
```

```
<400> SEQUENCE: 69
gtaccggatc ttcatccact tcagaatcgg ctgtgaaaac ctgaccttcc agggaggcct      60
cgaggatatc gcggccgc                                                   78

<210> SEQ ID NO 70
<211> LENGTH: 38
<212> TYPE: DNA
<213> ORGANISM: Artificial Sequence
<220> FEATURE:
<223> OTHER INFORMATION: Primer

<400> SEQUENCE: 70
agatcccgga tccgctcgag gccggacccc gcgctggc                             38

<210> SEQ ID NO 71
<211> LENGTH: 41
<212> TYPE: DNA
<213> ORGANISM: Artificial Sequence
<220> FEATURE:
<223> OTHER INFORMATION: Primer

<400> SEQUENCE: 71
aggggaggaa gccatctcga gagattggaa atacaggttt t                         41
```

TRANSCRIPTIONAL REGULATORY FUSION POLYPEPTIDE

CROSS-REFERENCE TO RELATED APPLICATIONS

This application is a National Stage application of PCT/JP2017/044266, filed Dec. 11, 2017, which claims priority from Japanese application JP 2016-240097, filed Dec. 12, 2016.

The instant application contains a Sequence Listing which has been submitted in ASCII format via EFS-WEB and is hereby incorporated by reference in its entirety. Said ASCII copy, created on May 30, 2019, is named sequence.txt and is 378,694 bytes.

TECHNICAL FIELD

The present invention relates to a transcriptional regulatory fusion polypeptide.

BACKGROUND ART

As genome editing technologies, Zinc finger nuclease (ZFN) in which a nuclease is fused to zinc finger protein (ZFP), transcription activator-like effector nuclease (TALEN®), pentatricopeptide repeat (PPR) protein, and clustered regularly interspaced short palindromic repeats/CRISPR-associated proteins 9 (CRISPR/CAS9) have been reported (Proc. Natl. Acad. Sci. U.S.A., 1996, Vol. 93, p. 1156-1160; Genetics, 2010, Vol. 186, p. 757-761; Science, 2013, Vol. 339, p. 819-826; and Methods Mol. Biol., 2016, Vol. 1469, p. 147-155). It has been reported that, since ZFP, transcription activator-like effector (TALE) and PPR protein can bind to an arbitrary gene, a fusion polypeptide in which a transcriptional regulator is bound to the protein can bind to the nucleotide sequence of a target gene and thereby regulate the expression of the gene (Proc. Natl. Acad. Sci. U.S.A., 1996, Vol. 93, p. 1156-1160; Genetics, 2010, Vol. 186, p. 757-761; and Methods Mol. Biol., 2016, Vol. 1469, p. 147-155). It has been reported that, since gRNA used in the CRISPR/CAS9 system can bind to an arbitrary gene, and Cas9 can bind to gRNA (Methods Mol. Biol., 2016, Vol. 1469, p. 147-155), a fusion protein (also referred to as dCAS9-transcriptional inducer) in which a protein having transcription-inducing activity is bound to a CAS9 mutant deficient in nuclease activity (also referred to as nuclease-deficient Cas9 (dCAS9)) increases the expression of a target gene when used with gRNA (Nat. Methods, 2013, Vol. 10, p. 977-979).

Transcriptional activators such as VP16, VP64, p300 and VPR and transcriptional repressors such as Kruppel-associated box (KRAB) have been reported as transcription regulators to be bound to ZFP, TALE, PPR protein and dCas9 (Mol. Ther. Nucleic Acids, 2013, Vol. 2, p. e87; Nat. Biotechnol., 2015, Vol. 33, p. 510-517; Nat. Methods, 2015, Vol. 12, p. 326-328; and Mol. Cancer Res., 2010, Vol. 8, p. 246-253).

Cell-penetrating peptides are polypeptides having the function of penetrating a cell membrane and moving to the inside of the cell. A large number of sequences including human immunodeficiency virus (HIV)-derived TAT as well as penetratin, oligoarginine, transportan, membrane transduction sequence, and the like are known (Pharmacol. Ther., 2015, Vol. 154, p. 78-86). Also, a novel cell-penetrating peptide found from a peptide sequence comprised in viral protein R of HIV-1 has been reported (International Publication No. WO 2008/108505).

It has been reported that the cell-penetrating peptides can be used as tools for delivering genome editing proteins (e.g., ZFN, TALEN and CRISPR/CAS9) into cells (Non Patent Literature 1). For example, a fusion polypeptide comprising TALEN and TAT that binds to human CCR5 gene (Non Patent Literatures 2 and 3), and a fusion polypeptide comprising ZFP, TAT and VP16 that binds to the promoter region of VEGF (Non Patent Literature 4) have been reported.

A fusion polypeptide comprising ZFP and VP16 that binds to the promoter region or exon of human TERT has been reported as a fusion polypeptide targeting human telomerase reverse transcriptase (TERT) gene (Non Patent Literature 5). A fusion polypeptide comprising ZFP and KRAB that binds to the promoter region of human TERT has also been reported (Non Patent Literature 6).

CITATION LIST

Non Patent Literature

Non Patent Literature 1: "J. Control. Release" (NL), 2016, Vol. 226, p. 124-137
Non Patent Literature 2: "PLoS One" (USA), 2014, Vol. 9, e85755
Non Patent Literature 3: "Cell Regen. (Lond)" (UK), 2013, Vol. 2, p. 5-12
Non Patent Literature 4: "Proc. Natl. Acad. Sci. U.S.A." (USA), 2004, Vol. 101, p. 15225-15230
Non Patent Literature 5: "Mol. Ther. Nucleic Acids" (NL), 2013, Vol. 2, e87
Non Patent Literature 6: "Mol. Cancer Res." (USA), 2010, Vol. 8, p. 246-253

SUMMARY OF INVENTION

Technical Problem

An object of the present invention is to provide a novel fusion polypeptide that regulates the transcription of a target gene in cells merely by adding the fusion polypeptide to a medium of the cells.

Solution to Problem

The present inventors have conducted considerable ingenious studies on the preparation of a novel polypeptide that regulates the transcription of a target gene. The present inventors have consequently prepared a fusion polypeptide comprising: a cell-penetrating peptide; a DNA-binding polypeptide; and a transcriptional activator (Example 1), and found that the fusion polypeptide can activate the transcription of a target gene (Examples 2 to 4). As a result, the present inventors have provided the fusion polypeptide and completed the present invention.

Specifically, the present invention may include the following aspects as medically or industrially useful substances or methods.

[1]

A fusion polypeptide comprising: a cell-penetrating peptide; a DNA-binding polypeptide that binds to the nucleotide sequence represented by SEQ ID NO: 49; and a transcriptional activator.

[2]

The fusion polypeptide according to [1], wherein the transcriptional activator is VP64, VPR (fusion transcriptional activator comprising VP64, p65 and Rta), p300 or GCN5.

[3]

The fusion polypeptide according to [1], wherein the cell-penetrating peptide is a peptide consisting of the amino acid sequence represented by SEQ ID NO: 53, 54, 55, 56, 57 or 60.

[4]

The fusion polypeptide according to [1], wherein the cell-penetrating peptide is a peptide consisting of the amino acid sequence represented by SEQ ID NO: 56 or 60.

[5]

The fusion polypeptide according to [1], wherein the DNA-binding polypeptide is transcription activator-like effector (TALE).

[6]

The fusion polypeptide according to [5], wherein the DNA-binding polypeptide is TALE comprising an amino acid sequence consisting of amino acid numbers 7 to 784 of SEQ ID NO: 2.

[7]

The fusion polypeptide according to [1], wherein the DNA-binding polypeptide is a polypeptide consisting of the amino acid sequence represented by SEQ ID NO: 2.

[8]

The fusion polypeptide according to [1], wherein the cell-penetrating peptide is a peptide consisting of the amino acid sequence represented by SEQ ID NO: 56 or 60, the DNA-binding polypeptide is a polypeptide consisting of the amino acid sequence represented by SEQ ID NO: 2, and the transcriptional activator is VPR.

[9]

The fusion polypeptide according to [1], wherein the fusion polypeptide is a polypeptide consisting of the amino acid sequence represented by SEQ ID NO: 62.

[10]

A polynucleotide comprising a nucleotide sequence encoding a fusion polypeptide according to any of [1] to [9].

[11]

An expression vector comprising a polynucleotide according to [10].

[12]

A host cell transformed with an expression vector according to [11].

[13]

A method for producing a fusion polypeptide, comprising the step of culturing a host cell according to [12].

[14]

A method for increasing the expression of human telomerase reverse transcriptase (TERT) gene in a human somatic cell, comprising the step of culturing the human somatic cell in a medium containing a fusion polypeptide according to any of [1] to [9].

[15]

A method for proliferating human somatic cells, comprising the step of culturing the human somatic cells in a medium containing a fusion polypeptide according to any of [1] to [9].

Advantageous Effects of Invention

The fusion polypeptide of the present invention can be used for regulating the transcription of a target gene in cells merely by adding the fusion polypeptide to a medium for the culture of the cells.

BRIEF DESCRIPTION OF DRAWINGS

FIG. 1 shows an up-regulatory effect of NTP-TALE-TERT-1-Activator on human TERT mRNA expression. The ordinate shows the relative expression level of human TERT mRNA when the relative expression level of human TERT mRNA of a control supplemented with only a buffer solution was defined as 1. The error bar shows a standard deviation of the duplicate measurement values of 3 test samples.

FIG. 2 shows an up-regulatory effect of NTP-TALE-TERT-1-p300CD, NTP-TALE-TERT-2-p300CD and NTP-TALE-TERT-3-p300CD on human TERT mRNA expression. The ordinate shows the relative expression level of human TERT mRNA when the relative expression level of human TERT mRNA of a control unsupplemented with NTP-TALE-Activator was defined as 1. The error bar shows a standard deviation of the duplicate measurement values of 3 test samples.

FIG. 3 shows an up-regulatory effect of NTP-TALE-miR-346-1-VP64 on human miR-346 RNA expression. The ordinate shows the relative expression level of human miR-346 RNA when the relative expression level of human miR-346 RNA of a control unsupplemented with NTP-TALE-miR-346-1-VP64 was defined as 1. The error bar shows a standard deviation of the duplicate measurement values of 3 test samples.

FIG. 4 shows a cell growth-promoting effect of NTP-TALE-Activator. The ordinate shows the measurement value of luminescence intensity. The error bar shows a standard deviation of the duplicate measurement values of 3 test samples.

FIG. 5 shows a cell growth-promoting effect of NTP-TALE-TERT-1-VPR. The ordinate shows a cell count.

FIG. 6 shows an up-regulatory effect of ICQ2-TALE-TERT-1-VPR on human TERT mRNA expression. The ordinate shows the relative expression level of human TERT mRNA when the relative expression level of human TERT mRNA of a control was defined as 1. The error bar shows a standard deviation of the duplicate measurement values of 3 test samples.

FIG. 7 shows a cell growth-promoting effect of ICQ2-TALE-TERT-1-VPR. The ordinate shows a cell count.

DESCRIPTION OF EMBODIMENTS

Hereinafter, the present invention will be described in detail. The present specification encompasses the contents described in the specification and drawings of Japanese Patent Application No. 2016-240097 filed on Dec. 12, 2016 which is priority document of the present application.

1. Fusion Polypeptide of Present Invention

The fusion polypeptide of the present invention includes a polypeptide having the following feature:

a fusion polypeptide comprising: a cell-penetrating peptide; a DNA-binding polypeptide; and a transcriptional regulator.

A transcriptional activator or a transcriptional repressor can be used as the transcriptional regulator comprised in the fusion polypeptide of the present invention.

In one embodiment, the fusion polypeptide of the present invention is a fusion polypeptide comprising: a cell-penetrating peptide; a DNA-binding polypeptide; and a transcriptional activator.

The transcriptional activator used is not particularly limited as long as the fusion polypeptide of the present invention can activate the transcription of a target gene. For example, a transcriptional activator known in the art, such as VP16, VP64, VPR (fusion transcriptional activator comprising VP64, p65 and Rta), p300, GCN5, histone methyltransferase or TFIID-binding protein can be used (Mol. Ther. Nucleic Acids, 2013, Vol. 2, p. e87; Nucl. Acids Res., 2014, Vol. 42, p. 4375-4390; Nat. Methods, 2015, Vol. 12, p. 326-328; EMBO J., 1997, Vol. 16, p. 555-565; Nature, 2000, Vol. 406, p. 593-599; and Nature, 2000, Vol. 405, p. 701-704). In one embodiment, the transcriptional activator contained in the fusion polypeptide of the present invention is VP64, VPR, p300 or GCN5, preferably VPR.

In the present invention, the transcriptional activator includes not only wild type but an engineered mutant as long as the transcriptional activator has the ability to activate transcription.

As the transcriptional activator comprised in the fusion polypeptide of the present invention, for example, a transcriptional activator having histone acetyltransferase activity (HAT activity) can be used. For use of the transcriptional activator having HAT activity, such as p300 or GCN5, a polypeptide comprising a core region that exhibits the HAT activity of the transcriptional activator may be used. In the present invention, p300 also includes a polypeptide comprising the core region of p300. In one embodiment, the core region of p300 is a polypeptide consisting of an amino acid sequence from amino acid numbers 1048 to 1664 of Accession No. NP_001420.2. In the present invention, GCN5 also includes a polypeptide comprising the core region of GCN5. In one embodiment, the core region of GCN5 is a polypeptide consisting of an amino acid sequence from amino acid numbers 497 to 837 of Accession No. NP_066564.2.

In the present specification, the term "binding" used as to the DNA-binding polypeptide means not only direct binding to a target nucleotide sequence but indirect binding to a target nucleotide sequence through binding to a polynucleotide that binds to the target nucleotide sequence. Thus, the DNA-binding polypeptide comprised in the fusion polypeptide of the present invention includes not only a polypeptide that directly binds to a target nucleotide sequence but a polypeptide that indirectly binds to a target nucleotide sequence through binding to a polynucleotide that binds to the target nucleotide sequence.

In the present specification, the term "binding" used as to the DNA-binding polypeptide further means not only actual binding to a target nucleotide sequence but design so as to bind to a target nucleotide sequence. Thus, the DNA-binding polypeptide comprised in the fusion polypeptide of the present invention includes not only a DNA-binding polypeptide that actually binds to a target nucleotide sequence but a DNA-binding polypeptide designed so as to bind to a target nucleotide sequence.

Whether or not a test polypeptide can bind to a target nucleotide sequence or a polynucleotide that binds to the target nucleotide sequence can be confirmed by using a binding activity measurement method known in the art, such as gel shift assay or ChIP (chromatin immunoprecipitation)-seq assay.

Whether or not a test polypeptide has been designed so as to bind to a target nucleotide sequence can be confirmed on the basis of, for example, the presence or absence of an amino acid sequence reported to bind to the target nucleotide sequence, in the test polypeptide. Examples of the amino acid sequence reported to bind to the target nucleotide sequence include amino acid sequences described in Science, 2009, Vol. 326, p. 1509-1512, Nat. Biotechnol., 2011, Vol. 29, p. 143-148, Japanese Patent Laid-Open No. 2015/33365, Proc. Natl. Acad. Sci. U.S.A., 1996, Vol. 93, p. 1156-1160, and Methods Mol. Biol., 2016, Vol. 1469, p. 147-155. Alternatively, whether or not a test polypeptide has been designed so as to bind to a target nucleotide sequence may be confirmed by examining whether the test polypeptide actually binds to the target nucleotide sequence by using a binding activity measurement method known in the art, such as gel shift assay or ChIP-seq assay.

In one embodiment, the DNA-binding polypeptide comprised in the fusion polypeptide of the present invention is a DNA-binding polypeptide that binds to the transcriptional regulatory region of a target gene.

The transcriptional regulatory region is not particularly limited as long as the region is involved in the expression regulation of a target gene. Examples thereof include a promoter region and an enhancer region.

Examples of the target gene include, but are not particularly limited to, human TERT gene and human miR-346 gene.

In one embodiment, when the target gene is human TERT gene, the DNA-binding polypeptide comprised in the fusion polypeptide of the present invention is a DNA-binding polypeptide having the following feature:

a DNA-binding polypeptide that binds to the nucleotide sequence represented by SEQ ID NO: 49.

In one embodiment, when the target gene is human miR-346 gene, the DNA-binding polypeptide comprised in the fusion polypeptide of the present invention is a DNA-binding polypeptide having the following feature:

a DNA-binding polypeptide that binds to a complementary strand sequence of the nucleotide sequence represented by SEQ ID NO: 52.

As the DNA-binding polypeptide designed so as to bind to a target nucleotide sequence, for example, TALE (Science, 2009, Vol. 326, p. 1509-1512), ZFP (Proc. Natl. Acad. Sci. U.S.A., 1996, Vol. 93, p. 1156-1160) or PPR protein (Methods Mol. Biol., 2016, Vol. 1469, p. 147-155) can be used. Since techniques of preparing TALE, ZFP and PPR protein are known in the art, those skilled in the art can prepare a polypeptide designed so as to bind to a nucleotide sequence of interest on the basis of the techniques (Nat. Biotechnol., 2011, Vol. 29, p. 143-148; Proc. Natl. Acad. Sci. U.S.A., 1997, Vol. 94, p. 5525-5530; and Methods Mol. Biol., 2016, Vol. 1469, p. 147-155). Also, a method for preparing TALE having high binding activity against a nucleotide sequence can be used (Japanese Patent Laid-Open No. 2015/33365. Platinum Gate TALEN construction protocol (Yamamoto lab) Ver. 1.0).

As the DNA-binding polypeptide that indirectly binds to a target nucleotide sequence through binding to a polynucleotide that binds to the target nucleotide sequence, for example, CRISPR/CAS9 (Science, 2013, Vol. 339, p. 819-823) can be used. Since a technique of preparing CRISPR/CAS9 is known in the art, those skilled in the art can prepare a polynucleotide designed so as to bind to a target nucleotide sequence, and a polypeptide that binds to the polynucleotide on the basis of the technique (Science, 2013, Vol. 339, p. 819-823; and Science, 2013, Vol. 339, p. 823-826).

In one embodiment, when the target gene is human TERT gene, the DNA-binding polypeptide comprised in the fusion polypeptide of the present invention is a DNA-binding polypeptide having the following feature:

a DNA-binding polypeptide which is TALE that binds to the nucleotide sequence represented by SEQ ID NO: 49.

In one embodiment, when the target gene is human miR-346 gene, the DNA-binding polypeptide comprised in the fusion polypeptide of the present invention is a DNA-binding polypeptide having the following feature:

a DNA-binding polypeptide which is TALE that binds to a complementary strand sequence of the nucleotide sequence represented by SEQ ID NO: 52.

The term "TALE" used in the present specification means a polypeptide comprising an amino-terminal region comprising a DNA-binding repeat domain designed so as to bind to a target nucleotide sequence on the genome of interest by linking 10 to 30 repeats of structural units (modules) consisting of 34 amino acids, and a thymine-binding domain (RCSB Protein Data Bank, Molecule of the Month, 2014, No. 180; and Nat. Biotechnol., 2011, Vol. 29, p. 143-148). As the amino-terminal region comprising a DNA-binding repeat domain designed so as to bind to a target nucleotide sequence, and a thymine-binding domain, for example, an amino acid sequence known in the art can be used (Science, 2009, Vol. 326, p. 1509-1512; Nat. Biotechnol., 2011, Vol. 29, p. 143-148; and Japanese Patent Laid-Open No. 2015/33365).

Alternatively, TALE engineered to shorten a moiety other than the DNA-binding repeat domain and the thymine-binding domain (also referred to as truncated TALE) may be used in the fusion polypeptide of the present invention as long as the fusion polypeptide can bind to a target nucleotide sequence. Those skilled in the art can prepare truncated TALE on the basis of a technique known in the art (Sci. Rep., 2013, Vol. 3, p. 3379).

In one embodiment, when the target gene is human TERT gene, the DNA-binding polypeptide comprised in the fusion polypeptide of the present invention is TALE comprising the amino acid sequence represented by amino acid numbers (positions) 7 to 784 of SEQ ID NO: 2. In this context, the amino acid sequence represented by amino acid numbers 7 to 784 of SEQ ID NO: 2 refers to a polypeptide consisting of a DNA-binding repeat domain of TALE designed so as to bind to the nucleotide sequence represented by SEQ ID NO: 49, and a thymine-binding domain.

In one embodiment, when the target gene is human miR-346 gene, the DNA-binding polypeptide comprised in the fusion polypeptide of the present invention is TALE comprising the amino acid sequence represented by amino acid numbers 7 to 784 of SEQ ID NO: 8. In this context, the amino acid sequence represented by amino acid numbers 7 to 784 of SEQ ID NO: 8 refers to a polypeptide consisting of a DNA-binding repeat domain of TALE designed so as to bind to a complementary strand of the nucleotide sequence represented by SEQ ID NO: 52, and a thymine-binding domain.

In one embodiment, when the target gene is human TERT gene, the DNA-binding polypeptide comprised in the fusion polypeptide of the present invention is a DNA-binding polypeptide having the following feature:

a DNA-binding polypeptide consisting of the amino acid sequence represented by SEQ ID NO: 2.

In one embodiment, when the target gene is human miR-346 gene, the DNA-binding polypeptide comprised in the fusion polypeptide of the present invention is a DNA-binding polypeptide having the following feature:

a DNA-binding polypeptide consisting of the amino acid sequence represented by SEQ ID NO: 8.

The cell-penetrating peptide comprised in the fusion polypeptide of the present invention is not particularly limited by its amino acid sequence as long as the cell-penetrating peptide can pass through a cell membrane. Whether or not a test peptide can pass through a cell membrane can be confirmed by using a cell membrane pass-through evaluation system known in the art (International Publication No. WO 2008/108505).

As the cell-penetrating peptide comprised in the fusion polypeptide of the present invention, a cell-penetrating peptide known in the art can be used (International Publication No. WO 2008/108505; Pharmacol. Ther., 2015, Vol. 154, p. 78-86; and Database (Oxford), 2012, bas015). As the cell-penetrating peptide comprised in the fusion polypeptide of the present invention, for example, a polypeptide comprising amino acid sequences RI, FI and RIGC and having 25 or less amino acid residues can be used. In one embodiment, examples of the cell-penetrating peptide comprised in the fusion polypeptide of the present invention include a peptide consisting of the amino acid sequence represented by SEQ ID NO: 53 (RILQQLLFIHFRIGCRHSRI), a peptide consisting of the amino acid sequence represented by SEQ ID NO: 54 (RILQQLLFIHFRIGCRH), a peptide consisting of the amino acid sequence represented by SEQ ID NO: 55 (RILQQLLFIHFRIGC), a peptide consisting of the amino acid sequence represented by SEQ ID NO: 56 (RI-FIHFRIGC), and a peptide consisting of the amino acid sequence represented by SEQ ID NO: 57 (RIFIRIGC). A peptide consisting of the amino acid sequence represented by SEQ ID NO: 56 is preferred.

As the cell-penetrating peptide comprised in the fusion polypeptide of the present invention, the amino acid sequence represented by SEQ ID NO: 60 (RIFIHFRQGQ) can be used.

The positions of the cell-penetrating peptide, the DNA-binding peptide and the transcriptional activator are not limited as long as the fusion polypeptide of the present invention can activate the transcription of a target gene. Preferably, the cell-penetrating peptide is positioned on the N-terminal or C-terminal side of the fusion polypeptide of the present invention. More preferably, the cell-penetrating peptide is positioned on the N-terminal side of the fusion polypeptide of the present invention. In one embodiment, the fusion polypeptide of the present invention is constituted by the cell-penetrating peptide, the DNA-binding peptide and the transcriptional activator in this order from the N-terminal side.

In one embodiment, the fusion polypeptide of the present invention is a fusion polypeptide comprising: a cell-penetrating peptide; a DNA-binding polypeptide that binds to the transcriptional regulatory region of a target gene; and a transcriptional activator.

In one embodiment, the fusion polypeptide of the present invention is a fusion polypeptide comprising: a cell-penetrating peptide; a DNA-binding polypeptide that binds to the transcriptional regulatory region of TERT or miR-346; and a transcriptional activator.

In one embodiment, the fusion polypeptide of the present invention is a fusion polypeptide comprising: a cell-penetrating peptide; a DNA-binding polypeptide that binds to the promoter region or enhancer region of a target gene; and a transcriptional activator.

In one embodiment, the fusion polypeptide of the present invention is a fusion polypeptide comprising: a cell-penetrating peptide; a DNA-binding polypeptide that binds to the promoter region or enhancer region of TERT or miR-346; and a transcriptional activator.

In one embodiment, the fusion polypeptide of the present invention is a fusion polypeptide comprising: a cell-penetrating peptide; a DNA-binding polypeptide that binds to the nucleotide sequence represented by SEQ ID NO: 49; and a transcriptional activator.

In one embodiment, the fusion polypeptide of the present invention is a fusion polypeptide comprising: a cell-penetrating peptide; a DNA-binding polypeptide that binds to a complementary strand sequence of the nucleotide sequence represented by SEQ ID NO: 52; and a transcriptional activator.

In one embodiment, the fusion polypeptide of the present invention is a fusion polypeptide comprising: a cell-penetrating peptide; TALE that binds to the nucleotide sequence represented by SEQ ID NO: 49; and a transcriptional activator.

In one embodiment, the fusion polypeptide of the present invention is a fusion polypeptide comprising: a cell-penetrating peptide; TALE that binds to a complementary strand sequence of the nucleotide sequence represented by SEQ ID NO: 52; and a transcriptional activator.

In one embodiment, the fusion polypeptide of the present invention is a fusion polypeptide comprising: a cell-penetrating peptide; TALE comprising an amino acid sequence consisting of amino acid numbers 7 to 784 of SEQ ID NO: 2; and a transcriptional activator.

In one embodiment, the fusion polypeptide of the present invention is a fusion polypeptide comprising: a cell-penetrating peptide; TALE comprising an amino acid sequence consisting of amino acid numbers 7 to 784 of SEQ ID NO: 8; and a transcriptional activator.

In one embodiment, the fusion polypeptide of the present invention is a fusion polypeptide comprising: a cell-penetrating peptide; a polypeptide consisting of the amino acid sequence represented by SEQ ID NO: 2; and a transcriptional activator.

In one embodiment, the fusion polypeptide of the present invention is a fusion polypeptide comprising: a cell-penetrating peptide; a polypeptide consisting of the amino acid sequence represented by SEQ ID NO: 8; and a transcriptional activator.

In one embodiment, the fusion polypeptide of the present invention is a fusion polypeptide comprising: a cell-penetrating peptide; a DNA-binding polypeptide that binds to the nucleotide sequence represented by SEQ ID NO: 49; and a transcriptional activator selected from the group consisting of VP64, VPR, p300 and GCN5.

In one embodiment, the fusion polypeptide of the present invention is a fusion polypeptide comprising: a cell-penetrating peptide; a DNA-binding polypeptide that binds to a complementary strand sequence of the nucleotide sequence represented by SEQ ID NO: 52; and a transcriptional activator selected from the group consisting of VP64, VPR, p300 and GCN5.

In one embodiment, the fusion polypeptide of the present invention is a fusion polypeptide comprising: a cell-penetrating peptide; TALE that binds to the nucleotide sequence represented by SEQ ID NO: 49; and a transcriptional activator selected from the group consisting of VP64, VPR, p300 and GCN5.

In one embodiment, the fusion polypeptide of the present invention is a fusion polypeptide comprising: a cell-penetrating peptide; TALE that binds to a complementary strand sequence of the nucleotide sequence represented by SEQ ID NO: 52; and a transcriptional activator selected from the group consisting of VP64, VPR, p300 and GCN5.

In one embodiment, the fusion polypeptide of the present invention is a fusion polypeptide comprising: a cell-penetrating peptide; TALE comprising an amino acid sequence consisting of amino acid numbers 7 to 784 of SEQ ID NO: 2; and a transcriptional activator selected from the group consisting of VP64, VPR, p300 and GCN5.

In one embodiment, the fusion polypeptide of the present invention is a fusion polypeptide comprising: a cell-penetrating peptide; TALE comprising an amino acid sequence consisting of amino acid numbers 7 to 784 of SEQ ID NO: 8; and a transcriptional activator selected from the group consisting of VP64, VPR, p300 and GCN5.

In one embodiment, the fusion polypeptide of the present invention is a fusion polypeptide comprising: a cell-penetrating peptide; a DNA-binding polypeptide consisting of the amino acid sequence represented by SEQ ID NO: 2; and a transcriptional activator selected from the group consisting of VP64, VPR, p300 and GCN5.

In one embodiment, the fusion polypeptide of the present invention is a fusion polypeptide comprising: a cell-penetrating peptide; a DNA-binding polypeptide consisting of the amino acid sequence represented by SEQ ID NO: 8; and a transcriptional activator selected from the group consisting of VP64, VPR, p300 and GCN5.

In one embodiment, the fusion polypeptide of the present invention is a fusion polypeptide comprising: a cell-penetrating peptide consisting of the amino acid sequence represented by SEQ ID NO: 53, 54, 55, 56, 57 or 60; TALE that binds to the nucleotide sequence represented by SEQ ID NO: 49; and a transcriptional activator selected from the group consisting of VP64, VPR, p300 and GCN5.

In one embodiment, the fusion polypeptide of the present invention is a fusion polypeptide comprising: a cell-penetrating peptide consisting of the amino acid sequence represented by SEQ ID NO: 53, 54, 55, 56, 57 or 60; TALE that binds to a complementary strand sequence of the nucleotide sequence represented by SEQ ID NO: 52; and a transcriptional activator selected from the group consisting of VP64, VPR, p300 and GCN5.

In one embodiment, the fusion polypeptide of the present invention is a fusion polypeptide comprising: a cell-penetrating peptide consisting of the amino acid sequence represented by SEQ ID NO: 53, 54, 55, 56, 57 or 60; TALE comprising an amino acid sequence consisting of amino acid numbers 7 to 784 of SEQ ID NO: 2; and a transcriptional activator selected from the group consisting of VP64, VPR, p300 and GCN5.

In one embodiment, the fusion polypeptide of the present invention is a fusion polypeptide comprising: a cell-penetrating peptide consisting of the amino acid sequence represented by SEQ ID NO: 53, 54, 55, 56, 57 or 60; TALE comprising an amino acid sequence consisting of amino acid numbers 7 to 784 of SEQ ID NO: 8; and a transcriptional activator selected from the group consisting of VP64, VPR, p300 and GCN5.

In one embodiment, the fusion polypeptide of the present invention is a fusion polypeptide comprising: a cell-penetrating peptide consisting of the amino acid sequence represented by SEQ ID NO: 53, 54, 55, 56, 57 or 60; a DNA-binding polypeptide consisting of the amino acid sequence represented by SEQ ID NO: 2; and a transcriptional activator selected from the group consisting of VP64, VPR, p300 and GCN5.

In one embodiment, the fusion polypeptide of the present invention is a fusion polypeptide comprising: a cell-penetrating peptide consisting of the amino acid sequence represented by SEQ ID NO: 53, 54, 55, 56, 57 or 60; a DNA-binding polypeptide consisting of the amino acid sequence represented by SEQ ID NO: 8; and a transcriptional activator selected from the group consisting of VP64, VPR, p300 and GCN5.

In one embodiment, the fusion polypeptide of the present invention is a fusion polypeptide comprising: a cell-penetrating peptide consisting of the amino acid sequence represented by SEQ ID NO: 53, 54, 55, 56, 57 or 60; a DNA-binding polypeptide consisting of the amino acid sequence represented by SEQ ID NO: 2; and VPR.

In one embodiment, the fusion polypeptide of the present invention is a fusion polypeptide comprising: a cell-penetrating peptide consisting of the amino acid sequence represented by SEQ ID NO: 53, 54, 55, 56, 57 or 60; a DNA-binding polypeptide consisting of the amino acid sequence represented by SEQ ID NO: 8; and VP64.

In one embodiment, the fusion polypeptide of the present invention is a fusion polypeptide comprising: a cell-penetrating peptide consisting of the amino acid sequence represented by SEQ ID NO: 56 or 60; TALE that binds to the nucleotide sequence represented by SEQ ID NO: 49; and a transcriptional activator selected from the group consisting of VP64, VPR, p300 and GCN5.

In one embodiment, the fusion polypeptide of the present invention is a fusion polypeptide comprising: a cell-penetrating peptide consisting of the amino acid sequence represented by SEQ ID NO: 56 or 60; TALE that binds to a complementary strand sequence of the nucleotide sequence represented by SEQ ID NO: 52; and a transcriptional activator selected from the group consisting of VP64, VPR, p300 and GCN5.

In one embodiment, the fusion polypeptide of the present invention is a fusion polypeptide comprising: a cell-penetrating peptide consisting of the amino acid sequence represented by SEQ ID NO: 56 or 60; TALE comprising an amino acid sequence consisting of amino acid numbers 7 to 784 of SEQ ID NO: 2; and a transcriptional activator selected from the group consisting of VP64, VPR, p300 and GCN5.

In one embodiment, the fusion polypeptide of the present invention is a fusion polypeptide comprising: a cell-penetrating peptide consisting of the amino acid sequence represented by SEQ ID NO: 56 or 60; TALE comprising an amino acid sequence consisting of amino acid numbers 7 to 784 of SEQ ID NO: 8; and a transcriptional activator selected from the group consisting of VP64, VPR, p300 and GCN5.

In one embodiment, the fusion polypeptide of the present invention is a fusion polypeptide comprising: a cell-penetrating peptide consisting of the amino acid sequence represented by SEQ ID NO: 56 or 60; a DNA-binding polypeptide consisting of the amino acid sequence represented by SEQ ID NO: 2; and a transcriptional activator selected from the group consisting of VP64, VPR, p300 and GCN5.

In one embodiment, the fusion polypeptide of the present invention is a fusion polypeptide comprising: a cell-penetrating peptide consisting of the amino acid sequence represented by SEQ ID NO: 56 or 60; a DNA-binding polypeptide consisting of the amino acid sequence represented by SEQ ID NO: 8; and a transcriptional activator selected from the group consisting of VP64, VPR, p300 and GCN5.

In one embodiment, the fusion polypeptide of the present invention is a fusion polypeptide comprising: a cell-penetrating peptide consisting of the amino acid sequence represented by SEQ ID NO: 56 or 60; a DNA-binding polypeptide consisting of the amino acid sequence represented by SEQ ID NO: 2; and VPR.

In one embodiment, the fusion polypeptide of the present invention is a fusion polypeptide comprising: a cell-penetrating peptide consisting of the amino acid sequence represented by SEQ ID NO: 56 or 60; a DNA-binding polypeptide consisting of the amino acid sequence represented by SEQ ID NO: 8; and VP64.

The fusion polypeptide of the present invention may comprise a peptide such as a peptide linker between the cell-penetrating peptide, the DNA-binding peptide and the transcriptional activator as long as the fusion polypeptide can activate the transcription of a target gene.

The fusion polypeptide of the present invention may also comprise a peptide tag such as glutathione S-transferase (GST) tag or polyhistidine tag at the N or C terminus as long as the fusion polypeptide of the present invention can activate the transcription of a target gene.

In one embodiment, the fusion polypeptide of the present invention is a polypeptide consisting of the amino acid sequence represented by SEQ ID NO: 62.

The fusion polypeptide of the present invention includes, in addition to the polypeptide consisting of the amino acid sequence represented by SEQ ID NO: 62, a polypeptide consisting of an amino acid sequence mutated from the amino acid sequence represented by SEQ ID NO: 62 by the deletion, substitution, insertion, or addition of one or several amino acids, or a combination thereof, and having an activating effect on the transcription of TERT gene.

Examples of the amino acid sequence mutated from the amino acid sequence represented by SEQ ID NO: 62 by the deletion, substitution, insertion, or addition of one or several amino acids, or a combination thereof include (i) an amino acid sequence with deletion of 1 to 10 (e.g., 1 to 5, preferably 1 to 3, more preferably 1 or 2, further preferably 1) amino acids in the amino acid sequence represented by SEQ ID NO: 62, (ii) an amino acid sequence with substitution of 1 to 10 (e.g., 1 to 5, preferably 1 to 3, more preferably 1 or 2, further preferably 1) amino acids by other amino acids in the amino acid sequence represented by SEQ ID NO: 62, (iii) an amino acid sequence with insertion of 1 to 10 (e.g., 1 to 5, preferably 1 to 3, more preferably 1 or 2, further preferably 1) amino acids in the amino acid sequence represented by SEQ ID NO: 62, (iv) an amino acid sequence with addition of 1 to 10 (e.g., 1 to 5, preferably 1 to 3, more preferably 1 or 2, further preferably 1) amino acids in the amino acid sequence represented by SEQ ID NO: 62, and (v) an amino acid sequence mutated by any combination of (i) to (iv).

In the present invention, the phrase "activating effect on the transcription of TERT gene" means an increasing effect on the expression level of the TERT gene in cells. The "activating effect on the transcription of TERT gene" means that a test fusion polypeptide has an increasing effect on the expression level of TERT gene by 10% or more, 20% or more, 30% or more, or 40% or more, preferably 50% or more, compared with the expression level of the TERT gene in cells cultured in a medium unsupplemented with the test fusion polypeptide. The activating effect on the transcription of TERT gene can be confirmed, for example, by measuring the mRNA level of the TERT gene in cells cultured in a medium supplemented with the fusion peptide of the present invention by using a method known in the art, for example, real-time PCR. As a specific method, for example, a method as described in Example 2 mentioned later can be used.

The fusion peptide of the present invention also includes, in addition to the polypeptide consisting of the amino acid sequence represented by SEQ ID NO: 62, a polypeptide having an amino acid sequence having about 80% or higher, 85% or higher, 90% or higher, 95% or higher, 96% or higher, 97% or higher, 98% or higher, or 99% or higher identity to the amino acid sequence represented by SEQ ID NO: 62, and having the activating effect on the transcription of TERT gene.

The term "identity" in the present specification means Identity, which is a value obtained by the search of NEEDLE program (J. Mol. Biol., 1970, Vol. 48, p. 443-453) using parameters provided as defaults. The parameters are as follows.

Gap penalty=10
Extend penalty=0.5
Matrix=EBLOSUM62

In order to prepare the polypeptide having the mutation described above, a mutation can be introduced to a polynucleotide encoding the polypeptide by using a kit for mutation introduction based on a site-directed mutagenesis method such as Kunkel method or gapped duplex method, for example, QuikChange™ Site-Directed Mutagenesis Kit (Stratagene Corporation), GeneTailor™ Site-Directed Mutagenesis System (Thermo Fisher Scientific Inc.), or TaKaRa Site-Directed Mutagenesis System (Mutan-K, Mutan-Super Express Km, etc.; Takara Bio Inc.). Also, a method such as a site-directed mutagenesis method described in, for example, "Molecular Cloning, A Laboratory Manual (4th edition)" (Cold Spring Harbor Laboratory Press (2012)) can be used.

In one embodiment, the fusion polypeptide of the present invention is a polypeptide consisting of the amino acid sequence represented by SEQ ID NO: 22.

The fusion polypeptide of the present invention includes, in addition to the polypeptide consisting of the amino acid sequence represented by SEQ ID NO: 22, a polypeptide consisting of an amino acid sequence mutated from the amino acid sequence represented by SEQ ID NO: 22 by the deletion, substitution, insertion, or addition of one or several amino acids, or a combination thereof, and having an activating effect on transcription of miR-346 gene.

Examples of the amino acid sequence mutated from the amino acid sequence represented by SEQ ID NO: 22 by the deletion, substitution, insertion, or addition of one or several amino acids, or a combination thereof include (i) an amino acid sequence with deletion of 1 to 10 (e.g., 1 to 5, preferably 1 to 3, more preferably 1 or 2, further preferably 1) amino acids in the amino acid sequence represented by SEQ ID NO: 22, (ii) an amino acid sequence with substitution of 1 to 10 (e.g., 1 to 5, preferably 1 to 3, more preferably 1 or 2, further preferably 1) amino acids by other amino acids in the amino acid sequence represented by SEQ ID NO: 22, (iii) an amino acid sequence with insertion of 1 to 10 (e.g., 1 to 5, preferably 1 to 3, more preferably 1 or 2, further preferably 1) amino acids in the amino acid sequence represented by SEQ ID NO: 22, (iv) an amino acid sequence with addition of 1 to 10 (e.g., 1 to 5, preferably 1 to 3, more preferably 1 or 2, further preferably 1) amino acids in the amino acid sequence represented by SEQ ID NO: 22, and (v) an amino acid sequence mutated by any combination of (i) to (iv).

In the present invention, the phrase "the activating effect on the transcription of miR-346 gene" means an increasing effect on the expression level of the miR-346 gene in cells.

The "having the activating effect on the transcription of miR-346 gene" means that a test fusion polypeptide has an increasing effect on the expression level of miR-346 gene by 10% or more, 20% or more, 30% or more, or 40% or more, preferably 50% or more, compared with the expression level of the miR-346 gene in cells cultured in a medium unsupplemented with the test fusion polypeptide. The activating effect on the transcription of miR-346 gene can be confirmed, for example, by measuring the RNA level of the miR-346 in cells cultured in a medium supplemented with the fusion peptide of the present invention by using a method known in the art, for example, real-time PCR. As a specific method, for example, a method as described in Example 4 mentioned later can be used.

The fusion peptide of the present invention also includes, in addition to the polypeptide consisting of the amino acid sequence represented by SEQ ID NO: 22, a polypeptide having an amino acid sequence having about 80% or higher, 85% or higher, 90% or higher, 95% or higher, 96% or higher, 97% or higher, 98% or higher, or 99% or higher identity to the amino acid sequence represented by SEQ ID NO: 22, and having the activating effect on the transcription of miR-346 gene.

A method for searching for identity and a method for introducing a mutation are similar to the case of the polypeptide consisting of the amino acid sequence represented by SEQ ID NO: 62.

Those skilled in the art is capable of readily preparing the fusion polypeptide of the present invention by using a method known in the art on the basis of sequence information on the cell-penetrating peptide, the DNA-binding peptide and the transcriptional regulator, disclosed in the present specification. The fusion polypeptide of the present invention can be produced according to, for example, but not particularly limited to, a method described in "5. Method for producing fusion polypeptide of present invention" mentioned later.

2. Polynucleotide of Present Invention

The polynucleotide of the present invention includes a polynucleotide comprising a nucleotide sequence encoding the fusion polypeptide of the present invention.

Those skilled in the art are capable of readily preparing the polynucleotide of the present invention by using a method known in the art on the basis of the nucleotide sequence. The polynucleotide of the present invention may be synthesized by using, for example, a gene synthesis method known in the art.

3. Expression Vector of Present Invention

The expression vector of the present invention includes an expression vector comprising the polynucleotide comprising a nucleotide sequence encoding the fusion polypeptide of the present invention.

The expression vector for the expression of the polynucleotide of the present invention is not particularly limited as long as the polynucleotide comprising a nucleotide sequence encoding the fusion polypeptide of the present invention can be expressed in a reaction solution containing RNA polymerase and nucleoside triphosphate and the polypeptide encoded thereby can be produced in a wheat germ extract, or as long as the polynucleotide comprising a nucleotide sequence encoding the fusion polypeptide of the present invention can be expressed in various host cells such as eukaryotic cells (e.g., animal cells, insect cells, plant cells, and yeasts) and/or prokaryotic cells (e.g., *E. coli*) and the polypeptide encoded thereby can be produced. Examples of such an expression vector include plasmid vectors and virus vectors (e.g., adenovirus, adeno-associated virus, retrovirus, and hemagglutinating virus of Japan). Preferably, pEU-E01-MCS (CellFree Sciences Co., Ltd.), pET20b(+) (Novagen), or pCold vector-I (Takara Bio Inc. 3361) can be used.

The expression vector of the present invention may comprise a promoter operably linked to the polynucleotide of the present invention. Examples of the promoter for expression in a reaction solution containing RNA polymerase and nucleoside triphosphate include T3 promoter, T7 promoter, and SP6 promoter. Examples of the promoter for the expression of the polynucleotide of the present invention in animal cells include promoters derived from viruses such as cytomegalovirus (CMV), respiratory syncytial virus (RSV), and simian virus 40 (SV40), actin promoter, EF (elongation factor) 1α promoter, and heat shock promoter. Examples of the promoter for expression in bacteria (e.g., bacteria of the genus Escherichia) include trp promoter, lac promoter, λPL promoter, tac promoter, T3 promoter, T7 promoter, and SP6 promoter. Examples of the promoter for expression in yeasts include GAL1 promoter, GAL10 promoter, PH05 promoter, PGK promoter, GAP promoter, and ADH promoter.

In the case of using a reaction solution containing RNA polymerase and nucleoside triphosphate and a wheat germ extract, or in the case of using animal cells, insect cells, or yeasts as host cells, the expression vector of the present invention may comprise a start codon and a stop codon. In this case, the expression vector of the present invention may comprise an enhancer sequence, 5' and 3' untranslated regions of a gene encoding the fusion polypeptide of the present invention, a secretory signal sequence, a splicing junction, a polyadenylation site, or a replicable unit, etc. In the case of using E. coli as host cells, the expression vector of the present invention may comprise a start codon, a stop codon, a terminator region, and a replicable unit. In this case, the expression vector of the present invention may comprise a selective marker usually used according to a purpose (e.g., tetracycline resistance gene, ampicillin resistance gene, kanamycin resistance gene, neomycin resistance gene, and dihydrofolate reductase gene).

4. Transformed Host Cell of Present Invention

The transformed host cell of the present invention includes a host cell transformed with the expression vector of the present invention.

The host cell to be transformed is not particularly limited as long as the host cell is compatible with the expression vector used and can be transformed with the expression vector and express a protein. Examples of the host cell to be transformed include various cells such as natural cells and artificially established cells usually used in the technical field of the present invention (e.g., animal cells (e.g., CHO cells), insect cells (e.g., Sf9), bacteria (bacteria of the genus Escherichia, etc.), and yeasts (the genus of Saccharomyces, the genus Pichia, etc.)). Preferably, animal cells such as CHO cells, HEK293 cells, or NS0 cells or a bacterium of the genus Escherichia can be used.

The method for transforming the host cell is not particularly limited, and, for example, a calcium phosphate method or electroporation can be used.

5. Method for Producing Fusion Polypeptide of Present Invention

The method for producing the fusion polypeptide of the present invention includes a method for producing a fusion polypeptide, comprising the step of reacting mRNA synthesized in a reaction solution containing RNA polymerase and nucleoside triphosphate using the expression vector of the present invention, with a wheat germ extract to express the fusion polypeptide, or the step of culturing the host cell of the present invention to express the fusion polypeptide.

The method for producing the fusion polypeptide of the present invention is not particularly limited as long as the method comprises the step of synthesizing mRNA in a reaction solution containing RNA polymerase and nucleoside triphosphate using the expression vector of the present invention, and reacting the synthesized mRNA with a wheat germ extract to express the fusion polypeptide, or the step of culturing the transformed host cell of the present invention to express the fusion polypeptide. Examples of the reaction solution containing RNA polymerase and nucleoside triphosphate and the wheat germ extract for use in the method include reagents included in WEPRO7240G Expression Kit (CellFree Sciences Co., Ltd.). Preferred examples of the host cell for use in the method include the preferred transformed host cells of the present invention mentioned above.

The culture of the transformed host cell can be performed by a method known in the art. Culture conditions, for example, a temperature, medium pH and a culture time are appropriately selected. The host cell can be cultured to produce the fusion polypeptide of the present invention.

The method for producing the fusion polypeptide of the present invention can further comprise the step of recovering, preferably isolating or purifying the fusion polypeptide, in addition to the step of synthesizing mRNA in a reaction solution containing RNA polymerase and nucleoside triphosphate using the expression vector of the present invention, and the step of reacting the synthesized mRNA with a wheat germ extract to express the fusion polypeptide. As for the isolation or purification method, for example, affinity chromatography in which the fusion polypeptide of the present invention fused with GST tag or polyhistidine tag can be bound to glutathione sepharose beads, followed by eluting the fused polypeptide with excessive reduced glutathione to purify the fusion polypeptide.

The method for producing the fusion polypeptide of the present invention can further comprise the step of recovering, preferably isolating or purifying the fusion polypeptide from the transformed host cell, in addition to the step of culturing the transformed host cell of the present invention to express the fusion polypeptide. Examples of the isolation or purification method include: methods exploiting solubility, such as salting out and a solvent precipitation method; methods exploiting difference in molecular weight, such as dialysis, ultrafiltration, and gel filtration; methods exploiting charge, such as ion-exchange chromatography and hydroxyapatite chromatography; methods exploiting specific affinity, such as affinity chromatography; methods exploiting difference in hydrophobicity, such as reverse-phase high-performance liquid chromatography; methods exploiting the specific affinity of an antibody recognizing the endogenous structure of a particular tag or protein molecule; and methods exploiting difference in isoelectric point, such as isoelectric focusing. Preferably, the fusion polypeptide accumulated in a culture supernatant can be purified by various chromatography techniques.

The fusion polypeptide of the present invention also includes a fusion polypeptide produced by the method for producing the fusion polypeptide of the present invention.

6. Method for Regulating Transcription of Target Gene Using Fusion Polypeptide of Present Invention The method for regulating the transcription of a target gene using the fusion polypeptide of the present invention includes a method for regulating the transcription of a target gene in a cell, comprising the step of culturing the cell in a medium containing the fusion polypeptide of the present invention.

Examples of the target gene whose transcription is regulated by the method of the present invention include, but are not particularly limited to, genes related to cell growth (TERT and miR-346, preferably human TERT and human miR-346).

Examples of the fusion polypeptide for use in the method of the present invention include the fusion polypeptides described in "1. Fusion polypeptide of present invention".

Examples of the cell for use in the method of the present invention include, but are not particularly limited to, somatic cells (preferably human somatic cells). In the present specification, the term "somatic cell" means cells, other than germ cells, present in organisms. Examples of the somatic cell for use in the method of the present invention include, but are not particularly limited to, stem cells (preferably human stem cells) such as mesenchymal stem cells (MSC) (preferably human MSC), and fibroblasts (preferably human fibroblasts).

The medium for use in the method of the present invention is not particularly limited as long as the medium is usually used in the field of cell culture. Serum can be added to the medium according to the type of the cell.

The culture conditions for use in the method of the present invention can be appropriately selected by those skilled in the art according to the type of the cell.

The concentration of the fusion polypeptide of the present invention to be added to the medium differs depending on the type of the cell, a cell count, the transcriptional regulatory activity of the fusion polypeptide, etc. For example, a concentration on the order of 0.01 nM to 10 µM, preferably 0.5 nM to 5 µM, can be used.

The timing and the number of addition of the fusion polypeptide of the present invention are not particularly limited. The timing of addition of the fusion polypeptide of the present invention to the medium may be, for example, at the start of culture, or may be after the start of culture. In the case of adding the fusion polypeptide of the present invention to the medium after the start of culture, the fusion polypeptide may be added, for example, after 1 hour, after 5 hours, after 10 hours, after 15 hours, after 24 hours (after 1 day), after 36 hours, after 48 hours (after 2 days), after 3 days, after 4 days, or after 5 days from the start of culture.

Whether or not the fusion polypeptide of the present invention can regulate the transcription of a target gene can be confirmed by using a gene expression level measurement method known in the art. Examples of the method for measuring a gene expression level include methods such as real-time PCR. In the case of using real-time PCR, whether or not a test fusion polypeptide can regulate the transcription of a target gene can be confirmed by using TaqMan Fast Advanced Master Mix (Thermo Fisher Scientific Inc.) in an exemplary method. As a specific method for evaluating a gene expression level, for example, a method as described in Examples 2 to 4 mentioned later can be used.

7. Method for Proliferating Cells Using Fusion Polypeptide of Present Invention

The method for proliferating cells using the fusion polypeptide of the present invention includes a method for proliferating cells, comprising the step of culturing the cells in a medium containing the fusion polypeptide of the present invention which can promote the transcription of a gene involved in cell growth.

Examples of the gene involved in cell growth include genes known in the art, such as TERT and miR-346.

Examples of the fusion polypeptide for use in the method of the present invention include the fusion polypeptides described in "1. Fusion polypeptide of present invention".

Examples of the cell for use in the method of the present invention include, but are not particularly limited to, somatic cells (preferably human somatic cells). Examples of the somatic cells for use in the method of the present invention include, but are not particularly limited to, stem cells (preferably human stem cells) such as mesenchymal stem cells (MSC) (preferably human MSC), and fibroblasts (preferably human fibroblasts).

The medium for use in the method of the present invention, the culture conditions, the concentration of the fusion polypeptide of the present invention, and the timing and number of addition the fusion polypeptide are as described above in "6. Method for regulating transcription of target gene using fusion polypeptide of present invention".

Whether or not the fusion polypeptide of the present invention can proliferate cells can be confirmed by using a cell growth measurement method known in the art. Examples of the method for measuring cell growth include cell growth assay using an intracellular ATP quantification reagent CellTiter-Glo® Reagent (Promega Corp.), and cell counting. By using CellTiter-Glo® Reagent or measuring cell count with a cell counter Scepter (Merck Millipore), whether or not a test fusion polypeptide can proliferate cells can be confirmed. As a specific method for evaluating cell growth, for example, a method as described in Examples 5, 6 and 8 mentioned later can be used.

The present invention is generally described above. Particular Examples to be referred in order to obtain further understanding will be provided here. However, these examples are given merely for illustrative purposes and do not limit the present invention.

EXAMPLES

In sections using a commercially available kit or reagent, etc. an experiment was conducted according to the attached protocol unless otherwise specified. A concentration mol/L is represented by M for the sake of convenience. For example, a 1 M aqueous sodium hydroxide solution means a 1 mol/L aqueous sodium hydroxide solution.

Example 1

Preparation of CPP-TALE-Activator

Transcription activator-like effector (TALE) designed so as to specifically bind to the promoter or enhancer of each of human TERT and human miR-346 genes, was prepared. A fusion polypeptide (hereinafter, also referred to as NTP-TALE-Activator) comprising: TALE; a cell-penetrating peptide (also referred to as NTP) encoded by a polynucleotide consisting of the nucleotide sequence represented by SEQ ID NO: 23 (International Publication No. WO 2008/108505); and a transcriptional activator, and a fusion polypeptide (hereinafter, also referred to as ICQ2-TALE-Activator) comprising: TALE; a cell-penetrating peptide (also referred to as ICQ2) encoded by a polynucleotide consisting of the nucleotide sequence represented by SEQ ID NO: 67; and a transcriptional activator were prepared (NTP-TALE-Activator and ICQ2-TALE-Activator are also collectively referred to as CPP-TALE-Activator).

(1) Preparation of Expression Plasmid pEU-E01-GST-NTP-TEV

A polynucleotide (SEQ ID NO: 24) consisting of a nucleotide sequence encoding glutathione S-transferase (GST), a polynucleotide (SEQ ID NO: 23) consisting of a nucleotide sequence encoding NTP (consisting of an amino acid sequence RIFIHFRIGC (SEQ ID NO: 56)), and a polynucleotide (SEQ ID NO: 25) consisting of a nucleotide sequence encoding a target peptide (hereinafter, referred to as TEV) of TEV protease were inserted in order from the 5' side to the multicloning site of an expression plasmid pEU-E01-MCS (CellFree Sciences Co., Ltd.).

A polynucleotide was synthesized in which a restriction enzyme EcoRV site and a restriction enzyme BamHI site were added to the 5' and 3' ends, respectively, of the polynucleotide consisting of the nucleotide sequence represented by SEQ ID NO: 24. The polynucleotide was inserted to the multicloning site of the expression plasmid pEU-E01-MCS using EcoRV (Takara Bio Inc.) and BamHI (Takara Bio Inc.) to prepare an expression plasmid pEU-E01-GST. Next, a polynucleotide comprising a BamHI site sequence, the nucleotide sequence encoding NTP, the nucleotide sequence encoding TEV, a restriction enzyme XhoI site sequence, a restriction enzyme SgfI site sequence, a restriction enzyme PmeI site sequence, a restriction enzyme NotI site sequence, and a restriction enzyme SalI site sequence in order from the 5' end (provided that cytosine was inserted to between the XhoI site and the SgfI site in order to encode amino acid sequences in frame) was prepared. The polynucleotide was inserted to the expression plasmid pEU-E01-GST using BamHI and SalI (Takara Bio Inc.). Then, inverse PCR (PCR in which primers are designed from one region of a cyclic polynucleotide outward, and the whole cyclized polynucleotide is amplified) was performed using primers consisting of the nucleotide sequences represented by SEQ ID NOs: 26 and 27 to prepare an expression plasmid pEU-E01-GST-NTP-TEV.

(2) Preparation of Plasmid pEU-E01-GST-NTP-TEV-ΔTALE-VP64V

A polynucleotide (comprising a nucleotide sequence encoding a portion of TALE and a nucleotide sequence encoding VP64 (SEQ ID NO: 29); referred to as ΔTALE-VP64) consisting of the nucleotide sequence represented by SEQ ID NO: 28 was integrated immediately downstream of the nucleotide sequence encoding TEV in the expression plasmid pEU-E01-GST-NTP-TEV prepared in (1) using In-Fusion® HD Cloning Plus kit (Takara Bio Inc.) to obtain a plasmid pEU-E01-GST-NTP-TEV-ΔTALE-VP64V. This designation ended in V because valine was added to the C terminus of VP64.

(3) Preparation of TALE Targeting Human TERT Gene

A surrounding sequence of a telomerase subunit human TERT gene (Accession No. AH007699.2) was searched for in a database Ensembl genome browser known in the art to select a nucleotide sequence from nucleotide numbers 49444 to 49461 of Accession No. AH007699.2 (nucleotide sequence represented by SEQ ID NO: 49) as a target nucleotide sequence of TALE, from a gene region of about 40000 base pairs (hereinafter, abbreviated to bp) downstream of the transcription initiation point of the gene, predicted to act as an enhancer. A polynucleotide (polynucleotide comprising a nucleotide sequence from nucleotide numbers 429 to 2064 of SEQ ID NO: 1) comprising a nucleotide sequence encoding a DNA-binding polypeptide designed so as to specifically bind to the nucleotide sequence represented by SEQ ID NO: 49 was prepared by a method known in the art (Platinum Gate TALEN construction protocol (Yamamoto lab) Ver. 1.0). Then, a polynucleotide consisting of a nucleotide sequence from nucleotide numbers 435 to 889 of SEQ ID NO: 28 comprised in the plasmid pEU-E01-GST-NTP-TEV-ΔTALE-VP64V prepared in (2) was replaced with the aforementioned polynucleotide consisting of a nucleotide sequence from nucleotide numbers 429 to 2064 of SEQ ID NO: 1 using T4 DNA Ligase (New England BioLabs, Inc.). As a result, a plasmid comprising a polynucleotide (consisting of the nucleotide sequence represented by SEQ ID NO: 1) consisting of a nucleotide sequence encoding a DNA-binding polypeptide (also referred to as TALE_TERT-1) consisting of the amino acid sequence of SEQ ID NO: 2 was obtained. The amino acid sequence represented by amino acid numbers 7 to 784 of SEQ ID NO: 2 is a polypeptide moiety comprising a DNA-binding repeat domain of TALE designed so as to bind to the nucleotide sequence represented by SEQ ID NO: 49, and a thymine-binding domain.

Likewise, a surrounding sequence of the human TERT gene (Accession No. AH007699.2) was searched for in Ensembl genome browser. As a result, a nucleotide sequence from nucleotide numbers 11029 to 11046 of Accession No. AH007699.2 (nucleotide sequence represented by SEQ ID NO: 50) was selected as a target nucleotide sequence of TALE from a gene region predicted to act as a promoter, and a nucleotide sequence from nucleotide numbers 6501 to 6518 of Accession No. AH007699.2 (nucleotide sequence represented by SEQ ID NO: 51) was selected as another target nucleotide sequence of TALE from a gene region predicted to act as an enhancer. Then, polynucleotides (polynucleotide comprising a nucleotide sequence from nucleotide numbers 429 to 2064 of SEQ ID NO: 3 and polynucleotide comprising a nucleotide sequence from nucleotide numbers 429 to 2064 of SEQ ID NO: 5) comprising a nucleotide sequence encoding each DNA-binding polypeptide designed so as to specifically bind to the nucleotide sequence represented by SEQ ID NO: 50 or the nucleotide sequence represented by SEQ ID NO: 51 was prepared. Next, a polynucleotide consisting of a nucleotide sequence from nucleotide numbers 435 to 889 of SEQ ID NO: 28 comprised in the plasmid pEU-E01-GST-NTP-TEV-ΔTALE-VP64V prepared in (2) was replaced with the aforementioned polynucleotide consisting of a nucleotide sequence from nucleotide numbers 429 to 2064 of SEQ ID NO: 3 or SEQ ID NO: 5. As a result, plasmids comprising polynucleotides (consisting of the nucleotide sequence represented by SEQ ID NOs: 3 and 5, respectively) consisting of nucleotide sequences encoding DNA-binding polypeptides (also referred to as TALE_TERT-2 and TALE_TERT-3, respectively) consisting of the amino acid sequences represented by SEQ ID NO: 4 and SEQ ID NO: 6 were obtained.

(4) Preparation of TALE Targeting Human miR-346 Gene

Human miR-346 gene is known to promote the expression of human TERT gene (Sci. Rep., 2015, Vol. 5, p. 15793). A surrounding sequence of human microRNA miR-346 gene (Accession No. NR_029907.1) was searched for in Ensembl genome browser to select a gene region consisting of a nucleotide sequence from nucleotide numbers 13529 to 13546 of Accession No. AMYH02023475.1 (nucleotide sequence represented by SEQ ID NO: 52) as a target nucleotide sequence of TALE, from a gene region of 1000 bp upstream of the transcription initiation point of the gene, predicted to act as a promoter. A plasmid comprising a polynucleotide (consisting of the nucleotide sequence represented by SEQ ID NO: 7) consisting of a nucleotide sequence encoding a DNA-binding polypeptide (consisting of the amino acid sequence represented by SEQ ID NO: 8 (also referred to as TALE_miR-346-1)) designed so as to bind to a complementary strand sequence of the nucleotide sequence represented by SEQ ID NO: 52 was obtained in a similar way to the method described above in (3).

The plasmid comprising the polynucleotide consisting of a nucleotide sequence encoding each TALE, prepared in (3)

and (4) was collectively referred to as an expression plasmid pEU-E01-GST-NTP-TEV-TALE-VP64V.

(5) Preparation of Expression Plasmid Encoding NTP-TALE-Activator

An expression plasmid pEU-E01-GST-NTP-TEV-TALE-VP64 was prepared by the method given below using the expression plasmid pEU-E01-GST-NTP-TEV-TALE-VP64V prepared in (3) and (4). Further, the nucleotide sequence encoding VP64 of the expression plasmid pEU-E01-GST-NTP-TEV-TALE-VP64 was replaced with each nucleotide sequence encoding VPR, a p300 core region (hereinafter, referred to as p300CD) or a GCN5 core region (hereinafter, referred to as GCN5CD).

PCR was performed using the expression plasmid pEU-E01-GST-NTP-TEV-TALE-VP64V prepared in (3) and (4) as a template and using PrimeSTAR® Max DNA Polymerase (Takara Bio Inc.) and primers consisting of the nucleotide sequences represented by SEQ ID NOs: 30 and 31. Thereby, a polynucleotide in which a SgfI site sequence and a NotI site sequence were added to the 5' and 3' ends, respectively, of a polynucleotide comprising a polynucleotide consisting of the nucleotide sequences encoding TALE and VP64 was prepared. This polynucleotide was designated as TALE-VP64. This TALE-VP64 was cleaved with SgfI (Takara Bio Inc.) and NotI (Takara Bio Inc.) and inserted to between the restriction enzyme sites SgfI and NotI of the expression plasmid pEU-E01-GST-NTP-TEV prepared in (1) to prepare an expression plasmid pEU-E01-GST-NTP-TEV-TALE-VP64.

PCR was performed using SP-dCas9-VPR (Addgene) as a template and using PrimeSTAR® Max DNA Polymerase (Takara Bio Inc.) and primers consisting of the nucleotide sequences represented by SEQ ID NOs: 32 and 33. Thereby, CGCGCGTCAGCCAGC (SEQ ID NO: 58) and GTTTAAACTGCGGCC (SEQ ID NO: 59) were added to the 5' and 3' ends, respectively, of a polynucleotide consisting of the nucleotide sequence encoding VPR (SEQ ID NO: 34). This polynucleotide was designated as VPR-PCR.

Next, PCR was performed using pEU-E01-GST-NTP-TEV-TALE-VP64 as a template and primers consisting of the nucleotide sequences represented by SEQ ID NOs: 35 and 36. Thereby, a polynucleotide in which the nucleotide sequence encoding VP64 was removed and CGCGCGTCAGCCAGC (SEQ ID NO: 58) and GTTTAAACTGCGGCC (SEQ ID NO: 59) were added to the 3' and 5' sides, respectively, was prepared. This polynucleotide was designated as pEU-E01-GST-NTP-TEV-TALE-PCR.

pEU-E01-GST-NTP-TEV-TALE-PCR and VPR-PCR were linked at a molar ratio of 1:10 using In-Fusion® HD Cloning Plus kit. As a result, an expression plasmid encoding VPR as the transcriptional activator was prepared. This expression plasmid was designated as pEU-E01-GST-NTP-TEV-TALE-VPR. Of this, pEU-E01-GST-NTP-TEV-TALE-VPR encoding TALE_TERT-1 as the DNA-binding polypeptide was designated as pEU-E01-GST-NTP-TALE-TERT-1-VPR. The expression plasmid was subjected to agarose electrophoresis and sequence analysis to confirm that the desired construct was cloned.

Likewise, as for the p300 core region (p300CD), PCR was performed using 1246 pCMVb p300HA (Addgene, 10718) as a template and primers consisting of the nucleotide sequences represented by SEQ ID NOs: 37 and 38 to add CGCGCGTCAGCCAGC (SEQ ID NO: 58) and GTTTAAACTGCGGCC (SEQ ID NO: 59) to the 5' and 3' ends, respectively, of a polynucleotide consisting of the nucleotide sequence encoding p300CD (SEQ ID NO: 39). This polynucleotide was designated as p300CD-PCR.

Likewise, as for the GCN5CD core region (GCN5CD), PCR was performed using Flexi ORF clone FXC03762 (Kazusa DNA Research Institute) as a template and primers consisting of the nucleotide sequences represented by SEQ ID NOs: 40 and 41 to add CGCGCGTCAGCCAGC (SEQ ID NO: 58) and GTTTAAACTGCGGCC (SEQ ID NO: 59) to the 5' and 3' ends, respectively, of a polynucleotide consisting of the nucleotide sequence encoding GCN5CD (SEQ ID NO: 42). This polynucleotide was designated as GCN5CD-PCR.

Each of these polynucleotides p300CD-PCR and GCN5CD-PCR was linked to pEU-E01-GST-NTP-TEV-TALE-PCR using In-Fusion® HD Cloning Plus kit, as in the case of VPR. As a result, an expression plasmid encoding p300CD as the transcriptional activator, and an expression plasmid encoding GCN5CD as the transcriptional activator were prepared. These expression plasmids were designated as pEU-E01-GST-NTP-TEV-TALE-p300CD and pEU-E01-GST-NTP-TEV-TALE-GCN5CD, respectively. The prepared expression plasmids comprising two types of transcriptional activators were each subjected to agarose electrophoresis and sequence analysis to confirm that the desired construct was cloned.

(6) Preparation of Expression Plasmid Encoding NTP-TEV-TALE_scramble-VPR or GST-NTP-EGFP Expression plasmids encoding GST-NTP-EGFP and NTP-TEV-TALE_scramble-VPR, respectively, were prepared as negative controls of Examples 6 and 8.

Next, an expression plasmid pGEX6p-1 (GE Healthcare Japan Corp.) was cleaved with a restriction enzyme EcoNI (New England Biolabs, Inc.), and a polynucleotide consisting of the nucleotide sequence represented by SEQ ID NO: 68 was inserted thereto as a linker. The obtained vector was cleaved with EcoRV and BamHI to excise a polynucleotide fragment. The excised fragment was inserted to pEU-E01-MCS cleaved with EcoRV and BamHI using T4 DNA Ligase. The vector was further cleaved with BamHI and SalI, and a polynucleotide consisting of the nucleotide sequence represented by SEQ ID NO: 69 encoding a NTP and TEV recognition sequence was inserted thereto using T4 DNA Ligase. The obtained vector was cleaved with XhoI and NotI, and a polynucleotide (consisting of the nucleotide sequence represented by SEQ ID NO: 65) consisting of a nucleotide sequence encoding highly sensitive green fluorescence protein (EGFP) in which XhoI and NotI sites were added to both ends, respectively, was inserted thereto using T4 DNA ligase to prepare an expression plasmid pEU-E01-GST-NTP-EGFP. pEU-E01-GST-NTP-EGFP comprises a polynucleotide consisting of a nucleotide sequence encoding a fusion polypeptide comprising GST, NTP and EGFP (also referred to as GST-NTP-EGFP).

Inverse PCR was performed using pEU-E01-GST-NTP-TALE-TERT-1-VPR prepared in (5) as a template and primers consisting of the nucleotide sequences represented by SEQ ID NOs: 70 and 71. The obtained PCR fragment was mixed with a polynucleotide consisting of the nucleotide sequence represented by SEQ ID NO: 63 (polynucleotide consisting of a nucleotide sequence encoding a polypeptide (also referred to as TALE_scramble) consisting of the amino acid sequence of SEQ ID NO: 64) and linked using In-Fusion® HD Cloning Plus kit. Thereby, a polynucleotide consisting of a nucleotide sequence from nucleotide numbers 1 to 2139 of SEQ ID NO: 1 encoding TALE_TERT-1, comprised in pEU-E01-GST-NTP-TALE-TERT-1-VPR was replaced with a polynucleotide consisting of the nucleotide sequence represented by SEQ ID NO: 63. As a result, an expression plasmid pEU-E01-GST-NTP-TALE_scramble- VPR comprising a polynucleotide encoding TALE_scramble was obtained. In this context, TALE_scramble is TALE targeting a gene in which a sequence except for T at both ends was randomly scrambled into a nucleotide sequence having composition with seven A, three T, three G, and three C, for example, TGCGTACAAAGTATACAT, and used as a negative control for the TALE moiety targeting human TERT.

(7) Preparation of Expression Plasmid pEU-E01-GST-ICQ2-TALE-TERT-1-VPR pEU-E01-GST-NTP-TALE-TERT-1-VPR prepared in (5) was treated with a restriction enzyme AsiSI (New England Biolabs, Inc.) and a restriction enzyme SwaI (Takara Bio Inc.).

Next, a polynucleotide (comprising a polynucleotide encoding ICQ2 (amino acid sequence: RIFIHFRQGQ (SEQ ID NO: 60))) consisting of the nucleotide sequence represented by SEQ ID NO: 66 was synthesized and treated with AsiSI and SwaI. Agarose electrophoresis was performed to excise a polynucleotide fragment of about 340 bases, which was then purified using FastGene gel/PCR extraction kit (Nippon Genetics Co., Ltd., FG91202). This polynucleotide fragment was linked to the expression plasmid pEU-E01-GST-NTP-TEV-TALE-VPR cleaved with AsiSI and SwaI using T4 DNA ligase (Mighty Mix, Takara Bio Inc., 6023). The plasmid thus obtained by linking was transferred to competent cells (Stbl, New England Biolabs, Inc.) by heat treatment. The cells were cultured overnight at 30° C. in a LB medium agar plate (aqueous solution containing 10 g/L Bacto Tryptone (Becton, Dickinson and Company), 5 g/L Bacto Yeast Extract (Becton, Dickinson and Company), 10 g/L sodium chloride (Wako Pure Chemical Industries, Ltd.) and 1.5% agarose (Wako Pure Chemical Industries, Ltd.)) containing 100 µg/mL ampicillin (Sigma-Aldrich Co. LLC) (hereinafter, referred to as a LA plate). A plasmid was purified from the obtained colony to obtain pEU-E01-GST-ICQ2-TALE-TERT-1-VPR in which a polynucleotide consisting of the nucleotide sequence encoding NTP in the expression plasmid pEU-E01-GST-NTP-TEV-TALE-VPR was replaced with a polynucleotide consisting of the nucleotide sequence represented by SEQ ID NO: 67. Sequence analysis was conducted to confirm that the construct was correctly prepared. pEU-E01-GST-ICQ2-TALE-TERT-1-VPR comprises a polynucleotide consisting of a nucleotide sequence encoding a fusion polypeptide comprising ICQ2, TALE_TERT-1 and VPR (also referred to as ICQ2-TALE-TERT-1-VPR).

(8) Preparation of NTP-TALE-Activator, ICQ2-TALE-TERT-1-VPR and GST-NTP-EGFP

Each CPP-TALE-Activator and GST-NTP-EGFP were synthesized using each expression plasmid encoding CPP-TALE-Activator or GST-NTP-EGFP, prepared in (5) to (7), as a template, and using a wheat cell-free protein synthesis kit (CellFree Sciences Co., Ltd.), and purified.

Each protein was synthesized at a scale of 0.29 mL as the amount of a reaction solution using 1 µg of each expression plasmid prepared in (5) to (7) and using WEPRO7240G Expression Kit (CellFree Sciences Co., Ltd.). After the synthesis, 0.1% Empigen (Sigma-Aldrich Co. LLC) was added with respect to the amount of the reaction solution. Further, 60 µL of Glutathione Sepharose 4B (GE Healthcare Japan Corp.) saturated with phosphate-buffered saline was added thereto, and the mixture was shaken at 4° C. for 2 hours. Glutathione Sepharose was recovered by centrifugation and suspended in 1 mL of ice-cold phosphate-buffered saline. The procedure of centrifugation again was repeated twice. Glutathione Sepharose thus recovered was suspended in 1 mL of phosphate-buffered saline containing 150 mM sodium chloride. Glutathione Sepharose was separated by centrifugation again.

Next, in order to extract CPP-TALE-Activator and GST-NTP-EGFP bound with Glutathione Sepharose, the following operation was performed: 60 µL of a 50 mM Tris-HCl buffer solution (pH 8.0) containing 30 mM reduced glutathione (Wako Pure Chemical Industries, Ltd.) was added to the aforementioned Glutathione Sepharose. After shaking at room temperature for 1 minute, a supernatant was recovered by centrifugation. The same procedure was repeated twice. A supernatant was recovered to obtain CPP-TALE-Activator and GST-NTP-EGFP. Glycerin (Nacalai Tesque, Inc.) (final concentration: 20%) and a protease inhibitor (Halt Protease and Phosphatase Inhibitor Cocktail, Thermo Fisher Scientific Inc.) (final concentration: 1%) were added to the recovered supernatant, and the mixture was preserved on ice. The concentration of the CPP-TALE-Activator protein contained in this supernatant was calculated from comparison with concurrently migrated BSA (Sigma-Aldrich Co. LLC, fraction V) by using SDS polyacrylamide electrophoresis and Coomassie Brilliant Blue staining. The aqueous solution containing 30 mM reduced glutathione, a 50 mM Tris-HCl buffer solution (pH 8.0), 20% glycerin and 1% protease inhibitor for the elution of these purified proteins is referred to as an elution buffer solution.

The name of each CPP-TALE-Activator obtained in this Example, SEQ ID NO of its nucleotide sequence and SEQ ID NO of an amino acid sequence encoded thereby will be shown.

TABLE 1

(Name and SEQ ID NO of each CPP-TALE-Activator)
CPP-TALE-Activator

| Name | Cell-penetrating peptide | TALE | Transcriptional activator | SEQ ID NO Nucleotide sequence | SEQ ID NO Amino acid Sequence |
|---|---|---|---|---|---|
| NTP-TALE-TERT-1-VP64 | NTP | TERT-1 | VP64 | SEQ ID NO: 9 | SEQ ID NO: 10 |
| NTP-TALE-TERT-1-VPR | NTP | TERT-1 | VPR | SEQ ID NO: 11 | SEQ ID NO: 12 |
| NTP-TALE-TERT-1-p300CD | NTP | TERT-1 | p300CD | SEQ ID NO: 13 | SEQ ID NO: 14 |

TABLE 1-continued (Name and SEQ ID NO of each CPP-TALE-Activator)
CPP-TALE-Activator

| Name | Cell-penetrating peptide | TALE | Transcriptional activator | SEQ ID NO Nucleotide sequence | SEQ ID NO Amino acid Sequence |
|---|---|---|---|---|---|
| NTP-TALE-TERT-1-GCN5CD | NTP | TERT-1 | GCN5CD | SEQ ID NO: 15 | SEQ ID NO: 16 |
| NTP-TALE-TERT-2-p300CD | NTP | TERT-2 | p300CD | SEQ ID NO: 17 | SEQ ID NO: 18 |
| NTP-TALE-TERT-3-p300CD | NTP | TERT-3 | p300CD | SEQ ID NO: 19 | SEQ ID NO: 20 |
| NTP-TALE-miR-346-1-VP64 | NTP | miR-346-1 | VP64 | SEQ ID NO: 21 | SEQ ID NO: 22 |
| ICQ2-TALE-TERT-1-VPR | ICQ2 | TERT-1 | VPR | SEQ ID NO: 61 | SEQ ID NO: 62 |

Example 2

Measurement of Intracellular Human TERT mRNA Expression Level when NTP-TALE-Activator is Added—(1)

The expression level of human TERT mRNA in cultured cells was evaluated using NTP-TALE-Activator targeting human TERT.

Human umbilical cord matrix-derived mesenchymal stem cells (PromoCell GmbH, C-12971; hereinafter, referred to as UC-MSC) were suspended in DMEM medium (Thermo Fisher Scientific Inc.) containing 10% fetal bovine serum (HyClone), 1% penicillin-streptomycin (Thermo Fisher Scientific Inc.) and 2 mM L-GlutaMax (Thermo Fisher Scientific Inc.) and seeded in a 96-well transparent culture plate (Iwaki Glass Co., Ltd.) at $0.4 \times 10^4$ cells/100 μL/well. The plate was left standing for 12 hours in a $CO_2$ incubator set to a $CO_2$ concentration of 5% at 37° C.

Each NTP-TALE-Activator prepared in Example 1 (NTP-TALE-TERT-1-VP64, NTP-TALE-TERT-1-VPR, NTP-TALE-TERT-1-p300CD, and NTP-TALE-TERT-1-GCN5CD) was diluted to 0.3 nM, 1.0 nM or 3.0 nM (intrawell final concentration at the time of the experiment) with an elution buffer solution and added at 1 μL to each well. The elution buffer solution was added as a control instead of NTP-TALE-Activator. The plate was left standing for 24 hours in an incubator at 37° C. and a $CO_2$ concentration of 5%. Each well was washed once with 100 μL of ice-cold phosphate-buffered saline. Then, the culture plate was treated with liquid nitrogen to freeze the cells.

The aforementioned culture plate was left standing on ice for thawing. At the same time therewith, 30 μL of a lysis solution (mixed solution of 29.7 μL of Lysis solution and 0.3 μL of DNase I) attached to TaqMan® Gene Expression Cells-to-CT™ kit (Thermo Fisher Scientific Inc.) was added to each well and mixed with the cells. The plate was left standing at room temperature for 5 minutes. Then, 3 μL of Stop solution attached to the kit was added to each well, and the plate was left standing at room temperature for 5 minutes. Thereby, a cell lysate containing RNA extracted from the cells was obtained.

Real-time PCR was performed using the cell lysate as a template and TaqMan® Fast Advanced Master Mix (Thermo Fisher Scientific Inc.) with 7900HT Fast Real Time PCR System (Thermo Fisher Scientific Inc.) to measure a human TERT mRNA level. The measurement value was indicated by a ratio to the mRNA level of human actin beta (ACTB) gene as an endogenous control gene. A value determined by dividing the human TERT mRNA level by the human ACTB mRNA level was used as the relative expression level of human TERT mRNA. The relative expression level of human TERT mRNA in each group was calculated when the relative expression level of human TERT mRNA of the control was defined as 1. The wells for the same sample were measured in triplicate.

TERT FAM (Thermo Fisher Scientific Inc., Hs00972648_g1) was used as a primer set for human TERT, and ACTB VIC (Thermo Fisher Scientific Inc., Hs99999903_m1) was used as a primer set for human ACTB.

As shown in FIGS. 1(1) and 1(2), NTP-TALE-TERT-1-VP64, NTP-TALE-TERT-1-VPR, NTP-TALE-TERT-1-p300CD and NTP-TALE-TERT-1-GCN5CD were found to increase the expression level of human TERT mRNA (increase the expression of the human TERT gene) as compared with the control group.

These results demonstrated that the fusion polypeptide of the present invention can increase the expression of a target gene in cells merely by adding the fusion polypeptide to a medium for the culture of the cells, without using a cell transfection reagent or electroporation.

Example 3

Measurement of Intracellular Human TERT mRNA Expression Level when NTP-TALE-Activator is Added—(2)

Each NTP-TALE-Activator (NTP-TALE-TERT-1-p300CD, NTP-TALE-TERT-2-p300CD and NTP-TALE-TERT-3-p300CD) targeting human TERT, prepared in Example 1 was dialyzed at 4° C. for 3 hours against OPTI-MEM medium (Thermo Fisher Scientific Inc.) in a microdialysis column (Tomy Seiko Co., Ltd.). The concentrations after purification were 40 nM NTP-TALE-TERT-1-p300CD, 55 nM NTP-TALE-TERT-2-p300CD, and 55 nM NTP-TALE-TERT-3-p300CD. Human T cells (obtained by separation from peripheral mononuclear cells in blood collected from a healthy person) were suspended in 100 µL of KBM550 (Kohjin Bio Co., Ltd.) and seeded in a 96-well plate at $0.5 \times 10^4$ cells/well.

The human T cells were separated as follows: blood was collected from a test subject, and centrifuged at 1500 rpm at room temperature for 20 minutes within 2 hours after the blood collection to collect an intermediate layer (mononuclear cell layer). The intermediate layer was washed twice with phosphate-buffered saline and suspended in 10 mL of KBM550 medium for lymphocyte culture (Kohjin Bio Co., Ltd., 16025500) warmed to 37° C. The cells were seeded in a culture dish of 10 cm in diameter (Corning Inc.) coated with an anti-CD3 antibody (Becton, Dickinson and Company, 555336, Clone HIT3a) at $2 \times 10^7$ cells. Then, the culture dish was left standing in an incubator at 37° C. and a $CO_2$ concentration of 5%. The coating was performed by adding a solution of the anti-CD3 antibody diluted to 10 µg/mL with phosphate-buffered saline so as to cover the surface of the culture dish, followed by incubation at 37° C. for 1 hour. Immediately before use, the antibody dilution was removed, and the culture dish was washed once with phosphate-buffered saline. The cells that became confluent in the culture dish were dissociated by pipetting. After centrifugation at 1000 rpm at room temperature for 5 minutes, a supernatant was removed. The cells were suspended in KBM550 medium for lymphocyte culture and seeded in a 6-well culture plate (Corning Inc.) coated with the aforementioned anti-CD3 antibody solution at $1.5 \times 10^6$ cells/well. The plate was left standing for 24 hours in an incubator at 37° C. and a $CO_2$ concentration of 5%. Then, colony formation by the growth of T lymphocytes was confirmed, and the colony was separated and obtained.

The obtained human T cells were cultured for 12 hours. Then, each NTP-TALE-Activator dialyzed as mentioned above was added at 3.0 nM (final concentration) to each well (as a result of conducting studies beforehand with a plurality of concentrations, the concentration at which each NTP-TALE-Activator was most responsive was 3.0 nM). Wells to which NTP-TALE-Activator was not added were prepared as a control. The plate was left standing for 24 hours in an incubator at 37° C. and a $CO_2$ concentration of 5%.

An intracellular human TERT mRNA expression level was measured 24 hours later by the following method: a culture supernatant was removed from each well of the cultured cells mentioned above, and the well was washed once with ice-cold phosphate-buffered saline. Then, 25 µL of a lysis solution (mixed solution of 24.5 µL of Lysis solution and 0.5 µL of DNase I) attached to Ambion® Power SYBR Cells-to-CT™ kit (Thermo Fisher Scientific Inc.) was added to each well and mixed with the cells. The plate was left standing at room temperature for 5 minutes. Then, 2.5 µL of Stop solution attached to the kit was added to each well, and the plate was left standing at room temperature for 2 minutes. As a result, a cell lysate containing RNA extracted from the cells was obtained.

cDNA was prepared from RNA using the cell lysate as a template and reverse transcriptase attached to the kit according to the attached protocol. Subsequently, real-time PCR was performed in CFX96 Touch real-time PCR analysis system (Bio-Rad Laboratories, Inc.) using the primers given below and Power SYBR Green PCR Master Mix attached to the kit to measure a human TERT mRNA level. A human actin beta (ACTB) mRNA level was measured for an endogenous control gene. A value determined by dividing the human TERT mRNA level by the human ACTB mRNA level was used as the relative expression level of human TERT mRNA. The relative expression level of human TERT mRNA in each group was calculated when the relative expression level of human TERT mRNA of the control was defined as 1. The wells for the same sample were measured in triplicate.

As a forward primer for TERT and a reverse primer for TERT, primers consisting of the nucleotide sequences represented by SEQ ID NOs: 43 and 44 were used, respectively. As a forward primer for ACTB and a reverse primer for ACTB, primers consisting of the nucleotide sequences represented by SEQ ID NOs: 45 and 46 were used, respectively.

As shown in FIG. 2, NTP-TALE-TERT-1-p300CD, NTP-TALE-TERT-2-p300CD and NTP-TALE-TERT-3-p300CD increased the expression level of human TERT mRNA to about 17 times, about 3.5 times, and about 2 times, respectively, as compared with the control group. Their activity was found to be higher in the order of NTP-TALE-TERT-1-p300CD, NTP-TALE-TERT-2-p300CD and NTP-TALE-TERT-3-p300CD.

Example 4

Measurement of Intracellular Human miR-346 RNA Expression Level when NTP-TALE-miR-346-1-VP64 is Added Evaluation was conducted in a similar way to the method shown in Example 3 using human bone marrow-derived mesenchymal stem cells (PromoCell GmbH, C-12974; hereinafter, abbreviated to BM-MSC) except that Mesenchymal Stem Cell Growth Medium (Takara Bio Inc. C-28010) was used as a medium. NTP-TALE-miR-346-1-VP64 prepared in Example 1 mentioned above was dialyzed in a similar way to the method shown in Example 3 to adjust the concentration to 150 nM. This was added at 0.25 nM, 3 nM and 10 nM (intrawell final concentration at the time of the experiment) to BM-MSC, and an intracellular human miR-346 RNA expression level was measured 24 hours later. In real-time PCR, a primer consisting of the nucleotide sequence represented by SEQ ID NO: 47 was used as a forward primer, and a universal primer of miScript SYBR® Green PCR Kit (Merck Millipore) was used as a reverse primer.

A U6 RNA level was measured as an endogenous control gene. A value determined by dividing the human miR-346 RNA level by the U6 RNA level was used as the relative expression level of human miR-346 RNA. The relative expression level of human miR-346 RNA in each group was calculated when the relative expression level of human miR-346 RNA of the control was defined as 1. A primer consisting of the nucleotide sequence represented by SEQ ID NO: 48 was used as a forward primer for U6, and the aforementioned universal primer was used as a reverse primer.

As shown in FIG. 3, NTP-TALE-miR-346-1-VP64 increased the expression of human miR-346 RNA (i.e. increased the expression of human miR-346 gene) as compared with the control.

The results of Examples 2 to 4 demonstrated that the fusion polypeptide of the present invention can increase the expression of a target gene in cells merely by adding the fusion polypeptide to a medium for the culture of the cells, without using a cell transfection reagent or electroporation.

Example 5

Cell Growth Assay

The effect of NTP-TALE-Activator on cell growth was evaluated. UC-MSC cultured in the same medium as in Example 2 was seeded in a 96-well plate (Iwaki Glass Co., Ltd., 3860-096) at $0.1 \times 10^4$ cells/100 μL/well and cultured at 37° C. for 24 hours at a $CO_2$ concentration of 5%. Here, the culture time was prolonged because the amount of the cells seeded was smaller than that of Example 2. In the growth test, cells having reduced growth ability to grow at a passage number ranging from 10 to 20 were used for sufficiently confirming the effect of a test protein group. NTP-TALE-TERT-1-GCNSCD, NTP-TALE-TERT-1-VPR and NTP-TALE-miR-346-1-VP64 prepared in Example 1 were diluted to 0.5 nM (final concentration) with an elution buffer solution and each added at 1 μL to each well. An elution buffer solution was added as a control instead of NTP-TALE-Activator. The medium was replaced with a fresh one every 24 hours, and the culture was continued up to 72 hours. For the medium replacement, 1 μL of each NTP-TALE-Activator was added to each well to adjust the final concentration to 0.5 nM. An intracellular ATP quantification reagent CellTiter-Glo® Reagent was added at 100 μL/well every 24 hours from the start of addition of NTP-TALE-Activator. The plate was left standing at room temperature for 10 minutes. Then, 200 μL of the cell suspension was transferred to each well of a 96-well white plate (Corning Inc.). The luminescence intensity of each well was measured using TECAN Infinite® M1000 (Tecan Trading AG) to measure the growth ability of the cells. The wells for the same sample were measured in triplicate.

As shown in FIG. 4, NTP-TALE-Activator (NTP-TALE-TERT-1-GCN5CD ("TERT-1-GCN5CD" in FIG. 4), NTP-TALE-TERT-1-VPR ("TERT-1-VPR" in FIG. 4), and NTP-TALE-miR-346-1-VP64 ("miR-346-1-VP64" in FIG. 4)) increased the total amount of intracellular ATP as compared with the control and promoted the growth of the cells.

These results demonstrated that the fusion polypeptide of the present invention can markedly promote the growth of cells by culturing the cells in a medium containing the fusion polypeptide.

Example 6

Cell Growth Assay (Long-Term Culture Test Using Human Fibroblast)

Human fibroblasts MRC-5 (Riken Cell Bank) were cultured in alpha MEM medium (Thermo Fisher Scientific Inc.) containing 10% fetal bovine serum (Thermo Fisher Scientific Inc.) and 1% penicillin-streptomycin (Thermo Fisher Scientific Inc.). At the time of a passage number of 8, the cells were liberated with trypsin (Wako Pure Chemical Industries, Ltd.), and a cell count was measured using a cytometer. The cells were suspended in 0.5 mL of the medium and seeded in a collagen I-coated 6-well plate (Corning Inc.) at $1 \times 10^5$ cells/well. The plate was left standing for 24 hours in an incubator at 37° C. and a $CO_2$ concentration of 5%. Then, NTP-TALE-TERT-1-VPR prepared in Example 1 and GST-NTP-EGFP as a negative control were each diluted to 100 nM with the medium (referred to as diluted NTP-TALE-TERT-1-VPR and diluted GST-NTP-EGFP, respectively) and added at 5 μL to each well. Only the medium was added as a control group to wells. The plate was left standing in an incubator at 37° C. and a $CO_2$ concentration of 5%. The aforementioned diluted NTP-TALE-TERT-1-VPR and diluted GST-NTP-EGFP were each added at 5 μL/well every 24 hours. On the 3rd day, each well was washed twice with 1 mL of phosphate-buffered saline. Then, the cells were liberated from the plate by adding trypsin at 100 μL/well. The cells were suspended by adding the medium at 400 μL/well. Then, the cell count of each well was measured four independent times using a cytometer. Then, the cell suspension was diluted with the medium and reseeded in a 6-well plate at $1 \times 10^5$ cells/well. This procedure was repetitively performed until the cumulative passage number reached 21. The measured cell count was multiplied by the dilution ratio at the time of passage corresponding to the cumulative passage number and compared with the cell count at the start of the experiment. The resulting numeric value (average of 4 measurement values) is shown in FIG. 5. In FIG. 5, 8 to 22 on the abscissa of the graph represent the passage numbers of the cells.

As shown in FIG. 5, it was confirmed that the cell count was increased in the cell group supplemented with NTP-TALE-TERT-1-VPR as compared with the cell group supplemented with only the medium (indicated by control) and the cell group supplemented with GST-NTP-EGFP (indicated by NTP-EGFP). Thus, NTP-TALE-TERT-1-VPR was shown to have a cell growth promoting effect.

These results demonstrated that the fusion polypeptide of the present invention can proliferate somatic cells (promote the growth of somatic cells) by culturing the somatic cells in a medium containing the fusion polypeptide. Furthermore, the results of this Example demonstrated that the fusion polypeptide of the present invention can proliferate somatic cells merely by adding the fusion polypeptide to a medium for the culture of the somatic cells. Moreover, in consideration of the results of Example 2, it was suggested that the fusion polypeptide of the present invention can proliferate somatic cells by regulating the transcription of a target gene (TERT) in the somatic cells.

Example 7

Measurement of Intracellular Human TERT mRNA Expression Level when ICQ2-TALE-TERT-1-VPR is Added An intracellular human TERT mRNA expression level when NTP-TALE-TERT-1-VPR or ICQ2-TALE-TERT-1-VPR was added was measured in a similar way to the method of Example 3 except for an intrawell final concentration. The intrawell final concentrations of NTP-TALE-TERT-1-VPR and ICQ2-TALE-TERT-1-VPR were 0.25 nM, 1 nM, 3 nM, 10 nM and 30 nM for the evaluation.

As a result, as shown in FIG. 6, ICQ2-TALE-TERT-1-VPR was found to increase the mRNA expression of the target human TERT gene at a level equivalent to or greater than that of NTP-TALE-TERT-1-VPR.

Example 8

Cell Growth Assay (Long-Term Culture Test Using Human MSC)

The effect of ICQ2-TALE-TERT-1-VPR on cell growth was evaluated. The same cell species and medium as in Example 2 were used. The cells at a passage number of 16 were suspended in 0.5 mL of the medium and seeded in a collagen I-coated 6-well plate (Corning Inc.) at $1 \times 10^5$ cells/well. ICQ2-TALE-TERT-1-VPR and NTP-TALE-scramble-VPR prepared in Example 1 were each diluted to 100 nM with the medium (referred to as diluted ICQ2-TALE-TERT-1-VPR and diluted NTP-TALE-scramble-VPR, respectively) and added at 5 μL to each well (cell group supplemented with NTP-TALE-scramble-VPR is referred to as a control). The aforementioned diluted ICQ2-TALE-TERT-1-VPR and diluted NTP-TALE-scramble-VPR were each added at 5 μL/well every 24 hours. On the 3rd day, each well was washed twice with 1 mL of phosphate-buffered saline. Then, the cells were liberated from the plate by adding trypsin at 100 μL/well. The cells were suspended by adding the medium at 400 μL/well. Then, the cell count of each well was measured four independent times using a cytometer. Then, the cell suspension was suspended by dilution with the medium and reseeded in a 6-well plate at 1×10$^5$ cells/well. This procedure was repetitively performed until the cumulative passage number reached 19. The measured cell count was multiplied by the dilution ratio at the time of passage corresponding to the cumulative passage number and compared with the cell count at the start of the experiment. The resulting numeric value (average of 4 measurement values) is shown in FIG. 7. In FIG. 7, 16 to 19 on the abscissa of the graph represent the passage numbers of the cells.

As a result, as shown in FIG. 7, the growth of the cells cultured in the medium supplemented with ICQ2-TALE-TERT-1-VPR was promoted as compared with the control.

INDUSTRIAL APPLICABILITY

The fusion polypeptide of the present invention is expected to be useful for regulating the expression of a target gene. Also, the fusion polypeptide of the present invention is expected to be useful for promoting the growth of cells. Furthermore, the polynucleotide, the expression vector, the transformed host cell and the method for producing a protein according to the present invention are expected to be useful for producing the fusion polypeptide.

FREE TEXT OF SEQUENCE LISTING

"Artificial Sequence" will be described in numeric identifier <223> in the sequence listing given below. Specifically, the nucleotide sequences represented by SEQ ID NOs: 1, 3, 5 and 7 of the sequence listing are the nucleotide sequences of TALE_TERT-1, TALE_TERT-2, TALE_TERT-3 and TALE_miR-346-1, respectively, and the amino acid sequences represented by SEQ ID NOs: 2, 4, 6 and 8 are the amino acid sequences of TALE_TERT-1 encoded by the nucleotide sequence represented by SEQ ID NO: 1, TALE_TERT-2 encoded by the nucleotide sequence represented by SEQ ID NO: 3, TALE_TERT-3 encoded by the nucleotide sequence represented by SEQ ID NO: 5 and TALE_miR-346-1 encoded by the nucleotide sequence represented by SEQ ID NO: 7, respectively. The nucleotide sequences represented by SEQ ID NOs: 9, 11, 13, 15, 17, 19, 21 and 61 of the sequence listing are the nucleotide sequences of NTP-TALE-TERT-1-VP64, NTP-TALE-TERT-1-VPR, NTP-TALE-TERT-1-p300CD, NTP-TALE-TERT-1-GCN5CD, NTP-TALE-TERT-2-p300CD, NTP-TALE-TERT-3-p300CD, NTP-TALE-miR-346-1-VP64, and ICQ2-TALE-TERT-1-VPR, respectively, and the amino acid sequences represented by SEQ ID NOs: 10, 12, 14, 16, 18, 20, 22 and 62 are the amino acid sequences of NTP-TALE-TERT-1-VP64 encoded by the nucleotide sequence represented by SEQ ID NO: 9, NTP-TALE-TERT-1-VPR encoded by the nucleotide sequence represented by SEQ ID NO: 11, NTP-TALE-TERT-1-p300CD encoded by the nucleotide sequence represented by SEQ ID NO: 13, NTP-TALE-TERT-1-GCN5CD encoded by the nucleotide sequence represented by SEQ ID NO: 15, NTP-TALE-TERT-2-p300CD encoded by the nucleotide sequence represented by SEQ ID NO: 17, NTP-TALE-TERT-3-p300CD encoded by the nucleotide sequence represented by SEQ ID NO: 19, NTP-TALE-miR-346-1-VP64 encoded by the nucleotide sequence represented by SEQ ID NO: 21, and ICQ2-TALE-TERT-1-VPR encoded by the nucleotide sequence represented by SEQ ID NO: 61, respectively. The nucleotide sequence represented by SEQ ID NO: 23 is a nucleotide sequence encoding NTP (RIFIHFRIGC). The nucleotide sequence represented by SEQ ID NO: 25 is a nucleotide sequence encoding TEV. The nucleotide sequences represented by SEQ ID NOs: 26, 27, 30 to 33, 35 to 38, 40, 41, 43 to 48, 70 and 71 are the respective nucleotide sequences of primers. The nucleotide sequence represented by SEQ ID NO: 28 is the nucleotide sequence of ΔTALE-VP64. The amino acid sequence represented by SEQ ID NO: 29 is the amino acid sequence of VP64. The amino acid sequence represented by SEQ ID NO: 34 is the amino acid sequence of VPR. The amino acid sequences represented by SEQ ID NOs: 53 to 57 and 60 are the respective amino acid sequences of cell-penetrating peptides. The nucleotide sequences represented by SEQ ID NOs: 58 and 59 are the 5'-terminal and 3'-terminal nucleotide sequences, respectively, of VPR-PCR. The nucleotide sequence represented by SEQ ID NO: 63 is the nucleotide sequence of TALE_scramble, and the amino acid sequence represented by SEQ ID NO: 64 is the amino acid sequence of TALE_scramble encoded by the nucleotide sequence represented by SEQ ID NO: 63. The nucleotide sequence represented by SEQ ID NO: 65 is the nucleotide sequence of a polynucleotide encoding EGFP with a XhoI site and a NotI site added thereto. The nucleotide sequence represented by SEQ ID NO: 66 is the nucleotide sequence of a polynucleotide comprising a polynucleotide encoding ICQ2 (amino acid sequence: RIFIHFRQGQ). The nucleotide sequence represented by SEQ ID NO: 67 is a nucleotide sequence encoding ICQ2. The nucleotide sequence represented by SEQ ID NO: 68 is a nucleotide sequence encoding a linker. The nucleotide sequence represented by SEQ ID NO: 69 is the nucleotide sequence of a polynucleotide.

The invention claimed is:

1. A fusion polypeptide comprising: a cell-penetrating peptide; a DNA-binding polypeptide that binds to the nucleotide sequence represented by SEQ ID NO: 49; and a transcriptional activator, wherein the cell-penetrating peptide, the DNA-binding peptide and the transcriptional activator are in this order from the N-terminal side.

2. The fusion polypeptide according to claim 1, wherein the transcriptional activator is VP64, VPR, p300 or GCN5.

3. The fusion polypeptide according to claim 1, wherein the cell-penetrating peptide is a peptide consisting of the amino acid sequence represented by SEQ ID NO: 53, 54, 55, 56, 57 or 60.

4. The fusion polypeptide according to claim 1, wherein the cell-penetrating peptide is a peptide consisting of the amino acid sequence represented by SEQ ID NO: 56 or 60.

5. The fusion polypeptide according to claim 1, wherein the DNA-binding polypeptide is transcription activator-like effector (TALE).

6. The fusion polypeptide according to claim 5, wherein the DNA-binding polypeptide is TALE comprising an amino acid sequence consisting of amino acid numbers 7 to 784 of SEQ ID NO: 2.

7. The fusion polypeptide according to claim 1, wherein the DNA-binding polypeptide is a polypeptide consisting of the amino acid sequence represented by SEQ ID NO: 2.

8. The fusion polypeptide according to claim 1, wherein the cell-penetrating peptide is a peptide consisting of the amino acid sequence represented by SEQ ID NO: 56 or 60, the DNA-binding polypeptide is a polypeptide consisting of the amino acid sequence represented by SEQ ID NO: 2, and the transcriptional activator is VPR.

9. The fusion polypeptide according to claim 1, wherein the fusion polypeptide is a polypeptide consisting of the amino acid sequence represented by SEQ ID NO: 62.

10. A polynucleotide comprising a nucleotide sequence encoding a fusion polypeptide according to claim 1.

11. An expression vector comprising a polynucleotide according to claim 10.

12. A host cell transformed with an expression vector according to claim 11.

13. A method for producing a fusion polypeptide, comprising the step of culturing a host cell according to claim 12.

14. A method for increasing the expression of human telomerase reverse transcriptase (TERT) gene in a human somatic cell, comprising the step of culturing the human somatic cell in a medium containing a fusion polypeptide according to claim 1.

15. A method for proliferating human somatic cells, comprising the step of culturing the human somatic cells in a medium containing a fusion polypeptide according to claim 1.

* * * * *